US006596279B1

(12) United States Patent
Paoletti et al.

(10) Patent No.: US 6,596,279 B1
(45) Date of Patent: Jul. 22, 2003

(54) IMMUNODEFICIENCY RECOMBINANT POXVIRUS

(75) Inventors: Enzo Paoletti, Delmar, NY (US); James Tartaglia, Schenectady, NY (US); William I. Cox, East Greenbush, NY (US); Robert Gallo, Baltimore, MD (US); Genoveffa Franchini, Washington, DC (US)

(73) Assignee: Virogenetics Corporation, Troy, NY (US)

( * ) Notice: Subject to any disclaimer, the term of this patent is extended or adjusted under 35 U.S.C. 154(b) by 0 days.

(21) Appl. No.: 09/136,159

(22) Filed: Aug. 14, 1998

Related U.S. Application Data

(60) Division of application No. 08/417,210, filed on Apr. 5, 1995, now Pat. No. 5,863,542, which is a continuation-in-part of application No. 08/223,842, filed on Apr. 6, 1994, now abandoned, which is a continuation-in-part of application No. 07/897,382, filed on Jun. 11, 1992, now abandoned, which is a continuation-in-part of application No. 07/715,921, filed on Jun. 14, 1991, now abandoned, application No. 09/136,159, which is a continuation-in-part of application No. 08/105,483, filed on Aug. 12, 1993, now Pat. No. 5,494,807, which is a continuation of application No. 07/847,951, filed on Mar. 6, 1992, now abandoned, which is a continuation-in-part of application No. 07/713,967, filed on Jun. 11, 1991, now abandoned, which is a continuation-in-part of application No. 07/666,056, filed on Mar. 7, 1991, now abandoned.

(51) Int. Cl.[7] ................................................ A61K 39/12

(52) U.S. Cl. ................................ 424/199.1; 424/188.1; 424/208.1; 424/202.1; 424/232.1; 435/320.1

(58) Field of Search ............................. 435/69.1, 320.1; 424/188.1, 199.1, 202.1, 208.1, 232.1

(56) References Cited

U.S. PATENT DOCUMENTS

| | | | | | |
|---|---|---|---|---|---|
| 5,494,807 | A | * | 2/1996 | Paoletti et al. | 435/69.3 |
| 5,762,938 | A | * | 6/1998 | Paoletti et al. | 424/199.1 |

* cited by examiner

*Primary Examiner*—Laurie Scheiner
*Assistant Examiner*—Jeffrey S. Parkin
(74) *Attorney, Agent, or Firm*—Patrick J. Halloran

(57) ABSTRACT

Attenuated recombinant viruses containing DNA encoding an immunodeficiency virus and/or CTL antigen, as well as methods and compositions employing the viruses, expression products therefrom, and antibodies generated from the viruses or expression products, are disclosed and claimed. The recombinant viruses can be NYVAC or ALVAC recombinant viruses. The DNA can code for at least one of: HIV1gag(+pro)(IIIB), gp120(MN)(+transmembrane), nef (BRU)CTL, pol(IIIB)CTL, ELDKWA or LDKW epitopes, preferably HIV1gag(+pro)(IIIB), gp120(MN)(+transmembrane), two (2) nef(BRU)CTL and three (3) pol(IIIB)CTL etpitopes; or two ELDKWA in gp120 V3 or another region or in gp160. The two (2) nef(BRU)CTL and three (3) pol(IIIB)CTL epitopes are preferably CTL1, CTL2, pol1, pol2 and pol3. The recombinant viruses and gene products therefrom and antibodies generated by the viruses and gene products have several preventive, therapeutic and diagnostic uses. DNA from the recombinant viruses are useful as probes or, for generating PCR primers or for immunization. Also disclosed and claimed are HIV immunogens and modified gp160 and gp120.

23 Claims, 128 Drawing Sheets

| | | | |
|---|---|---|---|
| 1 | TGAATGTTAA | ATGTTATACT | TTGGATGAAG |
| 31 | CTATAAATAT | GCATTGGAAA | AATAATCCAT |
| 61 | TTAAAGAAAG | GATTCAAATA | CTACAAAACC |
| 91 | TAAGCGATAA | TATGTTAACT | AAGCTTATTC |
| 121 | TTAACGACGC | TTTAAATATA | CACAAATAAA |
| 151 | CATAATTTTT | GTATAACCTA | ACAAATAACT |
| 181 | AAAACATAAA | AATAATAAAA | GGAAATGTAA |
| 211 | TATCGTAATT | ATTTTACTCA | GGAATGGGGT |
| 241 | TAAATATTTA | TATCACGTGT | ATATCTATAC |
| 271 | TGTTATCGTA | TACACTTTAC | AATTACTATT |
| 301 | ACGAATATGC | AAGAGATAAT | AAGATTACGT |
| 331 | ATTTAAGAGA | ATCTTGTCAT | GATAATTGGG |
| 361 | TACGACATAG | TGATAAATGC | TATTTCGCAT |
| 391 | CGTTACATAA | AGTCAGTTGG | AAAGATGGAT |
| 421 | TTGACAGATG | TAACTTAATA | GGTGCAAAAA |
| 451 | TGTTAAATAA | CAGCATTCTA | TCGGAAGATA |
| 481 | GGATACCAGT | TATATTATAC | AAAAATCACT |
| 511 | GGTTGGATAA | AACAGATTCT | GCAATATTCG |
| 541 | TAAAAGATGA | AGATTACTGC | GAATTTGTAA |
| 571 | ACTATGACAA | TAAAAAGCCA | TTTATCTCAA |
| 601 | CGACATCGTG | TAATTCTTCC | ATGTTTTATG |
| 631 | TATGTGTTTC | AGATATTATG | AGATTACTAT |
| 661 | AAACTTTTTG | TATACTTATA | TTCCGTAAAC |
| 691 | TATATTAATC | ATGAAGAAAA | TGAAAAAGTA |
| 721 | TAGAAGCTGT | TCACGAGCGG | TTGTTGAAAA |
| 751 | CAACAAAATT | ATACATTCAA | GATGGCTTAC |
| 781 | ATATACGTCT | GTGAGGCTAT | CATGGATAAT |
| 811 | GACAATGCAT | CTCTAAATAG | GTTTTTGGAC |
| 841 | AATGGATTCG | ACCCTAACAC | GGAATATGGT |
| 871 | ACTCTACAAT | CTCCTCTTGA | AATGGCTGTA |
| 901 | ATGTTCAAGA | ATACCGAGGC | TATAAAAATC |
| 931 | TTGATGAGGT | ATGGAGCTAA | ACCTGTAGTT |
| 961 | ACTGAATGCA | CAACTTCTTG | TCTGCATGAT |
| 991 | GCGGTGTTGA | GAGACGACTA | CAAAATAGTG |
| 1021 | AAAGATCTGT | TGAAGAATAA | CTATGTAAAC |
| 1051 | AATGTTCTTT | ACAGCGGAGG | CTTTACTCCT |
| 1081 | TTGTGTTTGG | CAGCTTACCT | TAACAAAGTT |
| 1111 | AATTTGGTTA | AACTTCTATT | GGCTCATTCG |
| 1141 | GCGGATGTAG | ATATTTCAAA | CACGGATCGG |
| 1171 | TTAACTCCTC | TACATATAGC | CGTATCAAAT |
| 1201 | AAAAATTTAA | CAATGGTTAA | ACTTCTATTG |
| 1231 | AACAAAGGTG | CTGATACTGA | CTTGCTGGAT |
| 1261 | AACATGGGAC | GTACTCCTTT | AATGATCGCT |
| 1291 | GTACAATCTG | GAAATATTGA | AATATGTAGC |

FIG. 8B

| | | | |
|---|---|---|---|
| 1321 | ACACTACTTA | AAAAAAATAA | AATGTCAGAA |
| 1351 | CTGGGAAAAA | TTGATCTTGC | CAGCTGTAAT |
| 1381 | TCATGGTAGA | AAAGAAGTGC | TCAGGCTACT |
| 1411 | TTTCAACAAA | GGAGCAGATG | TAAACTACAT |
| 1441 | CTTTGAAAGA | AATGGAAAAT | CATATACTGT |
| 1471 | TTTGGAATTG | ATTAAAGAAA | GTTACTCTGA |
| 1501 | GACACAAAAG | AGGTAGCTGA | AGTGGTACTC |
| 1531 | TCAAAATGCA | GAACGATGAC | TGCGAAGCAA |
| 1561 | GAAGTAGAGA | AATAACACTT | TATGACTTTC |
| 1591 | TTAGTTGTAG | AAAAGATAGA | GATATAATGA |
| 1621 | TGGTCATAAA | TAACTCTGAT | ATTGCAAGTA |
| 1651 | AATGCAATAA | TAAGTTAGAT | TTATTTAAAA |
| 1681 | GGATAGTTAA | AAATAGAAAA | AAAGAGTTAA |
| 1711 | TTTGTAGGGT | TAAAATAATA | CATAAGATCT |
| 1741 | TAAAATTTAT | AAATACGCAT | AATAATAAAA |
| 1771 | ATAGATTATA | CTTATTACCT | TCAGAGATAA |
| 1801 | AATTTAAGAT | ATTTACTTAT | TTAACTTATA |
| 1831 | AAGATCTAAA | ATGCATAATT | TCTAAATAAT |
| 1861 | GAAAAAAAAG | TACATCATGA | GCAACGCGTT |
| 1891 | AGTATATTTT | ACAATGGAGA | TTAACGCTCT |
| 1921 | ATACCGTTCT | ATGTTTATTG | ATTCAGATGA |
| 1951 | TGTTTTAGAA | AAGAAAGTTA | TTGAATATGA |
| 1981 | AAACTTTAAT | GAAGATGAAG | ATGACGACGA |
| 2211 | TGATTATTGT | TGTAAATCTG | TTTTAGATGA |
| 2041 | AGAAGATGAC | GCGCTAAAGT | ATACTATGGT |
| 2071 | TACAAAGTAT | AAGTCTATAC | TACTAATGGC |
| 2101 | GACTTGTGCA | AGAAGGTATA | GTATAGTGAA |
| 2131 | AATGTTGTTA | GATTATGATT | ATGAAAAACC |
| 2161 | AAATAAATCA | GATCCATATC | TAAAGGTATC |
| 2191 | TCCTTTGCAC | ATAATTTCAT | CTATTCCTAG |
| 2221 | TTTAGAATAC | TTTTCATTAT | ATTTGTTTAC |
| 2251 | AGCTGAAGAC | GAAAAAAATA | TATCGATAAT |
| 2281 | AGAAGATTAT | GTTAACTCTG | CTAATAAGAT |
| 2311 | GAAATTGAAT | GAGTCTGTGA | TAATAGCTAT |
| 2341 | AATCAGAGAA | GTTCTAAAAG | GAAATAAAAA |
| 2371 | TCTAACTGAT | CAGGATATAA | AAACATTGGC |
| 2401 | TGATGAAATC | AACAAGGAGG | AACTGAATAT |
| 2431 | AGCTAAACTA | TTGTTAGATA | GAGGGGCCAA |
| 2461 | AGTAAATTAC | AAGGATGTTT | ACGGTTCTTC |
| 2491 | AGCTCTCCAT | AGAGCTGCTA | TTGGTAGGAA |
| 2521 | ACAGGATATG | ATAAAGCTGT | TAATCGATCA |
| 2551 | TGGAGCTGAT | GTAAACTCTT | TAACTATTGC |
| 2581 | TAAAGATAAT | CTTATTAAAA | AAAAATAATA |
| 2611 | TCACGTTTAG | TAATATTAAA | ATATATTAAT |

FIG. 8C

| | | | |
|---|---|---|---|
| 2641 | AACTCTATTA | CTAATAACTC | CAGTGGATAT |
| 2671 | GAACATAATA | CGAAGTTTAT | ACATTCTCAT |
| 2701 | CAAAATCTTA | TTGACATCAA | GTTAGATTGT |
| 2731 | GAAAATGAGA | TTATGAAATT | AAGGAATACA |
| 2761 | AAAATAGGAT | GTAAGAACTT | ACTAGAATGT |
| 2791 | TTTATCAATA | ATGATATGAA | TACAGTATCT |
| 2821 | AGGGCTATAA | ACAATGAAAC | GATTAAAAAT |
| 2851 | TATAAAAATC | ATTTCCCTAT | ATATAATACG |
| 2881 | CTCATAGAAA | AATTCATTTC | TGAAAGTATA |
| 2911 | CTAAGACACG | AATTATTGGA | TGGAGTTATA |
| 2941 | AATTCTTTTC | AAGGATTCAA | TAATAAATTG |
| 2971 | CCTTACGAGA | TTCAGTACAT | TATACTGGAG |
| 3001 | AATCTTAATA | ACCATGAACT | AAAAAAAATT |
| 3031 | TTAGATAATA | TACATTAAAA | AGGTAAATAG |
| 3061 | ATCATCTGTT | ATTATAAGCA | AAGATGCTTG |
| 3091 | TTGCCAATAA | TATACAACAG | GTATTTGTTT |
| 3121 | TTATTTTTAA | CTACATATTT | GATGTTCATT |
| 3151 | CTCTTTATAT | AGTATACACA | GAAAATTCAT |
| 3181 | AATCCACTTA | GAATTTCTAG | TTATCTAG |

| | | | |
|---|---|---|---|
| 1 | GATATCTGTG | GTCTATATAT | ACTACACCCT |
| 31 | ACCGATATTA | ACCAACGAGT | TTCTCACAAG |
| 61 | AAAACTTGTT | TAGTAGATAG | AGATTCTTTG |
| 91 | ATTGTGTTTA | AAAGAAGTAC | CAGTAAAAAG |
| 121 | TGTGGCATAT | GCATAGAAGA | AATAAACAAA |
| 151 | AAACATATTT | CCGAACAGTA | TTTTGGAATT |
| 181 | CTCCCAAGTT | GTAAACATAT | TTTTTGCCTA |
| 211 | TCATGTATAA | GACGTTGGGC | AGATACTACC |
| 241 | AGAAATACAG | ATACTGAAAA | TACGTGTCCT |
| 271 | GAATGTAGAA | TAGTTTTTCC | TTTCATAATA |
| 301 | CCCAGTAGGT | ATTGGATAGA | TAATAAATAT |
| 331 | GATAAAAAAA | TATTATATAA | TAGATATAAG |
| 361 | AAAATGATTT | TTACAAAAAT | ACCTATAAGA |
| 391 | ACAATAAAAA | TATAATTACA | TTTACGGAAA |
| 421 | ATAGCTGGTT | TTAGTTTACC | AACTTAGAGT |
| 451 | AATTATCATA | TTGAATCTAT | ATTGTTTTTT |
| 481 | AGTTATATAA | AAACATGATT | AGCCCCCAAT |
| 511 | CGGATGAAAA | TATAAAAGAT | GTTGAGAATT |
| 541 | TCGAATACAA | CAAAAAGAGG | AATCGTACGT |
| 571 | TGTCCATATC | CAAACATATA | AATAAAAATT |
| 601 | CAAAAGTAGT | ATTATACTGG | ATGTTTAGAG |
| 631 | ATCAACGTGT | ACAAGATAAT | TGGGCTTTAA |
| 661 | TTTACGCACA | ACGATTAGCG | TTAAAACTCA |
| 691 | AAATACCTCT | AAGAATATGC | TTTTGTGTCG |
| 721 | TGCCAAAATT | TCACACTACT | ACTTCTAGAC |
| 751 | ACTTTATGTT | TTTAATATCC | GGTCTTAAAG |
| 781 | AAGTCGCGGA | AGAATGTAAA | AGACTATGTA |
| 811 | TAGGGTTTTC | ATTGATATAT | GGCGTACCAA |
| 841 | AAGTAATAAT | TCCGTGTATA | GTAAAAAAAT |
| 871 | ACAGAGTCGG | AGTAATCATA | ACGGATTTCT |
| 901 | TTCCATTACG | TGTTCCCGAA | AGATTAATGA |
| 931 | AACAGACTGT | AATATCTCTT | CCAGATAACA |
| 961 | TACCTTTTAT | ACAAGTAGAC | GCTCATAATA |
| 991 | TAGTACCTTG | TTGGGAAGCT | TCTGATAAAG |
| 1021 | AAGAATACGG | TGCACGAACT | TTAAGAAAAA |
| 1051 | AGATATTTGA | TAAATTATAT | GAATATATGA |
| 1081 | CAGAATTTCC | TGTTGTTCGT | AAACATCCAT |
| 1111 | ACGGTCCATT | TTCTATATCT | ATTGCAAAAC |
| 1141 | CCAAAAATAT | ATCATTAGAC | AAGACGGTAT |
| 1171 | TACCCGTAAA | ATGGGCAACG | CCTGGAACAA |
| 1201 | AAGCTGGAAT | AATTGTTTTA | AAAGAATTTA |
| 1231 | TAAAAAACAG | ATTACCGTCA | TACGACGCGG |
| 1261 | ATCATAACAA | TCCTACGTGT | GACGCTTTGA |
| 1291 | GTAACTTATC | TCCGTGGCTA | CATTTTGGTC |

FIG. 11B

| | | | |
|---|---|---|---|
| 1321 | ATGTATCCGC | ACAACGTGTT | GCCTTAGAAG |
| 1351 | TATTAAAATG | TATACGAGAA | AGCAAAAAAA |
| 1381 | ACGTTGAAAC | GTTTATAGAT | GAAATAATTG |
| 1411 | TAAGAAGAGA | ACTATCGGAT | AATTTTTGTT |
| 1441 | ACTATAACAA | ACATTATGAT | AGTATCCAGT |
| 1471 | CTACTCATTC | ATGGGTTAGA | AAAACATTAG |
| 1501 | AAGATCACAT | TAATGATCCT | AGAAAGTATA |
| 1531 | TATATTCCAT | TAAACAACTC | GAAAAAGCGG |
| 1561 | AAACTCATGA | TCCTCTATGG | AACGCGTCAC |
| 1591 | AAATGCAGAT | GGTGAGAGAA | GGAAAAATGC |
| 1621 | ATAGTTTTTT | ACGAATGTAT | TGGGCTAAGA |
| 1651 | AGATACTTGA | ATGGACTAGA | ACACCTGAAG |
| 1681 | ACGCTTTGAG | TTATAGTATC | TATTTGAACA |
| 1711 | ACAAGTACGA | ACTAGACGGC | ACGGATCCTA |
| 1741 | ACGGATACGT | AGGTTGTATG | TGGTCTATTT |
| 1771 | GCGGATTACA | CGATAGAGCG | TGGAAAGCAA |
| 1801 | GACCGATATT | TGGAAAGATA | AGATATATGA |
| 1831 | ATTATGAGAG | TTCTAAGAAG | AAATTTGATG |
| 1861 | TTGCTGTATT | TATACAGAAA | TACAATTAAG |
| 1891 | ATAAATAATA | TACAGCATTG | TAACCATCGT |
| 1921 | CATCCGTTAT | ACGGGGAATA | ATATTACCAT |
| 1951 | ACAGTATTAT | TAAATTTTCT | TACGAAGAAT |
| 1981 | ATAGATCGGT | ATTTATCGTT | AGTTTATTTT |
| 2011 | ACATTTATTA | ATTAAACATG | TCTACTATTA |
| 2041 | CCTGTTATGG | AAATGACAAA | TTTAGTTATA |
| 2071 | TAATTTATGA | TAAAATTAAG | ATAATAATAA |
| 2101 | TGAAATCAAA | TAATTATGTA | AATGCTACTA |
| 2141 | GATTATGTGA | ATTACGAGGA | AGAAAGTTTA |
| 2161 | CGAACTGGAA | AAAATTAAGT | GAATCTAAAA |
| 2191 | TATTAGTCGA | TAATGTAAAA | AAAATAAATG |
| 2221 | ATAAAACTAA | CCAGTTAAAA | ACGGATATGA |
| 2251 | TTATATACGT | TAAGGATATT | GATCATAAAG |
| 2281 | GAAGAGATAC | TTGCGGTTAC | TATGTACACC |
| 2311 | AAGATCTGGT | ATCTTCTATA | TCAAATTGGA |
| 2341 | TATCTCCGTT | ATTCGCCGTT | AAGGTAAATA |
| 2371 | AAATTATTAA | CTATTATATA | TGTAATGAAT |
| 2401 | ATGATATACG | ACTTAGCGAA | ATGGAATCTG |
| 2431 | ATATGACAGA | AGTAATAGAT | GTAGTTGATA |
| 2461 | AATTAGTAGG | AGGATACAAT | GATGAAATAG |
| 2491 | CAGAAATAAT | ATATTTGTTT | AATAAATTTA |
| 2521 | TAGAAAAATA | TATTGCTAAC | ATATCGTTAT |
| 2551 | CAACTGAATT | ATCTAGTATA | TTAAATAATT |
| 2581 | TTATAAATTT | TATAAATTTT | AATAAAAAAT |
| 2611 | ACAATAACGA | CATAAAGATA | TTTAATCTTT |

FIG. 11C

| | | | |
|---|---|---|---|
| 2641 | AATTCTTGAT | CTGAAAAACA | CATCTATAAA |
| 2671 | ACTAGATAAA | AAGTTATTCG | ATAAAGATAA |
| 2701 | TAATGAATCG | AACGATGAAA | AATTGGAAAC |
| 2731 | AGAAGTTGAT | AAGCTAATTT | TTTTCATCTA |
| 2761 | AATAGTATTA | TTTTATTGAA | GTACGAAGTT |
| 2791 | TTACGTTAGA | TAAATAATAA | AGGTCGATTT |
| 2821 | TTACTTTGTT | AAATATCAAA | TATGTCATTA |
| 2851 | TCTGATAAAG | ATACAAAAAC | ACACGGTGAT |
| 2881 | TATCAACCAT | CTAACGAACA | GATATTACAA |
| 2911 | AAAATACGTC | GGACTATGGA | AAACGAAGCT |
| 2941 | GATAGCCTCA | ATAGAAGAAG | CATTAAAGAA |
| 2971 | ATTGTTGTAG | ATGTTATGAA | GAATTGGGAT |
| 3001 | CATCCTCAAC | GAAGAAATAG | ATAAAGTTCT |
| 3031 | AAACTGGAAA | AATGATACAT | TAAACGATTT |
| 3061 | AGATCATCTA | AATACAGATG | ATAATATTAA |
| 3091 | GGAAATCATA | CAATGTCTGA | TTAGAGAATT |
| 3121 | TGCGTTTAAA | AAGATCAATT | CTATTATGTA |
| 3151 | TAGTTATGCT | ATGGTAAAAC | TCAATTCAGA |
| 3181 | TAACGAACAT | TGAAAGATAA | AATTAAGGAT |
| 3211 | TATTTTATAG | AAACTATTCT | TAAAGACAAA |
| 3241 | CGTGGTTATA | AACAAAAGCC | ATTACCCGGA |
| 3271 | TTGGAAACTA | AAATACTAGA | TAGTATTATA |
| 3301 | AGATTTTAAA | AACATAAAAT | TAATAGGTTT |
| 3331 | TTATAGATTG | ACTTATTATA | TACAATATGG |
| 3361 | ATAAAAGATA | TATATCAACT | AGAAAGTTGA |
| 3391 | ATGACGGATT | CTTAATTTTA | TATTATGATT |
| 3421 | CAATAGAAAT | TATTGTCATG | TCGTGTAATC |
| 2451 | ATTTTATAAA | TATATCAGCG | TTACTAGCTA |
| 3481 | AGAAAAACAA | GGACTTTAAT | GAATGGCTAA |
| 3501 | AGATAGAATC | ATTTAGAGAA | ATAATAGATA |
| 3541 | CTTTAGATAA | AATTAATTAC | GATCTAGGAC |
| 3571 | AACGATATTG | TGAAGAACTT | ACGGCGCATC |
| 3601 | ACATTCCAGT | GTAATTATTG | AGGTCAAAGC |
| 3631 | TAGTAACTTA | ATAGATGACA | GGACAGCTG |

FIG. 12A

| FIG. 12A |
|---|
| FIG. 12B |

| | | | |
|---|---|---|---|
| 1 | TGTCTGGACT | AACTGATTTC | ATGGAACAAT |
| 31 | TTTCATCAAA | AATATCAGTT | ATACCTAGTT |
| 61 | CTACAAAGAC | AGAACTTTGA | TGTTATGTTT |
| 91 | GTGTTTGTAT | AGAAAATTTT | GGGATACTAA |
| 121 | CTGATATTTC | TGAATATTTC | TGAATATTTC |
| 151 | ATGTTACTTA | CTTACTCCTA | TCTTAGACGA |
| 181 | TAATAAAATT | CGAGGCGTAA | TATGTTTTTC |
| 211 | CAAATATTTG | AAATTCTTAT | ACGTATCGGC |
| 241 | GAAGAAAAGT | AACATACTAT | AAGTGTTATG |
| 271 | CAAGTAAGGT | ATGTTAATGA | TATTGGATTT |
| 301 | AATTTCATTG | ACAATACATA | TGTCCAAACA |
| 331 | TTCCACTCGT | AATTATGTAC | GGAACGACTT |
| 361 | TAGTTAAATA | CTTAGTCACA | AAAAACTTAT |
| 391 | GACTGTCATT | ATCTGAAAAC | GGTGATTCCC |
| 421 | ATAAATCAGA | ATACTTAATA | TTAAATAGAA |
| 461 | TGCTCGCTTC | TGGAGGTTTC | CGGATACTAG |
| 481 | ATAACATATC | TTCTGTATTA | TAGTTTAATT |
| 511 | CACTCATTTT | ATTACATAAT | ACAGTAACAT |
| 541 | CTCCCGAAAC | CAATGATGTT | ATATTAGATT |
| 571 | TACTTACATA | CTTCTTGTAA | CTATCATGAA |
| 601 | TACGTTTGTT | ATGATCTATA | AAGAAGATGG |
| 631 | ATGTATATTC | TGTTCTAGAT | AGCAAGTTCT |
| 661 | TTAAGTTATT | CTTTGTCTGT | ATTACTATCA |
| 691 | TCGTCTTCAT | CATCGTCTAA | AGGTAGCATT |
| 721 | ATATAATAAA | TCTAATAGTT | GATTTCTCGA |
| 751 | TCTATCAGTA | CTCGCTTTCA | ATAACATTTT |
| 781 | TACTATAAGC | ATAATAGAAG | GCGGTGATAT |
| 811 | CACTATATTT | TTATCGGGTA | TTCTTTTAGT |
| 841 | AATTAGTTAG | TTCGTAGAAT | TTCGTAGAGA |
| 871 | TAAAAGCCAA | TTTGTTGTTG | ATACTGCTTA |
| 901 | CGTTACTCAT | GTTTCTTGTT | TCTGTTAATT |
| 931 | AACAGGTATA | CCCTTACAAT | AAGTTTAATT |
| 961 | AACTTTTAGG | TTTTTGTGAA | GAACTTTTAG |
| 991 | CTTCTAGTTC | CCTTATCCAT | AATTGGGTCT |
| 1021 | TAGATCTAGA | TTCTTCCCAT | GTATAAAGGG |
| 1051 | GGACATACCC | AAAATCTTTA | AATGCTTTGT |
| 1081 | CCGTTTCTAT | AGTAAATGTC | GTACATTCCT |
| 1111 | TAATCAAAGT | ATAAGGATTT | AGTAAAGGCG |
| 1141 | TGTAAGAACA | AATAGGTGAT | AGTAATACTC |
| 1171 | TTAAACCTTT | ATTAATATTA | GCGATAAACC |
| 1201 | TTAAACACCA | TAAAGGAAGA | CATGTATTCC |
| 1231 | GTAGATCCAT | CCCTAATTGA | TTAAAGAAAT |
| 1261 | GCATGTTAAA | ATCATGATAA | TGTTCAGTAG |
| 1291 | GAGAGGTATC | GTAACAGTAA | TACACGTTAT |

FIG. 12B

| | | | |
|---|---|---|---|
| 1321 | TGCAGAGAGG | ACTATGTTGA | CCATTTTCTA |
| 1351 | TCATATTTCT | TGCTGCTAAA | ATATGCATCC |
| 1381 | AAGCTACGTT | TCCTGCATAG | ACTCTGCTAT |
| 1411 | GAAATACTTT | ATCATCCGCA | TATTTATACA |
| 1441 | TTTTCCTGCT | TTTATACGAT | CTTCTGTATA |
| 1471 | AAGTTTCTAG | TACTGGACAG | TATTCTCCGA |
| 1501 | AAACACCTAA | TGGGCGTAGC | GACAAGTGCA |
| 1531 | TAATCTAAGT | CCTATATTAG | ACATAGTACC |
| 1561 | GTTAGCTTCT | AGTATATATT | TCTCAGATAA |
| 1591 | CTTGTTTACT | AAGAGGATAA | GCCTCTTTAT |
| 1621 | GGTTAGATTG | ATAATACGTA | TTCTCGTTTC |
| 1651 | CTCTTATCAT | CGCATCTCCG | GAGAAAGTTA |
| 1681 | GGACCTACCG | CAGAATAACT | ACTCGTATAT |
| 1711 | ACTAAGACTC | TTACGCCGTT | ATACAGACAA |
| 1741 | GAATCTACTA | CGTTCTTCGT | TCCGTTGATA |
| 1771 | TTAACGTCCA | TTATAGAGTC | GTTAGTAAAC |
| 1801 | TTACCCGCTA | CATCATTTAT | CGAAGCAATA |
| 1831 | TGAATGACCA | CATCTGCTGA | TCTAAGCGCT |
| 1861 | TCGTCCAAAG | TACTTTTATT | TCTAACATCT |
| 1891 | CCAATCACGG | GAACTATCTT | TATTATATTA |
| 1921 | CATTTTTCTA | CAAGATCTAG | TAACCATTGG |
| 1951 | TCGATTCTAA | TATCGTAAAC | ACGAACTTCT |
| 1981 | TTTTAAAGAG | GATTCGAACA | AGATAAGATT |
| 2011 | ATTTATAATG | TGTCTACCTA | AAAATCCACA |
| 2041 | CCCTCCGGTT | ACCACGTATA | CTAGTGTACG |
| 2071 | CATTTTGAGT | ATTAACTATA | TAAGACCAAA |
| 2101 | ATTATATTTT | CATTTTCTGT | TATATTATAC |
| 2131 | TATATAATAA | AAACAAATAA | ATATACGAAT |
| 2161 | ATTATAAGAA | ATTTAGAACA | CGTTATTAAA |
| 2191 | GTATTGCCTT | TTTTATTAAC | GGCGTGTTCT |
| 2221 | TGTAATTGCC | GTTTAGAATA | GTCTTTATTT |
| 2251 | ACTTTAGATA | ACTCTTCTAT | CATAACCGTC |
| 2281 | TCCTTATTCC | AATCTTCTTC | AGAAGTACAT |
| 2311 | GAGTACTTAC | CGAAGTTTAT | CATCATAGAG |
| 2341 | ATTATATATG | AAGAAA | |

FIG. 14A-1

| | | | |
|---|---|---|---|
| TAATGTAGTA ATTACATCAT _____C3 | TACTAATATT ATGATTATAA FLANKING | AACTCACATT TTGAGTGTAA ARM____> | 30 |
| TGACTAATTA ACTGATTAAT _____C3 | GCTATAAAAA CGATATTTTT FLANKING | CCCGGGATCG GGGCCCTAGC ARM____> | 60 |
| ATTCTAGAAT TAAGATCTTA | AAAAATTATC TTTTTAATAG < | CCTGCCTAAC GGACGGATTG | 90 |
| TCTATTCACT AGATAAGTGA <____HIV1 | ACAGAGAGTA TGTCTCTCAT ENV  TRANS | CAGCAAAAAC GTCGTTTTTG MEMBRANE__ | 120 |
| TATTCTTAAA ATAAGAATTT <____HIV1 | CCTACCAAGC GGATGGTTCG ENV  TRANS | CTCCTACTAT GAGGATGATA MEMBRANE__ | 150 |
| CATTATGAAT GTAATACTTA < | AATCTTTTTT TTAGAAAAAA <_HIV1(MN) | CTCTCTGCAC GAGAGACGTG gp120____ | 180 |
| CACTCTTCTC GTGAGAAGAG <____HIV1 | TTTGCCTTGG AAACGGAACC (MN) GP120 | TGGGTGCTAC ACCCACGATG GENE___ | 210 |
| TCCTAATGGT AGGATTACCA <____HIV1 | TCAATTGTTA AGTTAACAAT (MN) GP120 | CTACTTTATA GATGAAATAT GENE___ | 240 |
| TTTATATAAT AAATATATTA <____HIV1 | TCACTTCTCC AGTGAAGAGG (MN) GP120 | AATTGTCCCT TTAACAGGGA GENE___ | 270 |
| CATATCTCCT GTATAGAGGA <____HIV1 | CCTCCAGGTC GGAGGTCCAG (MN) GP120 | TGAAGATCTC ACTTCTAGAG GENE___ | 300 |
| GGTGTCGTTC CCACAGCAAG <____HIV1 | GTGTCCGTGT CACAGGCACA (MN) GP120 | CCTTACCACC GGAATGGTGG GENE___ | 330 |

FIG. 14A-2

| | | | |
|---|---|---|---|
| TCTTAAAGTG<br>AGAATTTCAC<br><______HIV1 | TCATTCCATT<br>AGTAAGGTAA<br>(MN) GP120 | TTGCTCTACT<br>AACGAGATGA<br>GENE_______ | 690 |
| AATGTTACAA<br>TTACAATGTT<br><______HIV1 | TGTGCTTGTC<br>ACACGAACAG<br>(MN) GP120 | TTATAGTTCC<br>AATATCAAGG<br>GENE_______ | 720 |
| TATTATATTT<br>ATAATATAAA<br><______HIV1 | TTTGTTGTAT<br>AAACAACATA<br>(MN) GP120 | AAAATGCTCT<br>TTTTACGAGA<br>GENE_______ | 750 |
| CCCTGGTCCT<br>GGGACCAGGA<br><______HIV1 | ATATGTATCC<br>TATACATAGG<br>(MN) GP120 | TTTTTCTTTT<br>AAAAAGAAAA<br>GENE_______ | 780 |
| ATTGTAGTTG<br>TAACATCAAC<br><______HIV1 | GGTCTTGTAC<br>CCAGAACATG<br>(MN) GP120 | AATTAATTTG<br>TTAATTAAAC<br>GENE_______ | 810 |
| TACAGATTCA<br>ATGTCTAAGT<br><______HIV1 | TTCAGATGTA<br>AAGTCTACAT<br>(MN) GP120 | CTATGATGGT<br>GATACTACCA<br>GENE_______ | 840 |
| TTTAGCATTA<br>AAATCGTAAT<br><______HIV1 | TCATTGAAAT<br>AGTAACTTTA<br>(MN) GP120 | TCTCAGATCT<br>AGAGTCTAGA<br>GENE_______ | 870 |
| AATTACTACC<br>TTAATGATGG<br><______HIV1 | TCTTCTTCTG<br>AGAAGAAGAC<br>(MN) GP120 | CTAGACTGCC<br>GATCTGACGG<br>GENE_______ | 900 |
| ATTTAACAGC<br>TAAATTGTCG<br><______HIV1 | AGTTGAGTTG<br>TCAACTCAAC<br>(MN) GP120 | ATACTACTGG<br>TATGATGACC<br>GENE_______ | 930 |
| CCTAATTCCA<br>GGATTAAGGT<br><______HIV1 | TGTGTACATT<br>ACACATGTAA<br>(MN) GP120 | GTACTGTGCT<br>CATGACACGA<br>GENE_______ | 960 |
| GACATTTTTA<br>CTGTAAAAAT<br><______HIV1 | CATGATCCTT<br>GTACTAGGAA<br>(MN) GP120 | TTCCACTGAA<br>AAGGTGACTT<br>GENE_______ | 990 |

FIG. 14A-3

| | | | |
|---|---|---|---|
| ATCTCTTGTT | AATAGTAGCC | CTGTAATATT | 360 |
| TAGAGAACAA | TTATCATCGG | GACATTATAA | |
| <______HIV1 | (MN) GP120 | GENE_______ | |
| TGATGAACAT | CTAATTTGTC | CTTCAATGGG | 390 |
| ACTACTTGTA | GATTAAACAG | GAAGTTACCC | |
| <______HIV1 | (MN) GP120 | GENE_______ | |
| AGGGGCATAT | ATTGCTTTTC | CTACTTCCTG | 420 |
| TCCCCGTATA | TAACGAAAAG | GATGAAGGAC | |
| <______HIV1 | (MN) GP120 | GENE_______ | |
| CCACATGTTT | ATAATTTGTT | TTATTTTGCA | 450 |
| GGTGTACAAA | TATTAAACAA | AATAAAACGT | |
| <______HIV1 | (MN) GP120 | GENE_______ | |
| TTGAAGTGTG | ATATTGTTAT | TTGACCCTGT | 480 |
| AACTTCACAC | TATAACAATA | AACTGGGACA | |
| <______HIV1 | (MN) GP120 | GENE_______ | |
| AGTATTATTC | CAAGTATTAT | TACCATTCCA | 510 |
| TCATAATAAG | GTTCATAATA | ATGGTAAGGT | |
| <______HIV1 | (MN) GP120 | GENE_______ | |
| AGTACTATTA | AACAGTGGTG | ATGAATTACA | 540 |
| TCATGATAAT | TTGTCACCAC | TACTTAATGT | |
| <______HIV1 | (MN) GP120 | GENE_______ | |
| GTAGAAGAAT | TCCCCTCCAC | AATTAAAACT | 570 |
| CATCTTCTTA | AGGGGAGGTG | TTAATTTTGA | |
| <______HIV1 | (MN) GP120 | GENE_______ | |
| GTGCATTACA | ATTTCTGGGT | CCCCTCCTGA | 600 |
| CACGTAATGT | TAAAGACCCA | GGGGAGGACT | |
| <______HIV1 | (MN) GP120 | GENE_______ | |
| GGATTGATTA | AAGACTATTG | TTTTATTCTT | 630 |
| CCTAACTAAT | TTCTGATAAC | AAAATAAGAA | |
| <______HIV1 | (MN) GP120 | GENE_______ | |
| AAATTGTTCT | TTTAATTTGC | TAACTATCTG | 660 |
| TTTAACAAGA | AAATTAAACG | ATTGATAGAC | |
| <______HIV1 | (MN) GP120 | GENE_______ | |

FIG. 14A-4

| | | | |
|---|---|---|---|
| CTTTTTATCG | TTACACTTTA | GAATCGCAAA | 1020 |
| GAAAAATAGC | AATGTGAAAT | CTTAGCGTTT | |
| <_____HIV1 | (MN) GP120 | GENE_____ | |
| ACCAGCCGGG | GCACAATAGT | GTATGGGAAT | 1050 |
| TGGTCGGCCC | CGTGTTATCA | CATACCCTTA | |
| <_____HIV1 | (MN) GP120 | GENE_____ | |
| TGGCTCAAAG | GATATCTTTG | GACAAGCTTG | 1080 |
| ACCGAGTTTC | CTATAGAAAC | CTGTTCGAAC | |
| <_____HIV1 | (MN) GP120 | GENE_____ | |

| FIG. 14B-1 |
|---|
| FIG. 14B-2 |
| FIG. 14B-3 |
| FIG. 14B-4 |
| FIG. 14B-5 |

FIG. 14B-1

| | | | |
|---|---|---|---|
| TGTAATGACT<br>ACATTACTGA<br><______HIV1 | GAGGTATTAC<br>CTCCATAATG<br>(MN) GP120 | AACTTATCAA<br>TTGAATAGTT<br>GENE______ | 1110 |
| CCTATAGCTG<br>GGATATCGAC<br><______HIV1 | GTACTATCAT<br>CATGATAGTA<br>(MN) GP120 | TATTTATTGA<br>ATAAATAACT<br>GENE______ | 1140 |
| TACTATATCA<br>ATGATATAGT<br><______HIV1 | AGTTTATAAA<br>TCAAATATTT<br>(MN) GP120 | GAAGTGCATA<br>CTTCACGTAT<br>GENE______ | 1170 |
| TTCTTTCTGC<br>AAGAAAGACG<br><______HIV1 | ATCTTATCTC<br>TAGAATAGAG<br>(MN) GP120 | TTATGCTTGT<br>AATACGAACA<br>GENE______ | 1200 |
| GGTGATATTG<br>CCACTATAAC<br><______HIV1 | AAAGAGCAGT<br>TTTCTCGTCA<br>(MN) GP120 | TTTTCATTTC<br>AAAAGTAAAG<br>GENE______ | 1230 |
| TCCTCCCTTT<br>AGGAGGGAAA<br><______HIV1 | ATTGTTCCCT<br>TAACAAGGGA<br>(MN) GP120 | CGCTATTACT<br>GCGATAATGA<br>GENE______ | 1260 |
| ATTGTTATTA<br>TAACAATAAT<br><______HIV1 | GCAGTACTAT<br>CGTCATGATA<br>(MN) GP120 | TATTGGTATT<br>ATAACCATAA<br>GENE______ | 1290 |
| AGTAGTATTC<br>TCATCATAAG<br><______HIV1 | CTCAAATCAG<br>GAGTTTAGTC<br>(MN) GP120 | TGCAATTTAA<br>ACGTTAAATT<br>GENE______ | 1320 |
| AGTAACACAG<br>TCATTGTGTC<br><______HIV1 | AGTGGGGTTA<br>TCACCCCAAT<br>(MN) GP120 | ATTTTACACA<br>TAAAATGTGT<br>GENE______ | 1350 |
| TGGCTTTAGG<br>ACCGAAATCC<br><______HIV1 | CTTTGATCCC<br>GAAACTAGGG<br>(MN) GP120 | ATAAACTGAT<br>TATTTGACTA<br>GENE______ | 1380 |
| TATATCCTCA<br>ATATAGGAGT<br><______HIV1 | TGCATCTGTT<br>ACGTAGACAA<br>(MN) GP120 | CTACCATGTT<br>GATGGTACAA<br>GENE______ | 1410 |

FIG. 14B-2

| | | | |
|---|---|---|---|
| ATTTTTCCAC | ATGTTAAAAT | TTTCTGTCAC | 1440 |
| TAAAAAGGTG | TACAATTTTA | AAAGACAGTG | |
| <_____HIV1 | (MN) GP120 | GENE______ | |
| ATTTACCAAT | TCTACTTCTT | GTGGGTTGGG | 1470 |
| TAAATGGTTA | AGATGAAGAA | CACCCAACCC | |
| <_____HIV1 | (MN) GP120 | GENE______ | |
| GTCTGTGGGT | ACACAGGCAT | GTGTGGCCCA | 1500 |
| CAGACACCCA | TGTGTCCGTA | CACACCGGGT | |
| <_____HIV1 | (MN) GP120 | GENE______ | |
| AACATTATGT | ACCTCTGTAT | CATATGCTTT | 1530 |
| TTGTAATACA | TGGAGACATA | GTATACGAAA | |
| <_____HIV1 | (MN) GP120 | GENE______ | |
| AGCATCTGAT | GCACAAAATA | GAGTGGTGGT | 1560 |
| TCGTAGACTA | CGTGTTTTAT | CTCACCACCA | |
| <_____HIV1 | (MN) GP120 | GENE______ | |
| TGCTTCTTTC | CACACAGGTAC | CCCATAATA | 1590 |
| ACGAAGAAAG | GTGTGTCCATG | GGGTATTAT | |
| <_____HIV1 | (MN) GP120 | GENE______ | |
| GACTGTGACC | CACAATTTTT | CTGTAGCACT | 1620 |
| CTGACACTGG | GTGTTAAAAA | GACATCGTGA | |
| <_____HIV1 | (MN) GP120 | GENE______ | |
| ACAGATCATC | AACATCCCAA | GGAGCATGGT | 1650 |
| TGTCTAGTAG | TTGTAGGGTT | CCTCGTACCA | |
| <_____HIV1 | (MN) GP120 | GENE______ | |
| GCCCCATCTC | CACCCCCATC | TCCACAAGTG | 1680 |
| CGGGGTAGAG | GTGGGGGTAG | AGGTGTTCAC | |
| <_____HIV1 | (MN) GP120 | GENE______ | |
| CTGATATTTC | TCCTTCACTC | TCATTGCCAC | 1710 |
| GACTATAAAG | AGGAAGTGAG | AGTAACGGTG | |
| <_____HIV1 | (MN) GP120 | GENE______ | |
| TGTCTTCTGC | TCTTTCATAT | ACGATACAAA | 1740 |
| ACAGAAGACG | AGAAAGTATA | TGCTATGTTT | |
| <_HIV1 (MN) | gp120___ | | |
| | <__ | __________ | |

FIG. 14B-3

| | | | |
|---|---|---|---|
| CTTAACGCAT<br>GAATTGCGTA<br><_______H6 | ATCGCGATAA<br>TAGCGCTATT<br>PROMOTER_ | TGAAATAATT<br>ACTTTATTAA<br>__________ | 1770 |
| TATGATTATT<br>ATACTAATAA<br><_______H6 | TCTCGCTTTC<br>AGAGCGAAAG<br>PROMOTER_ | AATTTAACAC<br>TTAAATTGTG<br>__________ | 1800 |
| AACCCTCAAG<br>TTGGGAGTTC<br><_______H6 | AACCTTTGTA<br>TTGGAAACAT<br>PROMOTER_ | TTTATTTTCA<br>AAATAAAAGT<br>__________ | 1830 |
| CTTTTTAAGT<br>GAAAAATTCA<br><_______H6 | ATAGAATAAA<br>TATCTTATTT<br>PROMOTER_ | GAAGCTCTAA<br>CTTCGAGATT<br>___ | 1860 |
| TTAATTAAGC<br>AATTAATTCG | TACAAATAGT<br>ATGTTTATCA | TTCGTTTTCA<br>AAGCAAAAGT | 1890 |
| CCTTGTCTAA<br>GGAACAGATT | TAACTAATTA<br>ATTGATTAAT | ATTAACCCGG<br>TAATTGGGCC | 1920 |
| ATCTTGAGAT<br>TAGAACTCTA<br>______ | AAAGTGAAAA<br>TTTCACTTTT<br>I3L PROMOT | TATATATCAT<br>ATATATAGTA<br>ER________> | 1950 |
| TATATTACAA<br>ATATAATGTT<br>___________ | AGTACAATTA<br>TCATGTTAAT<br>I3L PROMOT | TTTAGGTTTA<br>AAATCCAAAT<br>ER________> | 1980 |
| ATCATGGGTG<br>TAGTACCCAC<br>___><br>___HIV1 | CGAGAGCGTC<br>GCTCTCGCAG<br><br>(IIIB)GAG/ | AGTATTAAGC<br>TCATAATTCG<br><br>PRO GENE__> | 2010 |
| GGGGGAGAAT<br>CCCCCTCTTA<br>______HIV1 | TAGATCGATG<br>ATCTAGCTAC<br>(IIIB)GAG/ | GGAAAAAATT<br>CCTTTTTTAA<br>PRO GENE__> | 2040 |
| CGGTTAAGGC<br>GCCAATTCCG<br>______HIV1 | CAGGGGGAAA<br>GTCCCCCTTT<br>(IIIB)GAG/ | GAAAAAATAT<br>CTTTTTTATA<br>PRO GENE__> | 2070 |

FIG. 14B-4

| | | | |
|---|---|---|---|
| AAATTAAAAC<br>TTTAATTTTG<br>______HIV1 | ATATAGTATG<br>TATATCATAC<br>(IIIB)GAG/ | GGCAAGCAGG<br>CCGTTCGTCC<br>PRO GENE__> | 2100 |
| GAGCTAGAAC<br>CTCGATCTTG<br>______HIV1 | GATTCGCAGT<br>CTAAGCGTCA<br>(IIIB)GAG/ | TAATCCTGGC<br>ATTAGGACCG<br>PRO GENE__> | 2130 |
| CTGTTAGAAA<br>GACAATCTTT<br>______HIV1 | CATCAGAAGG<br>GTAGTCTTCC<br>(IIIB)GAG/ | CTGTAGACAA<br>GACATCTGTT<br>PRO GENE__> | 2160 |
| ATACTGGGAC<br>TATGACCCTG<br>______HIV1 | AGCTACAACC<br>TCGATGTTGG<br>(IIIB)GAG/ | ATCCCTTCAG<br>TAGGGAAGTC<br>PRO GENE__> | 2190 |
| ACAGGATCAG<br>TGTCCTAGTC<br>______HIV1 | AAGAACTTAG<br>TTCTTGAATC<br>(IIIB)GAG/ | ATCATTATAT<br>TAGTAATATA<br>PRO GENE__> | 2220 |
| AATACAGTAG<br>TTATGTCATC<br>______HIV1 | CAACCCTCTA<br>GTTGGGAGAT<br>(IIIB)GAG/ | TTGTGTGCAT<br>AACACACGTA<br>PRO GENE__> | 2250 |
| CAAAGGATAG<br>GTTTCCTATC<br>______HIV1 | AGATAAAAGA<br>TCTATTTTCT<br>(IIIB)GAG/ | CACCAAGGAA<br>GTGGTTCCTT<br>PRO GENE__> | 2280 |
| GCTTTAGACA<br>CGAAATCTGT<br>______HIV1 | AGATAGAGGA<br>TCTATCTCCT<br>(IIIB)GAG/ | AGAGCAAAAC<br>TCTCGTTTTG<br>PRO GENE__> | 2310 |
| AAAAGTAAGA<br>TTTTCATTCT<br>______HIV1 | AAAAAGCACA<br>TTTTTCGTGT<br>(IIIB)GAG/ | GCAAGCAGCA<br>CGTTCGTCGT<br>PRO GENE__> | 2340 |
| GCTGACACAG<br>CGACTGTGTC<br>______HIV1 | GACACAGCAA<br>CTGTGTCGTT<br>(IIIB)GAG/ | TCAGGTCAGC<br>AGTCCAGTCG<br>PRO GENE__> | 2370 |
| CAAAATTACC<br>GTTTTAATGG<br>______HIV1 | CTATAGTGCA<br>GATATCACGT<br>(IIIB)GAG/ | GAACATCCAG<br>CTTGTAGGTC<br>PRO GENE__> | 2400 |

FIG. 14B-5

| | | | |
|---|---|---|---|
| GGGCAAATGG | TACATCAGGC | CATATCACCT | 2430 |
| CCCGTTTACC | ATGTAGTCCG | GTATAGTGGA | |
| ______HIV1 | (IIIB)GAG/ | PRO GENE__> | |
| AGAACTTTAA | ATGCATGGGT | AAAAGTAGTA | 2460 |
| TCTTGAAATT | TACGTACCCA | TTTTCATCAT | |
| ______HIV1 | (IIIB)GAG/ | PRO GENE__> | |
| GAAGAGAAGG | CTTTCAGCCC | AGAAGTGATA | 2490 |
| CTTCTCTTCC | GAAAGTCGGG | TCTTCACTAT | |
| ______HIV1 | (IIIB)GAG/ | PRO GENE__> | |
| CCCATGTTTT | CAGCATTATC | AGAAGGAGCC | 2520 |
| GGGTACAAAA | GTCGTAATAG | TCTTCCTCGG | |
| ______HIV1 | (IIIB)GAG/ | PRO GENE__> | |

| |
|---|
| FIG. 14C-1 |
| FIG. 14C-2 |
| FIG. 14C-3 |
| FIG. 14C-4 |

FIG. 14C-1

```
ACCCCACAAG    ATTTAAACAC    CATGCTAAAC    2550
TGGGGTGTTC    TAAATTTGTG    GTACGATTTG
_______HIV1   (IIIB)GAG/    PRO GENE__>

ACAGTGGGGG    GACATCAAGC    AGCCATGCAA    2580
TGTCACCCCC    CTGTAGTTCG    TCGGTACGTT
_______HIV1   (IIIB)GAG/    PRO GENE__>

ATGTTAAAAG    AGACCATCAA    TGAGGAAGCT    2610
TACAATTTTC    TCTGGTAGTT    ACTCCTTCGA
_______HIV1   (IIIB)GAG/    PRO GENE__>

GCAGAATGGG    ATAGAGTGCA    TCCAGTGCAT    2640
CGTCTTACCC    TATCTCACGT    AGGTCACGTA
_______HIV1   (IIIB)GAG/    PRO GENE__>

GCAGGGCCTA    TTGCACCAGG    CCAGATGAGA    2670
CGTCCCGGAT    AACGTGGTCC    GGTCTACTCT
_______HIV1   (IIIB)GAG/    PRO GENE__>

GAACCAAGGG    GAAGTGACAT    AGCAGGAACT    2700
CTTGGTTCCC    CTTCACTGTA    TCGTCCTTGA
_______HIV1   (IIIB)GAG/    PRO GENE__>

ACTAGTACCC    TTCAGGAACA    AATAGGATGG    2730
TGATCATGGG    AAGTCCTTGT    TTATCCTACC
_______HIV1   (IIIB)GAG/    PRO GENE__>

ATGACAAATA    ATCCACCTAT    CCCAGTAGGA    2760
TACTGTTTAT    TAGGTGGATA    GGGTCATCCT
_______HIV1   (IIIB)GAG/    PRO GENE__>

GAAATTTATA    AAAGATGGAT    AATCCTGGGA    2790
CTTTAAATAT    TTTCTACCTA    TTAGGACCCT
_______HIV1   (IIIB)GAG/    PRO GENE__>

TTAAATAAAA    TAGTAAGAAT    GTATAGCCCT    2820
AATTTATTTT    ATCATTCTTA    CATATCGGGA
_______HIV1   (IIIB)GAG/    PRO GENE__>

ACCAGCATTC    TGGACATAAG    ACAAGGACCA    2850
TGGTCGTAAG    ACCTGTATTC    TGTTCCTGGT
_______HIV1   (IIIB)GAG/    PRO GENE__>
```

FIG. 14C-2

| | | | |
|---|---|---|---|
| AAAGAACCCT | TTAGAGACTA | TGTAGACCGG | 2880 |
| TTTCTTGGGA | AATCTCTGAT | ACATCTGGCC | |
| ______HIV1 | (IIIB)GAG/ | PRO GENE__> | |
| TTCTATAAAA | CTCTAAGAGC | CGAGCAAGCT | 2910 |
| AAGATATTTT | GAGATTCTCG | GCTCGTTCGA | |
| ______HIV1 | (IIIB)GAG/ | PRO GENE__> | |
| TCACAGGAGG | TAAAAAATTG | GATGACAGAA | 2940 |
| AGTGTCCTCC | ATTTTTTAAC | CTACTGTCTT | |
| ______HIV1 | (IIIB)GAG/ | PRO GENE__> | |
| ACCTTGTTGG | TCCAAAATGC | GAACCCAGAT | 2970 |
| TGGAACAACC | AGGTTTTACG | CTTGGGTCTA | |
| ______HIV1 | (IIIB)GAG/ | PRO GENE__> | |
| TGTAAGACTA | TTTTAAAAGC | ATTGGGACCA | 3000 |
| ACATTCTGAT | AAAATTTTCG | TAACCCTGGT | |
| ______HIV1 | (IIIB)GAG/ | PRO GENE__> | |
| GCGGCTACAC | TAGAAGAAAT | GATGACAGCA | 3030 |
| CGCCGATGTG | ATCTTCTTTA | CTACTGTCGT | |
| ______HIV1 | (IIIB)GAG/ | PRO GENE__> | |
| TGTCAGGGAG | TAGGAGGACC | CGGCCATAAG | 3060 |
| ACAGTCCCTC | ATCCTCCTGG | GCCGGTATTC | |
| ______HIV1 | (IIIB)GAG/ | PRO GENE__> | |
| GCAAGAGTTT | TGGCTGAAGC | AATGAGCCAA | 3090 |
| CGTTCTCAAA | ACCGACTTCG | TTACTCGGTT | |
| ______HIV1 | (IIIB)GAG/ | PRO GENE__> | |
| GTAACAAATT | CAGCTACCAT | AATGATGCAG | 3120 |
| CATTGTTTAA | GTCGATGGTA | TTACTACGTC | |
| ______HIV1 | (IIIB)GAG/ | PRO GENE__> | |
| AGAGGCAATT | TTAGGAACCA | AAGAAAGATT | 3150 |
| TCTCCGTTAA | AATCCTTGGT | TTCTTTCTAA | |
| ______HIV1 | (IIIB)GAG/ | PRO GENE__> | |
| GTTAAGTGTT | TCAATTGTGG | CAAAGAAGGG | 3180 |
| CAATTCACAA | AGTTAACACC | GTTTCTTCCC | |
| ______HIV1 | (IIIB)GAG/ | PRO GENE__> | |

FIG. 14C-3

| | | | |
|---|---|---|---|
| CACACAGCCA<br>GTGTGTCGGT<br>_______HIV1 | GAAATTGCAG<br>CTTTAACGTC<br>(IIIB)GAG/ | GGCCCCTAGG<br>CCGGGGATCC<br>PRO GENE__> | 3210 |
| AAAAAGGGCT<br>TTTTTCCCGA<br>_______HIV1 | GTTGGAAATG<br>CAACCTTTAC<br>(IIIB)GAG/ | TGGAAAGGAA<br>ACCTTTCCTT<br>PRO GENE__> | 3240 |
| GGACACCAAA<br>CCTGTGGTTT<br>_______HIV1 | TGAAAGATTG<br>ACTTTCTAAC<br>(IIIB)GAG/ | TACTGAGAGA<br>ATGACTCTCT<br>PRO GENE__> | 3270 |
| CAGGCTAATT<br>GTCCGATTAA<br>_______HIV1 | TTTTAGGGAA<br>AAAATCCCTT<br>(IIIB)GAG/ | GATCTGGCCT<br>CTAGACCGGA<br>PRO GENE__> | 3300 |
| TCCTACAAGG<br>AGGATGTTCC<br>_______HIV1 | GAAGGCCAGG<br>CTTCCGGTCC<br>(IIIB)GAG/ | GAATTTTCTT<br>CTTAAAAGAA<br>PRO GENE__> | 3330 |
| CAGAGCAGAC<br>GTCTCGTCTG<br>_______HIV1 | CAGAGCCAAC<br>GTCTCGGTTG<br>(IIIB)GAG/ | AGCCCCACCA<br>TCGGGGTGGT<br>PRO GENE__> | 3360 |
| GAAGAGAGCT<br>CTTCTCTCGA<br>_______HIV1 | TCAGGTCTGG<br>AGTCCAGACC<br>(IIIB)GAG/ | GGTAGAGACA<br>CCATCTCTGT<br>PRO GENE__> | 3390 |
| ACAACTCCCC<br>TGTTGAGGGG<br>_______HIV1 | CTCAGAAGCA<br>GAGTCTTCGT<br>(IIIB)GAG/ | GGAGCCGATA<br>CCTCGGCTAT<br>PRO GENE__> | 3420 |
| GACAAGGAAC<br>CTGTTCCTTG<br>_______HIV1 | TGTATCCTTT<br>ACATAGGAAA<br>(IIIB)GAG/ | AACTTCCCTC<br>TTGAAGGGAG<br>PRO GENE__> | 3450 |
| AGATCACTCT<br>TCTAGTGAGA<br>_______HIV1 | TTGGCAACGA<br>AACCGTTGCT<br>(IIIB)GAG/ | CCCCTCGTCA<br>GGGGAGCAGT<br>PRO GENE__> | 3480 |
| CAATAAAGAT<br>GTTATTTCTA<br>_______HIV1 | AGGGGGGCAA<br>TCCCCCCGTT<br>(IIIB)GAG/ | CTAAAGGAAG<br>GATTTCCTTC<br>PRO GENE__> | 3510 |

FIG. 14C-4

| | | | |
|---|---|---|---|
| CTCTATTAGA<br>GAGATAATCT<br>______HIV1 | TACAGGAGCA<br>ATGTCCTCGT<br>(IIIB)GAG/ | GATGATACAG<br>CTACTATGTC<br>PRO GENE__> | 3540 |
| TATTAGAAGA<br>ATAATCTTCT<br>______HIV1 | AATGAGTTTG<br>TTACTCAAAC<br>(IIIB)GAG/ | CCAGGAAGAT<br>GGTCCTTCTA<br>PRO GENE__> | 3570 |
| GGAAACCAAA<br>CCTTTGGTTT<br>______HIV1 | AATGATAGGG<br>TTACTATCCC<br>(IIIB)GAG/ | GGAATTGGAG<br>CCTTAACCTC<br>PRO GENE__> | 3600 |
| GTTTTATCAA<br>CAAAATAGTT<br>______HIV1 | AGTAAGACAG<br>TCATTCTGTC<br>(IIIB)GAG/ | TATGATCAGA<br>ATACTAGTCT<br>PRO GENE__> | 3630 |
| TACTCATAGA<br>ATGAGTATCT<br>______HIV1 | AATCTGTGGA<br>TTAGACACCT<br>(IIIB)GAG/ | CATAAAGCTA<br>GTATTTCGAT<br>PRO GENE__> | 3660 |
| TAGGTACAGT<br>ATCCATGTCA<br>______HIV1 | ATTAGTAGGA<br>TAATCATCCT<br>(IIIB)GAG/ | CCTACACCTG<br>GGATGTGGAC<br>PRO GENE__> | 3690 |
| TCAACATAAT<br>AGTTGTATTA<br>______HIV1 | TGGAAGAAAT<br>ACCTTCTTTA<br>(IIIB)GAG/ | CTGTTGACTC<br>GACAACTGAG<br>PRO GENE__> | 3720 |
| AGATTGGTTG<br>TCTAACCAAC<br>_HIV1(IIIB) | CACTTTAAAT<br>GTGAAATTTA<br>GAG/PRO | TTTTAACCCG<br>AAAATTGGGC<br>GENE__> | 3750 |
| GGGGATCCCG<br>CCCCTAGGGC<br>______C3 | ATTTTTATGA<br>TAAAAATACT<br>FLANKING | CTAGTTAATC<br>GATCAATTAG<br>ARM_______> | 3780 |
| AAATAAAAAG<br>TTTATTTTTC<br>_______C3 | CATACAAGCT<br>GTATGTTCGA<br>FLANKING | ATTGCTTC<br>TAACGAAG<br>ARM_____> | 3808 |

FIG. 15A-1

| | | | |
|---|---|---|---|
| AGATATTTGT | TAGCTTCTGC | CGGAGATACC | 30 |
| TCTATAAACA | ATCGAAGACG | GCCTCTATGG | |
| _____C3 | FLANKING | ARM_____> | |
| GTGAAAATCT | ATTTTCTGGA | AGGAAAGGGA | 60 |
| CACTTTTAGA | TAAAAGACCT | TCCTTTCCCT | |
| _____C3 | FLANKING | ARM_____> | |
| GGTCTTATCT | ATTCTGTCAG | CAGAGTAGGT | 90 |
| CCAGAATAGA | TAAGACAGTC | GTCTCATCCA | |
| _____C3 | FLANKING | ARM_____> | |
| TCCTCTAATG | ACGAAGACAA | TAGTGAATAC | 120 |
| AGGAGATTAC | TGCTTCTGTT | ATCACTTATG | |
| _____C3 | FLANKING | ARM_____> | |
| TTGCATGAAG | GTCACTGTGT | AGAGTTCAAA | 150 |
| AACGTACTTC | CAGTGACACA | TCTCAAGTTT | |
| _____C3 | FLANKING | ARM_____> | |
| ACTGATCATC | AGTGTTTGAT | AACTCTAGCG | 180 |
| TGACTAGTAG | TCACAAACTA | TTGAGATCGC | |
| _____C3 | FLANKING | ARM_____> | |
| TGTACGAGTC | CTTCTAACAC | TGTGGTTTAT | 210 |
| ACATGCTCAG | GAAGATTGTG | ACACCAAATA | |
| _____C3 | FLANKING | ARM_____> | |
| TGGCTGGAAT | AAAAGGATAA | AGACACCTAT | 240 |
| ACCGACCTTA | TTTTCCTATT | TCTGTGGATA | |
| _____C3 | FLANKING | ARM_____> | |
| ACTGATTCAT | TTTCATCTGT | CAACGTTTCT | 270 |
| TGACTAAGTA | AAAGTAGACA | GTTGCAAAGA | |
| _____C3 | FLANKING | ARM_____> | |
| CTAAGAGATT | CATAGGTATT | ATTATTACAT | 300 |
| GATTCTCTAA | GTATCCATAA | TAATAATGTA | |
| _____C3 | FLANKING | ARM_____> | |
| CGATCTAGAA | GTCTAATAAC | TGCTAAGTAT | 330 |
| GCTAGATCTT | CAGATTATTG | ACGATTCATA | |
| _____C3 | FLANKING | ARM_____> | |

FIG. 15A-2

| | | | |
|---|---|---|---|
| ATTATTGGAT<br>TAATAACCTA<br>______C3 | TTAACGCGCT<br>AATTGCGCGA<br>FLANKING | ATAAACGCAT<br>TATTTGCGTA<br>ARM______> | 360 |
| CCAAAACCTA<br>GGTTTTGGAT<br>______C3 | CAAATATAGG<br>GTTTATATCC<br>FLANKING | AGAAGCTTCT<br>TCTTCGAAGA<br>ARM______> | 390 |
| CTTATGAAAC<br>GAATACTTTG<br>______C3 | TTCTTAAAGC<br>AAGAATTTCG<br>FLANKING | TTTACTCTTA<br>AAATGAGAAT<br>ARM______> | 420 |
| CTATTACTAC<br>GATAATGATG<br>______C3 | TCAAAAGAGA<br>AGTTTTCTCT<br>FLANKING | TATTACATTA<br>ATAATGTAAT<br>ARM______> | 450 |
| ATTATGTGAT<br>TAATACACTA<br>______C3 | GAGGCATCCA<br>CTCCGTAGGT<br>FLANKING | ACATATAAAG<br>TGTATATTTC<br>ARM______> | 480 |
| AAGACTAAAG<br>TTCTGATTTC<br>______C3 | CTGTAGAAGC<br>GACATCTTCG<br>FLANKING | TGTTATGAAG<br>ACAATACTTC<br>ARM______> | 510 |
| AATATCTTAT<br>TTATAGAATA<br>______C3 | CAGATATATT<br>GTCTATATAA<br>FLANKING | AGATGCATTG<br>TCTACGTAAC<br>ARM______> | 540 |
| TTAGTTCTGT<br>AATCAAGACA<br>______C3 | AGATCAGTAA<br>TCTAGTCATT<br>FLANKING | CGTATAGCAT<br>GCATATCGTA<br>ARM______> | 570 |
| ACGAGTATAA<br>TGCTCATATT<br>______C3 | TTATCGTAGG<br>AATAGCATCC<br>FLANKING | TAGTAGGTAT<br>ATCATCCATA<br>ARM______> | 600 |
| CCTAAAATAA<br>GGATTTTATT<br>______C3 | ATCTGATACA<br>TAGACTATGT<br>FLANKING | GATAATAACT<br>CTATTATTGA<br>ARM______> | 630 |
| TTGTAAATCA<br>AACATTTAGT<br>__________> | | | 640 |

| FIG. 15B-1 |
|---|
| FIG. 15B-2 |
| FIG. 15B-3 |

FIG. 15B-1

| | | | |
|---|---|---|---|
| ATTCAGCAAT | TTCTCTATTA | TCATGATAAT | 670 |
| TAAGTCGTTA | AAGAGATAAT | AGTACTATTA | |
| ________C3 | FLANKING | ARM________> | |
| GATTAATACA | CAGCGTGTCG | TTATTTTTTG | 700 |
| CTAATTATGT | GTCGCACAGC | AATAAAAAAC | |
| ________C3 | FLANKING | ARM________> | |
| TTACGATAGT | ATTTCTAAAG | TAAAGAGCAG | 730 |
| AATGCTATCA | TAAAGATTTC | ATTTCTCGTC | |
| ________C3 | FLANKING | ARM________> | |
| GAATCCCTAG | TATAATAGAA | ATAATCCATA | 760 |
| CTTAGGGATC | ATATTATCTT | TATTAGGTAT | |
| ________C3 | FLANKING | ARM________> | |
| TGAAAAATAT | AGTAATGTAC | ATATTTCTAA | 790 |
| ACTTTTTATA | TCATTACATG | TATAAAGATT | |
| ________C3 | FLANKING | ARM________> | |
| TGTTAACATA | TTTATAGGTA | AATCCAGGAA | 820 |
| ACAATTGTAT | AAATATCCAT | TTAGGTCCTT | |
| ________C3 | FLANKING | ARM________> | |
| GGGTAATTTT | TACATATCTA | TATACGCTTA | 850 |
| CCCATTAAAA | ATGTATAGAT | ATATGCGAAT | |
| ________C3 | FLANKING | ARM________> | |
| TTACAGTTAT | TAAAAATATA | CTTGCAAACA | 880 |
| AATGTCAATA | ATTTTTATAT | GAACGTTTGT | |
| ________C3 | FLANKING | ARM________> | |
| TGTTAGAAGT | AAAAAAGAAA | GAACTAATTT | 910 |
| ACAATCTTCA | TTTTTTCTTT | CTTGATTAAA | |
| ________C3 | FLANKING | ARM________> | |
| TACAAAGTGC | TTTACCAAAA | TGCCAATGGA | 940 |
| ATGTTTCACG | AAATGGTTTT | ACGGTTACCT | |
| ________C3 | FLANKING | ARM________> | |
| AATTACTTAG | TATGTATATA | ATGTATAAAG | 970 |
| TTAATGAATC | ATACATATAT | TACATATTTC | |
| ________C3 | FLANKING | ARM________> | |

FIG. 15B-2

```
GTATGAATAT  CACAAACAGC  AAATCGGCTA   1000
CATACTTATA  GTGTTTGTCG  TTTAGCCGAT
________C3  FLANKING    ARM_______>

TTCCCAAGTT  GAGAAACGGT  ATAATAGATA   1030
AAGGGTTCAA  CTCTTTGCCA  TATTATCTAT
________C3  FLANKING    ARM_______>

TATTTCTAGA  TACCATTAAT  AACCTTATAA   1060
ATAAAGATCT  ATGGTAATTA  TTGGAATATT
________C3  FLANKING    ARM_______>

GCTTGACGTT  TCCTATAATG  CCTACTAAGA   1090
CGAACTGCAA  AGGATATTAC  GGATGATTCT
________C3  FLANKING    ARM_______>

AAACTAGAAG  ATACATACAT  ACTAACGCCA   1120
TTTGATCTTC  TATGTATGTA  TGATTGCGGT
________C3  FLANKING    ARM_______>

TACGAGAGTA  ACTACTCATC  GTATAACTAC   1150
ATGCTCTCAT  TGATGAGTAG  CATATTGATG
________C3  FLANKING    ARM_______>

TGTTGCTAAC  AGTGACACTG  ATGTTATAAC   1180
ACAACGATTG  TCACTGTGAC  TACAATATTG
________C3  FLANKING    ARM_______>

TCATCTTTGA  TGTGGTATAA  ATGTATAATA   1210
AGTAGAAACT  ACACCATATT  TACATATTAT
________C3  FLANKING    ARM_______>

ACTATATTAC  ACTGGTATTT  TATTTCAGTT   1240
TGATATAATG  TGACCATAAA  ATAAAGTCAA
________C3  FLANKING    ARM_______>

ATATACTATA  TAGTATTAAA  AATTATATTT   1270
TATATGATAT  ATCATAATTT  TTAATATAAA
________C3  FLANKING    ARM_______>

GTATAATTAT  ATTATTATAT  TCAGTGTAGA   1300
CATATTAATA  TAATAATATA  AGTCACATCT
________C3  FLANKING    ARM_______>
```

FIG. 15B-3

| | | | |
|---|---|---|---|
| AAGTAAAATA<br>TTCATTTTAT<br>__________C3 | CTATAAATAT<br>GATATTTATA<br>FLANKING | GTATCTCTTA<br>CATAGAGAAT<br>ARM________> | 1330 |
| TTTATAACTT<br>AAATATTGAA<br>__________C3 | ATTAGTAAAG<br>TAATCATTTC<br>FLANKING | TATGTACTAT<br>ATACATGATA<br>ARM________> | 1360 |
| TCAGTTATAT<br>AGTCAATATA<br>__________C3 | TGTTTTATAA<br>ACAAAATATT<br>FLANKING | AAGCTAAATG<br>TTCGATTTAC<br>ARM________> | 1390 |
| CTACTAGATT<br>GATGATCTAA<br>__________C3 | GATATAAATG<br>CTATATTTAC<br>FLANKING | AATATGTAAT<br>TTATACATTA<br>ARM________> | 1420 |
| AAATTAGTAA<br>TTTAATCATT<br>__C3 FLANK | TGTAGTATAC<br>ACATCATATG<br>ING ARM___> | | 1440 |

| FIG. 15C-1 |
|---|
| FIG. 15C-2 |
| FIG. 15C-3 |

FIG. 15C-1

| | | | |
|---|---|---|---|
| TAATATTAAC<br>ATTATAATTG<br>___C3 FLAN | TCACATTTGA<br>AGTGTAAACT<br>KING ARM__ | CTAATTAGCT<br>GATTAATCGA<br>><br>___CLONING | 1470 |
| ATAAAAACCC<br>TATTTTTGGG<br>_________ | GGGCTGCAGG<br>CCCGACGTCC<br>CLONING | AATTCCTCGA<br>TTAAGGAGCT<br>SITES_____> | 1500 |
| GTACGATACA<br>CATGCTATGT<br>_><br>________H6 | AACTTAACGG<br>TTGAATTGCC<br>PROMOTER__ | ATATCGCGAT<br>TATAGCGCTA<br>____________> | 1530 |
| AATGAAATAA<br>TTACTTTATT<br>_________H6 | TTTATGATTA<br>AAATACTAAT<br>PROMOTER__ | TTTCTCGCTT<br>AAAGAGCGAA<br>____________> | 1560 |
| TCAATTTAAC<br>AGTTAAATTG<br>_________H6 | ACAACCCTCA<br>TGTTGGGAGT<br>PROMOTER__ | AGAACCTTTG<br>TCTTGGAAAC<br>____________> | 1590 |
| TATTTATTTT<br>ATAAATAAAA<br>_________H6 | CACTTTTTAA<br>GTGAAAAATT<br>PROMOTER__ | GTATAGAATA<br>CATATCTTAT<br>____________> | 1620 |
| AAGAAGCTCT<br>TTCTTCGAGA<br>___________ | AATTAATTAA<br>TTAATTAATT | GCTACAAATA<br>CGATGTTTAT | 1650 |
| GTTTCGTTTT<br>CAAAGCAAAA | CACCTTGTCT<br>GTGGAACAGA | AATAACTAAT<br>TTATTGATTA | 1680 |
| TAATTAACCC<br>ATTAATTGGG | GGATCCCGAT<br>CCTAGGGCTA | TTTTATGACT<br>AAAATACTGA | 1710 |
| AGTTAATCAA<br>TCAATTAGTT<br>__C3 | ATAAAAAGCA<br>TATTTTTCGT<br>FLANKING | TACAAGCTAT<br>ATGTTCGATA<br>ARM________> | 1740 |

FIG. 15C-2

| | | | |
|---|---|---|---|
| TGCTTCGCTA<br>ACGAAGCGAT<br>__________C3 | TCGTTACAAA<br>AGCAATGTTT<br>FLANKING | ATGGCAGGAA<br>TACCGTCCTT<br>ARM__________> | 1770 |
| TTTTGTGTAA<br>AAAACACATT<br>__________C3 | ACTAAGCCAC<br>TGATTCGGTG<br>FLANKING | ATACTTGCCA<br>TATGAACGGT<br>ARM__________> | 1800 |
| ATGAAAAAAA<br>TACTTTTTTT<br>__________C3 | TAGTAGAAAG<br>ATCATCTTTC<br>FLANKING | GATACTATTT<br>CTATGATAAA<br>ARM__________> | 1830 |
| TAATGGGATT<br>ATTACCCTAA<br>__________C3 | AGATGTTAAG<br>TCTACAATTC<br>FLANKING | GTTCCTTGGG<br>CAAGGAACCC<br>ARM__________> | 1860 |
| ATTATAGTAA<br>TAATATCATT<br>__________C3 | CTGGGCATCT<br>GACCCGTAGA<br>FLANKING | GTTAACTTTT<br>CAATTGAAAA<br>ARM__________> | 1890 |
| ACGACGTTAG<br>TGCTGCAATC<br>__________C3 | GTTAGATACT<br>CAATCTATGA<br>FLANKING | GATGTTACAG<br>CTACAATGTC<br>ARM__________> | 1920 |
| ATTATAATAA<br>TAATATTATT<br>__________C3 | TGTTACAATA<br>ACAATGTTAT<br>FLANKING | AAATACATGA<br>TTTATGTACT<br>ARM__________> | 1950 |
| CAGGATGTGA<br>GTCCTACACT<br>__________C3 | TATTTTTCCT<br>ATAAAAAGGA<br>FLANKING | CATATAACTC<br>GTATATTGAG<br>ARM__________> | 1980 |
| TTGGAATAGC<br>AACCTTATCG<br>__________C3 | AAATATGGAT<br>TTTATACCTA<br>FLANKING | CAATGTGATA<br>GTTACACTAT<br>ARM__________> | 2010 |
| GATTTGAAAA<br>CTAAACTTTT<br>__________C3 | TTTCAAAAAG<br>AAAGTTTTTC<br>FLANKING | CAAATAACTG<br>GTTTATTGAC<br>ARM__________> | 2040 |
| ATCAAGATTT<br>TAGTTCTAAA<br>__________C3 | ACAGACTATT<br>TGTCTGATAA<br>FLANKING | TCTATAGTCT<br>AGATATCAGA<br>ARM__________> | 2070 |

FIG. 15C-3

| | | | |
|---|---|---|---|
| GTAAAGAAGA<br>CATTTCTTCT<br>_________C3 | GATGTGTTTT<br>CTACACAAAA<br>FLANKING | CCTCAGAGTA<br>GGAGTCTCAT<br>ARM________> | 2100 |
| ACGCCTCTAA<br>TGCGGAGATT<br>_________C3 | ACAGTTGGGA<br>TGTCAACCCT<br>FLANKING | GCGAAAGGAT<br>CGCTTTCCTA<br>ARM________> | 2130 |
| GCGCTGTAGT<br>CGCGACATCA<br>_________C3 | TATGAAACTG<br>ATACTTTGAC<br>FLANKING | GAGGTATCTG<br>CTCCATAGAC<br>ARM________> | 2160 |
| ATGAACTTAG<br>TACTTGAATC<br>_________C3 | AGCCCTAAGA<br>TCGGGATTCT<br>FLANKING | AATGTTCTGC<br>TTACAAGACG<br>ARM________> | 2190 |
| TGAATGCGGT<br>ACTTACGCCA<br>_________C3 | ACCCTGTTCG<br>TGGGACAAGC<br>FLANKING | AAGGACGTGT<br>TTCCTGCACA<br>ARM________> | 2220 |
| TTGGTGATAT<br>AACCACTATA<br>__C3 FLANK | CACAGTAGAT<br>GTGTCATCTA<br>ING ARM___> | | 2240 |

FIG. 15D-1

| | | | |
|---|---|---|---|
| AATCCGTGGA TTAGGCACCT ‾‾‾‾‾‾‾‾C3 | ATCCTCACAT TAGGAGTGTA FLANKING | AACAGTAGGA TTGTCATCCT ARM_____> | 2270 |
| TATGTTAAGG ATACAATTCC ‾‾‾‾‾‾‾‾C3 | AGGACGATGT TCCTGCTACA FLANKING | CGAAAACAAG GCTTTTGTTC ARM_____> | 2300 |
| AAACGCCTAA TTTGCGGATT ‾‾‾‾‾‾‾‾C3 | TGGAGTGCAT ACCTCACGTA FLANKING | GTCCAAGTTT CAGGTTCAAA ARM_____> | 2330 |
| AGGGGGCAAG TCCCCCGTTC ‾‾‾‾‾‾‾‾C3 | AAATACAAGT TTTATGTTCA FLANKING | TCTAGGATGG AGATCCTACC ARM_____> | 2360 |
| TATTAATAAG ATAATTATTC ‾‾‾‾‾‾‾‾C3 | TATCTAAGTA ATAGATTCAT FLANKING | TTTGGTATAA AAACCATATT ARM_____> | 2390 |
| TTTATTAAAT AAATAATTTA ‾‾‾‾‾‾‾‾C3 | AGTATAATTA TCATATTAAT FLANKING | TAACAAATAA ATTGTTTATT ARM_____> | 2420 |
| TAAATAACAT ATTTATTGTA ‾‾‾‾‾‾‾‾C3 | GATAACGGTT CTATTGCCAA FLANKING | TTTATTAGAA AAATAATCTT ARM_____> | 2450 |
| TAAAATAGAG ATTTTATCTC ‾‾‾‾‾‾‾‾C3 | ATAATATCAT TATTATAGTA FLANKING | AATGATATAT TTACTATATA ARM_____> | 2480 |
| AATACTTCAT TTATGAAGTA ‾‾‾‾‾‾‾‾C3 | TACCAGAAAT ATGGTCTTTA FLANKING | GAGTAATGGA CTCATTACCT ARM_____> | 2510 |
| AGACTTATAA TCTGAATATT ‾‾‾‾‾‾‾‾C3 | ATGAACTGCA TACTTGACGT FLANKING | TAAAGCTATA ATTTCGATAT ARM_____> | 2540 |
| AGGTATAGAG TCCATATCTC ‾‾‾‾‾‾‾‾C3 | ATATAAATTT TATATTTAAA FLANKING | AGTAAGGTAT TCATTCCATA ARM_____> | 2570 |

FIG. 15D-2

| | | | |
|---|---|---|---|
| ATACTTAAAA | AATGCAAATA | CAATAACGTA | 2600 |
| TATGAATTTT | TTACGTTTAT | GTTATTGCAT | |
| __________C3 | FLANKING | ARM__________> | |
| AATATACTAT | CAACGTCTTT | GTATTTAGCC | 2630 |
| TTATATGATA | GTTGCAGAAA | CATAAATCGG | |
| __________C3 | FLANKING | ARM__________> | |
| GTAAGTATTT | CTGATATAGA | AATGGTAAAA | 2660 |
| CATTCATAAA | GACTATATCT | TTACCATTTT | |
| __________C3 | FLANKING | ARM__________> | |
| TTATTACTAG | AACACGGTGC | CGATATTTTA | 2690 |
| AATAATGATC | TTGTGCCACG | GCTATAAAAT | |
| __________C3 | FLANKING | ARM__________> | |
| AAATGTAAAA | ATCCTCCTCT | TCATAAAGCT | 2720 |
| TTTACATTTT | TAGGAGGAGA | AGTATTTCGA | |
| __________C3 | FLANKING | ARM__________> | |
| GCTAGTTTAG | ATAATACAGA | AATTGCTAAA | 2750 |
| CGATCAAATC | TATTATGTCT | TTAACGATTT | |
| __________C3 | FLANKING | ARM__________> | |
| CTACTAATAG | ATTCTGGCGC | TGACATAGAA | 2780 |
| GATGATTATC | TAAGACCGCG | ACTGTATCTT | |
| __________C3 | FLANKING | ARM__________> | |
| CAGATACATT | CTGGAAATAG | TCCGTTATAT | 2710 |
| GTCTATGTAA | GACCTTTATC | AGGCAATATA | |
| __________C3 | FLANKING | ARM__________> | |
| ATTTCTGTAT | ATAGAAACAA | TAAGTCATTA | 2840 |
| TAAAGACATA | TATCTTTGTT | ATTCAGTAAT | |
| __________C3 | FLANKING | ARM__________> | |
| ACTAGATATT | TATTAAAAAA | AGGTGTTAAT | 2870 |
| TGATCTATAA | ATAATTTTTT | TCCACAATTA | |
| __________C3 | FLANKING | ARM__________> | |
| TGTAATAGAT | TCTTTCTAAA | TTATTACGAT | 2890 |
| ACATTATCTA | AGAAAGATTT | AATAATGCTA | |
| __________C3 | FLANKING | ARM__________> | |

FIG. 15D-3

| | | | |
|---|---|---|---|
| GTACTGTATG<br>CATGACATAC<br>_________C3 | ATAAGATATC<br>TATTCTATAG<br>FLANKING | TGATGATATG<br>ACTACTATAC<br>ARM________> | 2930 |
| TATAAAATAT<br>ATATTTTATA<br>_________C3 | TTATAGATTT<br>AATATCTAAA<br>FLANKING | TAATATTGAT<br>ATTATAACTA<br>ARM________> | 2960 |
| CTTAATATAC<br>GAATTATATG<br>_________C3 | AAACTAGAAA<br>TTTGATCTTT<br>FLANKING | TTTTGAAACT<br>AAAACTTTGA<br>ARM________> | 2990 |
| CCGTTACATT<br>GGCAATGTAA<br>_________C3 | ACGCTATAAA<br>TGCGATATTT<br>FLANKING | GTATAAGAAT<br>CATATTCTTA<br>ARM________> | 3020 |
| ATAGATTTAA<br>TATCTAAATT<br>__C3 FLANK | TTAGGATATT<br>AATCCTATAA<br>ING ARM___> | | 3040 |

| |
|---|
| FIG. 15E-1 |
| FIG. 15E-2 |
| FIG. 15E-3 |

FIG. 15E-1

| | | | |
|---|---|---|---|
| GTTAGATAAT<br>CAATCTATTA<br>________C3 | AGTATTAAAA<br>TCATAATTTT<br>FLANKING | TAGATAAAAG<br>ATCTATTTTC<br>ARM________> | 3070 |
| TTTATTTTTG<br>AAATAAAAAC<br>________C3 | CATAAACAGT<br>GTATTTGTCA<br>FLANKING | ATCTCATAAA<br>TAGAGTATTT<br>ARM________> | 3100 |
| GGCACTTAAA<br>CCGTGAATTT<br>________C3 | AATAATTGTA<br>TTATTAACAT<br>FLANKING | GTTACGATAT<br>CAATGCTATA<br>ARM________> | 3130 |
| AATAGCGTTA<br>TTATCGCAAT<br>________C3 | CTTATAAATC<br>GAATATTTAG<br>FLANKING | ACGGAGTGCC<br>TGCCTCACGG<br>ARM________> | 3160 |
| TATAAACGAA<br>ATATTTGCTT<br>________C3 | CAAGATGATT<br>GTTCTACTAA<br>FLANKING | TAGGTAAAAC<br>ATCCATTTTG<br>ARM________> | 3190 |
| CCCATTACAT<br>GGGTAATGTA<br>________C3 | CATTCGGTAA<br>GTAAGCCATT<br>FLANKING | TTAATAGAAG<br>AATTATCTTC<br>ARM________> | 3220 |
| AAAAGATGTA<br>TTTTCTACAT<br>________C3 | ACAGCACTTC<br>TGTCGTGAAG<br>FLANKING | TGTTAAATCT<br>ACAATTTAGA<br>ARM________> | 3250 |
| AGGAGCTGAT<br>TCCTCGACTA<br>________C3 | ATAAACGTAA<br>TATTTGCATT<br>FLANKING | TAGATGACTG<br>ATCTACTGAC<br>ARM________> | 3280 |
| TATGGGCAGT<br>ATACCCGTCA<br>________C3 | CCCTTACATT<br>GGGAATGTAA<br>FLANKING | ACGCTGTTTC<br>TGCGACAAAG<br>ARM________> | 3310 |
| ACGTAACGAT<br>TGCATTGCTA<br>________C3 | ATCGAAACAA<br>TAGCTTTGTT<br>FLANKING | CAAAGACACT<br>GTTTCTGTGA<br>ARM________> | 3340 |
| TTTAGAAAGA<br>AAATCTTTCT<br>________C3 | GGATCTAATG<br>CCTAGATTAC<br>FLANKING | TTAATGTGGT<br>AATTACACCA<br>ARM________> | 3370 |

FIG. 15E-2

| | | | |
|---|---|---|---|
| TAATAATCAT | ATAGATACCG | TTCTAAATAT | 3400 |
| ATTATTAGTA | TATCTATGGC | AAGATTTATA | |
| __________C3 | FLANKING | ARM__________> | |
| AGCTGTTGCA | TCTAAAAACA | AAACTATAGT | 3430 |
| TCGACAACGT | AGATTTTTGT | TTTGATATCA | |
| __________C3 | FLANKING | ARM__________> | |
| AAACTTATTA | CTGAAGTACG | GTACTGATAC | 3460 |
| TTTGAATAAT | GACTTCATGC | CATGACTATG | |
| __________C3 | FLANKING | ARM__________> | |
| AAAGTTGGTA | GGATTAGATA | AACATGTTAT | 3490 |
| TTTCAACCAT | CCTAATCTAT | TTGTACAATA | |
| __________C3 | FLANKING | ARM__________> | |
| TCACATAGCT | ATAGAAATGA | AAGATATTAA | 3520 |
| AGTGTATCGA | TATCTTTACT | TTCTATAATT | |
| __________C3 | FLANKING | ARM__________> | |
| TATACTGAAT | GCGATCTTAT | TATATGGTTG | 3550 |
| ATATGACTTA | CGCTAGAATA | ATATACCAAC | |
| __________C3 | FLANKING | ARM__________> | |
| CTATGTAAAC | GTCTATAATC | ATAAAGGTTT | 3580 |
| GATACATTTG | CAGATATTAG | TATTTCCAAA | |
| __________C3 | FLANKING | ARM__________> | |
| CACTCCTCTA | TACATGGCAG | TTAGTTCTAT | 3610 |
| GTGAGGAGAT | ATGTACCGTC | AATCAAGATA | |
| __________C3 | FLANKING | ARM__________> | |
| GAAAACAGAA | TTTGTTAAAC | TCTTACTTGA | 3640 |
| CTTTTGTCTT | AAACAATTTG | AGAATGAACT | |
| __________C3 | FLANKING | ARM__________> | |
| CCACGGTGCT | TACGTAAATG | CTAAAGCTAA | 3670 |
| GGTGCCACGA | ATGCATTTAC | GATTTCGATT | |
| __________C3 | FLANKING | ARM__________> | |
| GTTATCTGGA | AATACTCCTT | TACATAAAGC | 3700 |
| CAATAGACCT | TTATGAGGAA | ATGTATTTCG | |
| __________C3 | FLANKING | ARM__________> | |

FIG. 15E-3

| | | | |
|---|---|---|---|
| TATGTTATCT<br>ATACAATAGA<br>__________C3 | AATAGTTTTA<br>TTATCAAAAT<br>FLANKING | ATAATATAAA<br>TATTATATTT<br>ARM_________> | 3730 |
| ATTACTTTTA<br>TAATGAAAAT<br>__________C3 | TCTTATAACG<br>AGAATATTGC<br>FLANKING | CCGACTATAA<br>GGCTGATATT<br>ARM_________> | 3760 |
| TTCTCTAAAT<br>AAGAGATTTA<br>__________C3 | AATCACGGTA<br>TTAGTGCCAT<br>FLANKING | ATACGCCTCT<br>TATGCGGAGA<br>ARM_________> | 3790 |
| AACTTGTGTT<br>TTGAACACAA<br>__________C3 | AGCTTTTTAG<br>TCGAAAAATC<br>FLANKING | ATGACAAGAT<br>TACTGTTCTA<br>ARM_________> | 3820 |
| AGCTATTATG<br>TCGATAATAC<br>___C3 FLANK | ATAATATCTA<br>TATTATAGAT<br>ING ARM____> | | 3840 |

| | | | |
|---|---|---|---|
| AAATGATGTT<br>TTTACTACAA<br>__________C3 | AGAAATATCT<br>TCTTTATAGA<br>FLANKING | AAAAATCCTG<br>TTTTTAGGAC<br>ARM__________> | 3870 |
| AAATAGCTAA<br>TTTATCGATT<br>__________C3 | TTCAGAAGGT<br>AAGTCTTCCA<br>FLANKING | TTTATAGTAA<br>AAATATCATT<br>ARM__________> | 3900 |
| ACATGGAACA<br>TGTACCTTGT<br>__________C3 | TATAAACAGT<br>ATATTTGTCA<br>FLANKING | AATAAAAGAC<br>TTATTTTCTG<br>ARM__________> | 3930 |
| TACTATCTAT<br>ATGATAGATA<br>__________C3 | AAAAGAATCA<br>TTTTCTTAGT<br>FLANKING | TGCGAAAAAG<br>ACGCTTTTTC<br>ARM__________> | 3960 |
| AACTAGATGT<br>TTGATCTACA<br>__________C3 | TATAACACAT<br>ATATTGTGTA<br>FLANKING | ATAAAGTTAA<br>TATTTCAATT<br>ARM__________> | 3990 |
| ATTCTATATA<br>TAAGATATAT<br>__________C3 | TTCTTTTAAT<br>AAGAAAATTA<br>FLANKING | ATCTTTCTTG<br>TAGAAAGAAC<br>ARM__________> | 4020 |
| ACAATAACAT<br>TGTTATTGTA<br>__________C3 | AGATCTTATG<br>TCTAGAATAC<br>FLANKING | GTAAAGTTCG<br>CATTTCAAGC<br>ARM__________> | 4050 |
| TAACTAATCC<br>ATTGATTAGG<br>__________C3 | TAGAGTTAAT<br>ATCTCAATTA<br>FLANKING | AAGATACCTG<br>TTCTATGGAC<br>ARM__________> | 4080 |
| CATGTATACG<br>GTACATATGC<br>__________C3 | TATATATAGG<br>ATATATATCC<br>FLANKING | GAATTAATAC<br>CTTAATTATG<br>ARM__________> | 4110 |
| GGAAAAATAA<br>CCTTTTTATT<br>__________C3 | ATCATTAGCT<br>TAGTAATCGA<br>FLANKING | TTTCATAGAC<br>AAAGTATCTG<br>ARM__________> | 4140 |
| ATCAGCTAAT<br>TAGTCGATTA<br>__________C3 | AGTTAAAGCT<br>TCAATTTCGA<br>FLANKING | GTAAAAGAGA<br>CATTTTCTCT<br>ARM__________> | 4170 |

FIG. 15F-2

```
GTAAGAATCT  AGGAATAATA  GGTAGGTTAC   4200
CATTCTTAGA  TCCTTATTAT  CCATCCAATG
_________C3 FLANKING    ARM________>

CTATAGATAT  CAAACATATA  ATAATGGAAC   4230
GATATCTATA  GTTTGTATAT  TATTACCTTG
_________C3 FLANKING    ARM________>

TATTAAGTAA  TAATGATTTA  CATTCTGTTA   4260
ATAATTCATT  ATTACTAAAT  GTAAGACAAT
_________C3 FLANKING    ARM________>

TCACCAGCTG  TTGTAACCCA  GTAGTATAAA   4290
AGTGGTCGAC  AACATTGGGT  CATCATATTT
_________C3 FLANKING    ARM________>

G                                    4291
C
_>
```

| FIG. 16A |
|---|
| FIG. 16B |
| FIG. 16C |

FIG. 16A

| | | | |
|---|---|---|---|
| AGTACAATAA<br>TCATGTTATT<br>___C6 LEFT | AAAGTATTAA<br>TTTCATAATT<br>ARM________ | ATAAAAATAC<br>TATTTTTATG<br>____________> | 30 |
| TTACTTACGA<br>AATGAATGCT<br>___C6 LEFT | AAAAATGACT<br>TTTTTACTGA<br>ARM________ | AATTAGCTAT<br>TTAATCGATA<br>_> | 60 |
| AAAAACCCGG<br>TTTTTGGGCC | GCTGCAGCTC<br>CGACGTCGAG | GAGGATCCTC<br>CTCCTAGGAG | 90 |
| TAGATTAACA<br>ATCTAATTGT<br><C<br><___ | ATTTTTAAAA<br>TAAAAATTTT<br>N K F<br>_NEF CTL2_ | TATTCAGGAT<br>ATAAGTCCTA<br>Y E P H<br>__________ | 120 |
| GTAATTCTCT<br>CATTAAGAGA<br><L E R<br><__________ | AGCTACGTGA<br>TCGATGCACT<br>A V H<br>_NEF CTL2_ | TGAAATGCTA<br>ACTTTACGAT<br>H F A L<br>__________ | 150 |
| ATCTAGAATC<br>TAGATCTTAG<br><R S D<br><__________ | AAATCTCCAC<br>TTTAGAGGTG<br>F R W<br>_NEF CTL2_ | TCCATGATTA<br>AGGTACTAAT<br>E M<br>_____<br><_____ | 180 |
| AACCTAAATA<br>TTGGATTTAT<br><_______I3L | ATTGTACTTT<br>TAACATGAAA<br>PROMOTER__ | GTAATATAAT<br>CATTATATTA<br>__________ | 210 |
| GATATATATT<br>CTATATATAA<br><_______I3L | TTCACTTTAT<br>AAGTGAAATA<br>PROMOTER__ | CTCATTTGAG<br>GAGTAAACTC<br>__________ | 240 |
| AATAAAAATG<br>TTATTTTTAC<br><_______I3L | TTTTTGTTTA<br>AAAAACAAAT<br>PROMOTER__ | ACCACTGCAT<br>TGGTGACGTA<br>__________ | 270 |
| GATGTCTAAT<br>CTACAGATTA<br><_____ | TAATTAAGCT<br>ATTAATTCGA | ACAAATAGTT<br>TGTTTATCAA | 300 |

FIG. 16B

| | | | |
|---|---|---|---|
| TCGTTTTCAC<br>AGCAAAAGTG | CTTGTCTAAT<br>GAACAGATTA | AACTAATTAA<br>TTGATTAATT | 330 |
| TTAAGCTTCT<br>AATTCGAAGA<br>__H6 | TTATTCTATA<br>AATAAGATAT<br>PROMOTER__ | CTTAAAAAGT<br>GAATTTTTCA<br>__________> | 360 |
| GAAAATAAAT<br>CTTTTATTTA<br>__________H6 | ACAAAGGTTC<br>TGTTTCCAAG<br>PROMOTER__ | TTGAGGGTTG<br>AACTCCCAAC<br>__________> | 390 |
| TGTTAAATTG<br>ACAATTTAAC<br>__________H6 | AAAGCGAGAA<br>TTTCGCTCTT<br>PROMOTER__ | ATAATCATAA<br>TATTAGTATT<br>__________> | 420 |
| ATTATTTCAT<br>TAATAAAGTA<br>__________H6 | TATCGCGATA<br>ATAGCGCTAT<br>PROMOTER__ | TCCGTTAAGT<br>AGGCAATTCA<br>__________> | 450 |
| TTGTATCGTA<br>AACATAGCAT<br>__________ | ATGGTAGGTT<br>TACCATCCAA<br>M V G<br>><br>_NEF CTL1_ | TTCCAGTAAC<br>AAGGTCATTG<br>F P V T><br>__________> | 480 |
| ACCTCAAGTA<br>TGGAGTTCAT<br>P Q V<br>__________ | CCTTTAAGAC<br>GGAAATTCTG<br>P L R<br>_NEF CTL1_ | CAATGACTTA<br>GTTACTGAAT<br>P M T Y<br>__________> | 510 |
| CAAAGCAGCT<br>GTTTCGTCGA<br>K A A<br>__________ | GTAGATCTTT<br>CATCTAGAAA<br>V D L<br>_NEF CTL1_ | CTCACTTTTT<br>GAGTGAAAAA<br>S H F L<br>__________> | 540 |
| AAAAGAAAAA<br>TTTTCTTTTT<br>K E K<br>__________ | GGAGGTTTAG<br>CCTCCAAATC<br>G G L<br>_NEF CTL1_ | AAGGGCTAAT<br>TTCCCGATTA<br>E G L I<br>__________> | 570 |
| TCATTCTCAA<br>AGTAAGAGTT<br>H S Q<br>__________ | CGAAGACAAG<br>GCTTCTGTTC<br>R R Q<br>_NEF CTL1_ | ATATTCTTGA<br>TATAAGAACT<br>D I L D><br>__________> | 600 |

FIG. 16C

| | | | |
|---|---|---|---|
| TTTGTGGATT<br>AAACACCTAA<br>L W I | TATCATACAC<br>ATAGTATGTG<br>Y H T<br>_NEF CTL1_ | AAGGATATTT<br>TTCCTATAAA<br>Q G Y F<br>> | 630 |
| TCCTGATTGG<br>AGGACTAACC<br>P D W | CAGAATTACA<br>GTCTTAATGT<br>Q N Y<br>_NEF CTL1_ | CACCAGGACC<br>GTGGTCCTGG<br>T P G P<br>> | 660 |
| AGGAGTCAGA<br>TCCTCAGTCT<br>G V R | TACCCATTAA<br>ATGGGTAATT<br>Y P L<br>_NEF CTL1_ | CCTTTGGTTG<br>GGAAACCAAC<br>T F G W<br>> | 690 |
| GTGCTACAAG<br>CACGATGTTC<br>C Y K<br>__NEF CTL1 | CTAGTACCAT<br>GATCATGGTA<br>L V P><br>> | AATTTTTCTC<br>TTAAAAAGAG | 720 |
| GAGGAATTCT<br>CTCCTTAAGA | TTTTATTGAT<br>AAAATAACTA | TAACTAGTCA<br>ATTGATCAGT | 750 |
| AATGAGTATA<br>TTACTCATAT | TATAATTGAA<br>ATATTAACTT<br>__C6 RIGHT | AAAGTAAAAT<br>TTTCATTTTA<br>ARM | 780 |
| ATAAATCATA<br>TATTTAGTAT<br>C6 | TAATAATGAA<br>ATTATTACTT<br>RIGHT ARM | A<br>T<br>_> | 801 |

| FIG. 17A-1 |
|---|
| FIG. 17A-2 |

FIG. 17A-1

| | | | |
|---|---|---|---|
| GAGCTCGCGG<br>CTCGAGCGCC<br>C6 | CCGCCTATCA<br>GGCGGATAGT<br>FLANKING | AAAGTCTTAA<br>TTTCAGAATT<br>ARM > | 30 |
| TGAGTTAGGT<br>ACTCAATCCA<br>C6 | GTAGATAGTA<br>CATCTATCAT<br>FLANKING | TAGATATTAC<br>ATCTATAATG<br>ARM > | 60 |
| TACAAAGGTA<br>ATGTTTCCAT<br>C6 | TTCATATTTC<br>AAGTATAAAG<br>FLANKING | CTATCAATTC<br>GATAGTTAAG<br>ARM > | 90 |
| TAAAGTAGAT<br>ATTTCATCTA<br>C6 | GATATTAATA<br>CTATAATTAT<br>FLANKING | ACTCAAAGAT<br>TGAGTTTCTA<br>ARM > | 120 |
| GATGATAGTA<br>CTACTATCAT<br>C6 | GATAATAGAT<br>CTATTATCTA<br>FLANKING | ACGCTCATAT<br>TGCGAGTATA<br>ARM > | 150 |
| AATGACTGCA<br>TTACTGACGT<br>C6 | AATTTGGACG<br>TTAAACCTGC<br>FLANKING | GTTCACATTT<br>CAAGTGTAAA<br>ARM > | 180 |
| TAATCATCAC<br>ATTAGTAGTG<br>C6 | GCGTTCATAA<br>CGCAAGTATT<br>FLANKING | GTTTCAACTG<br>CAAAGTTGAC<br>ARM > | 210 |
| CATAGATCAA<br>GTATCTAGTT<br>C6 | AATCTCACTA<br>TTAGAGTGAT<br>FLANKING | AAAAGATAGC<br>TTTTCTATCG<br>ARM > | 240 |
| CGATGTATTT<br>GCTACATAAA<br>C6 | GAGAGAGATT<br>CTCTCTCTAA<br>FLANKING | GGACATCTAA<br>CCTGTAGATT<br>ARM > | 270 |
| CTACGCTAAA<br>GATGCGATTT<br>C6 | GAAATTACAG<br>CTTTAATGTC<br>FLANKING | TTATAAATAA<br>AATATTTATT<br>ARM > | 300 |
| TACATAATGG<br>ATGTATTACC<br>C6 | ATTTTGTTAT<br>TAAAACAATA<br>FLANKING | CATCAGTTAT<br>GTAGTCAATA<br>ARM > | 330 |

FIG. 17A-2

```
ATTTAACATA   AGTACAATAA   AAAGTATTAA      360
TAAATTGTAT   TCATGTTATT   TTTCATAATT
________C6   flanking     arm_______>

ATAAAAATAC   TTACTTACGA   AAAAATGACT      390
TATTTTTATG   AATGAATGCT   TTTTTACTGA
________C6   flanking     arm_____>
                                  __>

AATTAGCTAT   AAAAACCCGG   GCTGCAGCTC      420
TTAATCGATA   TTTTTGGGCC   CGACGTCGAG
__________   __Cloning    sites_____>

GAGGAATTCT   TTTTATTGAT   TAACTAGTCA      450
CTCCTTAAGA   AAAATAACTA   ATTGATCAGT
__________   __Cloning    sites__>
                                 ____>

AATGAGTATA   TATAATTGAA   AAAGTAAAAT      480
TTACTCATAT   ATATTAACTT   TTTCATTTTA
________C6   flanking     arm_______>

ATAAATCATA   TAATAATGAA   ACGAAATATC      510
TATTTAGTAT   ATTATTACTT   TGCTTTATAG
________C6   flanking     arm_______>

AGTAATAGAC   AGGAACTGGC   AGATTCTTCT      540
TCATTATCTG   TCCTTGACCG   TCTAAGAAGA
________C6   flanking     arm_______>

TCTAATGAAG   TAAGTACTGC   TAAATCTCCA      570
AGATTACTTC   ATTCATGACG   ATTTAGAGGT
________C6   flanking     arm_______>

AAATTAGATA   AAAATGATAC   AGCAAATACA      600
TTTAATCTAT   TTTTACTATG   TCGTTTATGT
________C6   flanking     arm_______>

GCTTCATTCA   ACGAATTACC   TTTTAATTTT      630
CGAAGTAAGT   TGCTTAATGG   AAAATTAAAA
________C6   flanking     arm_______>
```

FIG. 17B-1

| | | | |
|---|---|---|---|
| TTCAGACACA AAGTCTGTGT _____C6 | CCTTATTACA GGAATAATGT flanking | AACTAACTAA TTGATTGATT arm_____> | 660 |
| GTCAGATGAT CAGTCTACTA _____C6 | GAGAAAGTAA CTCTTTCATT flanking | ATATAAATTT TATATTTAAA arm_____> | 690 |
| AACTTATGGG TTGAATACCC _____C6 | TATAATATAA ATATTATATT flanking | TAAAGATTCA ATTTCTAAGT arm_____> | 720 |
| TGATATTAAT ACTATAATTA _____C6 | AATTTACTTA TTAAATGAAT flanking | ACGATGTTAA TGCTACAATT arm_____> | 750 |
| TAGACTTATT ATCTGAATAA _____C6 | CCATCAACCC GGTAGTTGGG flanking | CTTCAAACCT GAAGTTTGGA arm_____> | 780 |
| TTCTGGATAT AAGACCTATA _____C6 | TATAAAATAC ATATTTTATG flanking | CAGTTAATGA GTCAATTACT arm_____> | 810 |
| TATTAAAATA ATAATTTTAT _____C6 | GATTGTTTAA CTAACAAATT flanking | GAGATGTAAA CTCTACATTT arm_____> | 840 |
| TAATTATTTG ATTAATAAAC _____C6 | GAGGTAAAGG CTCCATTTCC flanking | ATATAAAATT TATATTTTAA arm_____> | 870 |
| AGTCTATCTT TCAGATAGAA _____C6 | TCACATGGAA AGTGTACCTT flanking | ATGAATTACC TACTTAATGG arm_____> | 900 |
| TAATATTAAT ATTATAATTA _____C6 | AATTATGATA TTAATACTAT flanking | GGAATTTTTT CCTTAAAAAA arm_____> | 930 |
| AGGATTTACA TCCTAAATGT _____C6 | GCTGTTATAT CGACAATATA flanking | GTATCAACAA CATAGTTGTT arm_____> | 960 |

FIG. 17B-2

```
TACAGGCAGA   TCTATGGTTA   TGGTAAAACA    990
ATGTCCGTCT   AGATACCAAT   ACCATTTTGT
_________C6  flanking     arm_______>

CTGTAACGGG   AAGCAGCATT   CTATGGTAAC   1020
GACATTGCCC   TTCGTCGTAA   GATACCATTG
_________C6  flanking     arm_______>

TGGCCTATGT   TTAATAGCCA   GATCATTTTA   1050
ACCGGATACA   AATTATCGGT   CTAGTAAAAT
_________C6  flanking     arm_______>

CTCTATAAAC   ATTTTACCAC   AAATAATAGG   1080
GAGATATTTG   TAAAATGGTG   TTTATTATCC
_________C6  flanking     arm_______>

ATCCTCTAGA   TATTTAATAT   TATATCTAAC   1110
TAGGAGATCT   ATAAATTATA   ATATAGATTG
_________C6  flanking     arm_______>

AACAACAAAA   AAATTTAACG   ATGTATGGCC   1140
TTGTTGTTTT   TTTAAATTGC   TACATACCGG
_________C6  flanking     arm_______>

AGAAGTATTT   TCTACTAATA   AAGATAAAGA   1170
TCTTCATAAA   AGATGATTAT   TTCTATTTCT
_________C6  flanking     arm_______>

TAGTCTATCT   TATCTACAAG   ATATGAAAGA   1200
ATCAGATAGA   ATAGATGTTC   TATACTTTCT
_________C6  flanking     arm_______>

AGATAATCAT   TTAGTAGTAG   CTACTAATAT   1230
TCTATTAGTA   AATCATCATC   GATGATTATA
_________C6  flanking     arm_______>

GGAAAGAAAT   GTATACAAAA   ACGTGGAAGC   1260
CCTTTCTTTA   CATATGTTTT   TGCACCTTCG
_________C6  flanking     arm_______>

TTTTATATTA   AATAGCATAT   TACTAGAAGA   1290
AAAATATAAT   TTATCGTATA   ATGATCTTCT
_________C6  flanking     arm_______>
```

FIG. 17B-3

| | | | |
|---|---|---|---|
| AGGAATAAGC<br>TCCTTATTCG<br>_________C6 | AATATGCCAA<br>TTATACGGTT<br>flanking | TTATGTCTAA<br>AATACAGATT<br>arm________> | 1440 |
| TATTTTAACT<br>ATAAAATTGA<br>_________C6 | TTAGAACTAA<br>AATCTTGATT<br>flanking | AACGTTCTAC<br>TTGCAAGATG<br>arm________> | 1470 |
| CAATACTAAA<br>GTTATGATTT<br>_________C6 | AATAGGATAC<br>TTATCCTATG<br>flanking | GTGATAGGCT<br>CACTATCCGA<br>arm________> | 1500 |
| GTTAAAAGCT<br>CAATTTTCGA<br>_________C6 | GCAATAAATA<br>CGTTATTTAT<br>flanking | GTAAGGATGT<br>CATTCCTACA<br>arm________> | 1530 |
| AGAAGAAATA<br>TCTTCTTTAT<br>_________C6 | CTTTGTTCTA<br>GAAACAAGAT<br>flanking | TACCTTCGGA<br>ATGGAAGCCT<br>arm________> | 1560 |
| GGAAAGAACT<br>CCTTTCTTGA<br>_________C6 | TTAGAACAAC<br>AATCTTGTTG<br>flanking | TTAAGTTTAA<br>AATTCAAATT<br>arm________> | 1590 |
| TCAAACTTGT<br>AGTTTGAACA<br>_________C6 | ATTTATGAAG<br>TAAATACTTC<br>flanking | GTACC<br>CATGG<br>arm__> | 1615 |

FIG. 17C

| | | | |
|---|---|---|---|
| TTTAAAATCT<br>AAATTTTAGA<br>________C6 | AGACTTAGTA<br>TCTGAATCAT<br>flanking | TAACAAAACA<br>ATTGTTTTGT<br>arm_______> | 1320 |
| GTTAAATGCC<br>CAATTTACGG<br>________C6 | AATATCGATT<br>TTATAGCTAA<br>flanking | CTATATTTCA<br>GATATAAAGT<br>arm_______> | 1350 |
| TCATAACAGT<br>AGTATTGTCA<br>________C6 | AGTACATTAA<br>TCATGTAATT<br>flanking | TCAGTGATAT<br>AGTCACTATA<br>arm_______> | 1380 |
| ACTGAAACGA<br>TGACTTTGCT<br>________C6 | TCTACAGACT<br>AGATGTCTGA<br>flanking | CAACTATGCA<br>GTTGATACGT<br>arm_______> | 1410 |

| FIG. 18A-1 |
|---|
| FIG. 18A-2 |
| FIG. 18A-3 |

FIG. 18A-1

```
TTAGAAATTA    TGCATTTTAG    ATCTTTATAA       30
AATCTTTAAT    ACGTAAAATC    TAGAAATATT
_________C5   LEFT ARM__    ___________

GCGGCCGTGA    TTAACTAGTC    ATAAAAACCC       60
CGCCGGCACT    AATTGATCAG    TATTTTTGGG
___________   ___________   >

GGGATCGATT    CTAGACTCGA    GCTATTCAAT       90
CCCTAGCTAA    GATCTGAGCT    CGATAAGTTA

TAGGTTGTAA    GTCCCCACCT    CAACAGATGT      120
ATCCAACATT    CAGGGGTGGA    GTTGTCTACA
  <T  T  L     G  W  R       L  L  H
<__________   __POL 2___    ___________

TGTCTCAGCT    CCTCTATTTT    TGTTCTATGC      150
ACAGAGTCGA    GGAGATAAAA    ACAAGATACG
Q  R  L  E     E  I  K       T  R  H
<__________   __POL 2___    ___________

TGCCCTATTT    CTAAGTCAGA    TCCTACATAC      180
ACGGGATAAA    GATTCAGTCT    AGGATGTATG
Q  G  I  E     L  D  S       G  V  Y
<__________   __POL 2___    ___________

AAATCATCCA    TGTATTGATA    GATAACTATG      210
TTTAGTAGGT    ACATAACTAT    CTATTGATAC
L  D  D  M     Y  Q  Y       I  V  I
<__________   __POL 2___    ___________

TCTGGATTTT    GTTTTCTAAA    AGGCTCTAAG      240
AGACCTAAAA    CAAAAGATTT    TCCGAGATTC
D  P  N  Q     K  R  F       P  E  L
<__________   __POL 2___    ___________

ATTTTTGTCA    TGCTACTTTG    GAATATTGCC      270
TAAAAACAGT    ACGATGAAAC    CTTATAACGG
I  K  T  M     S  S  Q       F  I  A
<__________   __POL 2___    ___________
```

FIG. 18A-2

| | | | |
|---|---|---|---|
| ATGGCCCAAA | AGTTAAACAA | TGGCCATTGA | 570 |
| TACCGGGTTT | TCAATTTGTT | ACCGGTAACT | |
| D G P K | V K Q | W P L | |
| __________ | ___POL1___ | __________> | |
| CAGAAGAAAA | AATAAAAGCA | TTAGTAGAAA | 600 |
| GTCTTCTTTT | TTATTTTCGT | AATCATCTTT | |
| T E E K | I K A | L V E | |
| __________ | ___POL1___ | __________> | |
| TTTGTACAGA | GATGGAAAAG | GAAGGGAAAA | 630 |
| AAACATGTCT | CTACCTTTTC | CTTCCCTTTT | |
| I C T E | M E K | E G K | |
| __________ | ___POL1___ | __________> | |
| TTTCAAAAAT | TGGGCCTTAA | TTGATTAGAA | 660 |
| AAAGTTTTTA | ACCCGGAATT | AACTAATCTT | |
| I S K I | G P> | | |
| __________ | __POL1_> | | |
| TTCCTGCAGC | CCAGGTCAAA | AAAATATAAA | 690 |
| AAGGACGTCG | GGTCCAGTTT | TTTTATATTT | |
| | ___42K | PROMOTER__> | |
| TGATTCACCA | TCTGATAGAA | AAAAAATTTA | 720 |
| ACTAAGTGGT | AGACTATCTT | TTTTTTAAAT | |
| ________42K | PROMOTER__ | __________> | |
| TTGGGAAGAA | TATGATAATA | TTTTGGGATT | 750 |
| AACCCTTCTT | ATACTATTAT | AAAACCCTAA | |
| ________42K | PROMOTER__ | __________> | |
| TCAAAATTGA | AAATATATAA | TTACAATATA | 780 |
| AGTTTTAACT | TTTATATATT | AATGTTATAT | |
| ________42K | PROMOTER__ | __________> | |
| AAATGCCACT | AACAGAAGAA | GCAGAGCTAG | 810 |
| TTTACGGTGA | TTGTCTTCTT | CGTCTCGATC | |
| M P L | T E E | A E L | |
| __> | | | |
| __________ | __POL 3___ | __________> | |
| AACTGGCAGA | AAACAGAGAG | ATTCTAAAAG | 840 |
| TTGACCGTCT | TTTGTCTCTC | TAAGATTTTC | |
| E L A E | N R E | I L K> | |
| __________ | __POL 3___ | __________> | |

FIG. 18A-3

```
ATGATTAAAC   CTAAATAATT   GTACTTTGTA        300
TACTAATTTG   GATTTATTAA   CATGAAACAT
M

<______I3L   PROMOTER__   __________

ATATAATGAT   ATATATTTTC   ACTTTATCTC        330
TATATTACTA   TATATAAAAG   TGAAATAGAG
<______I3L   PROMOTER__   __________

ATTTGAGAAT   AAAAATGTTT   TTGTTTAACC        360
TAAACTCTTA   TTTTTACAAA   AACAAATTGG
<______I3L   PROMOTER__   __________

ACTGCATGAT   GTAAGCTTCT   TTATTCTATA        390
TGACGTACTA   CATTCGAAGA   AATAAGATAT
<_________   __
                   ____   __________>

CTTAAAAAGT   GAAAATAAAT   ACAAAGGTTC        420
GAATTTTTCA   CTTTTATTTA   TGTTTCCAAG
________H6   PROMOTER__   __________>

TTGAGGGTTG   TGTTAAATTG   AAAGCGAGAA        450
AACTCCCAAC   ACAATTTAAC   TTTCGCTCTT
________H6   PROMOTER__   __________>

ATAATCATAA   ATTATTTCAT   TATCGCGATA        480
TATTAGTATT   TAATAAAGTA   ATAGCGCTAT
________H6   PROMOTER__   __________>

TCCGTTAAGT   TTGTATCGTA   ATGATTGAGA        510
AGGCAATTCA   AACATAGCAT   TACTAACTCT
                           M  I  E
________H6   PROMOTER__   >
                          __________>

CTGTACCAGT   AAAATTAAAG   CCAGGAATGG        540
GACATGGTCA   TTTTAATTTC   GGTCCTTACC
T  V  P  V    K  L  K      P  G  M
__________   ___POL1___   __________>
```

FIG. 18B

```
AACCAGTACA    TGGAGTGTAT    TATGACCCAT         870
TTGGTCATGT    ACCTCACATA    ATACTGGGTA
E  P  V  H     G  V  Y       Y  D  P
___________   __POL 3___    ___________>

CAAAAGACTT    AATAGCAGAA    ATACAGAAGC         900
GTTTTCTGAA    TTATCGTCTT    TATGTCTTCG
S  K  D  L     I  A  E       I  Q  K
___________   __POL 3___    ___________>

AGGGGCAAGG    CCAATGGACA    TATCAAATTT         930
TCCCCGTTCC    GGTTACCTGT    ATAGTTTAAA
Q  G  Q  G     Q  W  T       Y  Q  I
___________   __POL 3___    ___________>

ATCAAGAGCC    ATTTAAAAAT    CTGAAAACAG         960
TAGTTCTCGG    TAAATTTTTA    GACTTTTGTC
Y  Q  E  P     F  K  N       L  K  T>
___________   __POL 3___    ___________>

GATAATTTTT    ATGGATCCTT    TTTATAGCTA         990
CTATTAAAAA    TACCTAGGAA    AAATATCGAT
G>
__>
                                ______>

ATTAGTCACG    TACCTTTGAG    AGTACCACTT        1020
TAATCAGTGC    ATGGAAACTC    TCATGGTGAA
_________C5   RIGHT ARM_    ___________>

CAGCTACCTC    CTTTG                           1035
GTCGATGGAG    GAAAC
__C5 RIGHT    ARM__>
```

FIG. 19A-1

| FIG. 19A-1 |
|---|
| FIG. 19A-2 |
| FIG. 19A-3 |

```
GAATTGCGGC  CGCTGAATGT  TAAATGTTAT     30
CTTAACGCCG  GCGACTTACA  ATTTACAATA
_________C5 FLANKING    ARM________>

ACTTTGGATG  AAGCTATAAA  TATGCATTGG     60
TGAAACCTAC  TTCGATATTT  ATACGTAACC
_________C5 FLANKING    ARM________>

AAAAATAATC  CATTTAAAGA  AAGGATTCAA     90
TTTTTATTAG  GTAAATTTCT  TTCCTAAGTT
_________C5 FLANKING    ARM________>

ATACTACAAA  ACCTAAGCGA  TAATATGTTA    120
TATGATGTTT  TGGATTCGCT  ATTATACAAT
_________C5 FLANKING    ARM________>

ACTAAGCTTA  TTCTTAACGA  CGCTTTAAAT    150
TGATTCGAAT  AAGAATTGCT  GCGAAATTTA
_________C5 FLANKING    ARM________>

ATACACAAAT  AAACATAATT  TTTGTATAAC    180
TATGTGTTTA  TTTGTATTAA  AAACATATTG
_________C5 FLANKING    ARM________>

CTAACAAATA  ACTAAAACAT  AAAAATAATA    210
GATTGTTTAT  TGATTTTGTA  TTTTTATTAT
_________C5 FLANKING    ARM________>

AAAGGAAATG  TAATATCGTA  ATTATTTTAC    240
TTTCCTTTAC  ATTATAGCAT  TAATAAAATG
_________C5 FLANKING    ARM________>

TCAGGAATGG  GGTTAAATAT  TTATATCACG    270
AGTCCTTACC  CCAATTTATA  AATATAGTGC
_________C5 FLANKING    ARM________>

TGTATATCTA  TACTGTTATC  GTATACTCTT    300
ACATATAGAT  ATGACAATAG  CATATGAGAA
_________C5 FLANKING    ARM________>

TACAATTACT  ATTACGAATA  TGCAAGAGAT    330
ATGTTAATGA  TAATGCTTAT  ACGTTCTCTA
_________C5 FLANKING    ARM________>
```

FIG. 19A-2

| | | | |
|---|---|---|---|
| AATAAGATTA | CGTATTTAAG | AGAATCTTGT | 360 |
| TTATTCTAAT | GCATAAATTC | TCTTAGAACA | |
| ________C5 | FLANKING | ARM________> | |
| CATGATAATT | GGGTACGACA | TAGTGATAAA | 390 |
| GTACTATTAA | CCCATGCTGT | ATCACTATTT | |
| ________C5 | FLANKING | ARM________> | |
| TGCTATTTCG | CATCGTTACA | TAAAGTCAGT | 420 |
| ACGATAAAGC | GTAGCAATGT | ATTTCAGTCA | |
| ________C5 | FLANKING | ARM________> | |
| TGGAAAGATG | GATTTGACAG | ATGTAACTTA | 450 |
| ACCTTTCTAC | CTAAACTGTC | TACATTGAAT | |
| ________C5 | FLANKING | ARM________> | |
| ATAGGTGCAA | AAATGTTAAA | TAACAGCATT | 480 |
| TATCCACGTT | TTTACAATTT | ATTGTCGTAA | |
| ________C5 | FLANKING | ARM________> | |
| CTATCGGAAG | ATAGGATACC | AGTTATATTA | 510 |
| GATAGCCTTC | TATCCTATGG | TCAATATAAT | |
| ________C5 | FLANKING | ARM________> | |
| TACAAAAATC | ACTGGTTGGA | TAAAACAGAT | 540 |
| ATGTTTTTAG | TGACCAACCT | ATTTTGTCTA | |
| ________C5 | FLANKING | ARM________> | |
| TCTGCAATAT | TCGTAAAAGA | TGAAGATTAC | 570 |
| AGACGTTATA | AGCATTTTCT | ACTTCTAATG | |
| ________C5 | FLANKING | ARM________> | |
| TGCGAATTTG | TAAACTATGA | CAATAAAAAG | 600 |
| ACGCTTAAAC | ATTTGATACT | GTTATTTTTC | |
| ________C5 | FLANKING | ARM________> | |
| CCATTTATCT | CAACGACATC | GTGTAATTCT | 630 |
| GGTAAATAGA | GTTGCTGTAG | CACATTAAGA | |
| ________C5 | FLANKING | ARM________> | |
| TCCATGTTTT | ATGTATGTGT | TTCAGATATT | 660 |
| AGGTACAAAA | TACATACACA | AAGTCTATAA | |
| ________C5 | FLANKING | ARM________> | |

FIG. 19A-3

```
ATGAGATTAC   TATAAACTTT   TTGTATACTT         690
TACTCTAATG   ATATTTGAAA   AACATATGAA
_________C5   FLANKING     ARM________>

ATATTCCGTA   AACTATATTA   ATCATGAAGA         720
TATAAGGCAT   TTGATATAAT   TAGTACTTCT
_________C5   FLANKING     ARM________>
```

| FIG. 19B-1 |
|---|
| FIG. 19B-2 |
| FIG. 19B-3 |

FIG. 19B-1

| | | | |
|---|---|---|---|
| AAATGAAAAA | GTATAGAAGC | TGTTCACGAG | 750 |
| TTTACTTTTT | CATATCTTCG | ACAAGTGCTC | |
| ____C5 | FLANKING | ARM____> | |
| CGGTTGTTGA | AAACAACAAA | ATTATACATT | 780 |
| GCCAACAACT | TTTGTTGTTT | TAATATGTAA | |
| ____C5 | FLANKING | ARM____> | |
| CAAGATGGCT | TACATATACG | TCTGTGAGGC | 810 |
| GTTCTACCGA | ATGTATATGC | AGACACTCCG | |
| ____C5 | FLANKING | ARM____> | |
| TATCATGGAT | AATGACAATG | CATCTCTAAA | 840 |
| ATAGTACCTA | TTACTGTTAC | GTAGAGATTT | |
| ____C5 | FLANKING | ARM____> | |
| TAGGTTTTTG | GACAATGGAT | TCGACCCTAA | 870 |
| ATCCAAAAAC | CTGTTACCTA | AGCTGGGATT | |
| ____C5 | FLANKING | ARM____> | |
| CACGGAATAT | GGTACTCTAC | AATCTCCTCT | 900 |
| GTGCCTTATA | CCATGAGATG | TTAGAGGAGA | |
| ____C5 | FLANKING | ARM____> | |
| TGAAATGGCT | GTAATGTTCA | AGAATACCGA | 930 |
| ACTTTACCGA | CATTACAAGT | TCTTATGGCT | |
| ____C5 | FLANKING | ARM____> | |
| GGCTATAAAA | ATCTTGATGA | GGTATGGAGC | 960 |
| CCGATATTTT | TAGAACTACT | CCATACCTCG | |
| ____C5 | FLANKING | ARM____> | |
| TAAACCTGTA | GTTACTGAAT | GCACAACTTC | 990 |
| ATTTGGACAT | CAATGACTTA | CGTGTTGAAG | |
| ____C5 | FLANKING | ARM____> | |
| TTGTCTGCAT | GATGCGGTGT | TGAGAGACGA | 1020 |
| AACAGACGTA | CTACGCCACA | ACTCTCTGCT | |
| ____C5 | FLANKING | ARM____> | |
| CTACAAAATA | GTGAAAGATC | TGTTGAAGAA | 1050 |
| GATGTTTTAT | CACTTTCTAG | ACAACTTCTT | |
| ____C5 | FLANKING | ARM____> | |

FIG. 19B-2

| | | | |
|---|---|---|---|
| TAACTATGTA<br>ATTGATACAT<br>__________C5 | AACAATGTTC<br>TTGTTACAAG<br>FLANKING | TTTACAGCGG<br>AAATGTCGCC<br>ARM_________> | 1080 |
| AGGCTTTACT<br>TCCGAAATGA<br>__________C5 | CCTTTGTGTT<br>GGAAACACAA<br>FLANKING | TGGCAGCTTA<br>ACCGTCGAAT<br>ARM_________> | 1110 |
| CCTTAACAAA<br>GGAATTGTTT<br>__________C5 | GTTAATTTGG<br>CAATTAAACC<br>FLANKING | TTAAACTTCT<br>AATTTGAAGA<br>ARM_________> | 1140 |
| ATTGGCTCAT<br>TAACCGAGTA<br>__________C5 | TCGGCGGATG<br>AGCCGCCTAC<br>FLANKING | TAGATATTTC<br>ATCTATAAAG<br>ARM_________> | 1170 |
| AAACACGGAT<br>TTTGTGCCTA<br>__________C5 | CGGTTAACTC<br>GCCAATTGAG<br>FLANKING | CTCTACATAT<br>GAGATGTATA<br>ARM_________> | 1200 |
| AGCCGTATCA<br>TCGGCATAGT<br>__________C5 | AATAAAAATT<br>TTATTTTTAA<br>FLANKING | TAACAATGGT<br>ATTGTTACCA<br>ARM_________> | 1230 |
| TAAACTTCTA<br>ATTTGAAGAT<br>__________C5 | TTGAACAAAG<br>AACTTGTTTC<br>FLANKING | GTGCTGATAC<br>CACGACTATG<br>ARM_________> | 1260 |
| TGACTTGCTG<br>ACTGAACGAC<br>__________C5 | GATAACATGG<br>CTATTGTACC<br>FLANKING | GACGTACTCC<br>CTGCATGAGG<br>ARM_________> | 1290 |
| TTTAATGATC<br>AAATTACTAG<br>__________C5 | GCTGTACAAT<br>CGACATGTTA<br>FLANKING | CTGGAAATAT<br>GACCTTTATA<br>ARM_________> | 1320 |
| TGAAATATGT<br>ACTTTATACA<br>__________C5 | AGCACACTAC<br>TCGTGTGATG<br>FLANKING | TTAAAAAAAA<br>AATTTTTTTT<br>ARM_________> | 1350 |
| TAAAATGTCC<br>ATTTTACAGG<br>__________C5 | AGAACTGGGA<br>TCTTGACCCT<br>FLANKING | AAAATTGATC<br>TTTTAACTAG<br>ARM_________> | 1380 |

FIG. 19B-3

```
TTGCCAGCTG   TAATTCATGG   TAGAAAAGAA        1410
AACGGTCGAC   ATTAAGTACC   ATCTTTTCTT
_________C5  FLANKING     ARM________>

GTGCTCAGGC   TACTTTTCAA   CAAAGGAGCA        1440
CACGAGTCCG   ATGAAAAGTT   GTTTCCTCGT
_________C5  FLANKING     ARM________>

GATGTAAACT   ACATCTTTGA   AAGAAATGGA        1470
CTACATTTGA   TGTAGAAACT   TTCTTTACCT
_________C5  FLANKING     ARM________>

AAATCATATA   CTGTTTTGGA   ATTGATTAAA        1500
TTTAGTATAT   GACAAAACCT   TAACTAATTT
_________C5  FLANKING     ARM________>

GAAAGTTACT   CTGAGACACA                     1520
CTTTCAATGA   GACTCTGTGT
__C5 FLANK   ING ARM___>
```

FIG. 19C-1

| | | | |
|---|---|---|---|
| FIG.19C-1 | | | |
| FIG.19C-2 | | | |
| FIG.19C-3 | | | |

| | | | |
|---|---|---|---|
| AAAGAGGTAG<br>TTTCTCCATC<br>_____C5 | CTGAAGTGGT<br>GACTTCACCA<br>FLANKING | ACTCTCAAAG<br>TGAGAGTTTC<br>ARM_____> | 1550 |
| GTACGTGACT<br>CATGCACTGA<br>_____ | AATTAGCTAT<br>TTAATCGATA<br>CLONING | AAAAAGGATC<br>TTTTTCCTAG<br>SITES_____> | 1580 |
| CGGTACCCTC<br>GCCATGGGAG<br>_____ | GAGTCTAGAA<br>AGCTAGGGCC<br>CLONING | TCGATCCCGG<br>CAAAAATACT<br>SITES_____> | 1610 |
| GTTTTTATGA<br>CTCAGATCTT<br>_____ | CTAGTTAATC<br>GATCAATTAG<br>CLONING | ACGGCCGCTT<br>TGCCGGCGAA<br>SITES___> | 1640 |
| ATAAAGATCT<br>TATTTCTAGA<br>_____C5 | AAAATGCATA<br>TTTTACGTAT<br>FLANKING | ATTTCTAAAT<br>TAAAGATTTA<br>ARM_____> | 1670 |
| AATGAAAAAA<br>TTACTTTTTT<br>_____C5 | AAGTACATCA<br>TTCATGTAGT<br>FLANKING | TGAGCAACGC<br>ACTCGTTGCG<br>ARM_____> | 1700 |
| GTTAGTATAT<br>CAATCATATA<br>_____C5 | TTTACAATGG<br>AAATGTTACC<br>FLANKING | AGATTAACGC<br>TCTAATTGCG<br>ARM_____> | 1730 |
| TCTATACCGT<br>AGATATGGCA<br>_____C5 | TCTATGTTTA<br>AGATACAAAT<br>FLANKING | TTGATTCAGA<br>AACTAAGTCT<br>ARM_____> | 1760 |
| TGATGTTTTA<br>ACTACAAAAT<br>_____C5 | GAAAAGAAAG<br>CTTTTCTTTC<br>FLANKING | TTATTGAATA<br>AATAACTTAT<br>ARM_____> | 1790 |
| TGAAAACTTT<br>ACTTTTGAAA<br>_____C5 | AATGAAGATG<br>TTACTTCTAC<br>FLANKING | AAGATGACGA<br>TTCTACTGCT<br>ARM_____> | 1820 |

FIG. 19C-2

```
CGATGATTAT   TGTTGTAAAT   CTGTTTTAGA        1850
GCTACTAATA   ACAACATTTA   GACAAAATCT
_________C5  FLANKING     ARM________>

TGAAGAAGAT   GACGCGCTAA   AGTATACTAT        1880
ACTTCTTCTA   CTGCGCGATT   TCATATGATA
_________C5  FLANKING     ARM________>

GGTTACAAAG   TATAAGTCTA   TACTACTAAT        1910
CCAATGTTTC   ATATTCAGAT   ATGATGATTA
_________C5  FLANKING     ARM________>

GGCGACTTGT   GCAAGAAGGT   ATAGTATAGT        1940
CCGCTGAACA   CGTTCTTCCA   TATCATATCA
_________C5  FLANKING     ARM________>

GAAAATGTTG   TTAGATTATG   ATTATGAAAA        1970
CTTTTACAAC   AATCTAATAC   TAATACTTTT
_________C5  FLANKING     ARM________>

ACCAAATAAA   TCAGATCCAT   ATCTAAAGGT        2000
TGGTTTATTT   AGTCTAGGTA   TAGATTTCCA
_________C5  FLANKING     ARM________>

ATCTCCTTTG   CACATAATTT   CATCTATTCC        2030
TAGAGGAAAC   GTGTATTAAA   GTAGATAAGG
_________C5  FLANKING     ARM________>

TAGTTTAGAA   TACCTGCAG                      2049
ATCAAATCTT   ATGGACGTC
_C5  FLANK   ING ARM__>
```

FIG. 24
% SPECIFIC LYSIS
0
10
20
30
40
50
60
70
IgG
anti-CD4
anti-CD8
WR
WR-env (IIIB)
WR-env (MN)
WR-gag/pol
WR-nef
TARGET

FIG. 26A-1

| |
|---|
| FIG. 26A-1 |
| FIG. 26A-2 |
| FIG. 26A-3 |

pHIV59/vCP1307

| | | | |
|---|---|---|---|
| AGAAAGTTAC<br>TCTTTCAATG<br>_________C5 | TCTGAGACAC<br>AGACTCTGTG<br>FLANKING | AAAAGAGGTA<br>TTTTCTCCAT<br>ARM_______> | 30 |
| GCTGAAGTGG<br>CGACTTCACC<br>__C5 FLANK | TACTCTCAAA<br>ATGAGAGTTT<br>ING ARM___> | GGTACGTGAC<br>CCATGCACTG | 60 |
| TAATTAGCTA<br>ATTAATCGAT | TAAAAAGGAT<br>ATTTTTCCTA | CCGGGTTAAT<br>GGCCCAATTA | 90 |
| TAATTAGTCA<br>ATTAATCAGT | TCAGGCAGGG<br>AGTCCGTCCC | CGAGAACGAG<br>GCTCTTGCTC | 120 |
| ACTATCTGCT<br>TGATAGACGA | CGTTAATTAA<br>GCAATTAATT | TTAGAGCTTC<br>AATCTCGAAG<br>______> | 150 |
| TTTATTCTAT<br>AAATAAGATA<br>_________H6 | ACTTAAAAAG<br>TGAATTTTTC<br>PROMOTER__ | TGAAAATAAA<br>ACTTTTATTT<br>___________> | 180 |
| TACAAAGGTT<br>ATGTTTCCAA<br>_________H6 | CTTGAGGGTT<br>GAACTCCCAA<br>PROMOTER__ | GTGTTAAATT<br>CACAATTTAA<br>___________> | 210 |
| GAAAGCGAGA<br>CTTTCGCTCT<br>_________H6 | AATAATCATA<br>TTATTAGTAT<br>PROMOTER__ | AATTATTTCA<br>TTAATAAAGT<br>___________> | 240 |
| TTATCGCGAT<br>AATAGCGCTA<br>_________H6 | ATGCGTTAAG<br>TACGCAATTC<br>PROMOTER__ | TTTGTATCGT<br>AAACATAGCA<br>___________> | 270 |
| ATATGAAAGA<br>TATACTTTCT<br>M K E<br>_><br>____HIV1 | GCAGAAGACA<br>CGTCTTCTGT<br>Q K T<br><br>(MN) GP120 | GTGGCAATGA<br>CACCGTTACT<br>V A M><br><br>GENE_______> | 300<br><br>09 |

FIG. 26A-2

```
GAGTGAAGGA   GAAATATCAG   CACTTGTGGA        330
CTCACTTCCT   CTTTATAGTC   GTGAACACCT
R  V  K  E    K  Y  Q      H  L  W>          19
______HIV1   (MN) GP120   GENE______>

GATGGGGGTG   GAGATGGGGC   ACCATGCTCC        360
CTACCCCCAC   CTCTACCCCG   TGGTACGAGG
R  W  G  W    R  W  G      T  M  L>          29
_____HIV1    (MN) GP120   GENE______>

TTGGGATGTT   GATGATCTGT   AGTGCTACAG        390
AACCCTACAA   CTACTAGACA   TCACGATGTC
L  G  M  L    M  I  C      S  A  T>          39
______HIV1   (MN) GP120   GENE______>

AAAAATTGTG   GGTCACAGTC   TATTATGGGG        420
TTTTTAACAC   CCAGTGTCAG   ATAATACCCC
E  K  L  W    V  T  V      Y  Y  G>          49
______HIV1   (MN) GP120   GENE______>

TACCTGTGTG   GAAAGAAGCA   ACCACCACTC        450
ATGGACACAC   CTTTCTTCGT   TGGTGGTGAG
V  P  V  W    K  E  A      T  T  T>          59
______HIV1   (MN) GP120   GENE______>

TATTTTGTGC   ATCAGATGCT   AAAGCATATG        480
ATAAAACACG   TAGTCTACGA   TTTCGTATAC
L  F  C  A    S  D  A      K  A  Y>          69
______HIV1   (MN) GP120   GENE______>

ATACAGAGGT   ACATAATGTT   TGGGCCACAC        510
TATGTCTCCA   TGTATTACAA   ACCCGGTGTG
D  T  E  V    H  N  V      W  A  T>          79
______HIV1   (MN) GP120   GENE______>

ATGCCTGTGT   ACCCACAGAC   CCCAACCCAC        540
TACGGACACA   TGGGTGTCTG   GGGTTGGGTG
H  A  C  V    P  T  D      P  N  P>          89
______HIV1   (MN) GP120   GENE______>

AAGAAGTAGA   ATTGGTAAAT   GTGACAGAAA        570
TTCTTCATCT   TAACCATTTA   CACTGTCTTT
Q  E  V  E    L  V  N      V  T  E>          99
______HIV1   (MN) GP120   GENE______>
```

FIG. 26A-3

```
ATTTTAACAT   GTGGAAAAAT   AACATGGTAG          600
TAAAATTGTA   CACCTTTTTA   TTGTACCATC
N  F  N  M    W  K  N      N  M  V>           109
_______HIV1  (MN) GP120   GENE_______>

AACAGATGC    ATGAGGATATA  ATCAGTTTAT          630
TTGTCTACG    TACTCCTATAT  TAGTCAAATA
E  Q  M  H    E  D  I      I  S  L>           119
_______HIV1  (MN) GP120   GENE_______>

GGGATCAAAG   CCTAAAGCCA   TGTGTAAAAT          660
CCCTAGTTTC   GGATTTCGGT   ACACATTTTA
W  D  Q  S    L  K  P      C  V  K>           129
_______HIV1  (MN) GP120   GENE_______>

TAACCCCACT   CTGTGTTACT   TTAAATTGCA          690
ATTGGGGTGA   GACACAATGA   AATTTAACGT
L  T  P  L    C  V  T      L  N  C>           139
_______HIV1  (MN) GP120   GENE_______>

CTGATTTGAG   GAATACTACT   AATACCAATA          720
GACTAAACTC   CTTATGATGA   TTATGGTTAT
T  D  L  R    N  T  T      N  T  N>           149
_______HIV1  (MN) GP120   GENE_______>
```

| FIG. 26B-1 |
|---|
| FIG. 26B-2 |
| FIG. 26B-3 |

FIG. 26B-1 pHIV59/vCP1307

| | | | |
|---|---|---|---|
| ATAGTACTGC | TAATAACAAT | AGTAATAGCG | 750 |
| TATCATGACG | ATTATTGTTA | TCATTATCGC | |
| N S T A | N N N | S N S> | 159 |
| _______HIV1 | (MN) GP120 | GENE_______> | |
| AGGGAACAAT | AAAGGGAGGA | GAAATGAAAA | 780 |
| TCCCTTGTTA | TTTCCCTCCT | CTTTACTTTT | |
| E G T I | K G G | E M K> | 169 |
| _______HIV1 | (MN) GP120 | GENE_______> | |
| ACTGCTCTTT | CAATATCACC | ACAAGCATAA | 810 |
| TGACGAGAAA | GTTATAGTGG | TGTTCGTATT | |
| N C S F | N I T | T S I> | 179 |
| _______HIV1 | (MN) GP120 | GENE_______> | |
| GAGATAAGAT | GCAGAAAGAA | TATGCACTTC | 840 |
| CTCTATTCTA | CGTCTTTCTT | ATACGTGAAG | |
| R D K M | Q K E | Y A L> | 189 |
| _______HIV1 | (MN) GP120 | GENE_______> | |
| TTTATAAACT | TGATATAGTA | TCAATAAATA | 870 |
| AAATATTTGA | ACTATATCAT | AGTTATTTAT | |
| L Y K L | D I V | S I N> | 199 |
| _______HIV1 | (MN) GP120 | GENE_______> | |
| ATGATAGTAC | CAGCTATAGG | TTGATAAGTT | 900 |
| TACTATCATG | GTCGATATCC | AACTATTCAA | |
| N D S T | S Y R | L I S> | 209 |
| _______HIV1 | (MN) GP120 | GENE_______> | |
| GTAATACCTC | AGTCATTACA | CAAGCTTGTC | 930 |
| CATTATGGAG | TCAGTAATGT | GTTCGAACAG | |
| C N T S | V I T | Q A C> | 219 |
| _______HIV1 | (MN) GP120 | GENE_______> | |
| CAAAGATATC | CTTTGAGCCA | ATTCCCATAC | 960 |
| GTTTCTATAG | GAAACTCGGT | TAAGGGTATG | |
| P K I S | F E P | I P I> | 229 |
| _______HIV1 | (MN) GP120 | GENE_______> | |

FIG. 26B-2

| | | | |
|---|---|---|---|
| ACTATTGTGC | CCCGGCTGGT | TTTGCGATTC | 990 |
| TGATAACACG | GGGCCGACCA | AAACGCTAAG | |
| H Y C A | P A G | F A I> | 239 |
| ______HIV1 | (MN) GP120 | GENE______> | |
| TAAAGTGTAA | CGATAAAAAG | TTCAGTGGAA | 1020 |
| ATTTCACATT | GCTATTTTTC | AAGTCACCTT | |
| L K C N | D K K | F S G> | 249 |
| ______HIV1 | (MN) GP120 | GENE______> | |
| AAGGATCATG | TAAAAATGTC | AGCACAGTAC | 1050 |
| TTCCTAGTAC | ATTTTTACAG | TCGTGTCATG | |
| K G S C | K N V | S T V> | 259 |
| ______HIV1 | (MN) GP120 | GENE______> | |
| AATGTACACA | TGGAATTAGG | CCAGTAGTAT | 1080 |
| TTACATGTGT | ACCTTAATCC | GGTCATCATA | |
| Q C T H | G I R | P V V> | 269 |
| ______HIV1 | (MN) GP120 | GENE______> | |
| CAACTCAACT | GCTGTTAAAT | GGCAGTCTAG | 1110 |
| GTTGAGTTGA | CGACAATTTA | CCGTCAGATC | |
| S T Q L | L L N | G S L> | 279 |
| ______HIV1 | (MN) GP120 | GENE______> | |
| CAGAAGAAGA | GGTAGTAATT | AGATCTGAGA | 1140 |
| GTCTTCTTCT | CCATCATTAA | TCTAGACTCT | |
| A E E E | V V I | R S E> | 289 |
| ______HIV1 | (MN) GP120 | GENE______> | |
| ATTTCAATGA | TAATGCTAAA | ACCATCATAG | 1170 |
| TAAAGTTACT | ATTACGATTT | TGGTAGTATC | |
| N F N D | N A K | T I I> | 299 |
| ______HIV1 | (MN) GP120 | GENE______> | |
| TACATCTGAA | TGAATCTGTA | CAAATTAATT | 1200 |
| ATGTAGACTT | ACTTAGACAT | GTTTAATTAA | |
| V H L N | E S V | Q I N> | 309 |
| ______HIV1 | (MN) GP120 | GENE______> | |
| GTACAAGACC | CAACTACGAG | CTCGACAAAT | 1230 |
| CATGTTCTGG | GTTGATGCTC | GAGCTGTTTA | |
| C T R P | N Y E | L D K | 319 |
| ______GP120 | GENE__><KAT | EPITOPE___> | |

FIG. 26B-3

```
GGGCCCATAT   AGGACCAGGG   AGAGAATTGG        1260
CCCGGGTATA   TCCTGGTCCC   TCTCTTAACC
W  A  H  I    G  P  G      R  E  L           329
____><___GP120 GENE____   __><______

ATAAGTGGGC   GAATATAATA   GGAACTATAA        1290
TATTCACCCG   CTTATATTAT   CCTTGATATT
D  K  W  A    N  I  I      G  T  I>          339
KAT EPITOP   ><_____GP    120 GENE__>

GACAAGCACA   TTGTAACATT   AGTAGAGCAA        1320
CTGTTCGTGT   AACATTGTAA   TCATCTCGTT
R  Q  A  H    C  N  I      S  R  A>          349
______HIV1   (MN) GP120   GENE______>

AATGGAATGA   CACTTTAAGA   CAGATAGTTA        1350
TTACCTTACT   GTGAAATTCT   GTCTATCAAT
K  W  N  D    T  L  R      Q  I  V>          359
______HIV1   (MN) GP120   GENE______>

GCAAATTAAA   AGAACAATTT   AAGAATAAAA        1380
CGTTTAATTT   TCTTGTTAAA   TTCTTATTTT
S  K  L  K    E  Q  F      K  N  K>          369
______HIV1   (MN) GP120   GENE______>

CAATAGTCTT   TAATCAATCC   TCAGGAGGGG        1410
GTTATCAGAA   ATTAGTTAGG   AGTCCTCCCC
T  I  V  F    N  Q  S      S  G  G>          379
______HIV1   (MN) GP120   GENE______>

ACCCAGAAAT   TGTAATGCAC   AGTTTTAATT        1440
TGGGTCTTTA   ACATTACGTG   TCAAAATTAA
D  P  E  I    V  M  H      S  F  N>          389
______HIV1   (MN) GP120   GENE______>
```

FIG. 26C-1
FIG. 26C-2
FIG. 26C-3

FIG. 26C-1 pHIV59/vCP1307

```
GTGGAGGGGA   ATTCTTCTAC   TGTAATTCAT        1470
CACCTCCCCT   TAAGAAGATG   ACATTAAGTA
C  G  G  E    F  F  Y      C  N  S>          399
_______HIV1  (MN) GP120   GENE_______>

CACCACTGTT   TAATAGTACT   TGGAATGGTA        1500
GTGGTGACAA   ATTATCATGA   ACCTTACCAT
S  P  L  F    N  S  T      W  N  G>          409
_______HIV1  (MN) GP120   GENE_______>

ATAATACTTG   GAATAATACT   ACAGGGTCAA        1530
TATTATGAAC   CTTATTATGA   TGTCCCAGTT
N  N  T  W    N  N  T      T  G  S>          419
_______HIV1  (MN) GP120   GENE_______>

ATAACAATAT   CACACTTCAA   TGCAAAATAA        1560
TATTGTTATA   GTGTGAAGTT   ACGTTTTATT
N  N  N  I    T  L  Q      C  K  I>          429
_______HIV1  (MN) GP120   GENE_______>

AACAAATTAT   AAACATGTGG   CAGGAAGTAG        1590
TTGTTTAATA   TTTGTACACC   GTCCTTCATC
K  Q  I  I    N  M  W      Q  E  V>          439
_______HIV1  (MN) GP120   GENE_______>

GAAAAGCAAT   ATATGCCCCT   CCCATTGAAG        1620
CTTTTCGTTA   TATACGGGGA   GGGTAACTTC
G  K  A  I    Y  A  P      P  I  E>          449
_______HIV1  (MN) GP120   GENE_______>

GACAAATTAG   ATGTTCATCA   AATATTACAG        1650
CTGTTTAATC   TACAAGTAGT   TTATAATGTC
G  Q  I  R    C  S  S      N  I  T>          459
_______HIV1  (MN) GP120   GENE_______>

GGCTACTATT   AACAAGAGAT   GGTGGTAAGG        1680
CCGATGATAA   TTGTTCTCTA   CCACCATTCC
G  L  L  L    T  R  D      G  G  K>          469
_______HIV1  (MN) GP120   GENE_______>

ACACGGACAC   GAACGACACC   GAGATCTTCA        1710
TGTGCCTGTG   CTTGCTGTGG   CTCTAGAAGT
D  T  D  T    N  D  T      E  I  F>          479
_______HIV1  (MN) GP120   GENE_______>
```

FIG. 26C-2

```
GACCTGGAGG   AGGAGATATG   AGGGACAATT      1740
CTGGACCTCC   TCCTCTATAC   TCCCTGTTAA
R  P  G  G    G  D  M      R  D  N>        489
_______HIV1  (MN) GP120   GENE_______>

GGAGAAGTGA   ATTATATAAA   TATAAAGTAG      1770
CCTCTTCACT   TAATATATTT   ATATTTCATC
W  R  S  E    L  Y  K      Y  K  V>        499
_______HIV1  (MN) GP120   GENE_______>

TAACAATTGA   ACCATTAGGA   GTAGCACCCA      1800
ATTGTTAACT   TGGTAATCCT   CATCGTGGGT
V  T  I  E    P  L  G      V  A  P>        509
_______HIV1  (MN) GP120   GENE_______>

CCAAGGCAAA   GAGAAGAGTG   GTGCAGAGAG      1830
GGTTCCGTTT   CTCTTCTCAC   CACGTCTCTC
T  K  A  K    R  R  V      V  Q  R>        519
_______HIV1  (MN) GP120   GENE_______>

AAAAAAGATT   ATTCATAATG   ATAGTAGGAG      1860
TTTTTTCTAA   TAAGTATTAC   TATCATCCTC
E  K  R  L    F  I  M      I  V  G>        529
__________
          __ TRANSMEMBR   ANE REGION>

GCTTGGTAGG   TTTAAGAATA   GTTTTTGCTG      1890
CGAACCATCC   AAATTCTTAT   CAAAAACGAC
G  L  V  G    L  R  I      V  F  A>        539
_HIV1 TRAN   SMEMBRANE    REGION____>

TACTCTCTGT   AGTGAATAGA   GTTAGGCAGG      1920
ATGAGAGACA   TCACTTATCT   CAATCCGTCC
V  L  S  V    V  N  R      V  R  Q>        549
_HIV1 TRAN   SMEMBRANE    REGION____>

GATAATTTTT   ATTCTAGAAT   CGATCCCGGG      1950
CTATTAAAAA   TAAGATCTTA   GCTAGGGCCC
G  *>                                      550
______>

TTTTTATGAC   TAGTTAATCA   CGGCCGCTTA      1980
AAAAATACTG   ATCAATTAGT   GCCGGCGAAT
```

FIG. 26C-3

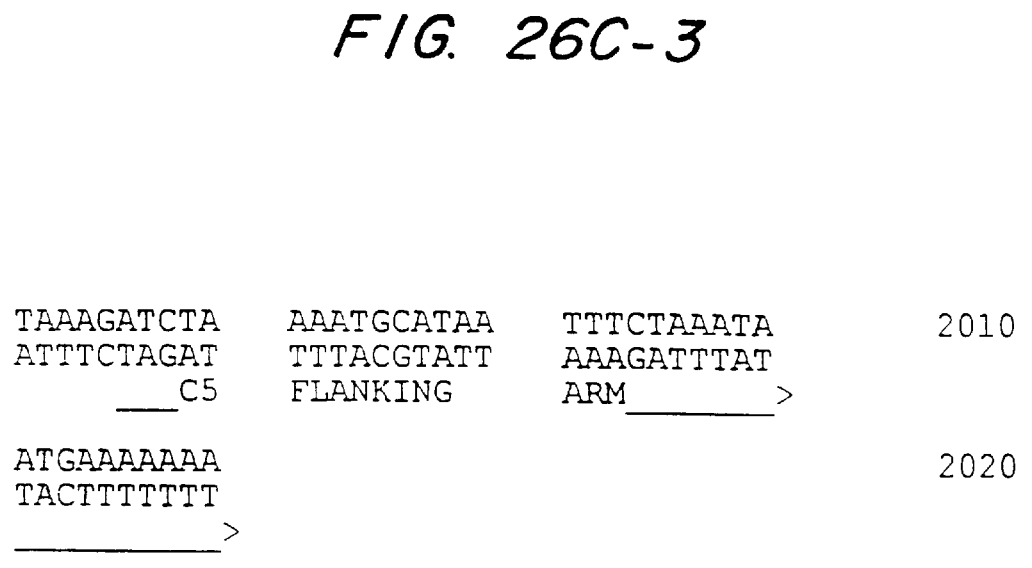

```
TAAAGATCTA   AAATGCATAA   TTTCTAAATA        2010
ATTTCTAGAT   TTTACGTATT   AAAGATTTAT
    ___C5    FLANKING     ARM________>

ATGAAAAAAA                                  2020
TACTTTTTTT
__________>
```

FIG.27a
FIG.27b
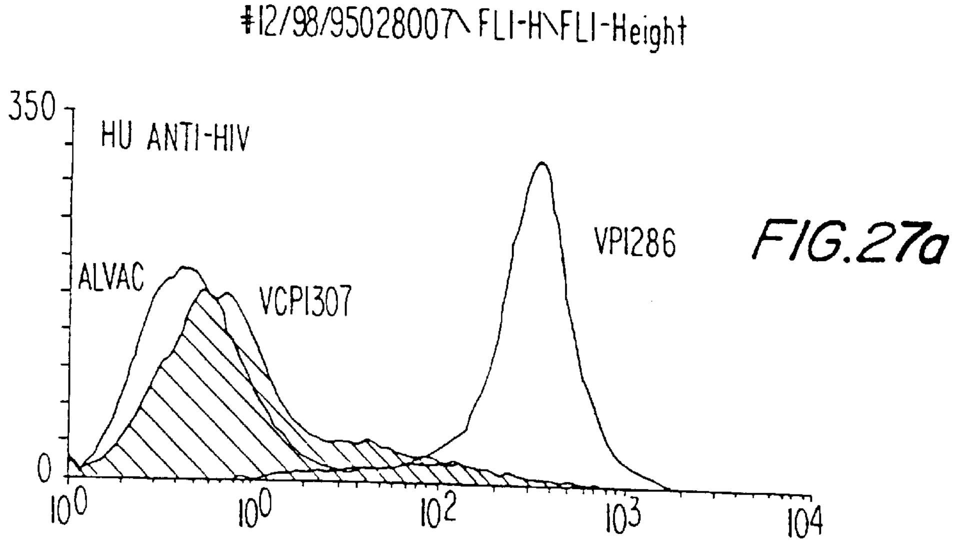
FIG.27a
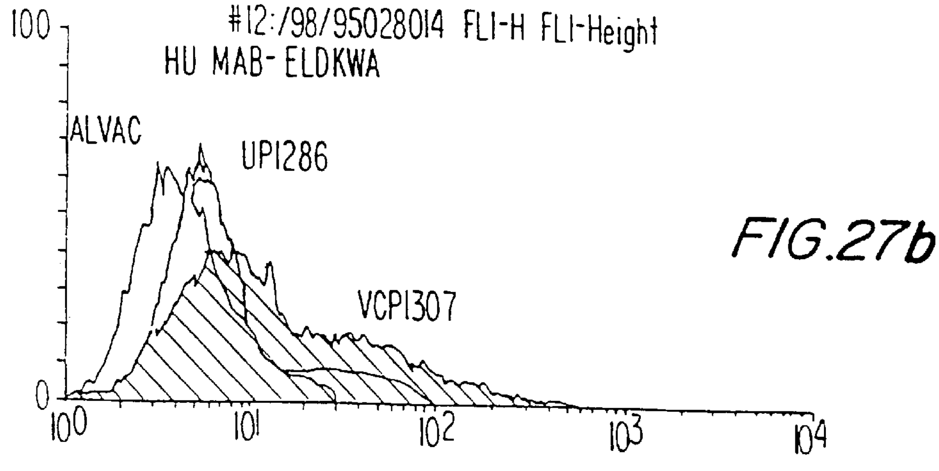
FIG.27b

FIG.28A-1
FIG.28A-2
FIG.28A-3

FIG. 28A-1 pHIV60/vP1313

```
TACTTTGTAA   TATAATGATA   TATATTTTCA     30
ATGAAACATT   ATATTACTAT   ATATAAAAGT
________14L  FLANKING     ARM________>

CTTTATCTCA   TTTGAGAATA   AAAAGATCAC     60
GAAATAGAGT   AAACTCTTAT   TTTTCTAGTG
________14L  FLANKING     ARM_>

AAAAATTAAC   TAATCAGGAT   CCGGGTTAAT     90
TTTTTAATTG   ATTAGTCCTA   GGCCCAATTA

TAATTAGTCA   TCAGGCAGGG   CGAGAACGAG    120
ATTAATCAGT   AGTCCGTCCC   GCTCTTGCTC

ACTATCTGCT   CGTTAATTAA   TTAGAGCTTC    150
TGATAGACGA   GCAATTAATT   AATCTCGAAG
                                ______>

TTTATTCTAT   ACTTAAAAAG   TGAAAATAAA    180
AAATAAGATA   TGAATTTTTC   ACTTTTATTT
_________H6  PROMOTER__   ___________>

TACAAAGGTT   CTTGAGGGTT   GTGTTAAATT    210
ATGTTTCCAA   GAACTCCCAA   CACAATTTAA
_________H6  PROMOTER__   ___________>

GAAAGCGAGA   AATAATCATA   AATTATTTCA    240
CTTTCGCTCT   TTATTAGTAT   TTAATAAAGT
_________H6  PROMOTER__   ___________>

TTATCGCGAT   ATGCGTTAAG   TTTGTATCGT    270
AATAGCGCTA   TACGCAATTC   AAACATAGCA
_________H6  PROMOTER__   ___________>

ATATGAAAGA   GCAGAAGACA   GTGGCAATGA    300
TATACTTTCT   CGTCTTCTGT   CACCGTTACT
   M  K  E     Q  K  T     V  A  M>
_>
  ____HIV1   (MN) GP120   GENE______>
```

FIG. 28A-2

```
GAGTGAAGGA   GAAATATCAG   CACTTGTGGA        330
CTCACTTCCT   CTTTATAGTC   GTGAACACCT
R  V  K  E    K  Y  Q      H  L  W>
_______HIV1  (MN) GP120   GENE_______>

GATGGGGGTG   GAGATGGGGC   ACCATGCTCC        360
CTACCCCCAC   CTCTACCCCG   TGGTACGAGG
R  W  G  W    R  W  G      T  M  L>
_______HIV1  (MN) GP120   GENE_______>

TTGGGATGTT   GATGATCTGT   AGTGCTACAG        390
AACCCTACAA   CTACTAGACA   TCACGATGTC
L  G  M  L    M  I  C      S  A  T>
_______HIV1  (MN) GP120   GENE_______>

AAAAATTGTG   GGTCACAGTC   TATTATGGGG        420
TTTTTAACAC   CCAGTGTCAG   ATAATACCCC
E  K  L  W    V  T  V      Y  Y  G>
_______HIV1  (MN) GP120   GENE_______>

TACCTGTGTG   GAAAGAAGCA   ACCACCACTC        450
ATGGACACAC   CTTTCTTCGT   TGGTGGTGAG
V  P  V  W    K  E  A      T  T  T>
_______HIV1  (MN) GP120   GENE_______>

TATTTTGTGC   ATCAGATGCT   AAAGCATATG        480
ATAAAACACG   TAGTCTACGA   TTTCGTATAC
L  F  C  A    S  D  A      K  A  Y>
_______HIV1  (MN) GP120   GENE_______>

ATACAGAGGT   ACATAATGTT   TGGGCCACAC        510
TATGTCTCCA   TGTATTACAA   ACCCGGTGTG
D  T  E  V    H  N  V      W  A  T>
_______HIV1  (MN) GP120   GENE_______>

ATGCCTGTGT   ACCCACAGAC   CCCAACCCAC        540
TACGGACACA   TGGGTGTCTG   GGGTTGGGTG
H  A  C  V    P  T  D      P  N  P>
_______HIV1  (MN) GP120   GENE_______>

AAGAAGTAGA   ATTGGTAAAT   GTGACAGAAA        570
TTCTTCATCT   TAACCATTTA   CACTGTCTTT
Q  E  V  E    L  V  N      V  T  E>
_______HIV1  (MN) GP120   GENE_______>
```

FIG. 28A-3

```
ATTTTAACAT   GTGGAAAAAT   AACATGGTAG      600
TAAAATTGTA   CACCTTTTTA   TTGTACCATC
N  F  N  M    W  K  N      N  M  V>
_______HIV1  (MN) GP120   GENE_______>

AACAGATGCA   TGAGGATATA   ATCAGTTTAT      630
TTGTCTACGT   ACTCCTATAT   TAGTCAAATA
E  Q  M  H    E  D  I      I  S  L>
_______HIV1  (MN) GP120   GENE_______>

GGGATCAAAG   CCTAAAGCCA   TGTGTAAAAT      660
CCCTAGTTTC   GGATTTCGGT   ACACATTTTA
W  D  Q  S    L  K  P      C  V  K>
_______HIV1  (MN) GP120   GENE_______>

TAACCCCACT   CTGTGTTACT   TTAAATTGCA      690
ATTGGGGTGA   GACACAATGA   AATTTAACGT
L  T  P  L    C  V  T      L  N  C>
_______HIV1  (MN) GP120   GENE_______>

CTGATTTGAG   GAATACTACT   AATACCAATA      720
GACTAAACTC   CTTATGATGA   TTATGGTTAT
T  D  L  R    N  T  T      N  T  N>
_______HIV1  (MN) GP120   GENE_______>
```

FIG. 28B-1

| FIG.28B-1 |
|---|
| FIG.28B-2 |
| FIG.28B-3 |

```
ATAGTACTGC   TAATAACAAT   AGTAATAGCG        750
TATCATGACG   ATTATTGTTA   TCATTATCGC
N  S  T  A    N  N  N      S  N  S>
_______HIV1  (MN) GP120   GENE_______>

AGGGAACAAT   AAAGGGAGGA   GAAATGAAAA        780
TCCCTTGTTA   TTTCCCTCCT   CTTTACTTTT
E  G  T  I    K  G  G      E  M  K>
_______HIV1  (MN) GP120   GENE_______>

ACTGCTCTTT   CAATATCACC   ACAAGCATAA        810
TGACGAGAAA   GTTATAGTGG   TGTTCGTATT
N  C  S  F    N  I  T      T  S  I>
_______HIV1  (MN) GP120   GENE_______>

GAGATAAGAT   GCAGAAAGAA   TATGCACTTC        840
CTCTATTCTA   CGTCTTTCTT   ATACGTGAAG
R  D  K  M    Q  K  E      Y  A  L>
_______HIV1  (MN) GP120   GENE_______>

TTTATAAACT   TGATATAGTA   TCAATAAATA        870
AAATATTTGA   ACTATATCAT   AGTTATTTAT
L  Y  K  L    D  I  V      S  I  N>
_______HIV1  (MN) GP120   GENE_______>

ATGATAGTAC   CAGCTATAGG   TTGATAAGTT        900
TACTATCATG   GTCGATATCC   AACTATTCAA
N  D  S  T    S  Y  R      L  I  S>
_______HIV1  (MN) GP120   GENE_______>

GTAATACCTC   AGTCATTACA   CAAGCTTGTC        930
CATTATGGAG   TCAGTAATGT   GTTCGAACAG
C  N  T  S    V  I  T      Q  A  C>
_______HIV1  (MN) GP120   GENE_______>

CAAAGATATC   CTTTGAGCCA   ATTCCCATAC        960
GTTTCTATAG   GAAACTCGGT   TAAGGGTATG
P  K  I  S    F  E  P      I  P  I>
_______HIV1  (MN) GP120   GENE_______>

ACTATTGTGC   CCCGGCTGGT   TTTGCGATTC        990
TGATAACACG   GGGCCGACCA   AAACGCTAAG
H  Y  C  A    P  A  G      F  A  I>
_______HIV1  (MN) GP120   GENE_______>
```

FIG. 28B-2

TAAAGTGTAA CGATAAAAAG TTCAGTGGAA 1020
ATTTCACATT GCTATTTTTC AAGTCACCTT
L K C N D K K F S G>
_______HIV1 (MN) GP120 GENE_______>

AAGGATCATG TAAAAATGTC AGCACAGTAC 1050
TTCCTAGTAC ATTTTTACAG TCGTGTCATG
K G S C K N V S T V>
_______HIV1 (MN) GP120 GENE_______>

AATGTACACA TGGAATTAGG CCAGTAGTAT 1080
TTACATGTGT ACCTTAATCC GGTCATCATA
Q C T H G I R P V V>
_______HIV1 (MN) GP120 GENE_______>

CAACTCAACT GCTGTTAAAT GGCAGTCTAG 1110
GTTGAGTTGA CGACAATTTA CCGTCAGATC
S T Q L L L N G S L>
_______HIV1 (MN) GP120 GENE_______>

CAGAAGAAGA GGTAGTAATT AGATCTGAGA 1140
GTCTTCTTCT CCATCATTAA TCTAGACTCT
A E E E V V I R S E>
_______HIV1 (MN) GP120 GENE_______>

ATTTCAATGA TAATGCTAAA ACCATCATAG 1170
TAAAGTTACT ATTACGATTT TGGTAGTATC
N F N D N A K T I I>
_______HIV1 (MN) GP120 GENE_______>

TACATCTGAA TGAATCTGTA CAAATTAATT 1200
ATGTAGACTT ACTTAGACAT GTTTAATTAA
V H L N E S V Q I N>
_______HIV1 (MN) GP120 GENE_______>

GTACAAGACC CAACTACGAG CTCGACAAAT 1230
CATGTTCTGG GTTGATGCTC GAGCTGTTTA
C T R P N Y E L D K>
______GP120 GENE___><KAT EPITOPE___>

GGGCCCATAT AGGACCAGGG AGAGAATTGG 1260
CCCGGGTATA TCCTGGTCCC TCTCTTAACC
W A H I G P G R E L>
_____><___GP 120 GENE___ ___><_______

FIG. 28B-3

```
ATAAGTGGGC   GAATATAATA   GGAACTATAA        1290
TATTCACCCG   CTTATATTAT   CCTTGATATT
D  K  W  A    N  I  I      G  T  I>
KAT EPITOP   ><_____GP    120 GENE__>

GACAAGCACA   TTGTAACATT   AGTAGAGCAA        1320
CTGTTCGTGT   AACATTGTAA   TCATCTCGTT
R  Q  A  H    C  N  I      S  R  A>
_______HIV1  (MN) GP120   GENE_______>

AATGGAATGA   CACTTTAAGA   CAGATAGTTA        1350
TTACCTTACT   GTGAAATTCT   GTCTATCAAT
K  W  N  D    T  L  R      Q  I  V>
_______HIV1  (MN) GP120   GENE_______>

GCAAATTAAA   AGAACAATTT   AAGAATAAAA        1380
CGTTTAATTT   TCTTGTTAAA   TTCTTATTTT
S  K  L  K    E  Q  F      K  N  K>
_______HIV1  (MN) GP120   GENE_______>

CAATAGTCTT   TAATCAATCC   TCAGGAGGGG        1410
GTTATCAGAA   ATTAGTTAGG   AGTCCTCCCC
T  I  V  F    N  Q  S      S  G  G>
_______HIV1  (MN) GP120   GENE_______>

ACCCAGAAAT   TGTAATGCAC   AGTTTTAATT        1440
TGGGTCTTTA   ACATTACGTG   TCAAAATTAA
D  P  E  I    V  M  H      S  F  N>
_______HIV1  (MN) GP120   GENE_______>
```

FIG. 28C-1

| | | | |
|---|---|---|---|
| GTGGAGGGGA<br>CACCTCCCCT<br>C  G  G  E<br>_____HIV1 | ATTCTTCTAC<br>TAAGAAGATG<br>F  F  Y<br>(MN) GP120 | TGTAATTCAT<br>ACATTAAGTA<br>C  N  S><br>GENE_____> | 1470 |
| CACCACTGTT<br>GTGGTGACAA<br>S  P  L  F<br>_____HIV1 | TAATAGTACT<br>ATTATCATGA<br>N  S  T<br>(MN) GP120 | TGGAATGGTA<br>ACCTTACCAT<br>W  N  G><br>GENE_____> | 1500 |
| ATAATACTTG<br>TATTATGAAC<br>N  N  T  W<br>_____HIV1 | GAATAATACT<br>CTTATTATGA<br>N  N  T<br>(MN) GP120 | ACAGGGTCAA<br>TGTCCCAGTT<br>T  G  S><br>GENE_____> | 1530 |
| ATAACAATAT<br>TATTGTTATA<br>N  N  N  I<br>_____HIV1 | CACACTTCAA<br>GTGTGAAGTT<br>T  L  Q<br>(MN) GP120 | TGCAAAATAA<br>ACGTTTTATT<br>C  K  I><br>GENE_____> | 1560 |
| AACAAATTAT<br>TTGTTTAATA<br>K  Q  I  I<br>_____HIV1 | AAACATGTGG<br>TTTGTACACC<br>N  M  W<br>(MN) GP120 | CAGGAAGTAG<br>GTCCTTCATC<br>Q  E  V><br>GENE_____> | 1590 |
| GAAAAGCAAT<br>CTTTTCGTTA<br>G  K  A  I<br>_____HIV1 | ATATGCCCCT<br>TATACGGGGA<br>Y  A  P<br>(MN) GP120 | CCCATTGAAG<br>GGGTAACTTC<br>P  I  E><br>GENE_____> | 1620 |
| GACAAATTAG<br>CTGTTTAATC<br>G  Q  I  R<br>_____HIV1 | ATGTTCATCA<br>TACAAGTAGT<br>C  S  S<br>(MN) GP120 | AATATTACAG<br>TTATAATGTC<br>N  I  T><br>GENE_____> | 1650 |
| GGCTACTATT<br>CCGATGATAA<br>G  L  L  L<br>_____HIV1 | AACAAGAGAT<br>TTGTTCTCTA<br>T  R  D<br>(MN) GP120 | GGTGGTAAGG<br>CCACCATTCC<br>G  G  K><br>GENE_____> | 1680 |
| ACACGGACAC<br>TGTGCCTGTG<br>D  T  D  T<br>_____HIV1 | GAACGACACC<br>CTTGCTGTGG<br>N  D  T<br>(MN) GP120 | GAGATCTTCA<br>CTCTAGAAGT<br>E  I  F><br>GENE_____> | 1710 |

FIG. 28C-2

```
GACCTGGAGG   AGGAGATATG   AGGGACAATT        1740
CTGGACCTCC   TCCTCTATAC   TCCCTGTTAA
R  P  G  G    G  D  M      R  D  N>
______HIV1   (MN) GP120   GENE______>

GGAGAAGTGA   ATTATATAAA   TATAAAGTAG        1770
CCTCTTCACT   TAATATATTT   ATATTTCATC
W  R  S  E    L  Y  K      Y  K  V>
______HIV1   (MN) GP120   GENE______>

TAACAATTGA   ACCATTAGGA   GTAGCACCCA        1800
ATTGTTAACT   TGGTAATCCT   CATCGTGGGT
V  T  I  E    P  L  G      V  A  P>
______HIV1   (MN) GP120   GENE______>

CCAAGGCAAA   GAGAAGAGTG   GTGCAGAGAG        1830
GGTTCCGTTT   CTCTTCTCAC   CACGTCTCTC
T  K  A  K    R  R  V      V  Q  R>
______HIV1   (MN) GP120   GENE______>

AAAAAAGATT   ATTCATAATG   ATAGTAGGAG        1860
TTTTTTCTAA   TAAGTATTAC   TATCATCCTC
E  K  R  L    F  I  M      I  V  G>
__________
        __   ____TRANS    MEMBRANE__>

GCTTGGTAGG   TTTAAGAATA   GTTTTTGCTG        1890
CGAACCATCC   AAATTCTTAT   CAAAAACGAC
G  L  V  G    L  R  I      V  F  A>
______HIV1   TRANSMEMBR   ANE_______>

TACTCTCTGT   AGTGAATAGA   GTTAGGCAGG        1920
ATGAGAGACA   TCACTTATCT   CAATCCGTCC
V  L  S  V    V  N  R      V  R  Q>
______HIV1   TRANSMEMBR   ANE_______>

GATAATTTTT   ATTCTAGAAT   CGATCCCGGG        1950
CTATTAAAAA   TAAGATCTTA   GCTAGGGCCC
G  *>
____>

AGATCTTAGC   TAACTGATTT   TTCTGGGAAA        1980
TCTAGAATCG   ATTGACTAAA   AAGACCCTTT
                                ___>
```

FIG. 28C-3

```
AAAATTATTT   AACTTTTCAT   TAATAGGGAT        2010
TTTTAATAAA   TTGAAAAGTA   ATTATCCCTA
_______14L   FLANKING     ARM________>

TTGACGTATG   TAGCGTAC                       2028
AACTGCATAC   ATCGCATG
_14L FLANK   ING ARM_>
```

FIG.29a
FIG.29b
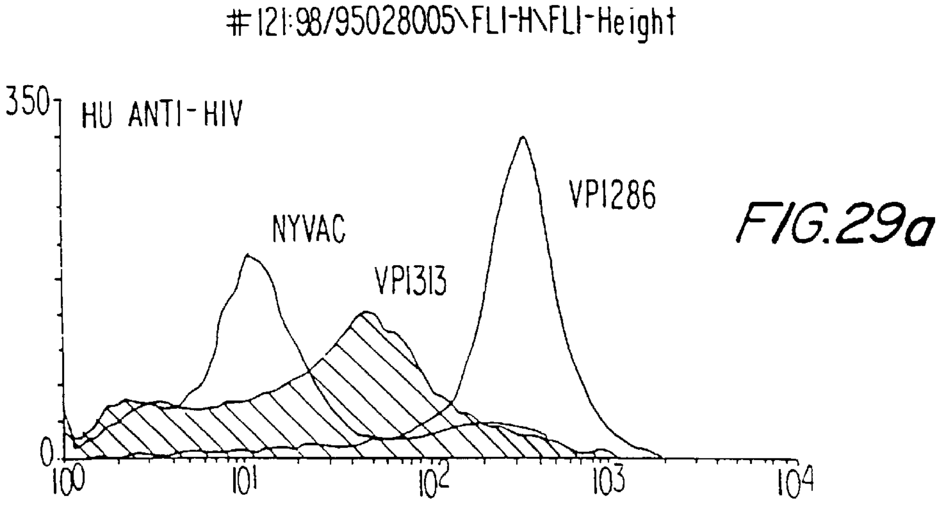
FIG.29a
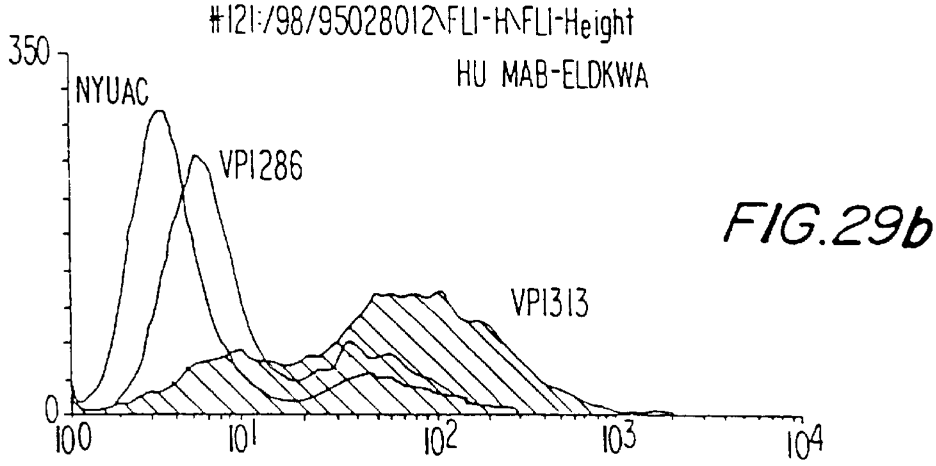
FIG.29b

| FIG. 30A-1 |
|---|
| FIG. 30A-2 |
| FIG. 30A-3 |

FIG. 30A-1 pHIV61/vCP1319

```
ATAAACCATT   AGATAAAGTT   GATCTCAAGC     30
TATTTGGTAA   TCTATTTCAA   CTAGAGTTCG
_______A24R  FLANKING     ARM________>

GCTCTTTTCT   GGTGTAATAA   AAATTAATTA     60
CGAGAAAAGA   CCACATTATT   TTTAATTAAT
__________   _________>

ATTACTCGAG   GGTACCGGAT   CCGGGTTAAT     90
TAATGAGCTC   CCATGGCCTA   GGCCCAATTA

TAATTAGTCA   TCAGGCAGGG   CGAGAACGAG    120
ATTAATCAGT   AGTCCGTCCC   GCTCTTGCTC

ACTATCTGCT   CGTTAATTAA   TTAGAGCTTC    150
TGATAGACGA   GCAATTAATT   AATCTCGAAG
                                ______>

TTTATTCTAT   ACTTAAAAAG   TGAAAATAAA    180
AAATAAGATA   TGAATTTTTC   ACTTTTATTT
________H6   PROMOTER__   __________>

TACAAAGGTT   CTTGAGGGTT   GTGTTAAATT    210
ATGTTTCCAA   GAACTCCCAA   CACAATTTAA
________H6   PROMOTER__   __________>

GAAAGCGAGA   AATAATCATA   AATTATTTCA    240
CTTTCGCTCT   TTATTAGTAT   TTAATAAAGT
________H6   PROMOTER__   __________>

TTATCGCGAT   ATGCGTTAAG   TTTGTATCGT    270
AATAGCGCTA   TACGCAATTC   AAACATAGCA
________H6   PROMOTER__   __________>

ATATGAAAGA   GCAGAAGACA   GTGGCAATGA    300
TATACTTTCT   CGTCTTCTGT   CACCGTTACT
    M  K  E    Q  K  T     V  A  M>    09
__>
  _____HIV1  (MN) GP120   GENE______
```

FIG. 30A-2

| | | | |
|---|---|---|---|
| GAGTGAAGGA | GAAATATCAG | CACTTGTGGA | 330 |
| CTCACTTCCT | CTTTATAGTC | GTGAACACCT | |
| R V K E | K Y Q | H L W> | 19 |
| ______HIV1 | (MN) GP120 | GENE______> | |
| GATGGGGGTG | GAGATGGGGC | ACCATGCTCC | 360 |
| CTACCCCCAC | CTCTACCCCG | TGGTACGAGG | |
| R W G W | R W G | T M L> | 29 |
| ______HIV1 | (MN) GP120 | GENE______> | |
| TTGGGATGTT | GATGATCTGT | AGTGCTACAG | 390 |
| AACCCTACAA | CTACTAGACA | TCACGATGTC | |
| L G M L | M I C | S A T> | 39 |
| ______HIV1 | (MN) GP120 | GENE______> | |
| AAAAATTGTG | GGTCACAGTC | TATTATGGGG | 420 |
| TTTTTAACAC | CCAGTGTCAG | ATAATACCCC | |
| E K L W | V T V | Y Y G> | 49 |
| ______HIV1 | (MN) GP120 | GENE______> | |
| TACCTGTGTG | GAAAGAAGCA | ACCACCACTC | 450 |
| ATGGACACAC | CTTTCTTCGT | TGGTGGTGAG | |
| V P V W | K E A | T T T> | 59 |
| ______HIV1 | (MN) GP120 | GENE______> | |
| TATTTTGTGC | ATCAGATGCT | AAAGCATATG | 480 |
| ATAAAACACG | TAGTCTACGA | TTTCGTATAC | |
| L F C A | S D A | K A Y> | 69 |
| ______HIV1 | (MN) GP120 | GENE______> | |
| ATACAGAGGT | ACATAATGTT | TGGGCCACAC | 510 |
| TATGTCTCCA | TGTATTACAA | ACCCGGTGTG | |
| D T E V | H N V | W A T> | 79 |
| ______HIV1 | (MN) GP120 | GENE______> | |
| ATGCCTGTGT | ACCCACAGAC | CCCAACCCAC | 540 |
| TACGGACACA | TGGGTGTCTG | GGGTTGGGTG | |
| H A C V | P T D | P N P> | 89 |
| ______HIV1 | (MN) GP120 | GENE______> | |
| AAGAAGTAGA | ATTGGTAAAT | GTGACAGAAA | 570 |
| TTCTTCATCT | TAACCATTTA | CACTGTCTTT | |
| Q E V E | L V N | V T E> | 99 |
| ______HIV1 | (MN) GP120 | GENE______> | |

FIG. 30A-3

```
ATTTTAACAT   GTGGAAAAAT   AACATGGTAG      600
TAAAATTGTA   CACCTTTTTA   TTGTACCATC
N  F  N  M    W  K  N      N  M  V>       109
_______HIV1  (MN) GP120   GENE_______>

AACAGATGC    ATGAGGATATA  ATCAGTTTAT      630
TTGTCTACG    TACTCCTATAT  TAGTCAAATA
E  Q  M  H    E  D  I      I  S  L>       119
_______HIV1  (MN) GP120   GENE_______>

GGGATCAAAG   CCTAAAGCCA   TGTGTAAAAT      660
CCCTAGTTTC   GGATTTCGGT   ACACATTTTA
W  D  Q  S    L  K  P      C  V  K>       129
_______HIV1  (MN) GP120   GENE_______>

TAACCCCACT   CTGTGTTACT   TTAAATTGCA      690
ATTGGGGTGA   GACACAATGA   AATTTAACGT
L  T  P  L    C  V  T      L  N  C>       139
_______HIV1  (MN) GP120   GENE_______>

CTGATTTGAG   GAATACTACT   AATACCAATA      720
GACTAAACTC   CTTATGATGA   TTATGGTTAT
T  D  L  R    N  T  T      N  T  N>       149
_______HIV1  (MN) GP120   GENE_______>
```

| FIG. 30B-1 |
|---|
| FIG. 30B-2 |
| FIG. 30B-3 |

FIG. 30B-1

```
ATAGTACTGC   TAATAACAAT   AGTAATAGCG        750
TATCATGACG   ATTATTGTTA   TCATTATCGC
N  S  T  A    N  N  N      S  N  S>          159
_______HIV1  (MN) GP120   GENE_______>

AGGGAACAAT   AAAGGGAGGA   GAAATGAAAA        780
TCCCTTGTTA   TTTCCCTCCT   CTTTACTTTT
E  G  T  I    K  G  G      E  M  K>          169
_______HIV1  (MN) GP120   GENE_______>

ACTGCTCTTT   CAATATCACC   ACAAGCATAA        810
TGACGAGAAA   GTTATAGTGG   TGTTCGTATT
N  C  S  F    N  I  T      T  S  I>          179
_______HIV1  (MN) GP120   GENE_______>

GAGATAAGAT   GCAGAAAGAA   TATGCACTTC        840
CTCTATTCTA   CGTCTTTCTT   ATACGTGAAG
R  D  K  M    Q  K  E      Y  A  L>          189
_______HIV1  (MN) GP120   GENE_______>

TTTATAAACT   TGATATAGTA   TCAATAAATA        870
AAATATTTGA   ACTATATCAT   AGTTATTTAT
L  Y  K  L    D  I  V      S  I  N>          199
_______HIV1  (MN) GP120   GENE_______>

ATGATAGTAC   CAGCTATAGG   TTGATAAGTT        900
TACTATCATG   GTCGATATCC   AACTATTCAA
N  D  S  T    S  Y  R      L  I  S>          209
_______HIV1  (MN) GP120   GENE_______>

GTAATACCTC   AGTCATTACA   CAAGCTTGTC        930
CATTATGGAG   TCAGTAATGT   GTTCGAACAG
C  N  T  S    V  I  T      Q  A  C>          219
_______HIV1  (MN) GP120   GENE_______>

CAAAGATATC   CTTTGAGCCA   ATTCCCATAC        960
GTTTCTATAG   GAAACTCGGT   TAAGGGTATG
P  K  I  S    F  E  P      I  P  I>          229
_______HIV1  (MN) GP120   GENE_______>

ACTATTGTGC   CCCGGCTGGT   TTTGCGATTC        990
TGATAACACG   GGGCCGACCA   AAACGCTAAG
H  Y  C  A    P  A  G      F  A  I>          239
_______HIV1  (MN) GP120   GENE_______>
```

FIG. 30B-2

| | | | |
|---|---|---|---|
| TAAAGTGTAA | CGATAAAAAG | TTCAGTGGAA | 1020 |
| ATTTCACATT | GCTATTTTTC | AAGTCACCTT | |
| L K C N | D K K | F S G> | 249 |
| ______HIV1 | (MN) GP120 | GENE______> | |
| AAGGATCATG | TAAAAATGTC | AGCACAGTAC | 1050 |
| TTCCTAGTAC | ATTTTTACAG | TCGTGTCATG | |
| K G S C | K N V | S T V> | 259 |
| ______HIV1 | (MN) GP120 | GENE______> | |
| AATGTACACA | TGGAATTAGG | CCAGTAGTAT | 1080 |
| TTACATGTGT | ACCTTAATCC | GGTCATCATA | |
| Q C T H | G I R | P V V> | 269 |
| ______HIV1 | (MN) GP120 | GENE______> | |
| CAACTCAACT | GCTGTTAAAT | GGCAGTCTAG | 1110 |
| GTTGAGTTGA | CGACAATTTA | CCGTCAGATC | |
| S T Q L | L L N | G S L> | 279 |
| ______HIV1 | (MN) GP120 | GENE______> | |
| CAGAAGAAGA | GGTAGTAATT | AGATCTGAGA | 1140 |
| GTCTTCTTCT | CCATCATTAA | TCTAGACTCT | |
| A E E E | V V I | R S E> | 289 |
| ______HIV1 | (MN) GP120 | GENE______> | |
| ATTTCAATGA | TAATGCTAAA | ACCATCATAG | 1170 |
| TAAAGTTACT | ATTACGATTT | TGGTAGTATC | |
| N F N D | N A K | T I I> | 299 |
| ______HIV1 | (MN) GP120 | GENE______> | |
| TACATCTGAA | TGAATCTGTA | CAAATTAATT | 1200 |
| ATGTAGACTT | ACTTAGACAT | GTTTAATTAA | |
| V H L N | E S V | Q I N> | 309 |
| ______HIV1 | (MN) GP120 | GENE______> | |
| GTACAAGACC | CAACTACGAG | CTCGACAAAT | 1230 |
| CATGTTCTGG | GTTGATGCTC | GAGCTGTTTA | |
| C T R P | N Y E | L D K | 319 |
| _____GP120 | GENE___><KAT | EPITOPE___> | |
| GGGCCCATAT | AGGACCAGGG | AGAGAATTGG | 1260 |
| CCCGGGTATA | TCCTGGTCCC | TCTCTTAACC | |
| W A H I | G P G | R E L | 329 |
| ____><___GP120 | GENE_____ | __><______ | |

FIG. 30B-3

```
ATAAGTGGGC   GAATATAATA   GGAACTATAA       1290
TATTCACCCG   CTTATATTAT   CCTTGATATT
D  K  W  A    N  I  I      G  T  I>         339
KAT EPITOP   ><_____GP    120 GENE__>

GACAAGCACA   TTGTAACATT   AGTAGAGCAA       1320
CTGTTCGTGT   AACATTGTAA   TCATCTCGTT
R  Q  A  H    C  N  I      S  R  A>         349
______HIV1   (MN) GP120   GENE______>

AATGGAATGA   CACTTTAAGA   CAGATAGTTA       1350
TTACCTTACT   GTGAAATTCT   GTCTATCAAT
K  W  N  D    T  L  R      Q  I  V>         359
______HIV1   (MN) GP120   GENE______>

GCAAATTAAA   AGAACAATTT   AAGAATAAAA       1380
CGTTTAATTT   TCTTGTTAAA   TTCTTATTTT
S  K  L  K    E  Q  F      K  N  K>         369
______HIV1   (MN) GP120   GENE______>

CAATAGTCTT   TAATCAATCC   TCAGGAGGGG       1410
GTTATCAGAA   ATTAGTTAGG   AGTCCTCCCC
T  I  V  F    N  Q  S      S  G  G>         379
______HIV1   (MN) GP120   GENE______>

ACCCAGAAAT   TGTAATGCAC   AGTTTTAATT       1440
TGGGTCTTTA   ACATTACGTG   TCAAAATTAA
D  P  E  I    V  M  H      S  F  N>         389
______HIV1   (MN) GP120   GENE______>
```

FIG. 30C-1

| | | | |
|---|---|---|---|
| GTGGAGGGGA | ATTCTTCTAC | TGTAATTCAT | 1470 |
| CACCTCCCCT | TAAGAAGATG | ACATTAAGTA | |
| C G G E | F F Y | C N S> | 399 |
| ___HIV1 | (MN) GP120 | GENE___> | |
| CACCACTGTT | TAATAGTACT | TGGAATGGTA | 1500 |
| GTGGTGACAA | ATTATCATGA | ACCTTACCAT | |
| S P L F | N S T | W N G> | 409 |
| ___HIV1 | (MN) GP120 | GENE___> | |
| ATAATACTTG | GAATAATACT | ACAGGGTCAA | 1530 |
| TATTATGAAC | CTTATTATGA | TGTCCCAGTT | |
| N N T W | N N T | T G S> | 419 |
| ___HIV1 | (MN) GP120 | GENE___> | |
| ATAACAATAT | CACACTTCAA | TGCAAAATAA | 1560 |
| TATTGTTATA | GTGTGAAGTT | ACGTTTTATT | |
| N N N I | T L Q | C K I> | 429 |
| ___HIV1 | (MN) GP120 | GENE___> | |
| AACAAATTAT | AAACATGTGG | CAGGAAGTAG | 1590 |
| TTGTTTAATA | TTTGTACACC | GTCCTTCATC | |
| K Q I I | N M W | Q E V> | 439 |
| ___HIV1 | (MN) GP120 | GENE___> | |
| GAAAAGCAAT | ATATGCCCCT | CCCATTGAAG | 1620 |
| CTTTTCGTTA | TATACGGGGA | GGGTAACTTC | |
| G K A I | Y A P | P I E> | 449 |
| ___HIV1 | (MN) GP120 | GENE___> | |
| GACAAATTAG | ATGTTCATCA | AATATTACAG | 1650 |
| CTGTTTAATC | TACAAGTAGT | TTATAATGTC | |
| G Q I R | C S S | N I T> | 459 |
| ___HIV1 | (MN) GP120 | GENE___> | |
| GGCTACTATT | AACAAGAGAT | GGTGGTAAGG | 1680 |
| CCGATGATAA | TTGTTCTCTA | CCACCATTCC | |
| G L L L | T R D | G G K> | 469 |
| ___HIV1 | (MN) GP120 | GENE___> | |
| ACACGGACAC | GAACGACACC | GAGATCTTCA | 1710 |
| TGTGCCTGTG | CTTGCTGTGG | CTCTAGAAGT | |
| D T D T | N D T | E I F> | 479 |
| ___HIV1 | (MN) GP120 | GENE___> | |

FIG. 30C-2

```
GACCTGGAGG   AGGAGATATG   AGGGACAATT        1740
CTGGACCTCC   TCCTCTATAC   TCCCTGTTAA
R  P  G  G    G  D  M      R  D  N>          489
_______HIV1  (MN) GP120   GENE_______>

GGAGAAGTGA   ATTATATAAA   TATAAAGTAG        1770
CCTCTTCACT   TAATATATTT   ATATTTCATC
W  R  S  E    L  Y  K      Y  K  V>          499
_______HIV1  (MN) GP120   GENE_______>

TAACAATTGA   ACCATTAGGA   GTAGCACCCA        1800
ATTGTTAACT   TGGTAATCCT   CATCGTGGGT
V  T  I  E    P  L  G      V  A  P>          509
_______HIV1  (MN) GP120   GENE_______>

CCAAGGCAAA   GAGAAGAGTG   GTGCAGAGAG        1830
GGTTCCGTTT   CTCTTCTCAC   CACGTCTCTC
T  K  A  K    R  R  V      V  Q  R>          519
_______HIV1  (MN) GP120   GENE_______>

AAAAAAGATT   ATTCATAATG   ATAGTAGGAG        1860
TTTTTTCTAA   TAAGTATTAC   TATCATCCTC
E  K  R  L    F  I  M      I  V  G>          529
___________  TRANSMEMBR   ANE REGION>

GCTTGGTAGG   TTTAAGAATA   GTTTTTGCTG        1890
CGAACCATCC   AAATTCTTAT   CAAAAACGAC
G  L  V  G    L  R  I      V  F  A>          539
_HIV1 TRAN   SMEMBRANE    REGION_____>

TACTCTCTGT   AGTGAATAGA   GTTAGGCAGG        1920
ATGAGAGACA   TCACTTATCT   CAATCCGTCC
V  L  S  V    V  N  R      V  R  Q>          549
_HIV1 TRAN   SMEMBRANE    REGION_____>

GATAATTTTT   ATTCGAGAAT   CGATCCCGGG        1950
CTATTAAAAA   TAAGATCTTA   GCTAGGGCCC
G  *                                         550
_____>

AATCGATTCG   CGATAGCTGA   TTAGTTTTTG        1980
TTAGCTAAGC   GCTATCGACT   AATCAAAAAC
```

FIG. 30C-3

```
TTAACAAAAA   TGTGGGAGAA   TCTAATTAGT      2010
AATTGTTTTT   ACACCCTCTT   AGATTAATCA
                              <_____

TTTTCTTTAC   ACAATTGACG   TACATGAGTC      2040
AAAAGAAATG   TGTTAACTGC   ATGTACTCAG
<______K1L   FLANKING     ARM_______

TGAGTTCCTT   GTTTTTGCTA                   2060
ACTCAAGGAA   CAAAAACGAT
<_K1L FLAN   KING ARM__
```

| FIG.31a |
|---|
| FIG.31b |
| FIG.31c |

Placebo
ERYTHROCYTES
Monkey #
1
2
3
4
m
20 weeks

ALVAC-HIV (vCP205)
Monkey #
5
6
7
8
m
20 weeks

MEAN CORPUSCLE VOLUME
Monkey #
1
2
3
4
m
20 weeks
Inoculations
fl

Monkey #
5
6
7
8
m
20 weeks
Inoculations

FIG.35a
FIG.35b
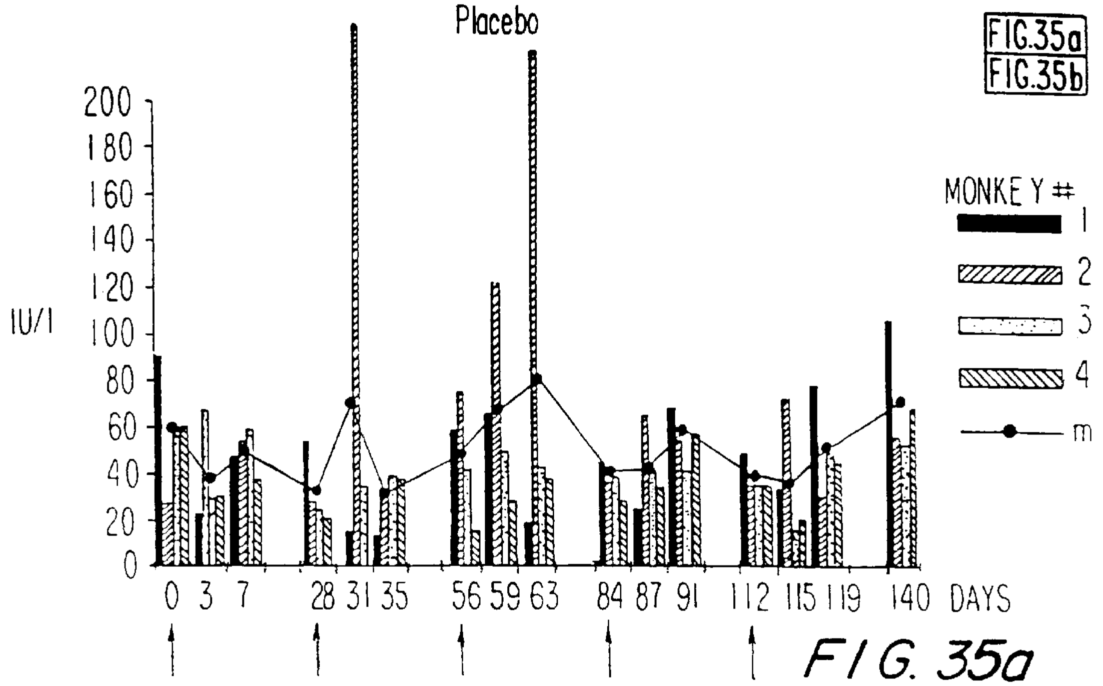
FIG. 35a
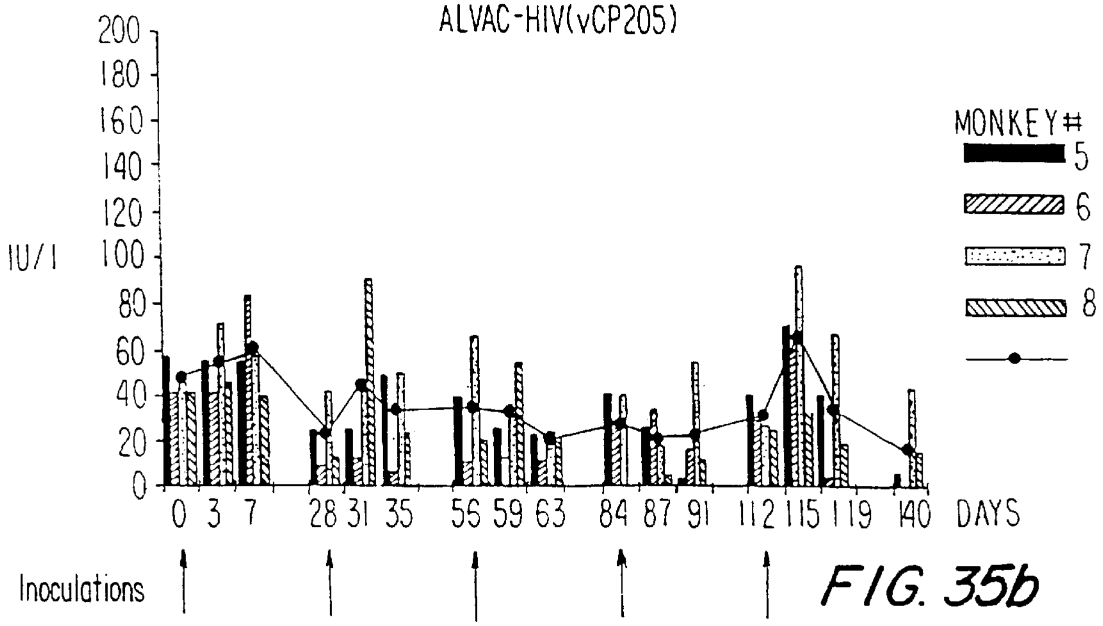
FIG. 35b

FIG.36a
FIG.36b
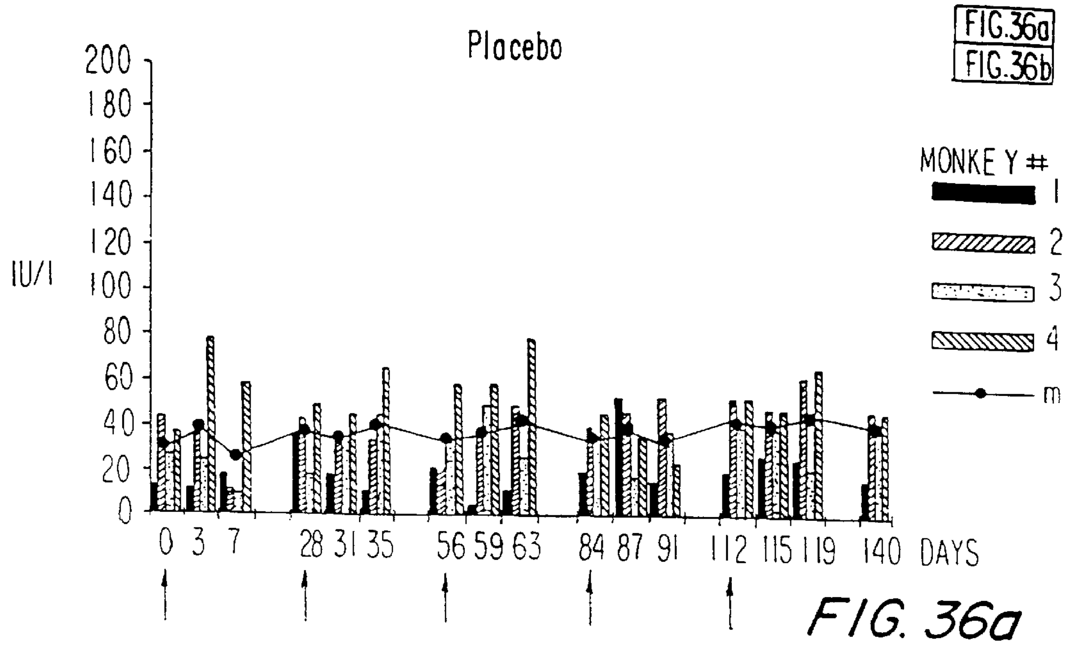
FIG. 36a
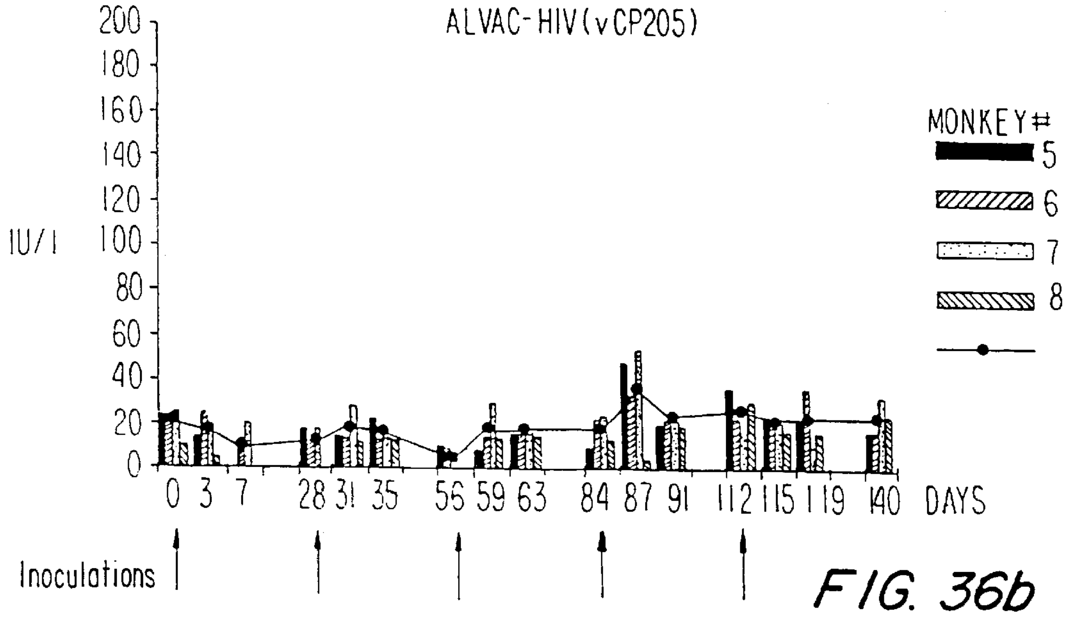
FIG. 36b

FIG. 40a Placebo
Individual WBC counts
giga/l
MONKEY#
1
2
3
4
5
168 Days
FIG. 40b ALVAC-HIV (vCP300)
Individual WBC counts
MONKEY#
5
6
7
8
m
168 Days Differential cell counts (average)
NEUTRO
LYMPHO
MONO
EOSINO
BASO
168 Days
Inoculations
I.M
I.M
I.M
I.M
I.M
I.V (vCP300)

Differential cell counts (average)
NEUTRO
LYMPHO
MONO
EOSINO
BASO
168 Days
Inoculations
I.M
I.M
I.M
I.M
I.M
I.V Placebo
ERYTHROCYTES
tera/15
Monkey #
FIG. 41a-2 ALVAC-HIV(vCP300)

MEAN CORPUSCLE VOLUME
femtol75 inoculations
I.M.
I.V.
(VCP300)
168 Days
FIG. 41a-1 | FIG. 41a-2
FIG. 41a-3 | FIG. 41a-4

FIG. 41b-1 Placebo
HEMATOCRITE
Monkey #
1
2
3
4
m
168 Days
FIG. 41b-2 ALVAC-HIV (vCP300)
Monkey #
5
6
7
8
m
FIG. 41b-1 | FIG. 41b-2
FIG. 41b-3 | FIG. 41b-4

HEMOGLOBIN
g/l
inoculations
I.M.
I.V. (vCP300)

I.V.
0
28
56
84
112
140

FIG.43a-1
FIG.43a-2
FIG.43a-3
FIG.43a-1
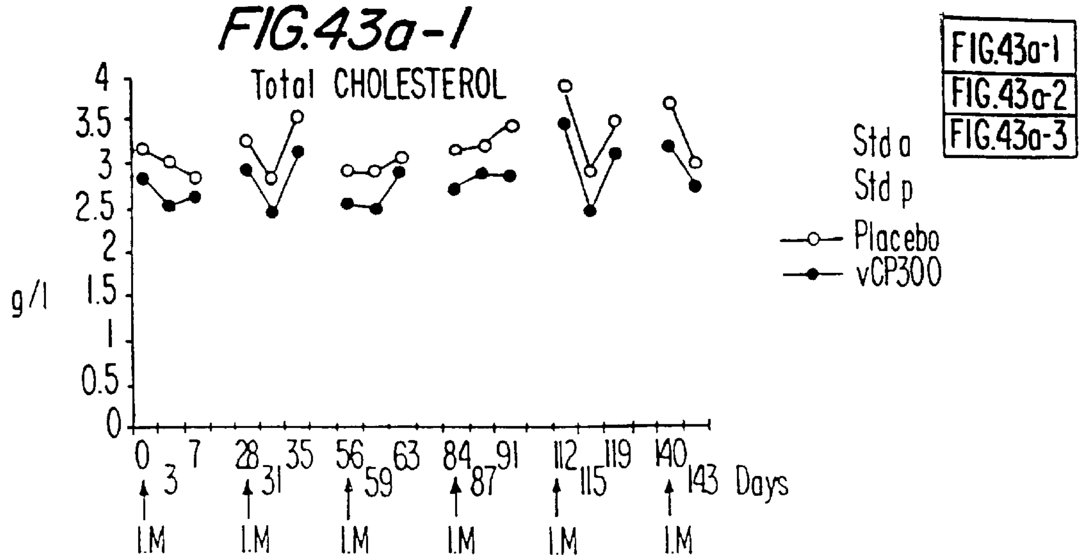
FIG.43a-2
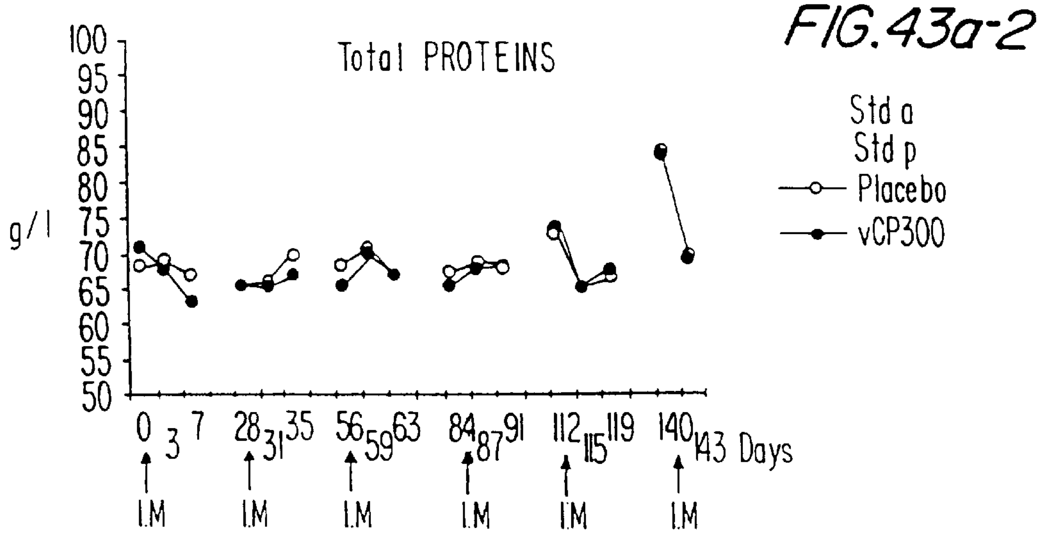
FIG.43a-3
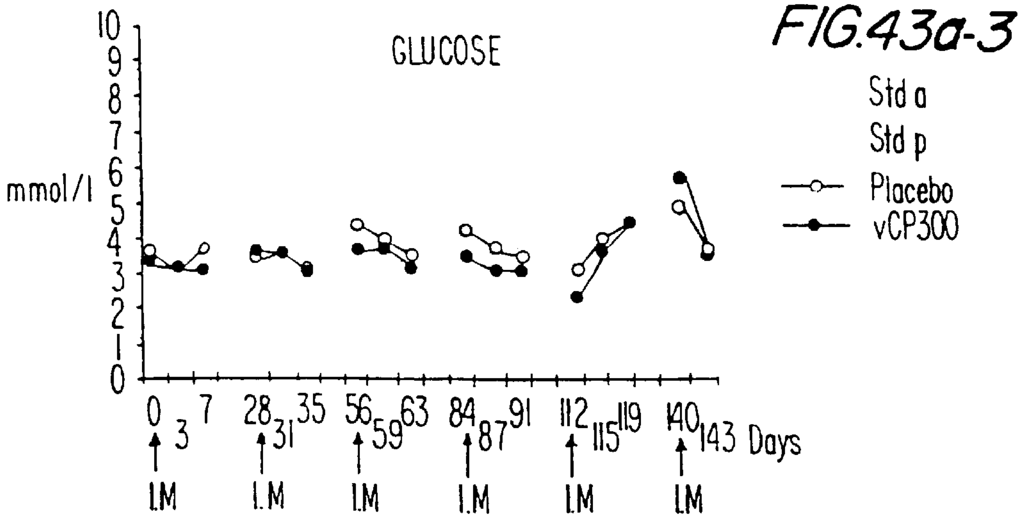

FIG. 43c-1
FIG. 43c-2
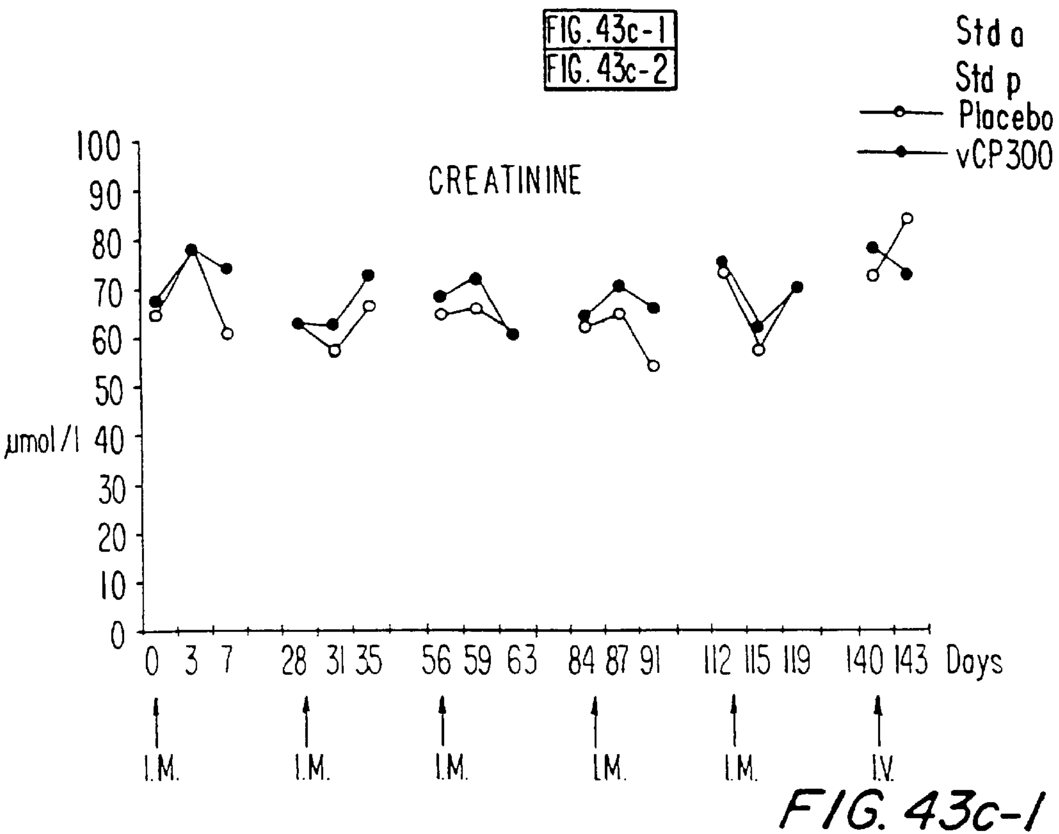
FIG. 43c-1
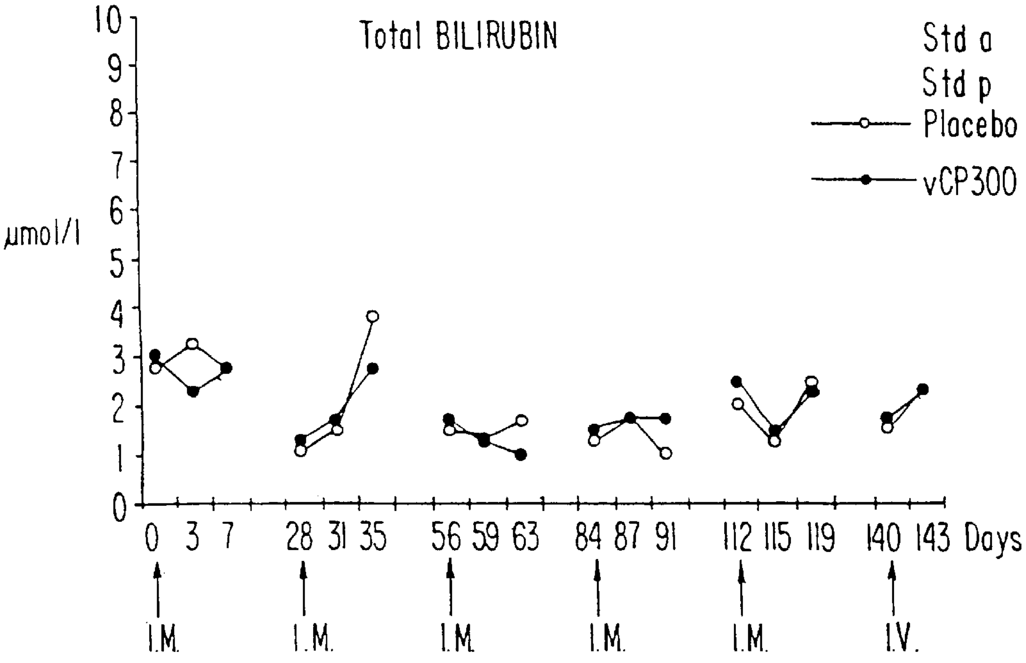
FIG. 43c-2

FIG. 43d-1
FIG. 43d-2
FIG. 43d-3
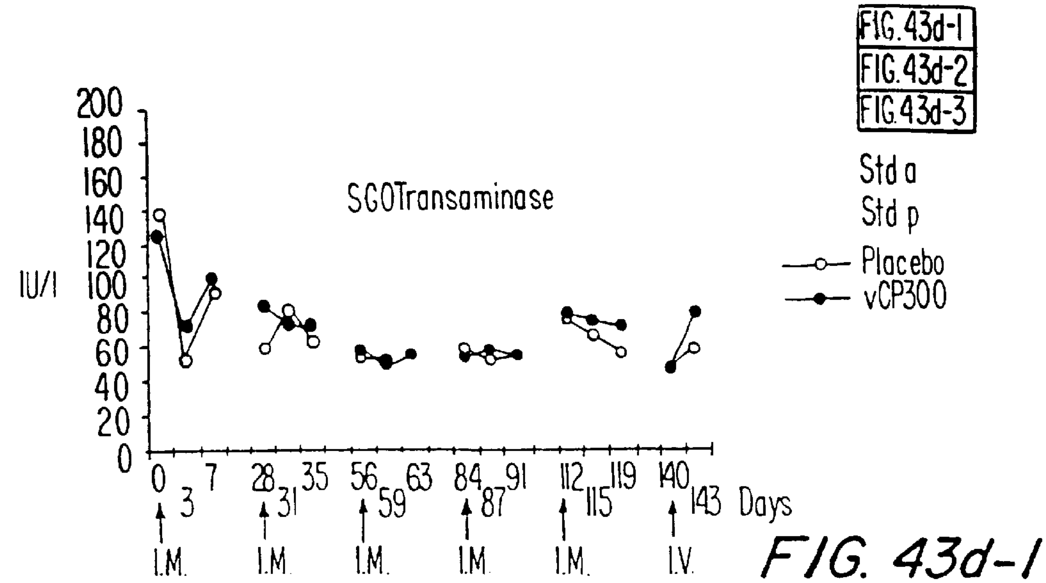
FIG. 43d-1
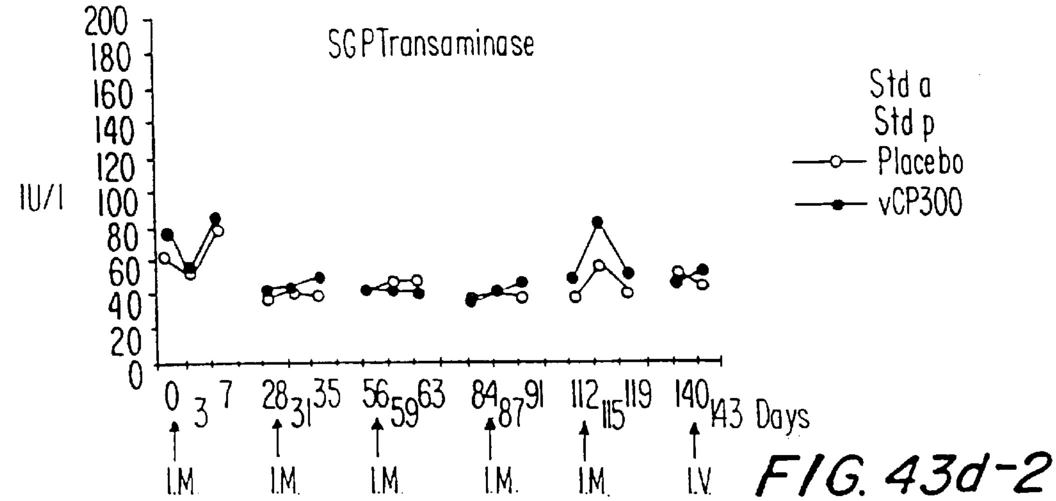
FIG. 43d-2
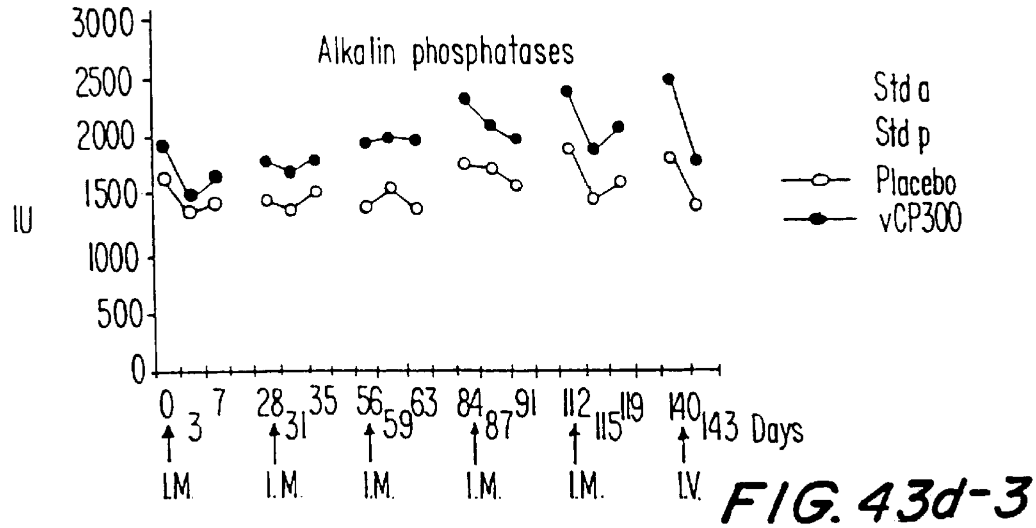
FIG. 43d-3

SEQUENCE LISTING

```
<160> NUMBER OF SEQ ID NOS: 149

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide referred to as
      MPSYN43

<400> SEQUENCE: 1

taattaacta gctacccggg                                              20


<210> SEQ ID NO 2
<211> LENGTH: 28
<212> TYPE: DNA
<213> ORGANISM: Artificial Sequence
```

-continued

```
<220> FEATURE:
<223> OTHER INFORMATION: Synthetic oligonucleotide referred to as
      MPSYN44

<400> SEQUENCE: 2

gtacattaat tgatcgatgg gcccttaa                                    28


<210> SEQ ID NO 3
<211> LENGTH: 73
<212> TYPE: DNA
<213> ORGANISM: Artificial Sequence
<220> FEATURE:
<223> OTHER INFORMATION: Synthetic oligonucleotide referred to as
      MPSYN45

<400> SEQUENCE: 3

agcttcccgg gtaagtaata cgtcaaggag aaaacgaaac gatctgtagt tagcggccgc     60

ctaattaact aat                                                    73


<210> SEQ ID NO 4
<211> LENGTH: 69
<212> TYPE: DNA
<213> ORGANISM: Artificial Sequence
<220> FEATURE:
<223> OTHER INFORMATION: Synthetic nucleotide referred to as MPSYN46

<400> SEQUENCE: 4

agggcccatt cattatgcag ttcctctttt gctttgctag acatcaatcg ccggcggatt     60

aattgatta                                                         69


<210> SEQ ID NO 5
<211> LENGTH: 20
<212> TYPE: DNA
<213> ORGANISM: Artificial Sequence
<220> FEATURE:
<223> OTHER INFORMATION: Complementary 20mer oligonucleotide referred to
      as MPSYN47

<400> SEQUENCE: 5

ttagttaatt aggcggccgc                                             20


<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide referred to as
      SD22mer

<400> SEQUENCE: 6

cgattactat gaaggatccg tt                                          22


<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide referred to as
      SD20mer

<400> SEQUENCE: 7

taatgatact tcctaggcaa                                             20


<210> SEQ ID NO 8
<211> LENGTH: 41
```

-continued

<212> TYPE: DNA
<213> ORGANISM: Artificial Sequence
<220> FEATURE:
<223> OTHER INFORMATION: Synthetic oligonucleotide referred to as
SD42mer

<400> SEQUENCE: 8
cgattactag atctgagctc cccgggctcg agggatccgt t 41

<210> SEQ ID NO 9
<211> LENGTH: 39
<212> TYPE: DNA
<213> ORGANISM: Artificial Sequence
<220> FEATURE:
<223> OTHER INFORMATION: Synthetic oligonucleotide referred to as
SD40mer

<400> SEQUENCE: 9
taatgatcta gactcgaggg gcccgagctc cctaggcaa 39

<210> SEQ ID NO 10
<211> LENGTH: 16
<212> TYPE: DNA
<213> ORGANISM: Artificial Sequence
<220> FEATURE:
<223> OTHER INFORMATION: Synthetic oligonucleotide referred to as HEM5

<400> SEQUENCE: 10
gatccgaatt ctagct 16

<210> SEQ ID NO 11
<211> LENGTH: 12
<212> TYPE: DNA
<213> ORGANISM: Artificial Sequence
<220> FEATURE:
<223> OTHER INFORMATION: Synthetic oligonucleotide referred to as HEM6

<400> SEQUENCE: 11
gcttaagatc ga 12

<210> SEQ ID NO 12
<211> LENGTH: 75
<212> TYPE: DNA
<213> ORGANISM: Artificial Sequence
<220> FEATURE:
<223> OTHER INFORMATION: Synthetic oligonucleotide referred to as ATI3

<400> SEQUENCE: 12
tatgagtaac ttaactcttt tgttaattaa aagtatattc aaaaaataag ttatataaat 60
agatctgaat tcgtt 75

<210> SEQ ID NO 13
<211> LENGTH: 73
<212> TYPE: DNA
<213> ORGANISM: Artificial Sequence
<220> FEATURE:
<223> OTHER INFORMATION: Synthetic oligonucleotide referred to as ATI4

<400> SEQUENCE: 13
actcattgaa ttgagaaaac aattaatttt catataagtt ttttattcaa tatatttatc 60
tagacttaag caa 73

<210> SEQ ID NO 14
<211> LENGTH: 49
<212> TYPE: DNA

-continued

<213> ORGANISM: Artificial Sequence
<220> FEATURE:
<223> OTHER INFORMATION: Synthetic oligonucleotide referred to as
MPSYN177

<400> SEQUENCE: 14
aaaatgggcg tggattgtta actttatata acttattttt tgaatatac 49

<210> SEQ ID NO 15
<211> LENGTH: 67
<212> TYPE: DNA
<213> ORGANISM: Artificial Sequence
<220> FEATURE:
<223> OTHER INFORMATION: Synthetic oligonucleotide referred to as
MPSYN59

<400> SEQUENCE: 15
acacgaatga ttttctaaag tatttggaaa gttttatagg tagttgatag aacaaaatac 60
ataattt 67

<210> SEQ ID NO 16
<211> LENGTH: 51
<212> TYPE: DNA
<213> ORGANISM: Artificial Sequence
<220> FEATURE:
<223> OTHER INFORMATION: Synthetic oligonucleotide referred to as
MPSYN62

<400> SEQUENCE: 16
tgtgcttact aaaagatttc ataaaccttt caaaatatcc atcaactatc t 51

<210> SEQ ID NO 17
<211> LENGTH: 46
<212> TYPE: DNA
<213> ORGANISM: Artificial Sequence
<220> FEATURE:
<223> OTHER INFORMATION: Synthetic oligonucleotide referred to as
MPSYN60

<400> SEQUENCE: 17
tgtaaaaata aatcactttt tatactaaga tctcccgggc tgcagc 46

<210> SEQ ID NO 18
<211> LENGTH: 66
<212> TYPE: DNA
<213> ORGANISM: Artificial Sequence
<220> FEATURE:
<223> OTHER INFORMATION: Synthetic oligonucleotide referred to as
MPSYN61

<400> SEQUENCE: 18
tgttttatgt attaaaacat ttttatttag tgaaaaatat gattctagag ggcccgacgt 60
cgccgg 66

<210> SEQ ID NO 19
<211> LENGTH: 50
<212> TYPE: DNA
<213> ORGANISM: Artificial Sequence
<220> FEATURE:
<223> OTHER INFORMATION: Synthetic oligonucleotide referred to as
MPSYN82

<400> SEQUENCE: 19
tttctgtata tttgcaccaa tttagatctt actcaaaata tgtaacaata 50

-continued

<210> SEQ ID NO 20
<211> LENGTH: 44
<212> TYPE: DNA
<213> ORGANISM: Artificial Sequence
<220> FEATURE:
<223> OTHER INFORMATION: Synthetic oligonucleotide referred to as MPSYN233

<400> SEQUENCE: 20
tgtcatttaa cactatactc atattaataa aaataatatt tatt 44

<210> SEQ ID NO 21
<211> LENGTH: 72
<212> TYPE: DNA
<213> ORGANISM: Artificial Sequence
<220> FEATURE:
<223> OTHER INFORMATION: Synthetic oligonucleotide referred to as 518A1

<400> SEQUENCE: 21
gatcctgagt actttgtaat ataatgatat atattttcac tttatctcat ttgagaataa 60
aaagatctta gg 72

<210> SEQ ID NO 22
<211> LENGTH: 72
<212> TYPE: DNA
<213> ORGANISM: Artificial Sequence
<220> FEATURE:
<223> OTHER INFORMATION: Synthetic oligonucleotide referred to as 518A2

<400> SEQUENCE: 22
gactcatgaa acattatatt actatatata aaagtgaaat agagtaaact cttatttttc 60
tagaatcctt aa 72

<210> SEQ ID NO 23
<211> LENGTH: 72
<212> TYPE: DNA
<213> ORGANISM: Artificial Sequence
<220> FEATURE:
<223> OTHER INFORMATION: Synthetic oligonucleotide referred to as 518B1

<400> SEQUENCE: 23
gatccagatc tcccgggaaa aaaattattt aacttttcat taatagggat ttgacgtatg 60
tagcgtacta gg 72

<210> SEQ ID NO 24
<211> LENGTH: 72
<212> TYPE: DNA
<213> ORGANISM: Artificial Sequence
<220> FEATURE:
<223> OTHER INFORMATION: Synthetic oligonucleotide referred to as 518B2

<400> SEQUENCE: 24
gtctagaggg cccttttttt aataaattga aaagtaatta tccctaaact gcatactacg 60
catgatcctt aa 72

<210> SEQ ID NO 25
<211> LENGTH: 40
<212> TYPE: DNA
<213> ORGANISM: Artificial Sequence
<220> FEATURE:
<223> OTHER INFORMATION: Synthetic oligonucleotide referred to as VQ1A

<400> SEQUENCE: 25
gggagatctc tcgagctgca gggcgccgga tcctttttct 40

-continued

<210> SEQ ID NO 26
<211> LENGTH: 40
<212> TYPE: DNA
<213> ORGANISM: Artificial Sequence
<220> FEATURE:
<223> OTHER INFORMATION: Synthetic oligonucleotide referred to as VQ1B

<400> SEQUENCE: 26
ccctctagag agctcgacgt cccgcggcct aggaaaaaga 40

<210> SEQ ID NO 27
<211> LENGTH: 59
<212> TYPE: DNA
<213> ORGANISM: Artificial Sequence
<220> FEATURE:
<223> OTHER INFORMATION: Oligonucleotide referred to as CE75

<400> SEQUENCE: 27
cgatatccgt taagtttgta tcgtaatggg ctccagatct tctaccagga tcccggtac 59

<210> SEQ ID NO 28
<211> LENGTH: 55
<212> TYPE: DNA
<213> ORGANISM: Artificial Sequence
<220> FEATURE:
<223> OTHER INFORMATION: Oligonucleotide referred to as CE76

<400> SEQUENCE: 28
cgggatcctg gtagaagatc tggagcccat tacgatacaa acttaacgga tatcg 55

<210> SEQ ID NO 29
<211> LENGTH: 17
<212> TYPE: DNA
<213> ORGANISM: Artificial Sequence
<220> FEATURE:
<223> OTHER INFORMATION: Oligonucleotide referred to as CE42

<400> SEQUENCE: 29
aattcgagct ccccggg 17

<210> SEQ ID NO 30
<211> LENGTH: 13
<212> TYPE: DNA
<213> ORGANISM: Artificial Sequence
<220> FEATURE:
<223> OTHER INFORMATION: Oligonucleotide referred to as CE43

<400> SEQUENCE: 30
cccggggagc tcg 13

<210> SEQ ID NO 31
<211> LENGTH: 26
<212> TYPE: DNA
<213> ORGANISM: Artificial Sequence
<220> FEATURE:
<223> OTHER INFORMATION: Oligonucleotide referred to as CE166

<400> SEQUENCE: 31
ctttttataa aaagttaact acgtag 26

<210> SEQ ID NO 32
<211> LENGTH: 34
<212> TYPE: DNA
<213> ORGANISM: Artificial Sequence
<220> FEATURE:

-continued

<223> OTHER INFORMATION: Oligonucleotide referred to as CE167

<400> SEQUENCE: 32
gatcctacgt agttaacttt ttataaaaag agct 34

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide referred to as CE182

<400> SEQUENCE: 33
cttaactcag ctgactatcc 20

<210> SEQ ID NO 34
<211> LENGTH: 44
<212> TYPE: DNA
<213> ORGANISM: Artificial Sequence
<220> FEATURE:
<223> OTHER INFORMATION: Oligonucleotide referred to as CE183

<400> SEQUENCE: 34
tacgtagtta actttttata aaaatcatat ttttgtagtg gctc 44

<210> SEQ ID NO 35
<211> LENGTH: 67
<212> TYPE: DNA
<213> ORGANISM: Artificial Sequence
<220> FEATURE:
<223> OTHER INFORMATION: Oligonucleotide referred to as CE162

<400> SEQUENCE: 35
aattcaggat cgttccttta ctagttgaga ttctcaagga tgatgggatt taatttttat 60
aagcttg 67

<210> SEQ ID NO 36
<211> LENGTH: 67
<212> TYPE: DNA
<213> ORGANISM: Artificial Sequence
<220> FEATURE:
<223> OTHER INFORMATION: Oligonucleotide referred to as CE163

<400> SEQUENCE: 36
aattcaagct tataaaaatt aaatcccatc atccttgaga atctcaacta gtaaaggaac 60
gatcctg 67

<210> SEQ ID NO 37
<211> LENGTH: 68
<212> TYPE: DNA
<213> ORGANISM: Artificial Sequence
<220> FEATURE:
<223> OTHER INFORMATION: Double-stranded oligonucleotide referred to as
JCA017

<400> SEQUENCE: 37
ctagacactt tatgtttttt aatatccggt cttaaaagct tcccggggat ccttatacgg 60
ggaataat 68

<210> SEQ ID NO 38
<211> LENGTH: 65
<212> TYPE: DNA
<213> ORGANISM: Artificial Sequence
<220> FEATURE:

-continued

<223> OTHER INFORMATION: Double-stranded oligonucleotide referred to as JCA018

<400> SEQUENCE: 38
attattcccc gtataaggat cccccgggaa gcttttaaga ccggatatta aaaaacataa 60
agtgt 65

<210> SEQ ID NO 39
<211> LENGTH: 29
<212> TYPE: DNA
<213> ORGANISM: Artificial Sequence
<220> FEATURE:
<223> OTHER INFORMATION: Replacement sequence for bases from 167 through position 455 of 880 bp canarypox PvuII fragment

<400> SEQUENCE: 39
gcttcccggg aattctagct agctagttt 29

<210> SEQ ID NO 40
<211> LENGTH: 46
<212> TYPE: DNA
<213> ORGANISM: Artificial Sequence
<220> FEATURE:
<223> OTHER INFORMATION: Synthetic oligonucleotide referred to as RW145

<400> SEQUENCE: 40
actctcaaaa gcttcccggg aattctagct agctagtttt tataaa 46

<210> SEQ ID NO 41
<211> LENGTH: 50
<212> TYPE: DNA
<213> ORGANISM: Artificial Sequence
<220> FEATURE:
<223> OTHER INFORMATION: Synthetic oligonucleotide referred to as RW146

<400> SEQUENCE: 41
gatctttata aaaactagct agctagaatt cccgggaagc ttttgagagt 50

<210> SEQ ID NO 42
<211> LENGTH: 71
<212> TYPE: DNA
<213> ORGANISM: Artificial Sequence
<220> FEATURE:
<223> OTHER INFORMATION: Oligonucleotide referred to as Oligonucleotide A

<400> SEQUENCE: 42
ctgaaattat ttcattatcg cgatatccgt taagtttgta tcgtaatggt tcctcaggct 60
ctcctgtttg t 71

<210> SEQ ID NO 43
<211> LENGTH: 48
<212> TYPE: DNA
<213> ORGANISM: Artificial Sequence
<220> FEATURE:
<223> OTHER INFORMATION: Oligonucleotide referred to as Oligonucleotide B

<400> SEQUENCE: 43
cattacgata caaacttaac ggatatcgcg ataatgaaat aatttcag 48

<210> SEQ ID NO 44
<211> LENGTH: 73
<212> TYPE: DNA
<213> ORGANISM: Artificial Sequence -continued

```
<220> FEATURE:
<223> OTHER INFORMATION: Oligonucleotide referred to as Oligonucleotide
      C

<400> SEQUENCE: 44

accccttctg gtttttccgt tgtgttttgg gaaattccct atttacacga tcccagacaa      60

gcttagatct cag                                                         73


<210> SEQ ID NO 45
<211> LENGTH: 51
<212> TYPE: DNA
<213> ORGANISM: Artificial Sequence
<220> FEATURE:
<223> OTHER INFORMATION: Oligonucleotide referred to as Oligonucleotide
      D

<400> SEQUENCE: 45

ctgagatcta agcttgtctg ggatcgtgta aatagggaat ttcccaaaac a               51


<210> SEQ ID NO 46
<211> LENGTH: 45
<212> TYPE: DNA
<213> ORGANISM: Artificial Sequence
<220> FEATURE:
<223> OTHER INFORMATION: Oligonucleotide referred to as Oligonucleotide
      E

<400> SEQUENCE: 46

caacggaaaa accagaaggg gtacaaacag gagagcctga ggaac                      45


<210> SEQ ID NO 47
<211> LENGTH: 11
<212> TYPE: DNA
<213> ORGANISM: Artificial Sequence
<220> FEATURE:
<223> OTHER INFORMATION: pRW824 sequence of BamHI followed by SmaI

<400> SEQUENCE: 47

ggatccccgg g                                                           11


<210> SEQ ID NO 48
<211> LENGTH: 60
<212> TYPE: DNA
<213> ORGANISM: Artificial Sequence
<220> FEATURE:
<223> OTHER INFORMATION: Oligonucleotide referred to as RW178

<400> SEQUENCE: 48

tcattatcgc gatatccgtg ttaactagct agctaatttt tattcccggg atccttatca      60


<210> SEQ ID NO 49
<211> LENGTH: 60
<212> TYPE: DNA
<213> ORGANISM: Artificial Sequence
<220> FEATURE:
<223> OTHER INFORMATION: Oligonucleotide referred to as RW179

<400> SEQUENCE: 49

gtataaggat cccgggaata aaaattagct agctagttaa cacggatatc gcgataatga      60


<210> SEQ ID NO 50
<211> LENGTH: 24
<212> TYPE: DNA
<213> ORGANISM: Artificial Sequence
<220> FEATURE:
<223> OTHER INFORMATION: Oligonucleotide referred to as F73PH2
```

-continued

<400> SEQUENCE: 50
gacaatctaa gtcctatatt agac 24

<210> SEQ ID NO 51
<211> LENGTH: 18
<212> TYPE: DNA
<213> ORGANISM: Artificial Sequence
<220> FEATURE:
<223> OTHER INFORMATION: Oligonucleotide referred to as F73PB

<400> SEQUENCE: 51
ggatttttag gtagacac 18

<210> SEQ ID NO 52
<211> LENGTH: 18
<212> TYPE: DNA
<213> ORGANISM: Artificial Sequence
<220> FEATURE:
<223> OTHER INFORMATION: Oligonucleotide referred to as F75PE

<400> SEQUENCE: 52
tcatcgtctt catcatcg 18

<210> SEQ ID NO 53
<211> LENGTH: 29
<212> TYPE: DNA
<213> ORGANISM: Artificial Sequence
<220> FEATURE:
<223> OTHER INFORMATION: Oligonucleotide referred to as F73PH1

<400> SEQUENCE: 53
gtcttaaact tattgtaagg gtatacctg 29

<210> SEQ ID NO 54
<211> LENGTH: 61
<212> TYPE: DNA
<213> ORGANISM: Artificial Sequence
<220> FEATURE:
<223> OTHER INFORMATION: Oligonucleotide referred to as F7MCSB

<400> SEQUENCE: 54
aacgattagt tagttactaa aagcttgctg cagcccgggt tttttattag tttagttagt 60
c 61

<210> SEQ ID NO 55
<211> LENGTH: 60
<212> TYPE: DNA
<213> ORGANISM: Artificial Sequence
<220> FEATURE:
<223> OTHER INFORMATION: Oligonucleotide referred to as F7MCSA

<400> SEQUENCE: 55
gactaactaa ctaataaaaa acccgggctg cagcaagctt tttgtaacta actaatcgtt 60

<210> SEQ ID NO 56
<211> LENGTH: 99
<212> TYPE: DNA
<213> ORGANISM: Artificial Sequence
<220> FEATURE:
<223> OTHER INFORMATION: Synthetic oligonucleotide referred to as RW152

<400> SEQUENCE: 56
gcacggaaca aagcttatcg cgatatccgt taagtttgta tcgtaatgct atcaatcacg 60

-continued

```
attctgttcc tgctcatagc agagggctca tctcagaat                              99


<210> SEQ ID NO 57
<211> LENGTH: 99
<212> TYPE: DNA
<213> ORGANISM: Artificial Sequence
<220> FEATURE:
<223> OTHER INFORMATION: Synthetic oligonucleotide referred to as RW153

<400> SEQUENCE: 57

attctgagat gagccctctg ctatgagcag gaacagaatc gtgattgata gcattacgat     60

acaaacttaa cggatatcgc gataagcttt gttccgtgc                              99


<210> SEQ ID NO 58
<211> LENGTH: 66
<212> TYPE: DNA
<213> ORGANISM: Artificial Sequence
<220> FEATURE:
<223> OTHER INFORMATION: Synthetic oligonucleotide referred to as RW10

<400> SEQUENCE: 58

gaaaaattta aagtcgacct gttttgttga gttgtttgcg tggtaaccaa tgcaaatctg     60

gtcact                                                                  66


<210> SEQ ID NO 59
<211> LENGTH: 66
<212> TYPE: DNA
<213> ORGANISM: Artificial Sequence
<220> FEATURE:
<223> OTHER INFORMATION: Synthetic oligonucleotide referred to as RW11

<400> SEQUENCE: 59

tctagcaaga ctgactattg caaaaagaag cactatttcc tccattacga tacaaactta     60

acggat                                                                  66


<210> SEQ ID NO 60
<211> LENGTH: 87
<212> TYPE: DNA
<213> ORGANISM: Artificial Sequence
<220> FEATURE:
<223> OTHER INFORMATION: Synthetic oligonucleotide referred to as RW12

<400> SEQUENCE: 60

atccgttaag tttgtatcgt aatggaggaa atagtgcttc tttttgcaat agtcagtctt     60

gctagaagtg accagatttg cattggt                                           87


<210> SEQ ID NO 61
<211> LENGTH: 49
<212> TYPE: DNA
<213> ORGANISM: Artificial Sequence
<220> FEATURE:
<223> OTHER INFORMATION: Synthetic oligonucleotide referred to as RW13

<400> SEQUENCE: 61

taccacgcaa acaactcaac aaaacaggtc gactttaaat ttttctgca                   49


<210> SEQ ID NO 62
<211> LENGTH: 132
<212> TYPE: DNA
<213> ORGANISM: Artificial Sequence
<220> FEATURE:
<223> OTHER INFORMATION: Synthetic oligonucleotide referred to as RW165

<400> SEQUENCE: 62
```

-continued gtacaggtcg acaagcttcc cgggtatcgc gatatccgtt aagtttgtat cgtaatgaat 60
actcaaattc taatactcac tcttgtggca gccattcaca caaatgcaga caaaatctgc 120
cttggacatc at 132

<210> SEQ ID NO 63
<211> LENGTH: 132
<212> TYPE: DNA
<213> ORGANISM: Artificial Sequence
<220> FEATURE:
<223> OTHER INFORMATION: Synthetic oligonucleotide referred to as RW166

<400> SEQUENCE: 63
atgatgtcca aggcagattt tgtctgcatt tgtgtgaatg gctgccacaa gagtgagtat 60
tagaatttga gtattcatta cgatacaaac ttaacggata tcgcgatacc cgggaagctt 120
gtcgacctgt ac 132

<210> SEQ ID NO 64
<211> LENGTH: 51
<212> TYPE: DNA
<213> ORGANISM: Artificial Sequence
<220> FEATURE:
<223> OTHER INFORMATION: Synthetic oligonucleotide referred to as RW227

<400> SEQUENCE: 64
ataacatgcg gtgcaccatt tgtatataag ttaacgaatt ccaagtcaag c 51

<210> SEQ ID NO 65
<211> LENGTH: 51
<212> TYPE: DNA
<213> ORGANISM: Artificial Sequence
<220> FEATURE:
<223> OTHER INFORMATION: Synthetic oligonucleotide referred to as RW228

<400> SEQUENCE: 65
gcttgacttg gaattcgtta acttatatac aaatggtgca ccgcatgtta t 51

<210> SEQ ID NO 66
<211> LENGTH: 3209
<212> TYPE: DNA
<213> ORGANISM: Canarypox virus

<400> SEQUENCE: 66
tgaatgttaa atgttatact ttggatgaag ctataaatat gcattggaaa aataatccat 60
ttaaagaaag gattcaaata ctacaaaacc taagcgataa tatgttaact aagcttattc 120
ttaacgacgc tttaaatata cacaaataaa cataattttt gtataaccta acaaataact 180
aaaacataaa aataataaaa ggaaatgtaa tatcgtaatt attttactca ggaatggggt 240
taaatattta tatcacgtgt atatctatac tgttatcgta tactctttac aattactatt 300
acgaatatgc aagagataat aagattacgt atttaagaga atcttgtcat gataattggg 360
tacgacatag tgataaatgc tatttcgcat cgttacataa agtcagttgg aaagatggat 420
ttgacagatg taacttaata ggtgcaaaaa tgttaaataa cagcattcta tcggaagata 480
ggataccagt tatattatac aaaaatcact ggttggataa aacagattct gcaatattcg 540
taaaagatga agattactgc gaatttgtaa actatgacaa taaaaagcca tttatctcaa 600
cgacatcgtg taattcttcc atgttttatg tatgtgtttc agatattatg agattactat 660
aaactttttg tatacttata ttccgtaaac tatattaatc atgaagaaaa tgaaaaagta 720

-continued

```
tagaagctgt tcacgagcgg ttgttgaaaa caacaaaatt atacattcaa gatggcttac     780
atatacgtct gtgaggctat catggataat gacaatgcat ctctaaatag gtttttggac     840
aatggattcg accctaacac ggaatatggt actctacaat ctcctcttga aatggctgta     900
atgttcaaga ataccgaggc tataaaaatc ttgatgaggt atggagctaa acctgtagtt     960
actgaatgca caacttcttg tctgcatgat gcggtgttga gagacgacta caaaatagtg    1020
aaagatctgt tgaagaataa ctatgtaaac aatgttcttt acagcggagg ctttactcct    1080
ttgtgtttgg cagcttacct taacaaagtt aatttggtta aacttctatt ggctcattcg    1140
gcggatgtag atatttcaaa cacggatcgg ttaactcctc tacatatagc cgtatcaaat    1200
aaaaatttaa caatggttaa acttctattg aacaaaggtg ctgatactga cttgctggat    1260
aacatgggac gtactccttt aatgatcgct gtacaatctg gaaatattga aatatgtagc    1320
acactactta aaaaaaataa aatgtccaga actgggaaaa attgatcttg ccagctgtaa    1380
ttcatggtag aaaagaagtg ctcaggctac ttttcaacaa aggagcagat gtaaactaca    1440
tctttgaaag aaatggaaaa tcatatactg ttttggaatt gattaaagaa agttactctg    1500
agacacaaaa gaggtagctg aagtggtact ctcaaaatgc agaacgatga ctgcgaagca    1560
agaagtagag aaataacact ttatgacttt cttagttgta gaaaagatag agatataatg    1620
atggtcataa ataactctga tattgcaagt aaatgcaata ataagttaga tttatttaaa    1680
aggatagtta aaaatagaaa aaaagagtta atttgtaggg ttaaaataat acataagatc    1740
ttaaaattta taaatacgca taataataaa aatagattat acttattacc ttcagagata    1800
aaatttaaga tatttactta tttaacttat aaagatctaa aatgcataat ttctaaataa    1860
tgaaaaaaaa gtacatcatg agcaacgcgt tagtatattt tacaatggag attaacgctc    1920
tataccgttc tatgtttatt gattcagatg atgttttaga aaagaaagtt attgaatatg    1980
aaaactttaa tgaagatgaa gatgacgacg atgattattg ttgtaaatct gttttagatg    2040
aagaagatga cgcgctaaag tatactatgg ttacaaagta taagtctata ctactaatgg    2100
cgacttgtgc aagaaggtat agtatagtga aaatgttgtt agattatgat tatgaaaaac    2160
caaataaatc agatccatat ctaaaggtat ctcctttgca cataatttca tctattccta    2220
gtttagaata cttttcatta tatttgttta cagctgaaga cgaaaaaaat atatcgataa    2280
tagaagatta tgttaactct gctaataaga tgaaattgaa tgagtctgtg ataatagcta    2340
taatcagaga agttctaaaa ggaaataaaa atctaactga tcaggatata aaaacattgg    2400
ctgatgaaat caacaaggag gaactgaata tagctaaact attgttagat agaggggcca    2460
aagtaaatta caaggatgtt tacggttctt cagctctcca tagagctgct attggtagga    2520
aacaggatat gataaagctg ttaatcgatc atggagctga tgtaaactct ttaactattg    2580
ctaaagataa tcttattaaa aaaaaataat atcacgttta gtaatattaa aatatattaa    2640
taactctatt actaataact ccagtggata tgaacataat acgaagttta tacattctca    2700
tcaaaatctt attgacatca agttagattg tgaaaatgag attatgaaat taaggaatac    2760
aaaaatagga tgtaagaact tactagaatg ttttatcaat aatgatatga atacagtatc    2820
tagggctata aacaatgaaa cgattaaaaa ttataaaaat catttcccta tatataatac    2880
gctcatagaa aaattcattt ctgaaagtat actaagacac gaattattgg atggagttat    2940
aaattctttt caaggattca ataataaatt gccttacgag attcagtaca ttatactgga    3000
gaatcttaat aaccatgaac taaaaaaaat tttagataat atacattaaa aaggtaaata    3060
gatcatctgt tattataagc aaagatgctt gttgccaata atatacaaca ggtatttgtt    3120
```

-continued

```
tttattttta actacatatt tgatgttcat tctctttata tagtatacac agaaaattca   3180

taatccactt agaatttcta gttatctag                                      3209


<210> SEQ ID NO 67
<211> LENGTH: 3659
<212> TYPE: DNA
<213> ORGANISM: Fowlpox virus

<400> SEQUENCE: 67

gatatctgtg gtctatatat actacaccct accgatatta accaacgagt ttctcacaag     60

aaaacttgtt tagtagatag agattctttg attgtgttta aaagaagtac cagtaaaaag    120

tgtggcatat gcatagaaga aataaacaaa aaacatattt ccgaacagta ttttggaatt    180

ctcccaagtt gtaaacatat tttttgccta tcatgtataa gacgttgggc agatactacc    240

agaaatacag atactgaaaa tacgtgtcct gaatgtagaa tagtttttcc tttcataata    300

cccagtaggt attggataga taataaatat gataaaaaaa tattatataa tagatataag    360

aaaatgattt ttacaaaaat acctataaga acaataaaaa tataattaca tttacggaaa    420

atagctggtt ttagtttacc aacttagagt aattatcata ttgaatctat attgtttttt    480

agttatataa aaacatgatt agcccccaat cggatgaaaa tataaaagat gttgagaatt    540

tcgaatacaa caaaaagagg aatcgtacgt tgtccatatc caaacatata aataaaaatt    600

caaaagtagt attatactgg atgtttagag atcaacgtgt acaagataat tgggctttaa    660

tttacgcaca acgattagcg ttaaaactca aaatacctct aagaatatgc ttttgtgtcg    720

tgccaaaatt tcacactact acttctagac actttatgtt tttaatatcc ggtcttaaag    780

aagtcgcgga agaatgtaaa agactatgta tagggttttc attgatatat ggcgtaccaa    840

aagtaataat tccgtgtata gtaaaaaaat acagagtcgg agtaatcata acggatttct    900

ttccattacg tgttcccgaa agattaatga aacagactgt aatatctctt ccagataaca    960

taccttttat acaagtagac gctcataata tagtaccttg ttgggaagct tctgataaag   1020

aagaatacgg tgcacgaact ttaagaaaaa agatatttga taaattatat gaatatatga   1080

cagaatttcc tgttgttcgt aaacatccat acggtccatt ttctatatct attgcaaaac   1140

ccaaaaatat atcattagac aagacggtat tacccgtaaa atgggcaacg cctggaacaa   1200

aagctggaat aattgtttta aaagaattta taaaaaacag attaccgtca tacgacgcgg   1260

atcataacaa tcctacgtgt gacgctttga gtaacttatc tccgtggcta cattttggtc   1320

atgtatccgc acaacgtgtt gccttagaag tattaaaatg tatacgagaa agcaaaaaaa   1380

acgttgaaac gtttatagat gaaataattg taagaagaga actatcggat aatttttgtt   1440

actataacaa acattatgat agtatccagt ctactcattc atgggttaga aaaacattag   1500

aagatcacat taatgatcct agaaagtata tatattccat taaacaactc gaaaaagcgg   1560

aaactcatga tcctctatgg aacgcgtcac aaatgcagat ggtgagagaa ggaaaaatgc   1620

atagtttttt acgaatgtat tgggctaaga agatacttga atggactaga acacctgaag   1680

acgctttgag ttatagtatc tatttgaaca acaagtacga actagacggc acggatccta   1740

acggatacgt aggttgtatg tggtctattt gcggattaca cgatagagcg tggaaagcaa   1800

gaccgatatt tggaaagata agatatatga attatgagag ttctaagaag aaatttgatg   1860

ttgctgtatt tatacagaaa tacaattaag ataaataata tacagcattg taaccatcgt   1920

catccgttat acggggaata atattaccat acagtattat taaattttct tacgaagaat   1980
```

-continued atagatcggt atttatcgtt agtttatttt acatttatta attaaacatg tctactatta 2040
cctgttatgg aaatgacaaa tttagttata taatttatga taaaattaag ataataataa 2100
tgaaatcaaa taattatgta aatgctacta gattatgtga attacgagga agaaagttta 2160
cgaactggaa aaaattaagt gaatctaaaa tattagtcga taatgtaaaa aaaataaatg 2220
ataaaactaa ccagttaaaa acggatatga ttatatacgt taaggatatt gatcataaag 2280
gaagagatac ttgcggttac tatgtacacc aagatctggt atcttctata tcaaattgga 2340
tatctccgtt attcgccgtt aaggtaaata aaattattaa ctattatata tgtaatgaat 2400
atgatatacg acttagcgaa atggaatctg atatgacaga agtaatagat gtagttgata 2460
aattagtagg aggatacaat gatgaaatag cagaaataat atatttgttt aataaattta 2520
tagaaaaata tattgctaac atatcgttat caactgaatt atctagtata ttaaataatt 2580
ttataaattt tataaatttt aataaaaaat acaataacga cataaagata tttaatcttt 2640
aattcttgat ctgaaaaaca catctataaa actagataaa aagttattcg ataaagataa 2700
taatgaatcg aacgatgaaa aattggaaac agaagttgat aagctaattt ttttcatcta 2760
aatagtatta ttttattgaa gtacgaagtt ttacgttaga taaataataa aggtcgattt 2820
ttactttgtt aaatatcaaa tatgtcatta tctgataaag atacaaaaac acacggtgat 2880
tatcaaccat ctaacgaaca gatattacaa aaaatacgtc ggactatgga aaacgaagct 2940
gatagcctca atagaagaag cattaaagaa attgttgtag atgttatgaa gaattgggat 3000
catcctcaac gaagaaatag ataaagttct aaactggaaa aatgatacat taaacgattt 3060
agatcatcta aatacagatg ataatattaa ggaaatcata caatgtctga ttagagaatt 3120
tgcgtttaaa aagatcaatt ctattatgta tagttatgct atggtaaaac tcaattcaga 3180
taacgaacat tgaaagataa aattaaggat tattttatag aaactattct taaagacaaa 3240
cgtggttata aacaaaagcc attacccgga ttggaaacta aaatactaga tagtattata 3300
agattttaaa aacataaaat taataggttt ttatagattg acttattata tacaatatgg 3360
ataaaagata tatatcaact agaaagttga atgacggatt cttaatttta tattatgatt 3420
caatagaaat tattgtcatg tcgtgtaatc attttataaa tatatcagcg ttactagcta 3480
agaaaaacaa ggactttaat gaatggctaa agatagaatc atttagagaa ataatagata 3540
ctttagataa aattaattac gatctaggac aacgatattg tgaagaactt acggcgcatc 3600
acattccagt gtaattattg aggtcaaagc tagtaactta atagatgaca ggacagctg 3659

<210> SEQ ID NO 68
<211> LENGTH: 2356
<212> TYPE: DNA
<213> ORGANISM: Fowlpox virus

<400> SEQUENCE: 68
tgtctggact aactgatttc atggaacaat tttcatcaaa aatatcagtt atacctagtt 60
ctacaaagac agaactttga tgttatgttt gtgtttgtat agaaaatttt gggatactaa 120
ctgatatttc tgaatatttc tgaatatttc atgttactta cttactccta tcttagacga 180
taataaaatt cgaggcgtaa tatgtttttc caaatatttg aaattcttat acgtatcggc 240
gaagaaaagt aacatactat aagtgttatg caagtaaggt atgttaatga tattggattt 300
aatttcattg acaatacata tgtccaaaca ttccactcgt aattatgtac ggaacgactt 360
tagttaaata cttagtcaca aaaaacttat gactgtcatt atctgaaaac ggtgattccc 420
ataaatcaga atacttaata ttaaatagaa tgctcgcttc tggaggtttc cggatactag 480

-continued

```
ataacatatc ttctgtatta tagtttaatt cactcatttt attacataat acagtaacat    540

ctcccgaaac caatgatgtt atattagatt tacttacata cttcttgtaa ctatcatgaa    600

tacgtttgtt atgatctata aagaagatgg atgtatattc tgttctagat agcaagttct    660

ttaagttatt ctttgtctgt attactatca tcgtcttcat catcgtctaa aggtagcatt    720

atataataaa tctaatagtt gatttctcga tctatcagta ctcgctttca ataacatttt    780

tactataagc ataatagaag gcggtgatat cactatattt ttatcgggta ttcttttagt    840

aattagttag ttcgtagaat ttcgtagaga taaaagccaa tttgttgttg atactgctta    900

cgttactcat gtttcttgtt tctgttaatt aacaggtata cccttacaat aagtttaatt    960

aacttttagg tttttgtgaa gaacttttag cttctagttc ccttatccat aattgggtct   1020

tagatctaga ttcttcccat gtataaaggg ggacataccc aaaatcttta aatgctttgt   1080

ccgtttctat agtaaatgtc gtacattcct taatcaaagt ataaggattt agtaaaggcg   1140

tgtaagaaca aataggtgat agtaatactc ttaaaccttt attaatatta gcgataaacc   1200

ttaaacacca taaaggaaga catgtattcc gtagatccat ccctaattga ttaaagaaat   1260

gcatgttaaa atcatgataa tgttcagtag gagaggtatc gtaacagtaa tacacgttat   1320

tgcagagagg actatgttga ccatttttcta tcatatttct tgctgctaaa atatgcatcc   1380

aagctacgtt tcctgcatag actctgctat gaaatacttt atcatccgca tatttataca   1440

ttttcctgct tttatacgat cttctgtata aagtttctag tactggacag tattctccga   1500

aaacacctaa tgggcgtagc gacaagtgca taatctaagt cctatattag acatagtacc   1560

gttagcttct agtatatatt tctcagataa cttgtttact aagaggataa gcctctttat   1620

ggttagattg ataatacgta ttctcgtttc ctcttatcat cgcatctccg gagaaagtta   1680

ggacctaccg cagaataact actcgtatat actaagactc ttacgccgtt atacagacaa   1740

gaatctacta cgttcttcgt tccgttgata ttaacgtcca ttatagagtc gttagtaaac   1800

ttacccgcta catcatttat cgaagcaata tgaatgacca catctgctga tctaagcgct   1860

tcgtccaaag tacttttatt tctaacatct ccaatcacgg gaactatctt tattatatta   1920

catttttcta caagatctag taaccattgg tcgattctaa tatcgtaaac acgaacttct   1980

ttttaaagag gattcgaaca agataagatt atttataatg tgtctaccta aaaatccaca   2040

ccctccggtt accacgtata ctagtgtacg cattttgagt attaactata taagaccaaa   2100

attatatttt cattttctgt tatattatac tatataataa aaacaaataa atatacgaat   2160

attataagaa atttagaaca cgttattaaa gtattgcctt ttttattaac ggcgtgttct   2220

tgtaattgcc gtttagaata gtctttattt actttagata actcttctat cataaccgtc   2280

tccttattcc aatcttcttc agaagtacat gagtacttac cgaagtttat catcatagag   2340

attatatatg aagaaa                                                   2356
```

<210> SEQ ID NO 69
<211> LENGTH: 16
<212> TYPE: DNA
<213> ORGANISM: Artificial Sequence
<220> FEATURE:
<223> OTHER INFORMATION: Oligonucleotide primer referred to as HIVP5

<400> SEQUENCE: 69
tgtggcaaag aagggc 16

<210> SEQ ID NO 70

-continued

<211> LENGTH: 26
<212> TYPE: DNA
<213> ORGANISM: Artificial Sequence
<220> FEATURE:
<223> OTHER INFORMATION: Oligonucleotide primer referred to as HIVP6

<400> SEQUENCE: 70
ttggatcctt attgtgacga ggggtc 26

<210> SEQ ID NO 71
<211> LENGTH: 106
<212> TYPE: DNA
<213> ORGANISM: Artificial Sequence
<220> FEATURE:
<223> OTHER INFORMATION: Oligonucleotide referred to as HIVL17

<400> SEQUENCE: 71
gatcttgaga taaagtgaaa atatatatca ttatattaca aagtacaatt atttaggttt 60
aatcatgggt gcgagagcgt cagtattaag cgggggagaa ttagat 106

<210> SEQ ID NO 72
<211> LENGTH: 104
<212> TYPE: DNA
<213> ORGANISM: Artificial Sequence
<220> FEATURE:
<223> OTHER INFORMATION: Oligonucleotide referred to HIVL18

<400> SEQUENCE: 72
cgatctaatt ctcccccgct taatactgac gctctcgcac ccatgattaa acctaaataa 60
ttgtactttg taatataatg atatatattt tcactttatc tcaa 104

<210> SEQ ID NO 73
<211> LENGTH: 68
<212> TYPE: DNA
<213> ORGANISM: Artificial Sequence
<220> FEATURE:
<223> OTHER INFORMATION: Oligonucleotide referred to as HIVL19

<400> SEQUENCE: 73
ctgacacagg acacagcaat caggtcagcc aaaattacta atttttatct cgaggtcgac 60
aggacccg 68

<210> SEQ ID NO 74
<211> LENGTH: 72
<212> TYPE: DNA
<213> ORGANISM: Artificial Sequence
<220> FEATURE:
<223> OTHER INFORMATION: Oligonucleotide referred to as HIVL20

<400> SEQUENCE: 74
gatccgggtc ctgtcgacct cgagataaaa attagtaatt ttggctgacc tgattgctgt 60
gtcctgtgtc ag 72

<210> SEQ ID NO 75
<211> LENGTH: 16
<212> TYPE: DNA
<213> ORGANISM: Artificial Sequence
<220> FEATURE:
<223> OTHER INFORMATION: Oligonucleotide primer referred to as HIVP7

<400> SEQUENCE: 75
aagaaaatta taggac 16

-continued

<210> SEQ ID NO 76
<211> LENGTH: 24
<212> TYPE: DNA
<213> ORGANISM: Artificial Sequence
<220> FEATURE:
<223> OTHER INFORMATION: Oligonucleotide primer referred to as HIVP8

<400> SEQUENCE: 76
ttggatccct aatcctcatc ctgt 24

<210> SEQ ID NO 77
<211> LENGTH: 36
<212> TYPE: DNA
<213> ORGANISM: Artificial Sequence
<220> FEATURE:
<223> OTHER INFORMATION: Oligonucleotide primer referred to as HIVP37

<400> SEQUENCE: 77
aaaggatccc ccgggttaaa aatttaaagt gcaacc 36

<210> SEQ ID NO 78
<211> LENGTH: 3807
<212> TYPE: DNA
<213> ORGANISM: Artificial Sequence
<220> FEATURE:
<223> OTHER INFORMATION: DNA sequence of plasmid referred to as pHIV32,
coding strand

<400> SEQUENCE: 78
taatgtagta tactaatatt aactcacatt tgactaatta gctataaaaa cccgggatcg 60
attctagaat aaaaattatc cctgcctaac tctattcact acagagagta cagcaaaaac 120
tattcttaaa cctaccaagc ctcctactat cattatgaat aatctttttt ctctctgcac 180
cactcttctc tttgccttgg tgggtgctac tcctaatggt tcaattgtta ctactttata 240
tttatataat tcacttctcc aattgtccct catatctcct cctccaggtc tgaagatctc 300
ggtgtcgttc gtgtccgtgt ccttaccacc atctcttgtt aatagtagcc ctgtaatatt 360
tgatgaacat ctaatttgtc cttcaatggg aggggcatat attgcttttc ctacttcctg 420
ccacatgttt ataatttgtt ttattttgca ttgaagtgtg atattgttat ttgaccctgt 480
agtattattc caagtattat taccattcca agtactatta aacagtggtg atgaattaca 540
gtagaagaat tcccctccac aattaaaact gtgcattaca atttctgggt cccctcctga 600
ggattgatta aagactattg ttttattctt aaattgttct tttaatttgc taactatctg 660
tcttaaagtg tcattccatt ttgctctact aatgttacaa tgtgcttgtc ttatagttcc 720
tattatattt tttgttgtat aaaatgctct ccctggtcct atatgtatcc tttttctttt 780
attgtagttg ggtcttgtac aattaatttg tacagattca ttcagatgta ctatgatggt 840
tttagcatta tcattgaaat tctcagatct aattactacc tcttcttctg ctagactgcc 900
atttaacagc agttgagttg atactactgg cctaattcca tgtgtacatt gtactgtgct 960
gacattttta catgatcctt ttccactgaa ctttttatcg ttacacttta gaatcgcaaa 1020
accagccggg gcacaatagt gtatgggaat tggctcaaag gatatctttg gacaagcttg 1080
tgtaatgact gaggtattac aacttatcaa cctatagctg gtactatcat tatttattga 1140
tactatatca agtttataaa gaagtgcata ttctttctgc atcttatctc ttatgcttgt 1200
ggtgatattg aaagagcagt ttttcatttc tcctcccttt attgttccct cgctattact 1260
attgttatta gcagtactat tattggtatt agtagtattc ctcaaatcag tgcaatttaa 1320
agtaacacag agtggggtta attttacaca tggctttagg ctttgatccc ataaactgat 1380

-continued

```
tatatcctca tgcatctgtt ctaccatgtt atttttccac atgttaaaat tttctgtcac   1440
atttaccaat tctacttctt gtgggttggg gtctgtgggt acacaggcat gtgtggccca   1500
aacattatgt acctctgtat catatgcttt agcatctgat gcacaaaata gagtggtggt   1560
tgcttctttc cacacaggta ccccataata gactgtgacc cacaattttt ctgtagcact   1620
acagatcatc aacatcccaa ggagcatggt gccccatctc caccccccatc tccacaagtg   1680
ctgatatttc tccttcactc tcattgccac tgtcttctgc tctttcatta cgatacaaac   1740
ttaacgcata tcgcgataat gaaataattt atgattattt ctcgctttca atttaacaca   1800
accctcaaga acctttgtat ttattttcac tttttaagta tagaataaag aagctctaat   1860
taattaagct acaaatagtt tcgttttcac cttgtctaat aactaattaa ttaacccgga   1920
tcttgagata aagtgaaaat atatatcatt atattacaaa gtacaattat ttaggtttaa   1980
tcatgggtgc gagagcgtca gtattaagcg ggggagaatt agatcgatgg gaaaaaattc   2040
ggttaaggcc agggggaaag aaaaaatata aattaaaaca tatagtatgg gcaagcaggg   2100
agctagaacg attcgcagtt aatcctggcc tgttagaaac atcagaaggc tgtagacaaa   2160
tactgggaca gctacaacca tcccttcaga caggatcaga agaacttaga tcattatata   2220
atacagtagc aaccctctat tgtgtgcatc aaaggataga gataaaagac accaaggaag   2280
ctttagacaa gatagaggaa gagcaaaaca aaagtaagaa aaaagcacag caagcagcag   2340
ctgacacagg acacagcaat caggtcagcc aaaattaccc tatagtgcag aacatccagg   2400
ggcaaatggt acatcaggcc atatcaccta gaactttaaa tgcatgggta aaagtagtag   2460
aagagaaggc tttcagccca gaagtgatac ccatgttttc agcattatca gaaggagcca   2520
ccccacaaga tttaaacacc atgctaaaca cagtgggggg acatcaagca gccatgcaaa   2580
tgttaaaaga gaccatcaat gaggaagctg cagaatggga tagagtgcat ccagtgcatg   2640
cagggcctat tgcaccaggc cagatgagag aaccaagggg aagtgacata gcaggaacta   2700
ctagtaccct tcaggaacaa ataggatgga tgacaaataa tccacctatc ccagtaggag   2760
aaatttataa aagatggata atcctgggat taaataaaat agtaagaatg tatagcccta   2820
ccagcattct ggacataaga caaggaccaa aagaaccctt tagagactat gtagaccggt   2880
tctataaaac tctaagagcc gagcaagctt cacaggaggt aaaaaattgg atgacagaaa   2940
ccttgttggt ccaaaatgcg aacccagatt gtaagactat tttaaaagca ttgggaccag   3000
cggctacact agaagaaatg atgacagcat gtcagggagt aggaggaccc ggccataagg   3060
caagagtttt ggctgaagca atgagccaag taacaaattc agctaccata atgatgcaga   3120
gaggcaattt taggaaccaa agaaagattg ttaagtgttt caattgtggc aaagaagggc   3180
acacagccag aaattgcagg gcccctagga aaaagggctg ttggaaatgt ggaaaggaag   3240
gacaccaaat gaaagattgt actgagagac aggctaattt tttagggaag atctggcctt   3300
cctacaaggg aaggccaggg aattttcttc agagcagacc agagccaaca gccccaccag   3360
aagagagctt caggtctggg gtagagacaa caactccccc tcagaagcag gagccgatag   3420
acaaggaact gtatccttta acttccctca gatcactctt tggcaacgac ccctcgtcac   3480
aataaagata ggggggcaac taaaggaagc tctattagat acaggagcag atgatacagt   3540
attagaagaa atgagtttgc caggaagatg gaaaccaaaa atgatagggg gaattggagg   3600
ttttatcaaa gtaagacagt atgatcagat actcatagaa atctgtggac ataaagctat   3660
aggtacagta ttagtaggac ctacacctgt caacataatt ggaagaaatc tgttgactca   3720
```

-continued gattggttgc actttaaatt tttaacccgg gggatcccga tttttatgac tagttaatca 3780
aataaaaagc atacaagcta ttgcttc 3807

<210> SEQ ID NO 79
<211> LENGTH: 3808
<212> TYPE: DNA
<213> ORGANISM: Artificial Sequence
<220> FEATURE:
<223> OTHER INFORMATION: DNA sequence of plasmid referred to as pHIV32, template strand

<400> SEQUENCE: 79
attacatcat atgattataa ttgagtgtaa actgattaat cgatattttt gggccctagc 60
taagatctta tttttaatag ggacggattg agataagtga tgtctctcat gtcgtttttg 120
ataagaattt ggatggttcg gaggatgata gtaatactta ttagaaaaaa gagagacgtg 180
gtgagaagag aaacggaacc acccacgatg aggattacca agttaacaat gatgaaatat 240
aaatatatta agtgaagagg ttaacaggga gtatagagga ggaggtccag acttctagag 300
ccacagcaag cacaggcaca ggaatggtgg tagagaacaa ttatcatcgg gacattataa 360
actacttgta gattaaacag gaagttaccc tccccgtata taacgaaaag gatgaaggac 420
ggtgtacaaa tattaaacaa aataaaacgt aacttcacac tataacaata aactgggaca 480
tcataataag gttcataata atggtaaggt tcatgataat ttgtcaccac tacttaatgt 540
catcttctta aggggaggtg ttaattttga cacgtaatgt taaagaccca ggggaggact 600
cctaactaat ttctgataac aaaataagaa tttaacaaga aaattaaacg attgatagac 660
agaatttcac agtaaggtaa aacgagatga ttacaatgtt acacgaacag aatatcaagg 720
ataatataaa aaacaacata ttttacgaga gggaccagga tatacatagg aaaaagaaaa 780
taacatcaac ccagaacatg ttaattaaac atgtctaagt aagtctacat gatactacca 840
aaatcgtaat agtaacttta agagtctaga ttaatgatgg agaagaagac gatctgacgg 900
taaattgtcg tcaactcaac tatgatgacc ggattaaggt acacatgtaa catgacacga 960
ctgtaaaaat gtactaggaa aaggtgactt gaaaaatagc aatgtgaaat cttagcgttt 1020
tggtcggccc cgtgttatca catacccta accgagtttc ctatagaaac ctgttcgaac 1080
acattactga ctccataatg ttgaatagtt ggatatcgac catgatagta ataaataact 1140
atgatatagt tcaaatattt cttcacgtat aagaaagacg tagaatagag aatacgaaca 1200
ccactataac tttctcgtca aaaagtaaag aggagggaaa taacaaggga gcgataatga 1260
taacaataat cgtcatgata ataaccataa tcatcataag gagtttagtc acgttaaatt 1320
tcattgtgtc tcaccccaat taaaatgtgt accgaaatcc gaaactaggg tatttgacta 1380
atataggagt acgtagacaa gatggtacaa taaaaaggtg tacaatttta aaagacagtg 1440
taaatggtta agatgaagaa cacccaaccc cagacaccca tgtgtccgta cacaccgggt 1500
ttgtaataca tggagacata gtatacgaaa tcgtagacta cgtgttttat ctcaccacca 1560
acgaagaaag gtgtgtccat ggggtattat ctgacactgg gtgttaaaaa gacatcgtga 1620
tgtctagtag ttgtagggtt cctcgtacca cggggtagag gtgggggtag aggtgttcac 1680
gactataaag aggaagtgag agtaacggtg acagaagacg agaaagtata tgctatgttt 1740
gaattgcgta tagcgctatt actttattaa atactaataa agagcgaaag ttaaattgtg 1800
ttgggagttc ttggaaacat aaataaaagt gaaaaattca tatcttattt cttcgagatt 1860
aattaattcg atgtttatca aagcaaaagt ggaacagatt attgattaat taattgggcc 1920

-continued

```
tagaactcta tttcactttt atatatagta atataatgtt tcatgttaat aaatccaaat   1980

tagtacccac gctctcgcag tcataattcg ccccctctta atctagctac ccttttttaa   2040

gccaattccg gtccccttt cttttttata tttaattttg tatatcatac ccgttcgtcc   2100

ctcgatcttg ctaagcgtca attaggaccg gacaatcttt gtagtcttcc gacatctgtt   2160

tatgaccctg tcgatgttgg tagggaagtc tgtcctagtc ttcttgaatc tagtaatata   2220

ttatgtcatc gttgggagat aacacacgta gtttcctatc tctattttct gtggttcctt   2280

cgaaatctgt tctatctcct tctcgttttg ttttcattct tttttcgtgt cgttcgtcgt   2340

cgactgtgtc ctgtgtcgtt agtccagtcg gttttaatgg gatatcacgt cttgtaggtc   2400

cccgtttacc atgtagtccg gtatagtgga tcttgaaatt tacgtaccca ttttcatcat   2460

cttctcttcc gaaagtcggg tcttcactat gggtacaaaa gtcgtaatag tcttcctcgg   2520

tggggtgttc taaatttgtg gtacgatttg tgtcaccccc ctgtagttcg tcggtacgtt   2580

tacaattttc tctggtagtt actccttcga cgtcttaccc tatctcacgt aggtcacgta   2640

cgtcccggat aacgtggtcc ggtctactct cttggttccc cttcactgta tcgtccttga   2700

tgatcatggg aagtccttgt ttatcctacc tactgtttat taggtggata gggtcatcct   2760

ctttaaatat tttctaccta ttaggaccct aatttatttt atcattctta catatcggga   2820

tggtcgtaag acctgtattc tgttcctggt tttcttggga aatctctgat acatctggcc   2880

aagatatttt gagattctcg gctcgttcga agtgtcctcc attttttaac ctactgtctt   2940

tggaacaacc aggttttacg cttgggtcta acattctgat aaaattttcg taaccctggt   3000

cgccgatgtg atcttcttta ctactgtcgt acagtccctc atcctcctgg gccggtattc   3060

cgttctcaaa accgacttcg ttactcggtt cattgtttaa gtcgatggta ttactacgtc   3120

tctccgttaa aatccttggt ttctttctaa caattcacaa agttaacacc gtttcttccc   3180

gtgtgtcggt ctttaacgtc ccggggatcc tttttcccga caacctttac acctttcctt   3240

cctgtggttt actttctaac atgactctct gtccgattaa aaaatccctt ctagaccgga   3300

aggatgttcc cttccggtcc cttaaaagaa gtctcgtctg gtctcggttg tcggggtggt   3360

cttctctcga agtccagacc ccatctctgt tgttgagggg gagtcttcgt cctcggctat   3420

ctgttccttg acataggaaa ttgaagggag tctagtgaga aaccgttgct ggggagcagt   3480

gttatttcta tccccccgtt gatttccttc gagataatct atgtcctcgt ctactatgtc   3540

ataatcttct ttactcaaac ggtccttcta cctttggttt ttactatccc ccttaacctc   3600

caaaatagtt tcattctgtc atactagtct atgagtatct ttagacacct gtatttcgat   3660

atccatgtca taatcatcct ggatgtggac agttgtatta accttcttta gacaactgag   3720

tctaaccaac gtgaaattta aaaattgggc cccctagggc taaaaatact gatcaattag   3780

tttatttttc gtatgttcga taacgaag                                       3808
```

<210> SEQ ID NO 80
<211> LENGTH: 4291
<212> TYPE: DNA
<213> ORGANISM: Artificial Sequence
<220> FEATURE:
<223> OTHER INFORMATION: Nucleotide sequence of C3 locus of ALVAC in the plasmid, pVQH6CP3L, coding strand

<400> SEQUENCE: 80

```
agatatttgt tagcttctgc cggagatacc gtgaaaatct attttctgga aggaaaggga     60

ggtcttatct attctgtcag cagagtaggt tcctctaatg acgaagacaa tagtgaatac    120
```

-continued

```
ttgcatgaag gtcactgtgt agagttcaaa actgatcatc agtgtttgat aactctagcg    180
tgtacgagtc cttctaacac tgtggtttat tggctggaat aaaaggataa agacacctat    240
actgattcat tttcatctgt caacgtttct ctaagagatt cataggtatt attattacat    300
cgatctagaa gtctaataac tgctaagtat attattggat ttaacgcgct ataaacgcat    360
ccaaaaccta caaatatagg agaagcttct cttatgaaac ttcttaaagc tttactctta    420
ctattactac tcaaaagaga tattacatta attatgtgat gaggcatcca acatataaag    480
aagactaaag ctgtagaagc tgttatgaag aatatcttat cagatatatt agatgcattg    540
ttagttctgt agatcagtaa cgtatagcat acgagtataa ttatcgtagg tagtaggtat    600
cctaaaataa atctgataca gataataact ttgtaaatca attcagcaat ttctctatta    660
tcatgataat gattaataca cagcgtgtcg ttattttttg ttacgatagt atttctaaag    720
taaagagcag gaatccctag tataatagaa ataatccata tgaaaaatat agtaatgtac    780
atatttctaa tgttaacata tttataggta aatccaggaa gggtaatttt tacatatcta    840
tatacgctta ttacagttat taaaaatata cttgcaaaca tgttagaagt aaaaaagaaa    900
gaactaattt tacaaagtgc tttaccaaaa tgccaatgga aattacttag tatgtatata    960
atgtataaag gtatgaatat cacaaacagc aaatcggcta ttcccaagtt gagaaacggt   1020
ataatagata tatttctaga taccattaat aaccttataa gcttgacgtt tcctataatg   1080
cctactaaga aaactagaag atacatacat actaacgcca tacgagagta actactcatc   1140
gtataactac tgttgctaac agtgacactg atgttataac tcatctttga tgtggtataa   1200
atgtataata actatattac actggtattt tatttcagtt atatactata tagtattaaa   1260
aattatattt gtataattat attattatat tcagtgtaga aagtaaaata ctataaatat   1320
gtatctctta tttataactt attagtaaag tatgtactat tcagttatat tgttttataa   1380
aagctaaatg ctactagatt gatataaatg aatatgtaat aaattagtaa tgtagtatac   1440
taatattaac tcacatttga ctaattagct ataaaaaccc gggctgcagg aattcctcga   1500
gtacgataca aacttaacgg atatcgcgat aatgaaataa tttatgatta tttctcgctt   1560
tcaatttaac acaaccctca agaacctttg tatttatttt cactttttaa gtatagaata   1620
aagaagctct aattaattaa gctacaaata gtttcgtttt caccttgtct aataactaat   1680
taattaaccc ggatcccgat tttatgact agttaatcaa ataaaaagca tacaagctat   1740
tgcttcgcta tcgttacaaa atggcaggaa ttttgtgtaa actaagccac atacttgcca   1800
atgaaaaaaa tagtagaaag gatactattt taatgggatt agatgttaag gttccttggg   1860
attatagtaa ctgggcatct gttaactttt acgacgttag gttagatact gatgttacag   1920
attataataa tgttacaata aaatacatga caggatgtga tatttttcct catataactc   1980
ttggaatagc aaatatggat caatgtgata gatttgaaaa tttcaaaaag caaataactg   2040
atcaagattt acagactatt tctatagtct gtaaagaaga gatgtgtttt cctcagagta   2100
acgcctctaa acagttggga gcgaaaggat gcgctgtagt tatgaaactg gaggtatctg   2160
atgaacttag agccctaaga aatgttctgc tgaatgcggt accctgttcg aaggacgtgt   2220
ttggtgatat cacagtagat aatccgtgga atcctcacat aacagtagga tatgttaagg   2280
aggacgatgt cgaaaacaag aaacgcctaa tggagtgcat gtccaagttt agggggcaag   2340
aaatacaagt tctaggatgg tattaataag tatctaagta tttggtataa tttattaaat   2400
agtataatta taacaaataa taaataacat gataacggtt tttattagaa taaaatagag   2460
ataatatcat aatgatatat aatacttcat taccagaaat gagtaatgga agacttataa   2520
```

-continued

```
atgaactgca taaagctata aggtatagag atataaattt agtaaggtat atacttaaaa   2580

aatgcaaata caataacgta aatatactat caacgtcttt gtatttagcc gtaagtattt   2640

ctgatataga aatggtaaaa ttattactag aacacggtgc cgatatttta aaatgtaaaa   2700

atcctcctct tcataaagct gctagtttag ataatacaga aattgctaaa ctactaatag   2760

attctggcgc tgacatagaa cagatacatt ctggaaatag tccgttatat atttctgtat   2820

atagaaacaa taagtcatta actagatatt tattaaaaaa aggtgttaat tgtaatagat   2880

tctttctaaa ttattacgat gtactgtatg ataagatatc tgatgatatg tataaaatat   2940

ttatagattt taatattgat cttaatatac aaactagaaa ttttgaaact ccgttacatt   3000

acgctataaa gtataagaat atagatttaa ttaggatatt gttagataat agtattaaaa   3060

tagataaaag tttatttttg cataaacagt atctcataaa ggcacttaaa aataattgta   3120

gttacgatat aatagcgtta cttataaatc acggagtgcc tataaacgaa caagatgatt   3180

taggtaaaac cccattacat cattcggtaa ttaatagaag aaaagatgta acagcacttc   3240

tgttaaatct aggagctgat ataaacgtaa tagatgactg tatgggcagt cccttacatt   3300

acgctgtttc acgtaacgat atcgaaacaa caaagacact tttagaaaga ggatctaatg   3360

ttaatgtggt taataatcat atagataccg ttctaaatat agctgttgca tctaaaaaca   3420

aaactatagt aaacttatta ctgaagtacg gtactgatac aaagttggta ggattagata   3480

aacatgttat tcacatagct atagaaatga aagatattaa tatactgaat gcgatcttat   3540

tatatggttg ctatgtaaac gtctataatc ataaaggttt cactcctcta tacatggcag   3600

ttagttctat gaaaacagaa tttgttaaac tcttacttga ccacggtgct tacgtaaatg   3660

ctaaagctaa gttatctgga aatactcctt tacataaagc tatgttatct aatagtttta   3720

ataatataaa attactttta tcttataacg ccgactataa ttctctaaat aatcacggta   3780

atacgcctct aacttgtgtt agctttttag atgacaagat agctattatg ataatatcta   3840

aaatgatgtt agaaatatct aaaaatcctg aaatagctaa ttcagaaggt tttatagtaa   3900

acatggaaca tataaacagt aataaaagac tactatctat aaaagaatca tgcgaaaaag   3960

aactagatgt tataacacat ataaagttaa attctatata ttcttttaat atctttcttg   4020

acaataacat agatcttatg gtaaagttcg taactaatcc tagagttaat aagatacctg   4080

catgtatacg tatatatagg gaattaatac ggaaaaataa atcattagct tttcatagac   4140

atcagctaat agttaaagct gtaaaagaga gtaagaatct aggaataata ggtaggttac   4200

ctatagatat caaacatata ataatggaac tattaagtaa taatgattta cattctgtta   4260

tcaccagctg ttgtaaccca gtagtataaa g                                  4291
```

<210> SEQ ID NO 81
<211> LENGTH: 4291
<212> TYPE: DNA
<213> ORGANISM: Artificial Sequence
<220> FEATURE:
<223> OTHER INFORMATION: Nucleotide sequence of C3 locus of ALVAC in the plasmid, pVQH6CP3L, template strand

<400> SEQUENCE: 81

```
tctataaaca atcgaagacg gcctctatgg cacttttaga taaaagacct tcctttccct     60

ccagaataga taagacagtc gtctcatcca aggagattac tgcttctgtt atcacttatg    120

aacgtacttc cagtgacaca tctcaagttt tgactagtag tcacaaacta ttgagatcgc    180

acatgctcag gaagattgtg acaccaaata accgacctta ttttcctatt tctgtggata    240
```

-continued

```
tgactaagta aaagtagaca gttgcaaaga gattctctaa gtatccataa taataatgta    300
gctagatctt cagattattg acgattcata taataaccta aattgcgcga tatttgcgta    360
ggttttggat gtttatatcc tcttcgaaga gaatactttg aagaatttcg aaatgagaat    420
gataatgatg agttttctct ataatgtaat taatacacta ctccgtaggt tgtatatttc    480
ttctgatttc gacatcttcg acaatacttc ttatagaata gtctatataa tctacgtaac    540
aatcaagaca tctagtcatt gcatatcgta tgctcatatt aatagcatcc atcatccata    600
ggattttatt tagactatgt ctattattga aacatttagt taagtcgtta aagagataat    660
agtactatta ctaattatgt gtcgcacagc aataaaaaac aatgctatca taaagatttc    720
atttctcgtc cttagggatc atattatctt tattaggtat actttttata tcattacatg    780
tataaagatt acaattgtat aaatatccat ttaggtcctt cccattaaaa atgtatagat    840
atatgcgaat aatgtcaata atttttatat gaacgtttgt acaatcttca ttttttcttt    900
cttgattaaa atgtttcacg aaatggtttt acggttacct ttaatgaatc atacatatat    960
tacatatttc catacttata gtgtttgtcg tttagccgat aagggttcaa ctctttgcca   1020
tattatctat ataaagatct atggtaatta ttggaatatt cgaactgcaa aggatattac   1080
ggatgattct tttgatcttc tatgtatgta tgattgcggt atgctctcat tgatgagtag   1140
catattgatg acaacgattg tcactgtgac tacaatattg agtagaaact acaccatatt   1200
tacatattat tgatataatg tgaccataaa ataaagtcaa tatatgatat atcataattt   1260
ttaatataaa catattaata taataatata agtcacatct ttcattttat gatatttata   1320
catagagaat aaatattgaa taatcatttc atacatgata agtcaatata acaaaatatt   1380
ttcgatttac gatgatctaa ctatatttac ttatacatta tttaatcatt acatcatatg   1440
attataattg agtgtaaact gattaatcga tatttttggg cccgacgtcc ttaaggagct   1500
catgctatgt ttgaattgcc tatagcgcta ttactttatt aaatactaat aaagagcgaa   1560
agttaaattg tgttgggagt tcttggaaac ataaataaaa gtgaaaaatt catatcttat   1620
ttcttcgaga ttaattaatt cgatgtttat caaagcaaaa gtggaacaga ttattgatta   1680
attaattggg cctagggcta aaaatactga tcaattagtt tatttttcgt atgttcgata   1740
acgaagcgat agcaatgttt taccgtcctt aaaacacatt tgattcggtg tatgaacggt   1800
tacttttttt atcatctttc ctatgataaa attaccctaa tctacaattc caaggaaccc   1860
taatatcatt gacccgtaga caattgaaaa tgctgcaatc caatctatga ctacaatgtc   1920
taatattatt acaatgttat tttatgtact gtcctacact ataaaaagga gtatattgag   1980
aaccttatcg tttataccta gttacactat ctaaactttt aaagtttttc gtttattgac   2040
tagttctaaa tgtctgataa agatatcaga catttcttct ctacacaaaa ggagtctcat   2100
tgcggagatt tgtcaaccct cgctttccta cgcgacatca atactttgac ctccatagac   2160
tacttgaatc tcgggattct ttacaagacg acttacgcca tgggacaagc ttcctgcaca   2220
aaccactata gtgtcatcta ttaggcacct taggagtgta ttgtcatcct atacaattcc   2280
tcctgctaca gcttttgttc tttgcggatt acctcacgta caggttcaaa tcccccgttc   2340
tttatgttca agatcctacc ataattattc atagattcat aaaccatatt aaataattta   2400
tcatattaat attgtttatt atttattgta ctattgccaa aaataatctt attttatctc   2460
tattatagta ttactatata ttatgaagta atggtcttta ctcattacct tctgaatatt   2520
tacttgacgt atttcgatat tccatatctc tatatttaaa tcattccata tatgaatttt   2580
```

-continued

```
ttacgtttat gttattgcat ttatatgata gttgcagaaa cataaatcgg cattcataaa   2640

gactatatct ttaccatttt aataatgatc ttgtgccacg gctataaaat tttacatttt   2700

taggaggaga agtatttcga cgatcaaatc tattatgtct ttaacgattt gatgattatc   2760

taagaccgcg actgtatctt gtctatgtaa gacctttatc aggcaatata taaagacata   2820

tatctttgtt attcagtaat tgatctataa ataatttttt tccacaatta acattatcta   2880

agaaagattt aataatgcta catgacatac tattctatag actactatac atattttata   2940

aatatctaaa attataacta gaattatatg tttgatcttt aaaactttga ggcaatgtaa   3000

tgcgatattt catattctta tatctaaatt aatcctataa caatctatta tcataatttt   3060

atctattttc aaataaaaac gtatttgtca tagagtattt ccgtgaattt ttattaacat   3120

caatgctata ttatcgcaat gaatatttag tgcctcacgg atatttgctt gttctactaa   3180

atccattttg ggtaatgta gtaagccatt aattatcttc ttttctacat tgtcgtgaag   3240

acaatttaga tcctcgacta tatttgcatt atctactgac atacccgtca gggaatgtaa   3300

tgcgacaaag tgcattgcta tagctttgtt gtttctgtga aaatctttct cctagattac   3360

aattacacca attattagta tatctatggc aagatttata tcgacaacgt agatttttgt   3420

tttgatatca tttgaataat gacttcatgc catgactatg tttcaaccat cctaatctat   3480

ttgtacaata agtgtatcga tatctttact ttctataatt atatgactta cgctagaata   3540

atataccaac gatacatttg cagatattag tatttccaaa gtgaggagat atgtaccgtc   3600

aatcaagata cttttgtctt aaacaatttg agaatgaact ggtgccacga atgcatttac   3660

gatttcgatt caatagacct ttatgaggaa atgtatttcg atacaataga ttatcaaaat   3720

tattatattt taatgaaaat agaatattgc ggctgatatt aagagattta ttagtgccat   3780

tatgcggaga ttgaacacaa tcgaaaaatc tactgttcta tcgataatac tattatagat   3840

tttactacaa tctttataga tttttaggac tttatcgatt aagtcttcca aaatatcatt   3900

tgtaccttgt atatttgtca ttattttctg atgatagata ttttcttagt acgctttttc   3960

ttgatctaca atattgtgta tatttcaatt taagatatat aagaaaatta tagaaagaac   4020

tgttattgta tctagaatac catttcaagc attgattagg atctcaatta ttctatggac   4080

gtacatatgc atatatatcc cttaattatg ccttttttatt tagtaatcga aaagtatctg   4140

tagtcgatta tcaatttcga cattttctct cattcttaga tccttattat ccatccaatg   4200

gatatctata gtttgtatat tattaccttg ataattcatt attactaaat gtaagacaat   4260

agtggtcgac aacattgggt catcatattt c                                  4291
```

<210> SEQ ID NO 82
<211> LENGTH: 88
<212> TYPE: DNA
<213> ORGANISM: Artificial Sequence
<220> FEATURE:
<223> OTHER INFORMATION: Oligonucleotide primer referred to as VQPCR13

<400> SEQUENCE: 82

```
atcatcaagc ttaattaatt agttattaga caaggtgaaa acgaaactat ttgtagctta     60

attattagac atcatgcagt ggttaaac                                        88
```

<210> SEQ ID NO 83
<211> LENGTH: 69
<212> TYPE: DNA
<213> ORGANISM: Artificial Sequence
<220> FEATURE:
<223> OTHER INFORMATION: Oligonucleotide primer referred to as I3PCRCTL -continued

<400> SEQUENCE: 83
ctagctacgt gatgaaatgc taatctagaa tcaaatctcc actccatgat taaacctaaa 60
taattgtac 69

<210> SEQ ID NO 84
<211> LENGTH: 77
<212> TYPE: DNA
<213> ORGANISM: Artificial Sequence
<220> FEATURE:
<223> OTHER INFORMATION: Oligonucleotide primer referred to as CTLPCR

<400> SEQUENCE: 84
gaattcctcg aggatcctct agattaacaa tttttaaaat attcaggatg taattctcta 60
gctacgtgat gaaatgc 77

<210> SEQ ID NO 85
<211> LENGTH: 35
<212> TYPE: DNA
<213> ORGANISM: Artificial Sequence
<220> FEATURE:
<223> OTHER INFORMATION: Oligonucleotide primer referred to as H6PCR1

<400> SEQUENCE: 85
actactaagc ttctttattc tatacttaaa aagtg 35

<210> SEQ ID NO 86
<211> LENGTH: 88
<212> TYPE: DNA
<213> ORGANISM: Artificial Sequence
<220> FEATURE:
<223> OTHER INFORMATION: Oligonucleotide primer referred to as NCCPCR1

<400> SEQUENCE: 86
cagctgcttt gtaagtcatt ggtcttaaag gtacttgagg tgttactgga aaacctacca 60
ttacgataca aacttaacgg atatcgcg 88

<210> SEQ ID NO 87
<211> LENGTH: 102
<212> TYPE: DNA
<213> ORGANISM: Artificial Sequence
<220> FEATURE:
<223> OTHER INFORMATION: Oligonucleotide referred to as NCC174A

<400> SEQUENCE: 87
acttacaaag cagctgtaga tctttctcac tttttaaaag aaaaaggagg tttagaaggg 60
ctaattcatt ctcaacgaag acaagatatt cttgatttgt gg 102

<210> SEQ ID NO 88
<211> LENGTH: 102
<212> TYPE: DNA
<213> ORGANISM: Artificial Sequence
<220> FEATURE:
<223> OTHER INFORMATION: Oligonucleotide referred to as NCC174B

<400> SEQUENCE: 88
ccacaaatca agaatatctt gtcttcgttg agaatgaatt agcccttcta aacctccttt 60
ttcttttaaa aagtgagaaa gatctacagc tgctttgtaa gt 102

<210> SEQ ID NO 89
<211> LENGTH: 54
<212> TYPE: DNA

-continued

<213> ORGANISM: Artificial Sequence
<220> FEATURE:
<223> OTHER INFORMATION: Oligonucleotide primer referred to as NCCPCR2

<400> SEQUENCE: 89
ctgccaatca ggaaaatatc cttgtgtatg ataaatccac aaatcaagaa tatc 54

<210> SEQ ID NO 90
<211> LENGTH: 79
<212> TYPE: DNA
<213> ORGANISM: Artificial Sequence
<220> FEATURE:
<223> OTHER INFORMATION: Oligonucleotide referred to as NCC291A

<400> SEQUENCE: 90
ggatattttc ctgattggca gaattacaca ccaggaccag gagtcagata cccattaacc 60
tttggttggt gctacaagc 79

<210> SEQ ID NO 91
<211> LENGTH: 79
<212> TYPE: DNA
<213> ORGANISM: Artificial Sequence
<220> FEATURE:
<223> OTHER INFORMATION: Oligonucleotide referred to as NCC291B

<400> SEQUENCE: 91
gcttgtagca ccaaccaaag gttaatgggt atctgactcc tggtcctggt gtgtaattct 60
gccaatcagg aaaatatcc 79

<210> SEQ ID NO 92
<211> LENGTH: 49
<212> TYPE: DNA
<213> ORGANISM: Artificial Sequence
<220> FEATURE:
<223> OTHER INFORMATION: Oligonucleotide primer referred to as NCCPCR3

<400> SEQUENCE: 92
actactgaat tctcgagaaa aattatggta ctagcttgta gcaccaacc 49

<210> SEQ ID NO 93
<211> LENGTH: 801
<212> TYPE: DNA
<213> ORGANISM: Artificial Sequence
<220> FEATURE:
<223> OTHER INFORMATION: DNA sequence of the plasmid, p2-60-HIV.3,
coding strand

<400> SEQUENCE: 93
agtacaataa aaagtattaa ataaaaatac ttacttacga aaaaatgact aattagctat 60
aaaaacccgg gctgcagctc gaggatcctc tagattaaca atttttaaaa tattcaggat 120
gtaattctct agctacgtga tgaaatgcta atctagaatc aaatctccac tccatgatta 180
aacctaaata attgtacttt gtaatataat gatatatatt ttcactttat ctcatttgag 240
aataaaaatg tttttgttta accactgcat gatgtctaat taattaagct acaaatagtt 300
tcgttttcac cttgtctaat aactaattaa ttaagcttct ttattctata cttaaaaagt 360
gaaaataaat acaaaggttc ttgagggttg tgttaaattg aaagcgagaa ataatcataa 420
attatttcat tatcgcgata tccgttaagt ttgtatcgta atggtaggtt ttccagtaac 480
acctcaagta cctttaagac caatgactta caaagcagct gtagatcttt ctcacttttt 540
aaaagaaaaa ggaggtttag aagggctaat tcattctcaa cgaagacaag atattcttga 600

-continued

```
tttgtggatt tatcatacac aaggatattt tcctgattgg cagaattaca caccaggacc    660

aggagtcaga tacccattaa cctttggttg gtgctacaag ctagtaccat aatttttctc    720

gaggaattct ttttattgat taactagtca aatgagtata tataattgaa aaagtaaaat    780

ataaatcata taataatgaa a                                              801
```

```
<210> SEQ ID NO 94
<211> LENGTH: 801
<212> TYPE: DNA
<213> ORGANISM: Artificial Sequence
<220> FEATURE:
<223> OTHER INFORMATION: DNA sequence of the plasmid, p2-60-HIV.3,
      template strand

<400> SEQUENCE: 94

tcatgttatt tttcataatt tatttttatg aatgaatgct tttttactga ttaatcgata     60

tttttgggcc cgacgtcgag ctcctaggag atctaattgt taaaaatttt ataagtccta    120

cattaagaga tcgatgcact actttacgat tagatcttag tttagaggtg aggtactaat    180

ttggatttat taacatgaaa cattatatta ctatatataa aagtgaaata gagtaaactc    240

ttatttttac aaaaacaaat tggtgacgta ctacagatta attaattcga tgtttatcaa    300

agcaaaagtg gaacagatta ttgattaatt aattcgaaga aataagatat gaatttttca    360

cttttattta tgtttccaag aactcccaac acaatttaac tttcgctctt tattagtatt    420

taataaagta atagcgctat aggcaattca aacatagcat taccatccaa aaggtcattg    480

tggagttcat ggaaattctg gttactgaat gtttcgtcga catctagaaa gagtgaaaaa    540

ttttcttttt cctccaaatc ttcccgatta agtaagagtt gcttctgttc tataagaact    600

aaacacctaa atagtatgtg ttcctataaa aggactaacc gtcttaatgt gtggtcctgg    660

tcctcagtct atgggtaatt ggaaaccaac cacgatgttc gatcatggta ttaaaaagag    720

ctccttaaga aaaataacta attgatcagt ttactcatat atattaactt tttcatttta    780

tatttagtat attattactt t                                              801
```

```
<210> SEQ ID NO 95
<211> LENGTH: 27
<212> TYPE: PRT
<213> ORGANISM: Human immunodeficiency virus type 1

<400> SEQUENCE: 95

Cys Asn Lys Phe Tyr Glu Pro His Leu Glu Arg Ala Val His His Phe
1               5                   10                  15

Ala Leu Arg Ser Asp Phe Arg Trp Glu Met Pro
            20                  25
```

```
<210> SEQ ID NO 96
<211> LENGTH: 83
<212> TYPE: PRT
<213> ORGANISM: Human immunodeficiency virus type 1

<400> SEQUENCE: 96

Met Val Gly Phe Pro Val Thr Pro Gln Val Pro Leu Arg Pro Met Thr
1               5                   10                  15

Tyr Lys Ala Ala Val Asp Leu Ser His Phe Leu Lys Glu Lys Gly Gly
            20                  25                  30

Leu Glu Gly Leu Ile His Ser Gln Arg Arg Gln Asp Ile Leu Asp Leu
        35                  40                  45

Trp Ile Tyr His Thr Gln Gly Tyr Phe Pro Asp Trp Gln Asn Tyr Thr
```

-continued

```
    50                  55                  60

Pro Gly Pro Gly Val Arg Tyr Pro Leu Thr Phe Gly Trp Cys Tyr Lys
65                  70                  75                  80

Leu Val Pro
```

<210> SEQ ID NO 97
<211> LENGTH: 1615
<212> TYPE: DNA
<213> ORGANISM: Artificial Sequence
<220> FEATURE:
<223> OTHER INFORMATION: Nucleotide sequence of the ALVAC C6 locus in the plasmid, pC6L, coding strand

<400> SEQUENCE: 97

```
gagctcgcgg ccgcctatca aaagtcttaa tgagttaggt gtagatagta tagatattac     60

tacaaaggta ttcatatttc ctatcaattc taaagtagat gatattaata actcaaagat    120

gatgatagta gataatagat acgctcatat aatgactgca aatttggacg gttcacattt    180

taatcatcac gcgttcataa gtttcaactg catagatcaa aatctcacta aaaagatagc    240

cgatgtattt gagagagatt ggacatctaa ctacgctaaa gaaattacag ttataaataa    300

tacataatgg attttgttat catcagttat atttaacata agtacaataa aaagtattaa    360

ataaaaatac ttacttacga aaaaatgact aattagctat aaaaacccgg gctgcagctc    420

gaggaattct tttattgat taactagtca aatgagtata tataattgaa aaagtaaaat    480

ataaatcata taataatgaa acgaaatatc agtaatagac aggaactggc agattcttct    540

tctaatgaag taagtactgc taaatctcca aaattagata aaaatgatac agcaaataca    600

gcttcattca acgaattacc ttttaatttt ttcagacaca ccttattaca aactaactaa    660

gtcagatgat gagaaagtaa atataaattt aacttatggg tataatataa taaagattca    720

tgatattaat aatttactta acgatgttaa tagacttatt ccatcaaccc cttcaaacct    780

ttctggatat tataaaatac cagttaatga tattaaaata gattgtttaa gagatgtaaa    840

taattatttg gaggtaaagg atataaaatt agtctatctt tcacatggaa atgaattacc    900

taatattaat aattatgata ggaatttttt aggatttaca gctgttatat gtatcaacaa    960

tacaggcaga tctatggtta tggtaaaaca ctgtaacggg aagcagcatt ctatggtaac   1020

tggcctatgt ttaatagcca gatcatttta ctctataaac attttaccac aaataatagg   1080

atcctctaga tatttaatat tatatctaac aacaacaaaa aaatttaacg atgtatggcc   1140

agaagtattt tctactaata aagataaaga tagtctatct tatctacaag atatgaaaga   1200

agataatcat ttagtagtag ctactaatat ggaaagaaat gtatacaaaa acgtggaagc   1260

ttttatatta aatagcatat tactagaaga tttaaaatct agacttagta taacaaaaca   1320

gttaaatgcc aatatcgatt ctatatttca tcataacagt agtacattaa tcagtgatat   1380

actgaaacga tctacagact caactatgca aggaataagc aatatgccaa ttatgtctaa   1440

tattttaact ttagaactaa aacgttctac caatactaaa aataggatac gtgataggct   1500

gttaaaagct gcaataaata gtaaggatgt agaagaaata ctttgttcta taccttcgga   1560

ggaaagaact ttagaacaac ttaagtttaa tcaaacttgt atttatgaag gtacc        1615
```

<210> SEQ ID NO 98
<211> LENGTH: 1615
<212> TYPE: DNA
<213> ORGANISM: Artificial Sequence
<220> FEATURE:
<223> OTHER INFORMATION: Nucleotide sequence of the ALVAC C6 locus in -continued the plasmid, pC6L, template strand

<400> SEQUENCE: 98

```
ctcgagcgcc ggcggatagt tttcagaatt actcaatcca catctatcat atctataatg     60
atgtttccat aagtataaag gatagttaag atttcatcta ctataattat tgagtttcta    120
ctactatcat ctattatcta tgcgagtata ttactgacgt ttaaacctgc caagtgtaaa    180
attagtagtg cgcaagtatt caaagttgac gtatctagtt ttagagtgat tttctatcg     240
gctacataaa ctctctctaa cctgtagatt gatgcgattt ctttaatgtc aatatttatt    300
atgtattacc taaaacaata gtagtcaata taaattgtat tcatgttatt tttcataatt    360
tatttttatg aatgaatgct tttttactga ttaatcgata tttttgggcc cgacgtcgag    420
ctccttaaga aaaataacta attgatcagt ttactcatat atattaactt tttcatttta    480
tatttagtat attattactt tgctttatag tcattatctg tccttgaccg tctaagaaga    540
agattacttc attcatgacg atttagaggt tttaatctat ttttactatg tcgtttatgt    600
cgaagtaagt tgcttaatgg aaaattaaaa aagtctgtgt ggaataatgt ttgattgatt    660
cagtctacta ctctttcatt tatatttaaa ttgaataccc atattatatt atttctaagt    720
actataatta ttaaatgaat tgctacaatt atctgaataa ggtagttggg gaagtttgga    780
aagacctata atattttatg gtcaattact ataattttat ctaacaaatt ctctacattt    840
attaataaac ctccatttcc tatattttaa tcagatagaa agtgtacctt tacttaatgg    900
attataatta ttaatactat ccttaaaaaa tcctaaatgt cgacaatata catagttgtt    960
atgtccgtct agataccaat accattttgt gacattgccc ttcgtcgtaa gataccattg   1020
accggataca aattatcggt ctagtaaaat gagatatttg taaaatggtg tttattatcc   1080
taggagatct ataaattata atatagattg ttgttgtttt tttaaattgc tacataccgg   1140
tcttcataaa agatgattat ttctatttct atcagataga atagatgttc tatactttct   1200
tctattagta aatcatcatc gatgattata cctttcttta catatgtttt tgcaccttcg   1260
aaaatataat ttatcgtata atgatcttct aaattttaga tctgaatcat attgttttgt   1320
caatttacgg ttatagctaa gatataaagt agtattgtca tcatgtaatt agtcactata   1380
tgactttgct agatgtctga gttgatacgt tccttattcg ttatacggtt aatacagatt   1440
ataaaattga aatcttgatt ttgcaagatg gttatgattt ttatcctatg cactatccga   1500
caattttcga cgttatttat cattcctaca tcttctttat gaaacaagat atggaagcct   1560
cctttcttga aatcttgttg aattcaaatt agtttgaaca taaatacttc catgg        1615
```

<210> SEQ ID NO 99
<211> LENGTH: 43
<212> TYPE: DNA
<213> ORGANISM: Artificial Sequence
<220> FEATURE:
<223> OTHER INFORMATION: Oligonucleotide primer referred to as P1A

<400> SEQUENCE: 99

```
tttgtatcgt aatgattgag actgtaccag taaaattaaa gcc                       43
```

<210> SEQ ID NO 100
<211> LENGTH: 66
<212> TYPE: DNA
<213> ORGANISM: Artificial Sequence
<220> FEATURE:
<223> OTHER INFORMATION: Oligonucleotide primer referred to as P1B

<400> SEQUENCE: 100

-continued gggctgcagg aattctaatc aattaaggcc caatttttga aattttccct tccttttcca 60
tctctg 66

<210> SEQ ID NO 101
<211> LENGTH: 53
<212> TYPE: DNA
<213> ORGANISM: Artificial Sequence
<220> FEATURE:
<223> OTHER INFORMATION: Oligonucleotide primer referred to as P2A

<400> SEQUENCE: 101
acaaagtaca attatttagg tttaatcatg gcaatattcc aaagtagcat gac 53

<210> SEQ ID NO 102
<211> LENGTH: 44
<212> TYPE: DNA
<213> ORGANISM: Artificial Sequence
<220> FEATURE:
<223> OTHER INFORMATION: Oligonucleotide primer referred to as P2B

<400> SEQUENCE: 102
atcatcctcg agaaaaatta ggtaagtccc cacctcaaca gatg 44

<210> SEQ ID NO 103
<211> LENGTH: 58
<212> TYPE: DNA
<213> ORGANISM: Artificial Sequence
<220> FEATURE:
<223> OTHER INFORMATION: Oligonucleotide primer referred to as P3A

<400> SEQUENCE: 103
aaaatatata attacaatat aaaatgccac taacagaaga agcagagcta gaactggc 58

<210> SEQ ID NO 104
<211> LENGTH: 60
<212> TYPE: DNA
<213> ORGANISM: Artificial Sequence
<220> FEATURE:
<223> OTHER INFORMATION: Oligonucleotide primer referred to as P3B

<400> SEQUENCE: 104
atcatctcta gactcgagga tccataaaaa ttatcctgtt ttcagatttt taaatggctc 60

<210> SEQ ID NO 105
<211> LENGTH: 52
<212> TYPE: DNA
<213> ORGANISM: Artificial Sequence
<220> FEATURE:
<223> OTHER INFORMATION: Oligonucleotide primer referred to as P2IVH

<400> SEQUENCE: 105
gtcatgctac ttttgaatat tgccatgatt aaacctaaat aattgtactt tg 52

<210> SEQ ID NO 106
<211> LENGTH: 56
<212> TYPE: DNA
<213> ORGANISM: Artificial Sequence
<220> FEATURE:
<223> OTHER INFORMATION: Oligonucleotide primer referred to as IVHP1

<400> SEQUENCE: 106
tttaatttta ctggtacagt ctcaatcatt acgatacaaa cttaacggat atcgcg 56

<210> SEQ ID NO 107

-continued

<211> LENGTH: 44
<212> TYPE: DNA
<213> ORGANISM: Artificial Sequence
<220> FEATURE:
<223> OTHER INFORMATION: Oligonucleotide primer referred to as EPS42K

<400> SEQUENCE: 107
aattgattag aattcctgca gcccgggtca aaaaaatata aatg 44

<210> SEQ ID NO 108
<211> LENGTH: 58
<212> TYPE: DNA
<213> ORGANISM: Artificial Sequence
<220> FEATURE:
<223> OTHER INFORMATION: Oligonucleotide primer referred to as 42KP3B

<400> SEQUENCE: 108
ccagttctag ctctgcttct tctgttagtg gcattttata ttgtaattat atattttc 58

<210> SEQ ID NO 109
<211> LENGTH: 32
<212> TYPE: DNA
<213> ORGANISM: Artificial Sequence
<220> FEATURE:
<223> OTHER INFORMATION: Oligonucleotide primer referred to as I3PCR1

<400> SEQUENCE: 109
atcatcggat ccaagcttac atcatgcagt gg 32

<210> SEQ ID NO 110
<211> LENGTH: 45
<212> TYPE: DNA
<213> ORGANISM: Artificial Sequence
<220> FEATURE:
<223> OTHER INFORMATION: Oligonucleotide primer referred to as FIXPOL2

<400> SEQUENCE: 110
atcatcctcg agctattcaa ttaggttgta agtccccacc tcaac 45

<210> SEQ ID NO 111
<211> LENGTH: 1035
<212> TYPE: DNA
<213> ORGANISM: Artificial Sequence
<220> FEATURE:
<223> OTHER INFORMATION: DNA sequence of the plasmid, pC5POLT5A, coding
strand

<400> SEQUENCE: 111
ttagaaatta tgcattttag atctttataa gcggccgtga ttaactagtc ataaaaaccc 60
gggatcgatt ctagactcga gctattcaat taggttgtaa gtccccacct caacagatgt 120
tgtctcagct cctctatttt tgttctatgc tgccctattt ctaagtcaga tcctacatac 180
aaatcatcca tgtattgata gataactatg tctggatttt gttttctaaa aggctctaag 240
atttttgtca tgctactttg gaatattgcc atgattaaac ctaaataatt gtactttgta 300
atataatgat atatattttc actttatctc atttgagaat aaaaatgttt ttgtttaacc 360
actgcatgat gtaagcttct ttattctata cttaaaaagt gaaaataaat acaaaggttc 420
ttgagggttg tgttaaattg aaagcgagaa ataatcataa attatttcat tatcgcgata 480
tccgttaagt ttgtatcgta atgattgaga ctgtaccagt aaaattaaag ccaggaatgg 540
atggcccaaa agttaaacaa tggccattga cagaagaaaa aataaaagca ttagtagaaa 600
tttgtacaga gatggaaaag gaagggaaaa tttcaaaaat tgggccttaa ttgattagaa 660

-continued

```
ttcctgcagc ccaggtcaaa aaaatataaa tgattcacca tctgatagaa aaaaaattta    720

ttgggaagaa tatgataata ttttgggatt tcaaaattga aaatatataa ttacaatata    780

aaatgccact aacagaagaa gcagagctag aactggcaga aaacagagag attctaaaag    840

aaccagtaca tggagtgtat tatgacccat caaaagactt aatagcagaa atacagaagc    900

aggggcaagg ccaatggaca tatcaaattt atcaagagcc atttaaaaat ctgaaaacag    960

gataattttt atggatcctt tttatagcta attagtcacg tacctttgag agtaccactt   1020

cagctacctc ctttg                                                     1035
```

<210> SEQ ID NO 112
<211> LENGTH: 1035
<212> TYPE: DNA
<213> ORGANISM: Artificial Sequence
<220> FEATURE:
<223> OTHER INFORMATION: DNA sequence of the plasmid, pC5POLT5A, template strand

<400> SEQUENCE: 112

```
aatctttaat acgtaaaatc tagaaatatt cgccggcact aattgatcag tatttttggg     60

ccctagctaa gatctgagct cgataagtta atccaacatt caggggtgga gttgtctaca    120

acagagtcga ggagataaaa acaagatacg acgggataaa gattcagtct aggatgtatg    180

tttagtaggt acataactat ctattgatac agacctaaaa caaaagattt tccgagattc    240

taaaaacagt acgatgaaac cttataacgg tactaatttg gatttattaa catgaaacat    300

tatattacta tatataaaag tgaaatagag taaactctta tttttacaaa aacaaattgg    360

tgacgtacta cattcgaaga aataagatat gaatttttca cttttattta tgtttccaag    420

aactcccaac acaatttaac tttcgctctt tattagtatt taataaagta atagcgctat    480

aggcaattca aacatagcat tactaactct gacatggtca ttttaatttc ggtccttacc    540

taccgggttt tcaatttgtt accggtaact gtcttctttt ttattttcgt aatcatcttt    600

aaacatgtct ctaccttttc cttccctttt aaagttttta acccggaatt aactaatctt    660

aaggacgtcg ggtccagttt ttttatattt actaagtggt agactatctt ttttttaaat    720

aacccttctt atactattat aaaaccctaa agttttaact tttatatatt aatgttatat    780

tttacggtga ttgtcttctt cgtctcgatc ttgaccgtct tttgtctctc taagattttc    840

ttggtcatgt acctcacata atactgggta gttttctgaa ttatcgtctt tatgtcttcg    900

tccccgttcc ggttacctgt atagtttaaa tagttctcgg taaattttta gacttttgtc    960

ctattaaaaa tacctaggaa aaatatcgat taatcagtgc atggaaactc tcatggtgaa   1020

gtcgatggag gaaac                                                     1035
```

<210> SEQ ID NO 113
<211> LENGTH: 60
<212> TYPE: PRT
<213> ORGANISM: Human immunodeficiency virus type 1

<400> SEQUENCE: 113

```
Thr Thr Leu Gly Trp Arg Leu Leu His Gln Arg Leu Glu Glu Ile Lys
1               5                   10                  15

Thr Arg His Gln Gly Ile Glu Leu Asp Ser Gly Val Tyr Leu Asp Asp
            20                  25                  30

Met Tyr Gln Tyr Ile Val Ile Asp Pro Asn Gln Lys Arg Phe Pro Glu
        35                  40                  45

Leu Ile Lys Thr Met Ser Ser Gln Phe Ile Ala Met
```

-continued 50 55 60

<210> SEQ ID NO 114
<211> LENGTH: 49
<212> TYPE: PRT
<213> ORGANISM: Human immunodeficiency virus type 1

<400> SEQUENCE: 114

Met Ile Glu Thr Val Pro Val Lys Leu Lys Pro Gly Met Asp Gly Pro
1 5 10 15

Lys Val Lys Gln Trp Pro Leu Thr Glu Glu Lys Ile Lys Ala Leu Val
20 25 30

Glu Ile Cys Thr Glu Met Glu Lys Glu Gly Lys Ile Ser Lys Ile Gly
35 40 45

Pro

<210> SEQ ID NO 115
<211> LENGTH: 59
<212> TYPE: PRT
<213> ORGANISM: Human immunodeficiency virus type 1

<400> SEQUENCE: 115

Met Pro Leu Thr Glu Glu Ala Glu Leu Glu Leu Ala Glu Asn Arg Glu
1 5 10 15

Ile Leu Lys Glu Pro Val His Gly Val Tyr Tyr Asp Pro Ser Lys Asp
20 25 30

Leu Ile Ala Glu Ile Gln Lys Gln Gly Gln Gly Gln Trp Thr Tyr Gln
35 40 45

Ile Tyr Gln Glu Pro Phe Lys Asn Leu Lys Thr
50 55

<210> SEQ ID NO 116
<211> LENGTH: 2049
<212> TYPE: DNA
<213> ORGANISM: Artificial Sequence
<220> FEATURE:
<223> OTHER INFORMATION: Nucleotide sequence of the ALVAC C5 locus of the plasmid, pNC5L-SP5, coding strand

<400> SEQUENCE: 116
gaattgcggc cgctgaatgt taaatgttat actttggatg aagctataaa tatgcattgg 60
aaaaataatc catttaaaga aaggattcaa atactacaaa acctaagcga taatatgtta 120
actaagctta ttcttaacga cgctttaaat atacacaaat aaacataatt tttgtataac 180
ctaacaaata actaaaacat aaaaataata aaaggaaatg taatatcgta attattttac 240
tcaggaatgg ggttaaatat ttatatcacg tgtatatcta tactgttatc gtatactctt 300
tacaattact attacgaata tgcaagagat aataagatta cgtatttaag agaatcttgt 360
catgataatt gggtacgaca tagtgataaa tgctatttcg catcgttaca taaagtcagt 420
tggaaagatg gatttgacag atgtaactta ataggtgcaa aaatgttaaa taacagcatt 480
ctatcggaag ataggatacc agttatatta tacaaaaatc actggttgga taaaacagat 540
tctgcaatat tcgtaaaaga tgaagattac tgcgaatttg taaactatga caataaaaag 600
ccatttatct caacgacatc gtgtaattct tccatgtttt atgtatgtgt ttcagatatt 660
atgagattac tataaacttt ttgtatactt atattccgta aactatatta atcatgaaga 720
aaatgaaaaa gtatagaagc tgttcacgag cggttgttga aaacaacaaa attatacatt 780
caagatggct tacatatacg tctgtgaggc tatcatggat aatgacaatg catctctaaa 840

-continued taggtttttg gacaatggat tcgaccctaa cacggaatat ggtactctac aatctcctct 900
tgaaatggct gtaatgttca agaataccga ggctataaaa atcttgatga ggtatggagc 960
taaacctgta gttactgaat gcacaacttc ttgtctgcat gatgcggtgt tgagagacga 1020
ctacaaaata gtgaaagatc tgttgaagaa taactatgta aacaatgttc tttacagcgg 1080
aggctttact cctttgtgtt tggcagctta ccttaacaaa gttaatttgg ttaaacttct 1140
attggctcat tcggcggatg tagatatttc aaacacggat cggttaactc ctctacatat 1200
agccgtatca aataaaaatt taacaatggt taaacttcta ttgaacaaag gtgctgatac 1260
tgacttgctg gataacatgg gacgtactcc tttaatgatc gctgtacaat ctggaaatat 1320
tgaaatatgt agcacactac ttaaaaaaaa taaaatgtcc agaactggga aaaattgatc 1380
ttgccagctg taattcatgg tagaaaagaa gtgctcaggc tacttttcaa caaaggagca 1440
gatgtaaact acatctttga aagaaatgga aaatcatata ctgttttgga attgattaaa 1500
gaaagttact ctgagacaca aaagaggtag ctgaagtggt actctcaaag gtacgtgact 1560
aattagctat aaaaaggatc cggtaccctc gagtctagaa tcgatcccgg gtttttatga 1620
ctagttaatc acggccgctt ataaagatct aaaatgcata atttctaaat aatgaaaaaa 1680
aagtacatca tgagcaacgc gttagtatat tttacaatgg agattaacgc tctataccgt 1740
tctatgttta ttgattcaga tgatgtttta gaaaagaaag ttattgaata tgaaaacttt 1800
aatgaagatg aagatgacga cgatgattat tgttgtaaat ctgttttaga tgaagaagat 1860
gacgcgctaa agtatactat ggttacaaag tataagtcta tactactaat ggcgacttgt 1920
gcaagaaggt atagtatagt gaaaatgttg ttagattatg attatgaaaa accaaataaa 1980
tcagatccat atctaaaggt atctcctttg cacataattt catctattcc tagtttagaa 2040
tacctgcag 2049

<210> SEQ ID NO 117
<211> LENGTH: 2049
<212> TYPE: DNA
<213> ORGANISM: Artificial Sequence
<220> FEATURE:
<223> OTHER INFORMATION: DNA sequence of the ALVAC C5 locus in the plasmid, pCN5L-SP5, template strand

<400> SEQUENCE: 117
cttaacgccg gcgacttaca atttacaata tgaaacctac ttcgatattt atacgtaacc 60
tttttattag gtaaatttct ttcctaagtt tatgatgttt tggattcgct attatacaat 120
tgattcgaat aagaattgct gcgaaattta tatgtgttta tttgtattaa aaacatattg 180
gattgtttat tgattttgta tttttattat tttcctttac attatagcat taataaaatg 240
agtccttacc ccaatttata aatatagtgc acatatagat atgacaatag catatgagaa 300
atgttaatga taatgcttat acgttctcta ttattctaat gcataaattc tcttagaaca 360
gtactattaa cccatgctgt atcactattt acgataaagc gtagcaatgt atttcagtca 420
acctttctac ctaaactgtc tacattgaat tatccacgtt tttacaattt attgtcgtaa 480
gatagccttc tatcctatgg tcaatataat atgtttttag tgaccaacct attttgtcta 540
agacgttata agcattttct acttctaatg acgcttaaac atttgatact gttatttttc 600
ggtaaataga gttgctgtag cacattaaga aggtacaaaa tacatacaca aagtctataa 660
tactctaatg atatttgaaa aacatatgaa tataaggcat ttgatataat tagtacttct 720
tttacttttt catatcttcg acaagtgctc gccaacaact tttgttgttt taatatgtaa 780

-continued

```
gttctaccga atgtatatgc agacactccg atagtaccta ttactgttac gtagagattt    840
atccaaaaac ctgttaccta agctgggatt gtgccttata ccatgagatg ttagaggaga    900
actttaccga cattacaagt tcttatggct ccgatatttt tagaactact ccatacctcg    960
atttggacat caatgactta cgtgttgaag aacagacgta ctacgccaca actctctgct   1020
gatgttttat cactttctag acaacttctt attgatacat ttgttacaag aaatgtcgcc   1080
tccgaaatga ggaaacacaa accgtcgaat ggaattgttt caattaaacc aatttgaaga   1140
taaccgagta agccgcctac atctataaag tttgtgccta gccaattgag gagatgtata   1200
tcggcatagt ttatttttaa attgttacca atttgaagat aacttgtttc cacgactatg   1260
actgaacgac ctattgtacc ctgcatgagg aaattactag cgacatgtta gacctttata   1320
actttataca tcgtgtgatg aatttttttt attttacagg tcttgaccct ttttaactag   1380
aacggtcgac attaagtacc atcttttctt cacgagtccg atgaaaagtt gtttcctcgt   1440
ctacatttga tgtagaaact ttctttacct tttagtatat gacaaaacct taactaattt   1500
ctttcaatga gactctgtgt tttctccatc gacttcacca tgagagtttc catgcactga   1560
ttaatcgata tttttcctag gccatgggag ctcagatctt agctagggcc caaaaatact   1620
gatcaattag tgccggcgaa tatttctaga ttttacgtat taaagattta ttactttttt   1680
ttcatgtagt actcgttgcg caatcatata aaatgttacc tctaattgcg agatatggca   1740
agatacaaat aactaagtct actacaaaat cttttctttc aataacttat acttttgaaa   1800
ttacttctac ttctactgct gctactaata acaacattta gacaaaatct acttcttcta   1860
ctgcgcgatt tcatatgata ccaatgtttc atattcagat atgatgatta ccgctgaaca   1920
cgttcttcca tatcatatca cttttacaac aatctaatac taatactttt tggtttattt   1980
agtctaggta tagatttcca tagaggaaac gtgtattaaa gtagataagg atcaaatctt   2040
atggacgtc                                                           2049
```

<210> SEQ ID NO 118
<211> LENGTH: 34
<212> TYPE: PRT
<213> ORGANISM: Artificial Sequence
<220> FEATURE:
<223> OTHER INFORMATION: Peptide referred to as CLTB-36, which is a small portion of the HIV1 gp120 envelope glycoprotein, the V3 loop.

<400> SEQUENCE: 118

```
Gly Pro Lys Glu Pro Phe Arg Asp Tyr Val Asp Arg Phe Tyr Lys Asn
1               5                   10                  15

Lys Arg Lys Arg Ile His Ile Gly Pro Gly Arg Ala Phe Tyr Thr Thr
            20                  25                  30

Lys Asn
```

<210> SEQ ID NO 119
<211> LENGTH: 26
<212> TYPE: PRT
<213> ORGANISM: Artificial Sequence
<220> FEATURE:
<223> OTHER INFORMATION: Synthetic peptide representing the HIV MN gp120 V3 loop

<400> SEQUENCE: 119

```
Cys Asn Lys Arg Lys Arg Ile His Ile Gly Pro Gly Arg Ala Phe Tyr
1               5                   10                  15
```

-continued

Thr Thr Lys Asn Ile Ile Gly Thr Ile Cys
20 25

<210> SEQ ID NO 120
<211> LENGTH: 26
<212> TYPE: PRT
<213> ORGANISM: Artificial Sequence
<220> FEATURE:
<223> OTHER INFORMATION: Synthetic peptide representing HIV MN gp120 V3 loop

<400> SEQUENCE: 120

Cys Asn Lys Arg Lys Arg Ile His Ile Gly Pro Gly Arg Ala Phe Tyr
1 5 10 15

Thr Thr Lys Asn Ile Ile Gly Thr Ile Cys
20 25

<210> SEQ ID NO 121
<211> LENGTH: 23
<212> TYPE: DNA
<213> ORGANISM: Artificial Sequence
<220> FEATURE:
<223> OTHER INFORMATION: Primer referred to as HIVP72

<400> SEQUENCE: 121
ttattaccat tccaagtact att 23

<210> SEQ ID NO 122
<211> LENGTH: 109
<212> TYPE: DNA
<213> ORGANISM: Artificial Sequence
<220> FEATURE:
<223> OTHER INFORMATION: Primer referred to as HIVP74

<400> SEQUENCE: 122
tctgtacaaa ttaattgtac aagacccaac tacgagctcg acaaatgggc ccatatagga 60
ccagggagag aattggataa gtgggcgaat ataataggaa ctataagac 109

<210> SEQ ID NO 123
<211> LENGTH: 20
<212> TYPE: DNA
<213> ORGANISM: Artificial Sequence
<220> FEATURE:
<223> OTHER INFORMATION: Oligonucleotide referred to as HIVMN6

<400> SEQUENCE: 123
gggttattaa tgatctgtag 20

<210> SEQ ID NO 124
<211> LENGTH: 37
<212> TYPE: DNA
<213> ORGANISM: Artificial Sequence
<220> FEATURE:
<223> OTHER INFORMATION: Oligonucleotide referred to as HIV3B2

<400> SEQUENCE: 124
gaattacagt agaagaattc ccctccacaa ttaaaac 37

<210> SEQ ID NO 125
<211> LENGTH: 37
<212> TYPE: DNA
<213> ORGANISM: Artificial Sequence
<220> FEATURE:
<223> OTHER INFORMATION: Oligonucleotide referred to as HIV3B1

<400> SEQUENCE: 125

-continued gttttaattg tggaggggaa ttcttctact gtaattc 37

<210> SEQ ID NO 126
<211> LENGTH: 24
<212> TYPE: DNA
<213> ORGANISM: Artificial Sequence
<220> FEATURE:
<223> OTHER INFORMATION: Oligonucleotide referred to as HIVMN4

<400> SEQUENCE: 126
atcatcgagc tcctatcgct gctc 24

<210> SEQ ID NO 127
<211> LENGTH: 30
<212> TYPE: DNA
<213> ORGANISM: Artificial Sequence
<220> FEATURE:
<223> OTHER INFORMATION: Oligonucleotide referred to as HIVMN5

<400> SEQUENCE: 127
atcatcgagc tctgttcctt gggttcttag 30

<210> SEQ ID NO 128
<211> LENGTH: 43
<212> TYPE: DNA
<213> ORGANISM: Artificial Sequence
<220> FEATURE:
<223> OTHER INFORMATION: Oligonucleotide referred to as HIVMN3P

<400> SEQUENCE: 128
atcatctcta gaataaaaat tatagcaaag ccctttccaa gcc 43

<210> SEQ ID NO 129
<211> LENGTH: 87
<212> TYPE: DNA
<213> ORGANISM: Artificial Sequence
<220> FEATURE:
<223> OTHER INFORMATION: Oligonucleotide referred to as HIVTM1

<400> SEQUENCE: 129
ttattcataa tgatagtagg aggcttggta ggtttaagaa tagtttttgc tgtactctct 60
gtagtgaata gagttaggca gggataa 87

<210> SEQ ID NO 130
<211> LENGTH: 87
<212> TYPE: DNA
<213> ORGANISM: Artificial Sequence
<220> FEATURE:
<223> OTHER INFORMATION: Oligonucleotide referred to as HIVTM2

<400> SEQUENCE: 130
ttatccctgc ctaactctat tcactacaga gagtacagca aaaactattc ttaaacctac 60
caagcctcct actatcatta tgaataa 87

<210> SEQ ID NO 131
<211> LENGTH: 43
<212> TYPE: DNA
<213> ORGANISM: Artificial Sequence
<220> FEATURE:
<223> OTHER INFORMATION: Oligonucleotide referred to as HIVTM3

<400> SEQUENCE: 131
atcatctcta gaataaaaat tatccctgcc taactctatt cac 43

-continued

<210> SEQ ID NO 132
<211> LENGTH: 39
<212> TYPE: DNA
<213> ORGANISM: Artificial Sequence
<220> FEATURE:
<223> OTHER INFORMATION: Oligonucleotide referred to as HIVMN18

<400> SEQUENCE: 132
gcctcctact atcattatga ataatctttt ttctctctg 39

<210> SEQ ID NO 133
<211> LENGTH: 24
<212> TYPE: DNA
<213> ORGANISM: Artificial Sequence
<220> FEATURE:
<223> OTHER INFORMATION: Primer referred to as HIVP69

<400> SEQUENCE: 133
tgatagtacc agctataggt tgat 24

<210> SEQ ID NO 134
<211> LENGTH: 33
<212> TYPE: DNA
<213> ORGANISM: Artificial Sequence
<220> FEATURE:
<223> OTHER INFORMATION: Primer referred to as HIVP75

<400> SEQUENCE: 134
tttgtcgagc tcgtagttgg gtcttgtaca att 33

<210> SEQ ID NO 135
<211> LENGTH: 2020
<212> TYPE: DNA
<213> ORGANISM: Artificial Sequence
<220> FEATURE:
<223> OTHER INFORMATION: DNA sequence of the H6-promoted HIV1 gp120 + TM
(with ELDKWA epitopes) gene between C5 flanking arms, coding
strand

<400> SEQUENCE: 135
agaaagttac tctgagacac aaaagaggta gctgaagtgg tactctcaaa ggtacgtgac 60
taattagcta taaaaaggat ccgggttaat taattagtca tcaggcaggg cgagaacgag 120
actatctgct cgttaattaa ttagagcttc tttattctat acttaaaaag tgaaaataaa 180
tacaaaggtt cttgagggtt gtgttaaatt gaaagcgaga aataatcata aattatttca 240
ttatcgcgat atgcgttaag tttgtatcgt atatgaaaga gcagaagaca gtggcaatga 300
gagtgaagga gaaatatcag cacttgtgga gatgggggtg gagatggggc accatgctcc 360
ttgggatgtt gatgatctgt agtgctacag aaaaattgtg ggtcacagtc tattatgggg 420
tacctgtgtg gaaagaagca accaccactc tattttgtgc atcagatgct aaagcatatg 480
atacagaggt acataatgtt tgggccacac atgcctgtgt acccacagac cccaacccac 540
aagaagtaga attggtaaat gtgacagaaa attttaacat gtggaaaaat aacatggtag 600
aacagatgca tgaggatata atcagtttat gggatcaaag cctaaagcca tgtgtaaaat 660
taaccccact ctgtgttact ttaaattgca ctgatttgag gaatactact aataccaata 720
atagtactgc taataacaat agtaatagcg agggaacaat aaagggagga gaaatgaaaa 780
actgctcttt caatatcacc acaagcataa gagataagat gcagaaagaa tatgcacttc 840
tttataaact tgatatagta tcaataaata atgatagtac cagctatagg ttgataagtt 900
gtaatacctc agtcattaca caagcttgtc caaagatatc ctttgagcca attcccatac 960

-continued

```
actattgtgc cccggctggt tttgcgattc taaagtgtaa cgataaaaag ttcagtggaa   1020

aaggatcatg taaaaatgtc agcacagtac aatgtacaca tggaattagg ccagtagtat   1080

caactcaact gctgttaaat ggcagtctag cagaagaaga ggtagtaatt agatctgaga   1140

atttcaatga taatgctaaa accatcatag tacatctgaa tgaatctgta caaattaatt   1200

gtacaagacc caactacgag ctcgacaaat gggcccatat aggaccaggg agagaattgg   1260

ataagtgggc gaatataata ggaactataa gacaagcaca ttgtaacatt agtagagcaa   1320

aatggaatga cactttaaga cagatagtta gcaaattaaa agaacaattt aagaataaaa   1380

caatagtctt taatcaatcc tcaggagggg acccagaaat tgtaatgcac agttttaatt   1440

gtggaggggga attcttctac tgtaattcat caccactgtt taatagtact tggaatggta   1500

ataatacttg gaataatact acagggtcaa ataacaatat cacacttcaa tgcaaaataa   1560

aacaaattat aaacatgtgg caggaagtag gaaaagcaat atatgcccct cccattgaag   1620

gacaaattag atgttcatca aatattacag ggctactatt aacaagagat ggtggtaagg   1680

acacggacac gaacgacacc gagatcttca gacctggagg aggagatatg agggacaatt   1740

ggagaagtga attatataaa tataaagtag taacaattga accattagga gtagcaccca   1800

ccaaggcaaa gagaagagtg gtgcagagag aaaaaagatt attcataatg atagtaggag   1860

gcttggtagg tttaagaata gtttttgctg tactctctgt agtgaataga gttaggcagg   1920

gataattttt attctagaat cgatcccggg tttttatgac tagttaatca cggccgctta   1980

taaagatcta aaatgcataa tttctaaata atgaaaaaaa                        2020
```

<210> SEQ ID NO 136
<211> LENGTH: 2020
<212> TYPE: DNA
<213> ORGANISM: Artificial Sequence
<220> FEATURE:
<223> OTHER INFORMATION: DNA sequence of the H6-promoted HIV1 gp120 + TM (with ELDKWA epitopes) gene between C5 flanking arms, template strand

<400> SEQUENCE: 136

```
tctttcaatg agactctgtg ttttctccat cgacttcacc atgagagttt ccatgcactg     60

attaatcgat atttttccta ggcccaatta attaatcagt agtccgtccc gctcttgctc    120

tgatagacga gcaattaatt aatctcgaag aaataagata tgaatttttc acttttattt    180

atgtttccaa gaactcccaa cacaatttaa ctttcgctct ttattagtat ttaataaagt    240

aatagcgcta tacgcaattc aaacatagca tatactttct cgtcttctgt caccgttact    300

ctcacttcct ctttatagtc gtgaacacct ctacccccac ctctaccccg tggtacgagg    360

aaccctacaa ctactagaca tcacgatgtc tttttaacac ccagtgtcag ataatacccc    420

atggacacac ctttcttcgt tggtggtgag ataaaacacg tagtctacga tttcgtatac    480

tatgtctcca tgtattacaa acccggtgtg tacggacaca tgggtgtctg gggttgggtg    540

ttcttcatct taaccattta cactgtcttt taaaattgta caccttttta ttgtaccatc    600

ttgtctacgt actcctatat tagtcaaata ccctagtttc ggatttcggt acacatttta    660

attggggtga gacacaatga aatttaacgt gactaaactc cttatgatga ttatggttat    720

tatcatgacg attattgtta tcattatcgc tcccttgtta tttccctcct ctttactttt    780

tgacgagaaa gttatagtgg tgttcgtatt ctctattcta cgtctttctt atacgtgaag    840

aaatatttga actatatcat agttatttat tactatcatg gtcgatatcc aactattcaa    900
```

-continued

```
cattatggag tcagtaatgt gttcgaacag gtttctatag gaaactcggt taagggtatg    960

tgataacacg gggccgacca aaacgctaag atttcacatt gctatttttc aagtcacctt   1020

ttcctagtac atttttacag tcgtgtcatg ttacatgtgt accttaatcc ggtcatcata   1080

gttgagttga cgacaattta ccgtcagatc gtcttcttct ccatcattaa tctagactct   1140

taaagttact attacgattt tggtagtatc atgtagactt acttagacat gtttaattaa   1200

catgttctgg gttgatgctc gagctgttta cccgggtata tcctggtccc tctcttaacc   1260

tattcacccg cttatattat ccttgatatt ctgttcgtgt aacattgtaa tcatctcgtt   1320

ttaccttact gtgaaattct gtctatcaat cgtttaattt tcttgttaaa ttcttatttt   1380

gttatcagaa attagttagg agtcctcccc tgggtcttta acattacgtg tcaaaattaa   1440

cacctcccct taagaagatg acattaagta gtggtgacaa attatcatga accttaccat   1500

tattatgaac cttattatga tgtcccagtt tattgttata gtgtgaagtt acgttttatt   1560

ttgtttaata tttgtacacc gtccttcatc cttttcgtta tatacgggga gggtaacttc   1620

ctgtttaatc tacaagtagt ttataatgtc ccgatgataa ttgttctcta ccaccattcc   1680

tgtgcctgtg cttgctgtgg ctctagaagt ctggacctcc tcctctatac tccctgttaa   1740

cctcttcact taatatattt atatttcatc attgttaact tggtaatcct catcgtgggt   1800

ggttccgttt ctcttctcac cacgtctctc ttttttctaa taagtattac tatcatcctc   1860

cgaaccatcc aaattcttat caaaaacgac atgagagaca tcacttatct caatccgtcc   1920

ctattaaaaa taagatctta gctagggccc aaaaatactg atcaattagt gccggcgaat   1980

atttctagat tttacgtatt aaagatttat tacttttttt                         2020
```

```
<210> SEQ ID NO 137
<211> LENGTH: 551
<212> TYPE: PRT
<213> ORGANISM: Artificial Sequence
<220> FEATURE:
<223> OTHER INFORMATION: HIV1 gp120 + TM (with ELDKWA epitopes)
      expressed by vCP1307-infected cells

<400> SEQUENCE: 137

Met Lys Glu Gln Lys Thr Val Ala Met Arg Val Lys Glu Lys Tyr Gln
1               5                   10                  15

His Leu Trp Arg Trp Gly Trp Arg Trp Gly Thr Met Leu Leu Gly Met
            20                  25                  30

Leu Met Ile Cys Ser Ala Thr Glu Lys Leu Trp Val Thr Val Tyr Tyr
        35                  40                  45

Gly Val Pro Val Trp Lys Glu Ala Thr Thr Thr Leu Phe Cys Ala Ser
    50                  55                  60

Asp Ala Lys Ala Tyr Asp Thr Glu Val His Asn Val Trp Ala Thr His
65                  70                  75                  80

Ala Cys Val Pro Thr Asp Pro Asn Pro Gln Glu Val Glu Leu Val Asn
                85                  90                  95

Val Thr Glu Asn Phe Asn Met Trp Lys Asn Asn Met Val Glu Gln Met
            100                 105                 110

His Glu Asp Ile Ile Ser Leu Trp Asp Gln Ser Leu Lys Pro Cys Val
        115                 120                 125

Lys Leu Thr Pro Leu Cys Val Thr Leu Asn Cys Thr Asp Leu Arg Asn
    130                 135                 140

Thr Thr Asn Thr Asn Asn Ser Thr Ala Asn Asn Asn Ser Asn Ser Glu
145                 150                 155                 160
```

-continued

```
Gly Thr Ile Lys Gly Gly Glu Met Lys Asn Cys Ser Phe Asn Ile Thr
                165                 170                 175

Thr Ser Ile Arg Asp Lys Met Gln Lys Glu Tyr Ala Leu Leu Tyr Lys
            180                 185                 190

Leu Asp Ile Val Ser Ile Asn Asn Asp Ser Thr Ser Tyr Arg Leu Ile
        195                 200                 205

Ser Cys Asn Thr Ser Val Ile Thr Gln Ala Cys Pro Lys Ile Ser Phe
    210                 215                 220

Glu Pro Ile Pro Ile His Tyr Cys Ala Pro Ala Gly Phe Ala Ile Leu
225                 230                 235                 240

Lys Cys Asn Asp Lys Lys Phe Ser Gly Lys Gly Ser Cys Lys Asn Val
                245                 250                 255

Ser Thr Val Gln Cys Thr His Gly Ile Arg Pro Val Val Ser Thr Gln
            260                 265                 270

Leu Leu Leu Asn Gly Ser Leu Ala Glu Glu Glu Val Val Ile Arg Ser
        275                 280                 285

Glu Asn Phe Asn Asp Asn Ala Lys Thr Ile Ile Val His Leu Asn Glu
    290                 295                 300

Ser Val Gln Ile Asn Cys Thr Arg Pro Asn Tyr Glu Leu Asp Lys Trp
305                 310                 315                 320

Ala His Ile Gly Pro Gly Arg Glu Leu Asp Lys Trp Ala Asn Ile Ile
                325                 330                 335

Gly Thr Ile Arg Gln Ala His Cys Asn Ile Ser Arg Ala Lys Trp Asn
            340                 345                 350

Asp Thr Leu Arg Gln Ile Val Ser Lys Leu Lys Glu Gln Phe Lys Asn
        355                 360                 365

Lys Thr Ile Val Phe Asn Gln Ser Ser Gly Gly Asp Pro Glu Ile Val
    370                 375                 380

Met His Ser Phe Asn Cys Gly Gly Glu Phe Phe Tyr Cys Asn Ser Ser
385                 390                 395                 400

Pro Leu Phe Asn Ser Thr Trp Asn Gly Asn Asn Thr Trp Asn Asn Thr
                405                 410                 415

Thr Gly Ser Asn Asn Asn Ile Thr Leu Gln Cys Lys Ile Lys Gln Ile
            420                 425                 430

Ile Asn Met Trp Gln Glu Val Gly Lys Ala Ile Tyr Ala Pro Pro Ile
        435                 440                 445

Glu Gly Gln Ile Arg Cys Ser Ser Asn Ile Thr Gly Leu Leu Leu Thr
    450                 455                 460

Arg Asp Gly Gly Lys Asp Thr Asp Thr Asn Asp Thr Glu Ile Phe Arg
465                 470                 475                 480

Pro Gly Gly Gly Asp Met Arg Asp Asn Trp Arg Ser Glu Leu Tyr Lys
                485                 490                 495

Tyr Lys Val Val Thr Ile Glu Pro Leu Gly Val Ala Pro Thr Lys Ala
            500                 505                 510

Lys Arg Arg Val Val Gln Arg Glu Lys Arg Leu Phe Ile Met Ile Val
        515                 520                 525

Gly Gly Leu Val Gly Leu Arg Ile Val Phe Ala Val Leu Ser Val Val
    530                 535                 540

Asn Arg Val Arg Gln Gly Asn
545                 550
```

<210> SEQ ID NO 138
<211> LENGTH: 2028
<212> TYPE: DNA

-continued

<213> ORGANISM: Artificial Sequence
<220> FEATURE:
<223> OTHER INFORMATION: Nucleotide sequence of H6-promoted HIV1 gp120 + TM (with ELDKWA epitopes) gene between I4L flanking arms, coding strand.

<400> SEQUENCE: 138

```
tactttgtaa tataatgata tatattttca ctttatctca tttgagaata aaaagatcac     60

aaaaattaac taatcaggat ccgggttaat taattagtca tcaggcaggg cgagaacgag    120

actatctgct cgttaattaa ttagagcttc tttattctat acttaaaaag tgaaaataaa    180

tacaaaggtt cttgagggtt gtgttaaatt gaaagcgaga aataatcata aattatttca    240

ttatcgcgat atgcgttaag tttgtatcgt atatgaaaga gcagaagaca gtggcaatga    300

gagtgaagga gaaatatcag cacttgtgga gatgggggtg gagatggggc accatgctcc    360

ttgggatgtt gatgatctgt agtgctacag aaaaattgtg ggtcacagtc tattatgggg    420

tacctgtgtg gaaagaagca accaccactc tattttgtgc atcagatgct aaagcatatg    480

atacagaggt acataatgtt tgggccacac atgcctgtgt acccacagac cccaacccac    540

aagaagtaga attggtaaat gtgacagaaa attttaacat gtggaaaaat aacatggtag    600

aacagatgca tgaggatata atcagtttat gggatcaaag cctaaagcca tgtgtaaaat    660

taaccccact ctgtgttact ttaaattgca ctgatttgag gaatactact aataccaata    720

atagtactgc taataacaat agtaatagcg agggaacaat aaagggagga gaaatgaaaa    780

actgctcttt caatatcacc acaagcataa gagataagat gcagaaagaa tatgcacttc    840

tttataaact tgatatagta tcaataaata atgatagtac cagctatagg ttgataagtt    900

gtaatacctc agtcattaca caagcttgtc caaagatatc ctttgagcca attcccatac    960

actattgtgc cccggctggt tttgcgattc taaagtgtaa cgataaaaag ttcagtggaa   1020

aaggatcatg taaaaatgtc agcacagtac aatgtacaca tggaattagg ccagtagtat   1080

caactcaact gctgttaaat ggcagtctag cagaagaaga ggtagtaatt agatctgaga   1140

atttcaatga taatgctaaa accatcatag tacatctgaa tgaatctgta caaattaatt   1200

gtacaagacc caactacgag ctcgacaaat gggcccatat aggaccaggg agagaattgg   1260

ataagtgggc gaatataata ggaactataa gacaagcaca ttgtaacatt agtagagcaa   1320

aatggaatga cactttaaga cagatagtta gcaaattaaa agaacaattt aagaataaaa   1380

caatagtctt taatcaatcc tcaggagggg acccagaaat tgtaatgcac agttttaatt   1440

gtggagggga attcttctac tgtaattcat caccactgtt taatagtact tggaatggta   1500

ataatacttg gaataatact acagggtcaa ataacaatat cacacttcaa tgcaaaataa   1560

aacaaattat aaacatgtgg caggaagtag gaaaagcaat atatgcccct cccattgaag   1620

gacaaattag atgttcatca aatattacag ggctactatt aacaagagat ggtggtaagg   1680

acacggacac gaacgacacc gagatcttca gacctggagg aggagatatg agggacaatt   1740

ggagaagtga attatataaa tataaagtag taacaattga accattagga gtagcaccca   1800

ccaaggcaaa gagaagagtg gtgcagagag aaaaaagatt attcataatg atagtaggag   1860

gcttggtagg tttaagaata gtttttgctg tactctctgt agtgaataga gttaggcagg   1920

gataattttt attctagaat cgatcccggg agatcttagc taactgattt ttctgggaaa   1980

aaaattattt aacttttcat taatagggat ttgacgtatg tagcgtac                2028
```

<210> SEQ ID NO 139
<211> LENGTH: 2028

-continued

<212> TYPE: DNA
<213> ORGANISM: Artificial Sequence
<220> FEATURE:
<223> OTHER INFORMATION: Nucleotide sequence of H6-promoted HIV1 gp120 + TM (with ELDKWA epitopes) gene between I4L flanking arms, template strand

<400> SEQUENCE: 139

```
atgaaacatt atattactat atataaaagt gaaatagagt aaactcttat ttttctagtg     60
tttttaattg attagtccta ggcccaatta attaatcagt agtccgtccc gctcttgctc    120
tgatagacga gcaattaatt aatctcgaag aaataagata tgaatttttc acttttattt    180
atgtttccaa gaactcccaa cacaatttaa ctttcgctct ttattagtat ttaataaagt    240
aatagcgcta tacgcaattc aaacatagca tatactttct cgtcttctgt caccgttact    300
ctcacttcct ctttatagtc gtgaacacct ctacccccac ctctaccccg tggtacgagg    360
aaccctacaa ctactagaca tcacgatgtc tttttaacac ccagtgtcag ataataccc     420
atggacacac ctttcttcgt tggtggtgag ataaaaacacg tagtctacga tttcgtatac   480
tatgtctcca tgtattacaa acccggtgtg tacggacaca tgggtgtctg gggttgggtg    540
ttcttcatct taaccattta cactgtcttt taaaattgta cacctttttta ttgtaccatc   600
ttgtctacgt actcctatat tagtcaaata ccctagtttc ggatttcggt acacatttta    660
attggggtga gacacaatga aatttaacgt gactaaactc cttatgatga ttatggttat    720
tatcatgacg attattgtta tcattatcgc tcccttgtta tttccctcct ctttactttt    780
tgacgagaaa gttatagtgg tgttcgtatt ctctattcta cgtctttctt atacgtgaag    840
aaatatttga actatatcat agttatttat tactatcatg gtcgatatcc aactattcaa    900
cattatggag tcagtaatgt gttcgaacag gtttctatag gaaactcggt taagggtatg    960
tgataacacg gggccgacca aaacgctaag atttcacatt gctatttttc aagtcacctt   1020
ttcctagtac atttttacag tcgtgtcatg ttacatgtgt accttaatcc ggtcatcata   1080
gttgagttga cgacaattta ccgtcagatc gtcttcttct ccatcattaa tctagactct   1140
taaagttact attacgattt tggtagtatc atgtagactt acttagacat gtttaattaa   1200
catgttctgg gttgatgctc gagctgttta cccgggtata tcctggtccc tctcttaacc   1260
tattcacccg cttatattat ccttgatatt ctgttcgtgt aacattgtaa tcatctcgtt   1320
ttaccttact gtgaaattct gtctatcaat cgtttaattt tcttgttaaa ttcttatttt   1380
gttatcagaa attagttagg agtcctcccc tgggtcttta acattacgtg tcaaaattaa   1440
cacctcccct taagaagatg acattaagta gtggtgacaa attatcatga accttaccat   1500
tattatgaac cttattatga tgtcccagtt tattgttata gtgtgaagtt acgttttatt   1560
ttgtttaata tttgtacacc gtccttcatc cttttcgtta tatacgggga gggtaacttc   1620
ctgtttaatc tacaagtagt ttataatgtc ccgatgataa ttgttctcta ccaccattcc   1680
tgtgcctgtg cttgctgtgg ctctagaagt ctggacctcc tcctctatac tccctgttaa   1740
cctcttcact taatatattt atatttcatc attgttaact tggtaatcct catcgtgggt   1800
ggttccgttt ctcttctcac cacgtctctc ttttttctaa taagtattac tatcatcctc   1860
cgaaccatcc aaattcttat caaaaacgac atgagagaca tcacttatct caatccgtcc   1920
ctattaaaaa taagatctta gctagggccc tctagaatcg attgactaaa aagacccttt   1980
ttttaataaa ttgaaaagta attatcccta aactgcatac atcgcatg                2028
```

<210> SEQ ID NO 140

-continued

```
<211> LENGTH: 550
<212> TYPE: PRT
<213> ORGANISM: Artificial Sequence
<220> FEATURE:
<223> OTHER INFORMATION: HIV1 gp120 + TM (with ELDKWA epitopes)
      expressed by vP1313-infected cells

<400> SEQUENCE: 140

Met Lys Glu Gln Lys Thr Val Ala Met Arg Val Lys Glu Lys Tyr Gln
1               5                   10                  15

His Leu Trp Arg Trp Gly Trp Arg Trp Gly Thr Met Leu Leu Gly Met
            20                  25                  30

Leu Met Ile Cys Ser Ala Thr Glu Lys Leu Trp Val Thr Val Tyr Tyr
        35                  40                  45

Gly Val Pro Val Trp Lys Glu Ala Thr Thr Thr Leu Phe Cys Ala Ser
    50                  55                  60

Asp Ala Lys Ala Tyr Asp Thr Glu Val His Asn Val Trp Ala Thr His
65                  70                  75                  80

Ala Cys Val Pro Thr Asp Pro Asn Pro Gln Glu Val Glu Leu Val Asn
                85                  90                  95

Val Thr Glu Asn Phe Asn Met Trp Lys Asn Asn Met Val Glu Gln Met
            100                 105                 110

His Glu Asp Ile Ile Ser Leu Trp Asp Gln Ser Leu Lys Pro Cys Val
        115                 120                 125

Lys Leu Thr Pro Leu Cys Val Thr Leu Asn Cys Thr Asp Leu Arg Asn
    130                 135                 140

Thr Thr Asn Thr Asn Asn Ser Thr Ala Asn Asn Asn Ser Asn Ser Glu
145                 150                 155                 160

Gly Thr Ile Lys Gly Gly Glu Met Lys Asn Cys Ser Phe Asn Ile Thr
                165                 170                 175

Thr Ser Ile Arg Asp Lys Met Gln Lys Glu Tyr Ala Leu Leu Tyr Lys
            180                 185                 190

Leu Asp Ile Val Ser Ile Asn Asn Asp Ser Thr Ser Tyr Arg Leu Ile
        195                 200                 205

Ser Cys Asn Thr Ser Val Ile Thr Gln Ala Cys Pro Lys Ile Ser Phe
    210                 215                 220

Glu Pro Ile Pro Ile His Tyr Cys Ala Pro Ala Gly Phe Ala Ile Leu
225                 230                 235                 240

Lys Cys Asn Asp Lys Lys Phe Ser Gly Lys Gly Ser Cys Lys Asn Val
                245                 250                 255

Ser Thr Val Gln Cys Thr His Gly Ile Arg Pro Val Val Ser Thr Gln
            260                 265                 270

Leu Leu Leu Asn Gly Ser Leu Ala Glu Glu Glu Val Val Ile Arg Ser
        275                 280                 285

Glu Asn Phe Asn Asp Asn Ala Lys Thr Ile Ile Val His Leu Asn Glu
    290                 295                 300

Ser Val Gln Ile Asn Cys Thr Arg Pro Asn Tyr Glu Leu Asp Lys Trp
305                 310                 315                 320

Ala His Ile Gly Pro Gly Arg Glu Leu Asp Lys Trp Ala Asn Ile Ile
                325                 330                 335

Gly Thr Ile Arg Gln Ala His Cys Asn Ile Ser Arg Ala Lys Trp Asn
            340                 345                 350

Asp Thr Leu Arg Gln Ile Val Ser Lys Leu Lys Glu Gln Phe Lys Asn
        355                 360                 365

Lys Thr Ile Val Phe Asn Gln Ser Ser Gly Gly Asp Pro Glu Ile Val
```

-continued

```
    370                 375                 380

Met His Ser Phe Asn Cys Gly Gly Glu Phe Phe Tyr Cys Asn Ser Ser
385                 390                 395                 400

Pro Leu Phe Asn Ser Thr Trp Asn Gly Asn Asn Thr Trp Asn Asn Thr
                405                 410                 415

Thr Gly Ser Asn Asn Asn Ile Thr Leu Gln Cys Lys Ile Lys Gln Ile
            420                 425                 430

Ile Asn Met Trp Gln Glu Val Gly Lys Ala Ile Tyr Ala Pro Pro Ile
        435                 440                 445

Glu Gly Gln Ile Arg Cys Ser Ser Asn Ile Thr Gly Leu Leu Leu Thr
    450                 455                 460

Arg Asp Gly Gly Lys Asp Thr Asp Thr Asn Asp Thr Glu Ile Phe Arg
465                 470                 475                 480

Pro Gly Gly Gly Asp Met Arg Asp Asn Trp Arg Ser Glu Leu Tyr Lys
                485                 490                 495

Tyr Lys Val Val Thr Ile Glu Pro Leu Gly Val Ala Pro Thr Lys Ala
            500                 505                 510

Lys Arg Arg Val Val Gln Arg Glu Lys Arg Leu Phe Ile Met Ile Val
        515                 520                 525

Gly Gly Leu Val Gly Leu Arg Ile Val Phe Ala Val Leu Ser Val Val
    530                 535                 540

Asn Arg Val Arg Gln Gly
545                 550


<210> SEQ ID NO 141
<211> LENGTH: 2060
<212> TYPE: DNA
<213> ORGANISM: Artificial Sequence
<220> FEATURE:
<223> OTHER INFORMATION: H6-promoted HIV1 gp120 + TM (with ELDKWA
      epitopes) gene between A24R and K1L flanking arms, coding
      sequence

<400> SEQUENCE: 141

ataaaccatt agataaagtt gatctcaagc gctcttttct ggtgtaataa aaattaatta     60

attactcgag ggtaccggat ccgggttaat taattagtca tcaggcaggg cgagaacgag    120

actatctgct cgttaattaa ttagagcttc tttattctat acttaaaaag tgaaaataaa    180

tacaaaggtt cttgagggtt gtgttaaatt gaaagcgaga aataatcata aattatttca    240

ttatcgcgat atgcgttaag tttgtatcgt atatgaaaga gcagaagaca gtggcaatga    300

gagtgaagga gaaatatcag cacttgtgga gatgggggtg gagatggggc accatgctcc    360

ttgggatgtt gatgatctgt agtgctacag aaaaattgtg ggtcacagtc tattatgggg    420

tacctgtgtg gaaagaagca accaccactc tattttgtgc atcagatgct aaagcatatg    480

atacagaggt acataatgtt tgggccacac atgcctgtgt acccacagac cccaacccac    540

aagaagtaga attggtaaat gtgacagaaa attttaacat gtggaaaaat aacatggtag    600

aacagatgca tgaggatata atcagtttat gggatcaaag cctaaagcca tgtgtaaaat    660

taaccccact ctgtgttact ttaaattgca ctgatttgag gaatactact aataccaata    720

atagtactgc taataacaat agtaatagcg agggaacaat aaagggagga gaaatgaaaa    780

actgctcttt caatatcacc acaagcataa gagataagat gcagaaagaa tatgcacttc    840

tttataaact tgatatagta tcaataaata atgatagtac cagctatagg ttgataagtt    900

gtaatacctc agtcattaca caagcttgtc caaagatatc ctttgagcca attcccatac    960
```

-continued

```
actattgtgc cccggctggt tttgcgattc taaagtgtaa cgataaaaag ttcagtggaa   1020

aaggatcatg taaaaatgtc agcacagtac aatgtacaca tggaattagg ccagtagtat   1080

caactcaact gctgttaaat ggcagtctag cagaagaaga ggtagtaatt agatctgaga   1140

atttcaatga taatgctaaa accatcatag tacatctgaa tgaatctgta caaattaatt   1200

gtacaagacc caactacgag ctcgacaaat gggcccatat aggaccaggg agagaattgg   1260

ataagtgggc gaatataata ggaactataa gacaagcaca ttgtaacatt agtagagcaa   1320

aatggaatga cactttaaga cagatagtta gcaaattaaa agaacaattt aagaataaaa   1380

caatagtctt taatcaatcc tcaggagggg acccagaaat tgtaatgcac agttttaatt   1440

gtggagggga attcttctac tgtaattcat caccactgtt taatagtact tggaatggta   1500

ataatacttg gaataatact acagggtcaa ataacaatat cacacttcaa tgcaaaataa   1560

aacaaattat aaacatgtgg caggaagtag gaaaagcaat atatgcccct cccattgaag   1620

gacaaattag atgttcatca aatattacag ggctactatt aacaagagat ggtggtaagg   1680

acacggacac gaacgacacc gagatcttca gacctggagg aggagatatg agggacaatt   1740

ggagaagtga attatataaa tataaagtag taacaattga accattagga gtagcaccca   1800

ccaaggcaaa gagaagagtg gtgcagagag aaaaaagatt attcataatg atagtaggag   1860

gcttggtagg tttaagaata gtttttgctg tactctctgt agtgaataga gttaggcagg   1920

gataattttt attcgagaat cgatcccggg aatcgattcg cgatagctga ttagtttttg   1980

ttaacaaaaa tgtgggagaa tctaattagt ttttctttac acaattgacg tacatgagtc   2040

tgagttcctt gtttttgcta                                               2060
```

<210> SEQ ID NO 142
<211> LENGTH: 2060
<212> TYPE: DNA
<213> ORGANISM: Artificial Sequence
<220> FEATURE:
<223> OTHER INFORMATION: H6-promoted HIV1 gp120 + TM (with ELDKWA epitopes) gene between A24R and K1L flanking arms, template strand

<400> SEQUENCE: 142

```
tatttggtaa tctatttcaa ctagagttcg cgagaaaaga ccacattatt tttaattaat     60

taatgagctc ccatggccta ggcccaatta attaatcagt agtccgtccc gctcttgctc    120

tgatagacga gcaattaatt aatctcgaag aaataagata tgaatttttc acttttattt    180

atgtttccaa gaactcccaa cacaatttaa ctttcgctct ttattagtat ttaataaagt    240

aatagcgcta tacgcaattc aaacatagca tatactttct cgtcttctgt caccgttact    300

ctcacttcct ctttatagtc gtgaacacct ctacccccac ctctaccccg tggtacgagg    360

aaccctacaa ctactagaca tcacgatgtc tttttaacac ccagtgtcag ataatacccc    420

atggacacac ctttcttcgt tggtggtgag ataaaacacg tagtctacga tttcgtatac    480

tatgtctcca tgtattacaa acccggtgtg tacggacaca tgggtgtctg gggttgggtg    540

ttcttcatct taaccattta cactgtcttt taaaattgta caccttttta ttgtaccatc    600

ttgtctacgt actcctatat tagtcaaata ccctagtttc ggatttcggt acacatttta    660

attggggtga gacacaatga aatttaacgt gactaaactc cttatgatga ttatggttat    720

tatcatgacg attattgtta tcattatcgc tcccttgtta tttccctcct ctttactttt    780

tgacgagaaa gttatagtgg tgttcgtatt ctctattcta cgtctttctt atacgtgaag    840

aaatatttga actatatcat agttatttat tactatcatg gtcgatatcc aactattcaa    900
```

-continued

```
cattatggag tcagtaatgt gttcgaacag gtttctatag gaaactcggt taagggtatg    960

tgataacacg gggccgacca aaacgctaag atttcacatt gctatttttc aagtcacctt   1020

ttcctagtac atttttacag tcgtgtcatg ttacatgtgt accttaatcc ggtcatcata   1080

gttgagttga cgacaattta ccgtcagatc gtcttcttct ccatcattaa tctagactct   1140

taaagttact attacgattt tggtagtatc atgtagactt acttagacat gtttaattaa   1200

catgttctgg gttgatgctc gagctgttta cccgggtata tcctggtccc tctcttaacc   1260

tattcacccg cttatattat ccttgatatt ctgttcgtgt aacattgtaa tcatctcgtt   1320

ttaccttact gtgaaattct gtctatcaat cgtttaattt tcttgttaaa ttcttatttt   1380

gttatcagaa attagttagg agtcctcccc tgggtcttta acattacgtg tcaaaattaa   1440

cacctcccct taagaagatg acattaagta gtggtgacaa attatcatga accttaccat   1500

tattatgaac cttattatga tgtcccagtt tattgttata gtgtgaagtt acgttttatt   1560

ttgtttaata tttgtacacc gtccttcatc cttttcgtta tatacgggga gggtaacttc   1620

ctgtttaatc tacaagtagt ttataatgtc ccgatgataa ttgttctcta ccaccattcc   1680

tgtgcctgtg cttgctgtgg ctctagaagt ctggacctcc tcctctatac tccctgttaa   1740

cctcttcact taatatattt atatttcatc attgttaact tggtaatcct catcgtgggt   1800

ggttccgttt ctcttctcac cacgtctctc ttttttctaa taagtattac tatcatcctc   1860

cgaaccatcc aaattcttat caaaaacgac atgagagaca tcacttatct caatccgtcc   1920

ctattaaaaa taagatctta gctagggccc ttagctaagc gctatcgact aatcaaaaac   1980

aattgttttt acaccctctt agattaatca aaaagaaatg tgttaactgc atgtactcag   2040

actcaaggaa caaaaacgat                                               2060
```

```
<210> SEQ ID NO 143
<211> LENGTH: 551
<212> TYPE: PRT
<213> ORGANISM: Artificial Sequence
<220> FEATURE:
<223> OTHER INFORMATION: HIV1 gp120 + TM (with ELDKWA epitopes)
      expressed by vP1319 infected cells

<400> SEQUENCE: 143

Met Lys Glu Gln Lys Thr Val Ala Met Arg Val Lys Glu Lys Tyr Gln
1               5                   10                  15

His Leu Trp Arg Trp Gly Trp Arg Trp Gly Thr Met Leu Leu Gly Met
            20                  25                  30

Leu Met Ile Cys Ser Ala Thr Glu Lys Leu Trp Val Thr Val Tyr Tyr
        35                  40                  45

Gly Val Pro Val Trp Lys Glu Ala Thr Thr Thr Leu Phe Cys Ala Ser
    50                  55                  60

Asp Ala Lys Ala Tyr Asp Thr Glu Val His Asn Val Trp Ala Thr His
65                  70                  75                  80

Ala Cys Val Pro Thr Asp Pro Asn Pro Gln Glu Val Glu Leu Val Asn
                85                  90                  95

Val Thr Glu Asn Phe Asn Met Trp Lys Asn Asn Met Val Glu Gln Met
            100                 105                 110

His Glu Asp Ile Ile Ser Leu Trp Asp Gln Ser Leu Lys Pro Cys Val
        115                 120                 125

Lys Leu Thr Pro Leu Cys Val Thr Leu Asn Cys Thr Asp Leu Arg Asn
    130                 135                 140

Thr Thr Asn Thr Asn Asn Ser Thr Ala Asn Asn Asn Ser Asn Ser Glu
```

-continued

```
145                 150                 155                 160

Gly Thr Ile Lys Gly Gly Glu Met Lys Asn Cys Ser Phe Asn Ile Thr
                165                 170                 175

Thr Ser Ile Arg Asp Lys Met Gln Lys Glu Tyr Ala Leu Leu Tyr Lys
            180                 185                 190

Leu Asp Ile Val Ser Ile Asn Asn Asp Ser Thr Ser Tyr Arg Leu Ile
        195                 200                 205

Ser Cys Asn Thr Ser Val Ile Thr Gln Ala Cys Pro Lys Ile Ser Phe
    210                 215                 220

Glu Pro Ile Pro Ile His Tyr Cys Ala Pro Ala Gly Phe Ala Ile Leu
225                 230                 235                 240

Lys Cys Asn Asp Lys Lys Phe Ser Gly Lys Gly Ser Cys Lys Asn Val
                245                 250                 255

Ser Thr Val Gln Cys Thr His Gly Ile Arg Pro Val Val Ser Thr Gln
            260                 265                 270

Leu Leu Leu Asn Gly Ser Leu Ala Glu Glu Glu Val Val Ile Arg Ser
        275                 280                 285

Glu Asn Phe Asn Asp Asn Ala Lys Thr Ile Ile Val His Leu Asn Glu
    290                 295                 300

Ser Val Gln Ile Asn Cys Thr Arg Pro Asn Tyr Glu Leu Asp Lys Trp
305                 310                 315                 320

Ala His Ile Gly Pro Gly Arg Glu Leu Asp Lys Trp Ala Asn Ile Ile
                325                 330                 335

Gly Thr Ile Arg Gln Ala His Cys Asn Ile Ser Arg Ala Lys Trp Asn
            340                 345                 350

Asp Thr Leu Arg Gln Ile Val Ser Lys Leu Lys Glu Gln Phe Lys Asn
        355                 360                 365

Lys Thr Ile Val Phe Asn Gln Ser Ser Gly Gly Asp Pro Glu Ile Val
    370                 375                 380

Met His Ser Phe Asn Cys Gly Gly Glu Phe Phe Tyr Cys Asn Ser Ser
385                 390                 395                 400

Pro Leu Phe Asn Ser Thr Trp Asn Gly Asn Asn Thr Trp Asn Asn Thr
                405                 410                 415

Thr Gly Ser Asn Asn Asn Ile Thr Leu Gln Cys Lys Ile Lys Gln Ile
            420                 425                 430

Ile Asn Met Trp Gln Glu Val Gly Lys Ala Ile Tyr Ala Pro Pro Ile
        435                 440                 445

Glu Gly Gln Ile Arg Cys Ser Ser Asn Ile Thr Gly Leu Leu Leu Thr
    450                 455                 460

Arg Asp Gly Gly Lys Asp Thr Asp Thr Asn Asp Thr Glu Ile Phe Arg
465                 470                 475                 480

Pro Gly Gly Gly Asp Met Arg Asp Asn Trp Arg Ser Glu Leu Tyr Lys
                485                 490                 495

Tyr Lys Val Val Thr Ile Glu Pro Leu Gly Val Ala Pro Thr Lys Ala
            500                 505                 510

Lys Arg Arg Val Val Gln Arg Glu Lys Arg Leu Phe Ile Met Ile Val
        515                 520                 525

Gly Gly Leu Val Gly Leu Arg Ile Val Phe Ala Val Leu Ser Val Val
    530                 535                 540

Asn Arg Val Arg Gln Gly Asn
545                 550
```

<210> SEQ ID NO 144

-continued

<211> LENGTH: 23
<212> TYPE: DNA
<213> ORGANISM: Artificial Sequence
<220> FEATURE:
<223> OTHER INFORMATION: Primer referred to as HIVP72

<400> SEQUENCE: 144
ttattaccat tccaagtact att 23

<210> SEQ ID NO 145
<211> LENGTH: 109
<212> TYPE: DNA
<213> ORGANISM: Artificial Sequence
<220> FEATURE:
<223> OTHER INFORMATION: Primer referred to as HIVP74

<400> SEQUENCE: 145
tctgtacaaa ttaattgtac aagacccaac tacgagctcg acaaatgggc ccatatagga 60
ccagggagag aattggataa gtgggcgaat ataataggaa ctataagac 109

<210> SEQ ID NO 146
<211> LENGTH: 20
<212> TYPE: DNA
<213> ORGANISM: Artificial Sequence
<220> FEATURE:
<223> OTHER INFORMATION: Oligonucleotide referred to as HIVMN6

<400> SEQUENCE: 146
gggttattaa tgatctgtag 20

<210> SEQ ID NO 147
<211> LENGTH: 6
<212> TYPE: PRT
<213> ORGANISM: Human immunodeficiency virus type 1

<400> SEQUENCE: 147

Glu Leu Asp Lys Trp Ala
1 5

<210> SEQ ID NO 148
<211> LENGTH: 4
<212> TYPE: PRT
<213> ORGANISM: Human immunodeficiency virus type 1

<400> SEQUENCE: 148

Leu Asp Lys Trp
1

<210> SEQ ID NO 149
<211> LENGTH: 5
<212> TYPE: PRT
<213> ORGANISM: Newcastle disease virus

<400> SEQUENCE: 149

Arg Arg Gln Arg Arg
1 5

IMMUNODEFICIENCY RECOMBINANT POXVIRUS

RELATED APPLICATIONS

This application is divisional of U.S. application Ser. No. 08/417,210, filed Apr. 5, 1995, now U.S. Pat. No. 5,863,542, which was a continuation-in-part of application Ser. No. 08/223,842, filed Apr. 6, 1994 now abandoned which in turn is a continuation-in-part of application Ser. No. 07/897,382, filed Jun. 11, 1992 now abandoned, which in turn is a continuation-in-part of application Ser. No. 07/715,921, filed Jun. 14, 1991. This application is also a continuation-in-part of application Ser. No. 08/105,483, filed Aug. 12, 1993, now U.S. Pat. No. 5,494,807 which in turn is a continuation of application Ser. No. 07/847,951, filed Mar. 6, 1992, which in turn is a continuation-in-part of application Ser. No. 07/713,967, filed Jun. 11, 1991, which in turn is a continuation in part of application Ser. No. 07/666,056, filed Mar. 7, 1991. Mention is also made of application Ser. No. 08/184,009, filed Jan. 19, 1994 as a continuation-in-part of application Ser. No. 08/007,115, filed Jan. 20, 1993. Each of the aforementioned and above-referenced applications is hereby incorporated herein by reference.

FIELD OF THE INVENTION

The present invention relates to a modified poxvirus and to methods of making and using the same. More in particular, the invention relates to improved vectors for the insertion and expression of foreign genes for use as safe immunization vehicles to elicit an immune response against immunodeficiency virus. Thus, the invention relates to a recombinant poxvirus, which virus expresses gene products of immunodeficiency virus and to immunogenic compositions which induce an immunological response against immunodeficiency virus infections when administered to a host, or in vitro (e.g. ex vivo modalities) as well as to the products of expression of the poxvirus which by themselves are useful for eliciting an immune response e.g., raising antibodies, which antibodies are useful against immunodeficiency virus infection, in either seropositive or seronegative individuals, or are useful if isolated from an animal or human for preparing a diagnostic kit, test or assay for the detection of the virus or infected cells.

Several publications are referenced in this application. Full citation to these references is found at the end of the specification immediately preceding the claims or where the publication is mentioned; and each of these publications is hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179,993, the disclosures of which are incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. $TK^-$ vaccinia virus is also capable of replication in vivo at the site of inoculation in a variety of hosts by a variety of routes.

It has been shown for herpes simplex virus type 2 that intravaginal inoculation of guinea pigs with $TK^-$ virus resulted in significantly lower virus titers in the spinal cord than did inoculation with $TK^+$ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of $TK^-$ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, $TK^-$ recombinant vaccinia generated equivalent anti-vaccinia neutralizing antibodies as compared with the parental $TK^+$ vaccinia virus, indicating that in this test system the loss of TK function does not significantly decrease immunogenicity of the vaccinia virus vector. Following intranasal inoculation of mice with $TK^-$ and $TK^+$ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmidtt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant $HA^-$ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipoxviruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993a,b; Taylor et al., 1992; 1991b; 1988b).

In 1983, human immunodeficiency virus type 1 (HIV1) was identified as the causative agent of AIDS. Twelve years later, despite a massive, worldwide effort, an effective HIV1 vaccine is still not available. Recently, however, several reports have suggested that an efficacious HIV1 vaccine may be attainable. For example, macaques have been protected against a simian immunodeficiency virus (SIV) challenge by a vaccination protocol involving a primary immunization with a vaccinia virus recombinant expressing the SIV gp160 glycoprotein and a booster immunization with purified SIV gp160 glycoprotein (Hu et al., 1992). In addition, chimpanzees have been protected against an HIV1 challenge with an HIV1 gp120 subunit vaccine (Berman et al, 1990). Chimps have also been protected against an HIV1 challenge by a vaccination protocol involving multiple injections of either inactivated HIV1, gp160 and/or V3 peptide or gp160, p17 (a Gag protein) and/or V3 peptide (Girard et al., 1991). A similar protocol involving multiple injections of gp160, p17, p24 (a Gag protein), Vif, Nef and/or V3 peptide has also protected chimps against a challenge of HIV1-infected cells (Fultz et al., 1992). Furthermore, chimps have been passively protected by the infusion of HIV1 V3-specific antibodies (Emini et al., 1992).

Most of these vaccination protocols have focused on eliciting an immune response against the HIV1 or SIV envelope glycoprotein, or more specifically, against the V3 epitope of the envelope glycoprotein. Unfortunately, different strains of HIV1 exhibit extensive genetic and antigenic variability, especially in the envelope glycoprotein. Therefore, an effective HIV1 vaccine may need to elicit an immune response against more than one HIV1 antigen, or one epitope of one HIV1 antigen.

Contrary to the extensive sequence variability observed in B-cell epitopes, T-cell epitopes are relatively conserved. For example, cytotoxic T-lymphocytes (CTL) clones, isolated from an HIV1-seronegative individual vaccinated with a vaccinia virus recombinant expressing HIV1 gp160 (LAI strain) and boosted with purified HIV1 gp160 (LAI), lyse target cells expressing the HIV1 MN or RF envelope glycoprotein as efficiently as cells expressing the HIV1 LAI envelope glycoprotein (Hammond et al., 1992). Therefore, a vaccine that elicits an immune response against relatively conserved T-cell epitopes may not only be more efficacious against a homologous challenge, but also more efficacious against a heterologous challenge.

HIV1-seronegative individuals have been vaccinated with an ALVAC recombinant (vCP125) expressing HIV1 gp160, in a prime-boost protocol similar to the regimen used to vaccinate macaques against SIV. These ALVAC-based protocols demonstrated the ability of vCP125 to elicit HIV1 envelope-specific $CD8^+$ CTLs and to enhance envelope-specific humoral responses observed following a subunit booster (Pialoux et al., 1995). These results justify the rationale for a recombinant ALVAC-based HIV1 vaccine.

Individuals infected with human immunodeficiency virus type 1 (HIV1) initially generate a relatively dynamic and extensive antiviral immune response, including HIV1-specific neutralizing antibodies and HIV1-specific CTLs. Despite these responses, however, the vast majority of HIV1-infected people eventually succumb to HIV1-associated diseases. Since the immune response generated by most HIV1-infected people is not protective, generation of an effective immune response may necessitate that the immune response be modulated or redirected against HIV1 epitopes that are not normally or efficiently seen by HIV1-infected individuals.

Approximately 40% of the HIV1-specific antibody in HIV1-seropositive individuals capable of binding HIV1-infected cells is specific to the third variable region (V3) of the HIV1 envelope glycoprotein (Spear et al, 1994). These results indicate that the V3 loop is 1) highly immunogenic and 2) exposed on the surface of infected cells. The amino acid sequence of the V3 loop varies considerably between different HIV1 isolates. Therefore, a moderate level of sequence variation does not appear to alter the structure or immunogenicity of this region of the envelope glycoprotein.

Since the V3 loop is highly immunogenic and its structure and immunogenicity is not severely affected by sequence variation, this region of the envelope glycoprotein may be useful as an immunogenic platform for presenting normally non-immunogenic linear HIV1 epitopes or heterologous epitopes to the immune system.

Sera from HIV1-seropositive individuals can neutralize lab-adapted strains of HIV1. These sera can also neutralize primary HIV1 isolates (although 100×higher titers are required). Conversely, sera from individuals vaccinated with HIV1 gp120 can neutralize lab-adapted strains of HIV1 (although 10×higher titers relative to sera from seropositive individuals are required), but can not neutralize (at assayable levels) primary isolates (Hanson, 1994). A significant portion of the neutralizing activity found in sera from seropositive and gp120-vaccinated individuals appears to be specific to the V3 loop (Spear et al., 1994; Berman et al., 1994). Since the V3 loop is hypervariable and since antibodies against this region may not neutralize primary isolates or heterologous strains of HIV1, it may be necessary to develop vaccines that elicit an immune response against epitopes other than the V3 loop, epitopes that can neutralize a broad spectrum of HIV1 strains, including primary isolates.

A monoclonal antibody capable of neutralizing primary HIV1 isolates, as well as a broad spectrum of lab-adapted HIV1 strains, has been isolated (Conley et al., 1994; Katinger et al., 1992). The epitope recognized by this monoclonal antibody has been mapped between amino acids 662 and 667 of HIV1 gp41 and has the amino acid sequence, ELDKWA (Buchacher et al, 1994). Approximately 80% of the HIV1 strains from which sequence information has been derived, including strains from the various HIV1 clades, express the core binding sequence of this epitope, LDKW (Conley et al., 1994). Therefore, unlike the V3 loop, this epitope appears to be relatively well conserved. Unfortunately, this epitope does not appear to be very immunogenic in its normal configuration. Only approximately 50% of HIV1-seropositive individuals have a detectable antibody response to the region of gp41 containing this epitope (Broliden et al., 1992).

It can thus be appreciated that provision of an immunodeficiency virus recombinant poxvirus, and of an immunogenic composition which induces an immunological response against immunodeficiency virus infections when administered to host, particularly a composition having enhanced safety such as NYVAC or ALVAC based recombinants containing coding for any or all of HIV1gag(+pro)(IIIB), gp120(MN)(+transmembrane), nef(BRU)CTL epitopes, pol(IIIB)CTL epitopes; for instance, HIV1gag(+pro)(IIIB), gp120(MN)(+transmembrane), nefCTL1, nefCTL2, pol1(PolCTL1), pol2(PolCTL2), pol3(PolCTL3), ELDKWA or LDKW epitopes (SEQ ID NOS: 147 and 148), especially in an immunogenic configuration, or any combination thereof, for example all of them in combination, would be a highly desirable advance over the current state of technology.

ALVAC, TROVAC, NYVAC, and vCP205(ALVAC-MN120TMG) were deposited under the terms of the Budapest Treaty with the American Type Culture Collection (ATCC), 12301 Parklawn Drive, Rockville, Md., 20852, USA: NYVAC under ATCC accession number VR-2559 on Mar. 6, 1997; vCP205 (ALVAC-MN120TMG) under ATCC accession number VR-2557 on Mar. 6, 1997; TROVAC under ATCC accession number VR-2553 on Feb. 6, 1997 and, ALVAC under ATCC accession number VR-2547 on Nov. 14, 1996.

OBJECTS AND SUMMARY OF THE INVENTION

It is therefore an object of this invention to provide modified recombinant viruses, which viruses have enhanced safety, and to provide a method of making such recombinant viruses.

It is an additional object of this invention to provide a recombinant poxvirus antigenic, vaccine or immunological composition having an increased level of safety compared to known recombinant poxvirus vaccines.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety.

These and other objects and advantages of the present invention will become more readily apparent after consideration of the following.

In one aspect, the present invention relates to a modified recombinant virus having inactivated virus-encoded genetic functions so that the recombinant virus has attenuated virulence and enhanced safety. The functions can be non-essential, or associated with virulence. The virus is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigen or epitope derived from immunodeficiency virus and/or CTL epitope such as, e.g., HIV1gag(+pro)(IIIB), gp120(MN)(+transmembrane), nef (BRU)CTL, pol(IIIB) CTL, ELDKWA, LDKW epitopes or any combination thereof, preferably all of them in combination.

In another aspect, the present invention relates to an antigenic, immunological or vaccine composition or a therapeutic composition for inducing an antigenic or immunological response in a host animal inoculated with the composition, said vaccine including a carrier and a modified recombinant virus having inactivated nonessential virus-encoded genetic functions so that the recombinant virus has attenuated virulence and enhanced safety. The virus used in the composition according to the present invention is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigenic protein, e.g., derived from immunodeficiency virus and/or CTL such as, HIV1gag(+pro)(IIIB), gp120(MN)(+transmembrane), nef(BRU) CTL, pol(IIIB) CTL, ELDKWA, LDKW epitopes or any combination thereof, preferably all of them in combination.

In yet another aspect, the present invention relates to an immunogenic composition containing a modified recombinant virus having inactivated nonessential virus-encoded genetic functions so that the recombinant virus has attenuated virulence and enhanced safety. The modified recombinant virus includes, within a non-essential region of the virus genome, a heterologous DNA sequence which encodes an antigenic protein (e.g., derived from an immunodeficiency virus and/or CTL such as, HIV1gag(+pro)(IIIB), gp120 (MN)(+transmembrane), nef(BRU)CTL, pol(IIIB)CTL, ELDKWA, LDKW epitopes or any combination thereof, preferably all of them in combination) wherein the composition, when administered to a host, is capable of inducing an immunological response specific to the antigen.

In a further aspect, the present invention relates to a method for expressing a gene product in a cell (e.g. peripheral blood mononuclear cells (PBMCs) or lymph node mononuclear cells (LNMC) in vitro by introducing into the cell a modified recombinant virus having attenuated virulence and coenhanced safety. The modified recombinant virus can include, within a nonessential region of the virus genome, a heterologous DNA sequence which encodes an antigenic protein, e.g. derived from an immunodeficiency virus such as HIV/gag (+pro) (IIIB), gp120(MN) (+transmembrane), nef(BRU) CTL, pol (IIIB) CTL, ELDKWA, LDKW epitopes or any combination thereof, preferably all of them in combination. The cells can then be reinfused directly into the individual or used to amplify specific $CD8^+$ CTL reactivities for reinfusion (Ex vivo therapy).

In a further aspect, the present invention relates to a method for expressing a gene product in a cell cultured in vitro by introducing into the cell a modified recombinant virus having attenuated virulence and enhanced safety. The modified recombinant virus can include, within a nonessential region of the virus genome, a heterologous DNA sequence which encodes an antigenic protein, e.g., derived from a immunodeficiency virus such as HIV1gag (+pro) (IIIB), gp120(MN)(+transmembrane), nef(BRU)CTL, pol (IIIB)CTL, ELDKWA, LDKW epitopes or any combination thereof, preferably all of them in combination. The product can then be administered to individuals or animals to stimulate an immune response. The antibodies raised can be useful in individuals for the prevention or treatment of immunodeficiency virus and, the antibodies from animals can be used in diagnostic kits, assays or tests to determine the presence or absence in a sample such as sera of immunodeficiency virus or CTL antigens (and therefore the absence or presence of the virus of an immune response to the virus or antibodies).

In a still further aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. The DNA can code for an immunodeficiency virus and/or CTL antigen such as HIV1gag(+pro)(IIIB), gp120(MN)(+ transmembrane), nef(BRU)CTL, pol(IIIB)CTL, ELDKWA, LDKW epitopes or any combination thereof, preferably all of them in combination. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. The modified Copenhagen strain of vaccinia virus is identified as NYVAC (Tartaglia et al., 1992). However, the COPAK strain can also be used in the practice of the invention.

Most preferably, in recombinant viruses of the invention, the exogenous DNA codes for HIV1gag(+pro)(IIIB), gp120 (MN)(+transmembrane), two (2) nef(BRU)CTL and three (3) pol(IIIB)CTL epitopes; or, the exogenous DNA codes for the ELDKWA or LDKW epitopes, and, is inserted so as to be expressed in a region of gp120 or gp160 (i.e., the exogenous DNA codes for a ELDKWA or LDKW modified gp120 or gp160, for instance ELDKWA or LDKW or repeats of either or both in the V3 loop) such that the epitope is expressed in an immunogenic configuration. In this most preferred embodiment it is even more preferred that the two (2) nef(BRU)CTL and three (3) pol(IIIB)CTL epitopes are CTL1, CTL2, pol1, pol2, and pol3. In another most preferred embodiment the exogenous DNA codes for HIV1 gp120+TM in which the V3 loop has been modified to contain at least one, and preferably two ELDKWA epitopes.

In further embodiments, the invention comprehends HIV immunogens and modified gp160 or gp120. Thus, the invention includes an HIV immunogen preferably selected from the group consisting of: HIV1gag(+pro)(IIIB), gp120(MN) (+transmembrane), nef(BRU)CTL, pol(IIIB)CTL, and ELDKWA or LDKW epitopes. The HIV immunogen of the invention can be part of gp160 or gp120. Thus the HIV immunogens ELKDKWA or LDKWA, for example, can be a part of a region of go120 or a region of gp160; for instance, part of gp120V3. Accordingly, the invention comprehends a gp120 or gp160 modified so as to contain an epitope not naturally occurring in gp160. The epitope can be a B-cell epitope. The epitope, more specifically, can be at least one of HIV1gag(+pro)(IIIB), gp120(MN)(+transmembrane), nef (BRU)CTL, pol(IIIB)CTL, and ELDKWA or LDKW epitopes. The gp120 can be modified in the V3 loop. The immunogen and modified gp120 or gp160 can be synthesized by any suitable vector, including a poxvirus, such as a recombinant of the invention; or, by any suitable chemical synthesis method such as the Merrifield Synthesis Method.

The invention in yet a further aspect relates to the product of expression of the inventive recombinant poxvirus and uses therefor, as well as to uses for the inventive immunogens and modified gp120 and sp160, such as to form antigenic, immunological or vaccine compositions for treatment, prevention, diagnosis or testing. The invention in still a further embodiment relates to the uses of DNA from the recombinants as probes for detecting the presence or absence of HIV DNA in a sample or for DNA immunization using an appropriate expression plasmid.

These and other embodiments are disclosed or are obvious from and encompassed by the following detailed description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 8 shows the DNA sequence (SEQ ID NO:66) of a canarypox PvuII fragment containing the C5 ORF.

FIG. 11 shows the nucleotide sequence (SEQ ID NO:67) of a fragment of TROVAC DNA containing an F8 ORF;

FIG. 12 shows the DNA sequence (SEQ ID NO:68) of a 2356 base pair fragment of TROVAC DNA containing the F7 ORF;

FIGS. 14A to 14C shows the nucleotide sequence of the H6-promoted HIV1 gp120(+transmembrane) gene and the I3L-promoted HIV1gag(+pro) gene contained in pHIV32 (SEQ ID NOS: 78 and 79);

FIGS. 15A to 15F shows the nucleotide sequence of the C3 locus in pVQH6CP3L (SEQ ID NOS: 80 and 81);

FIG. 16 shows the nucleotide sequence of the I3L-promoted nef CTL2 epitope and H6-promoted nef CTL1 epitope contained in p2-60-HIV.3 (SEQ ID NOS: 93–96);

FIGS. 17A to 17C shows the nucleotide sequence of the C6 locus in pC6L (SEQ ID NOS: 97 and 98);

FIGS. 18A to 18B shows the nucleotide sequence of the I3L-promoted pol2 epitope, H6-promoted pol1 epitope and 42K-promoted pol3 epitope contained in pC5POLT5A (SEQ ID NOS: 111–115);

FIGS. 19A to 19C shows the nucleotide sequence of the C5 locus in pNC5L-SP5 (SEQ ID NOS: 116 and 117);

FIGS. 26*a–c*, shows the nucleotide sequence of the H6-promoted HIV1 gp120+TM (with ELDKWA epitopes) gene (SEQ ID NOS: 135 and 136) contained in pHIV59 and vCP1307 and the protein expressed (SEQ ID NO: 137);

FIG. 27 shows FACS analysis of vCP1307-infected cells (FACS analysis was performed on HeLa cells infected with ALVAC, vP1286 or vCP1307 with sera from HIV1-seropositve humans (upper panel) or a human monoclonal antibody specific for the ELDKWA epitope, IAM41-2F5 (lower panel));

FIGS. 28*a–c* shows the nucleotide sequence of the H6-promoted HIV1 gp120+TM (with ELDKWA epitopes) gene (SEQ ID NOS: 138 and 139) contained in pHIV60 and vP1313 and the protein expressed (SEQ ID NOS: 140);

FIG. 29 shows FACS analysis of vP1313-infected cells (FACS analysis was performed on HeLa cells infected with NYVAC, vP1286 or vP1313 with sera from HIV1-seropositve humans (upper panel) or a human monoclonal antibody specific for the ELDKWA epitope, IAM41-2F5 (lower panel)).

FIGS. 30*a–c* shows the nucleotide sequence of the H6-promoted HIV1 gp120+TM (with ELDKWA epitopes) gene (SEQ ID NOS: 141 to [143] 142) contained in pHIV61 and vP1319 and the protein expressed (SEQ ID NO: 143);

FIGS. 32, 33*a*, 33*b*, 33*c*, 34, 35, 36, 37*a*, 37*b*, 37*c*, 38*a*, 38*b*, 38*c* show comparative body weights (FIG. 32), blood counts (FIGS. 33*a–c*), creatinine (FIG. 34), SGOT (35), SGPT (FIG. 36), ELISA (Anti-gp160 MN/BR, -v3MN, -p24, FIGS. 37*a–c*, 38*a–c*) of monkeys inoculated with vCP205 and placebo (FIG. 32). upper panel=monkeys 1–4, placebo; lower panel=monkeys 5–8 vCP205; monkeys: 1=open square, 2=open diamond, 3=open triangle, 4=open circle, 5=darkened square, 6=darkened diamond, 7=darkened triangle, 8—darkened circle; plots of Kg (wt) vs. weeks (inoculations indicated with arrow). FIG. 33*a*: leucoytes: left top and bottom panels=monkeys 1–4, placebo; right top and bottom panels=monkeys 5–8, vCP205; top panels individual WBC counts, key same as FIG. 32 except small darkened circle is mean (m); lower panels differential cell counts, darkened square=granulo, open square=lympho, darkened diamond=mono. FIG. 33*b*: same layout and keying as FIG. 33*a*, with upper panels indicating erythrocytes and lower panels indicating mean corpuscle volume and mean indicated by smaller darkened circle. FIG. 33*c*: same layout as FIG. 33*b* with upper panels indicating hematocrite and lower panels indicating hemoglobin. FIG. 34: upper bar graphs=monkeys 1–4, placebo; lower bar graph=monkeys 5–8, vCP205; mg/l vs. days, arrow indicates inoculation; monkeys 1 and 5=dark bars, monkeys 2 and 6=double stippling bars (slanted lines in opposite directions), monkeys 3 and 7=dotted bars, monkeys 4 and 8=single stippling bar (slant lines in one direction), mean is darkened circles. FIG. 35: same keying as FIG. 34, except IU/l vs. days. FIG. 36: same keying as FIG. 35. FIGS. 37*a–c* and 38*a–c*: ELISA in placebo administered monkeys (FIGS. 37*a–c*) and in vCP205 administered monkeys (FIGS. 38*a–c*), titer (log) vs. weeks, arrow indicates injection; FIGS. 37*a* and 38*a*=anti-gp160 MN/BRU, FIGS. 37*b* and 38*b*=anti-V3MN, FIGS. 37*c* and 38C=anti-p24; monkeys 1 and 5=open circle; monkeys 2 and 6=darkened circle; monkeys 3 and 7=open inverted triangle; monkeys 4 and 8=darkened inverted triangle);

FIG. 41*c*: layout and keying same as FIG. 41*b*, upper panels=reticulocytes, lower panels=thrombocytes. FIG. 43*a*: top=cholesterol, middle=proteins, lower=glucose; open circle=placebo, darkened circle= vCP300. FIG. 43*c*: top=creatinine, lower= bilirulain; keying same as FIG. 43*a*. FIG. 43*d*: top=SGOT, middle=SGPT, lower=alkaline phosphatases; keying same as FIG. 43*a*.

DETAILED DESCRIPTION OF THE INVENTION

Figure 1:
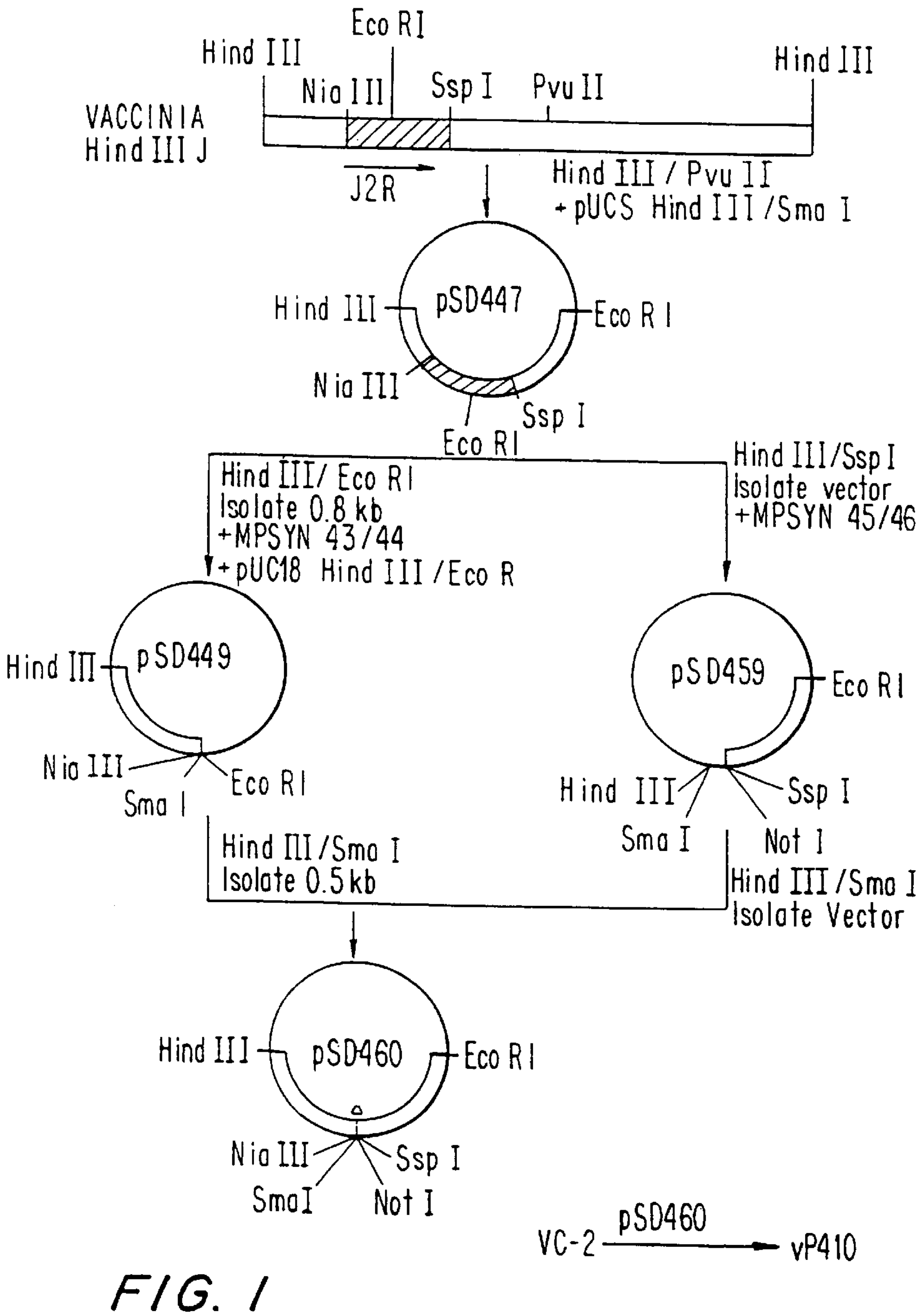
FIG. 1 schematically shows a method for the construction of plasmid pSD460 for deletion of thymidine kinase gene and generation of recombinant vaccinia virus vP410.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R+B14R) vP553;

(3) A type inclusion body region (ATI; A26L) vP618;

(4) hemagglutinin gene (HA; A56R) vP723;

(5) host range gene region (C7L–K1L) vP804; and (6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1992).

NYVAC, ALVAC and TROVAC have also been recognized as unique among all poxviruses in that the National Institutes of Health ("NIH")(U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

Both NYVAC- and ALVAC-based recombinant viruses have been shown to stimulate in vitro specific $CD8^+$ CTLs from human PBMCs (Tartaglia et al., 1993a). Mice immunized with NYVAC or ALVAC recombinants expressing various forms of the HIV-1 envelope glycoprotein generated both primary and memory HIV specific CTL responses which could be recalled by a second inoculation (Tartaglia et al., 1993a; Cox et al., 1993). ALVAC-env and NYVAC-env recombinants (expressing the HIV-1 envelope glycoprotein) stimulated strong HIV-specific CTL responses from peripheral blood mononuclear cells (PBMC) of HIV-1 infected individuals (Tartaglia et al., 1993a; Cox et al., 1993). Acutely infected autologous PBMC were used as stimulator cells for the remaining PBMC. After 10 days incubation in the absence of exogenous IL-2, the cells were evaluated for CTL activities. NYVAC-env and ALVAC-env stimulated high levels of anti-HIV activities in mice.

Applicants have generated an ALVAC recombinant, vCP300 (ALVAC-MN120TMGNP), that expresses numerous HIV1 antigens and HIV1 T-cell epitopes. vCP300 expresses the HIV1 (IIIB) gag (and protease) proteins. (Expression of the protease protein allows the gag polyprotein to be correctly processed.) vCP300 also expresses a form of the HIV1 (MN) envelope glycoprotein in which gp120 is fused to the transmembrane anchor sequence derived from gp41. vP300 also expresses two (2) HIV1 (BRU) nef CTL epitopes and three (3) HIV1 (IIIB) pol CTL epitopes. vCP300 does not, however, express a functional reverse transcriptase activity. vCP300 also does not express a functional nef gene product; a protein associated with pathogenicity in the SIV-macaque model system and HIV1 virulence (Miller et al, 1994; Spina et al, 1994). Therefore, vCP300 expresses immunologically important antigens and/or epitopes from gag, env, pol and nef, but does not express the potentially detrimental enzymatic and/or pathogenic activities associated with pol and nef.

As previously mentioned, vCP300 expresses a form of HIV1 envelope glycoprotein in which the vast majority of the gp41 sequence is deleted. Since most of the immunologically important epitopes associated with the HIV1 envelope glycoprotein are found on gp120, rather than gp41, it is assumed that the immunogenicity of the envelope glycoprotein expressed by this recombinant is not adversely affected. In fact, in a side-by-side analysis, an HIV1 gp120 subunit vaccine was able to protect chimpanzees against an HIV1 challenge, whereas an HIV1 gp160 subunit vaccine was not (Berman et al., 1990). It is not known why the efficacy of these two vaccines is different. However, it is known that antibodies against an epitope gp41 can enhance HIV1 infection in vitro (Robinson et al., 1990). Furthermore, it is known that antibodies to a putative immunosuppressive region of gp41 are associated with the absence of AIDS in HIV1-seropositive individuals, suggesting a potential role in pathogenicity for this region (Klasse et al., 1988). In addition, it is known that antibodies to the C-terminal region of gp41 can cross-react with HLA class II antigens (Golding et al., 1988) and inhibit antigen-specific lymphoproliferative responses (Golding et al., 1989). Since the envelope glycoprotein expressed by vCP300 does not contain any gp41 sequence, except for the 28 amino acids associated with the transmembrane region, the potentially detrimental effects associated with gp41 are avoided. Furthermore, the envelope glycoprotein expressed by vCP300 does not contain the immunodominant epitope on gp41 that is recognized by antisera from every HIV1-seropositive individual from every stage of an HIV1 infection (Shafferman et al., 1989). Therefore, diagnostic tests based upon reactivity against this epitope can be used to distinguish between vaccinated and infected individuals. The ability to differentiate vCP300-vaccinated individuals from HIV1-infected individuals with a gp41 antibody assay is important because the most commonly used diagnostic kit (which assays for the presence of HIV1 p24 antibodies) would be useless, since vCP300-vaccinated individuals would be expected to have a high level of p24 antibodies. Alternatively, HIV-1 infected individuals would be expected to make anti-gp41 antibodies but those vaccinated with vCP205 or vCP300 would not since gp41 is absent from vCP205 or vCP300.

Rabbits and guinea pigs have been inoculated with an ALVAC recombinant (vCP205; ALVAC-MN120TMG) expressing the same cell surface-associated form of HIV1 gp120 (120TM) and Gag/pro as expressed by vCP300. Rabbits and guinea pigs have also been inoculated with vCP205 and boosted with an HIV1 T-B peptide. Both ALVAC-based protocols were able to elicit HIV1 gp160- and V3 loop-specific antibodies, thereby indicating that an ALVAC recombinant expressing the cell surface form of HIV1 gp120 induces an HIV1-specific immune response.

vCP300 expresses the HIV1 Gag proteins, a cell surface-associated form of the HIV1 gp120 envelope glycoprotein, two (2) regions from HIV1 nef containing CTL epitopes and three (3) regions from HIV1 pol containing CTL epitopes. The expression of an HIV1 envelope glycoprotein that does not contain gp41 allows vaccinated individuals to be differentiated from HIV1-infected individuals via an assay for gp41 antibodies and eliminates potentially detrimental responses associated with various gp41 epitopes. Since a previous ALVAC recombinant expressing HIV1 gp160 has been shown to elicit HIV1-specific humoral and cellular immune responses in humans (Pialoux et al., 1995), the addition of Gag and the Pol and Nef epitopes (and the deletion of the potentially detrimental gp41 epitopes) heightens and broadens the immune response elicited by vP300, relative to vCP125, and, may provide an efficacious HIV1 vaccine, or immunological or antigenic composition.

In *Macaca fascicularis* (monkeys; macaques) immunized with vCP205 or vCP300, an antibody response (anti-HIV) was observed, thereby further demonstrating the utility and efficacy of these recombinants.

Since the ELDKWA or LDKW epitope does not appear to be very immunogenic in its normal configuration, to increase its immunogenicity, recombinants of the invention present it to the immune system in a more immunogenic setting, such as within the V3 loop of gp120 or within other regions of gp120 and/or as part of an intact gp160 envelope.

ALVAC recombinant (vCP1307), NYVAC recombinant (vP1313) and COPAK recombinant (vP1319) express a form of the HIV1 gp120+TM gene product in which the V3 loop has been modified to contain two copies of the ELDKWA epitope. The ELDKWA epitopes of this gp120+TM (with ELDKWA epitopes) gene product are expressed on the surface of vCP1307-, vP1313- and vP1319-infected cells.

The V3 loop of HIV1 gp120+TM (or gp160) can be used as an immunological platform for any linear epitope, not just linear HIV1 epitopes. The gp120+TM (with epitopes of interest) protein generated by these recombinants can also be isolated from poxvirus-infected cells and used to inoculate individuals in a subunit vaccine configuration (composition, or an antigenic or immunological composition). The proteins generated by the recombinants and antibodies elicited therefrom can also be used in assays to detect the presence or absence of HIV. Accordingly, the invention comprehends HIV immunogens and modified gp120 and gp160. Further, such envelope-based immunogens (HIV immunogens or unodified gp120 or gp160 (can be derived from any eukaryotic or prokaryotic expression vector and used as subunit preparations or can be administered through DNA immunization using an appropriate expression plasmid. Techniques for DNA immunization are known in the art. With respect to techniques for DNA immunization, mention is particularly made of Nabel and Felgner, "Direct gene transfer for immunotherapy and immunization", Tibtech, May 1993, 11;

211–215, and Webster et al, "protection of ferrets against influenza challenge with a DNA vaccine to the haemagglutinin", vaccine, 1994, 12(16): 1495–1498, incorporated herein by reference. Also, the DNA from the recombinants vP1313, vP1319 and vCP1307 can be used to probe for the presence of HIV DNA in a sample of interest using known hybridization techniques, or, to generate PCR primers using known techniques.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

The administration procedure for recombinant virus, immunogen, modified gp120 or gp160, DNA or expression product compositions of the invention such as immunological, antigenic or vaccine compositions or therapeutic compositions can be via a parenteral route (intradermal, intramuscular or subcutaneous). Such an administration enables a systemic immune response.

More generally, the inventive antigenic, immunological or vaccine compositions or therapeutic compositions (compositions containing the poxvirus recombinants, expression products, immunogens, DNA, modified gp120 or gp160 of the invention) can be prepared in accordance with standard techniques well known to those skilled in the pharmaceutical art. Such compositions can be administered in dosages and by techniques well known to those skilled in the medical arts taking into consideration such factors as the age, sex, weight, and condition of the particular patient, and the route of administration. The compositions can be administered alone, or can be co-administered or sequentially administered with compositions of the invention or with other immunological, antigenic or vaccine or therapeutic compositions in seropositive individuals. The compositions can be administered alone, or can be co-administered or sequentially administered with compositions of the invention or with other antigenic, immunological, vaccine or therapeutic compositions in seronegative individuals. Such other compositions can include purified antigens from immunodeficiency virus or from the expression of such antigens by a recombinant poxvirus or other vector system or, such other compositions can include a recombinant poxvirus which expresses other immunodeficiency antigens or biological response modifiers (e.g. cytokines; co-stimulating molecules). Again, co-administration is performed by taking into consideration such known factors as the age, sex, weight, and condition of the particular patient, and, the route of administration.

Examples of compositions of the invention include liquid preparations for orifice, e.g., oral, nasal, anal, vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant poxvirus, expression product, immunogen, DNA, or modified gp120 or gp160 may be in admixture with a suitable carrier, diluent, or excipient such as sterile water, physiological saline, glucose or the like.

Further, the products of expression of the inventive recombinant poxviruses can be used directly to stimulate an immune response in either seronegative or seropositive individuals or in animals. Thus, the expression products can be used in compositions of the invention instead or in addition to the inventive recombinant poxvirus in the aforementioned compositions. The immunogens of the invention can be similarly used.

Additionally, the inventive recombinant poxvirus and the expression products therefrom and immunogens and modified gp120 or gp160 of the invention stimulate an immune or antibody response in humans and animals. From those antibodies or by techniques well-known in the art, monoclonal antibodies can be prepared and, those monoclonal antibodies, can be employed in well known antibody binding assays, diagnostic kits or tests to determine the presence or absence of particular immunodeficiency virus antigen(s) and therefore the presence or absence of the virus, or to determine whether an immune response to the virus or antigen(s) has simply been stimulated. Those monoclonal antibodies can also be employed in immunoadsorption chromatography to recover immunodeficiency virus or expression products of the inventive recombinant poxvirus.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Furthermore, the inventive recombinant poxvirus or expression products therefrom or the inventive immunogens or modified gp120 or gp160 can be used to stimulate a response in cells such as lymphocytes or CTLs in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against immunodeficiency virus.

Additionally, the DNA from inventive recombinants can be used as probes to detect the presence of HIV DNA in a sample or, to generate PCR primers, or for DNA immunization using an appropriate expression plasmid, by methods known in the art. (See Nabel and Felger and Webster et al, supra)

Accordingly, the inventive recombinant poxvirus has several utilities: In antigenic, immunological or vaccine compositions such as for administration to seronegative individuals. In therapeutic compositions in seropositive individuals in need of therapy to stimulate or boost the immune system against immunodeficiency virus. In vitro to produce antigens or the inventive immunogens or the inventive modified gp120 or gp160 which can be further used in antigenic, immunological or vaccine compositions or in therapeutic compositions. To generate antibodies (either by direct administration or by administration of an expression product of the inventive recombinant poxvirus) which can be further used: in diagnosis, tests or kits to ascertain the presence or absence of antigens in a sample such as sera, for instance, to ascertain the presence or absence of immunodeficiency virus or CTLs in a sample such as sera or, to determine whether an immune response has elicited to the virus or, to particular antigen(s); or, in immunoadsorption chromatography (the inventive immunogens and modified gp120 or gp160 can also be used to generate antibodies which can be also so further used). To generate DNA for use as hybridization probes or to prepare PCR primers or for DNA immunization. And, the inventive recombinant poxvirus, expression products therefrom, immunogens and modified gp120 or gp160 can be used to generate stimulated cells which can be further used (reinfused) to stimulate an immune response (antigenic, or immunological response; or active immunization) or, to boost or stimulate the immune system (for instance, of an immunocompromised or seropositive individual). Other utilities also exist for embodiments of the invention.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of *E. coli* polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor-et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

Example 1

Construction of Plasmid pSD460 for Deletion of Thymidine Kinase Gene (J2R)

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:1/SEQ ID NO:2)

```
                                     SmaI
MPSYN43     5'      TAATTAACTAGCTACCCGGG      3'

MPSYN44     3' GTACATTAATTGATCGATGGGCCCTTAA 5'
               NlaIII                 EcoRI
```

were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

```
                HindIII SmaI                                                        NotI        SspI
MPSYN45    5'  AGCTTCCCGGGTAAGTAATACGTCAAGGAGAAAACGAAACGATCTGTAGTTAGCGGCCGCCTAATTAACTAAT 3'    MPSYN45

MPSYN46    3'      AGGGCCCATTCATTATGCAGTTCCTCTTTTGCTTTGCTAGACATCAATCGCCGGCGGATTAATTGATTA 5'    MPSYN46
```

generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}P$ labelled probe was synthesized by primer extension using MPSYN45 (SEQ ID NO:3) as template and the complementary 20mer oligonucleotide MPSYN47 (SEQ ID NO:5) (5' TTAGTTAATTAGGCGGCCGC 3') as primer. Recombinant virus vP410 was identified by plaque hybridization.

Example 2

Construction of Plasmid pSD486 for Deletion of Hemorrhagic Region (B13R+B14R)

Figure 2:
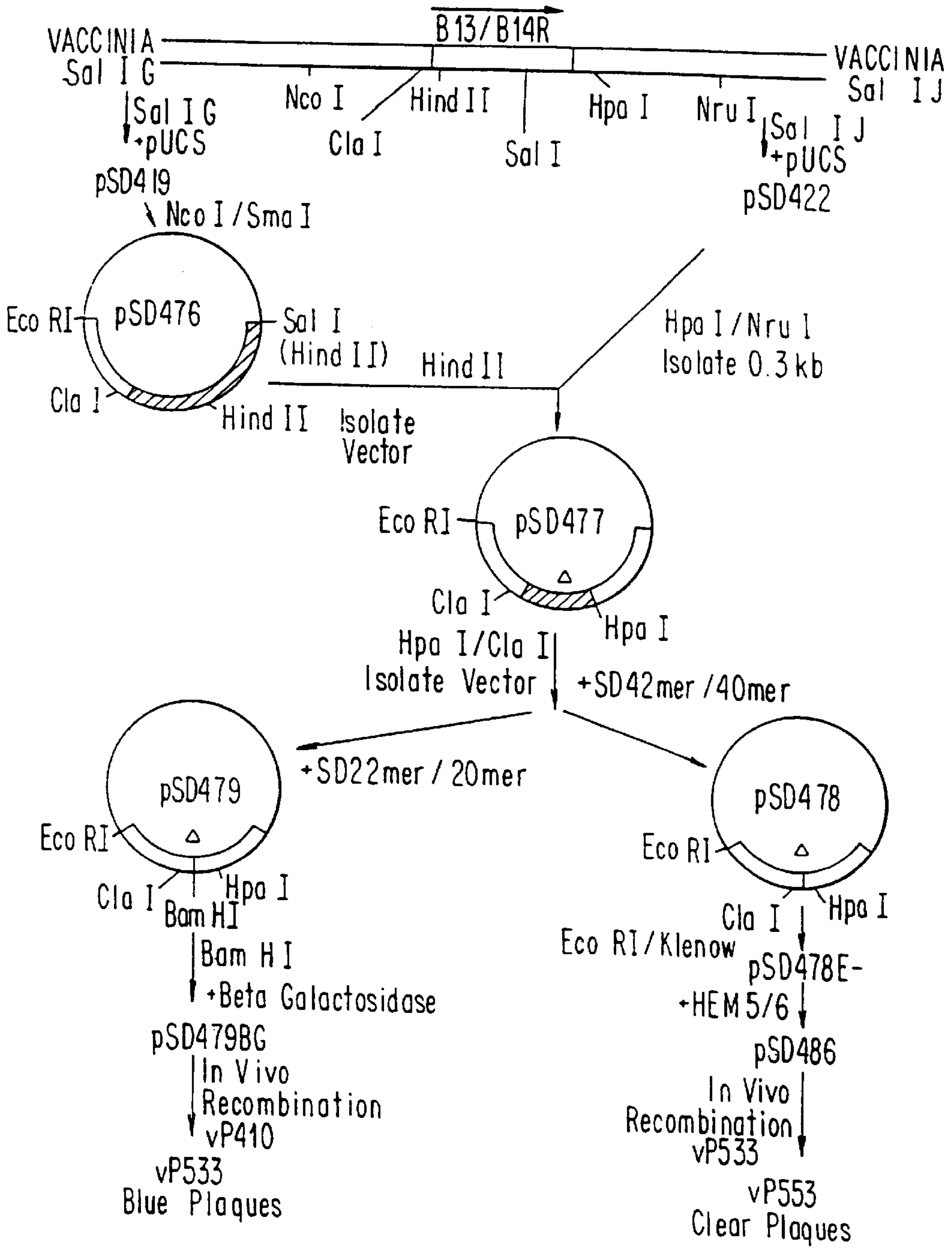
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of *E. coli* polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:6/SEQ ID NO:7)

```
               ClaI          BamHI HpaI
SD22mer    5' CGATTACTATGAAGGATCCGTT 3'

SD20mer    3'   TAATGATACTTCCTAGGCAA 5'
```

generating pSD479. pSD479 contains an initiation codon (underlined) followed by a BamHI site. To place *E. coli* Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

```
             ClaI          SacI          XhoI          HpaI
SD42mer    5' CGATTACTAGATCTGAGCTCCCCGGGCTCGAGGGATCCGTT 3'

SD40mer    3'   TAATGATCTAGACTCGAGGGGCCCGAGCTCCCTAGGCAA 5'
                    BglII         SmaI          BamHI
```

generating plasmid pSD478. Next the EcoRI site at the pUC/vaccinia junction was destroyed by digestion of pSD478 with EcoRI followed by blunt ending with Klenow fragment of *E. coli* polymerase and ligation, generating plasmid pSD478E⁻. pSD478E⁻ was digested with BamHI and HpaI and ligated with annealed synthetic oligonucleotides HEM5/HEM6 (SEQ ID NO:10/SEQ ID NO:11)

```
             BamHI EcoRI  HpaI
HEMS      5'  GATCCGAATTCTAGCT 3'

HEM6      3'      GCTTAAGATCGA 5'
```

generating plasmid pSD486. pSD486 was used as donor plasmid for recombination with recombinant vaccinia virus vP533, generating vP553, which was isolated as a clear plaque in the presence of X-gal.

Example 3

Construction of Plasmid pMP494Δ for Deletion of ATI Region (A26L)

Figure 3:
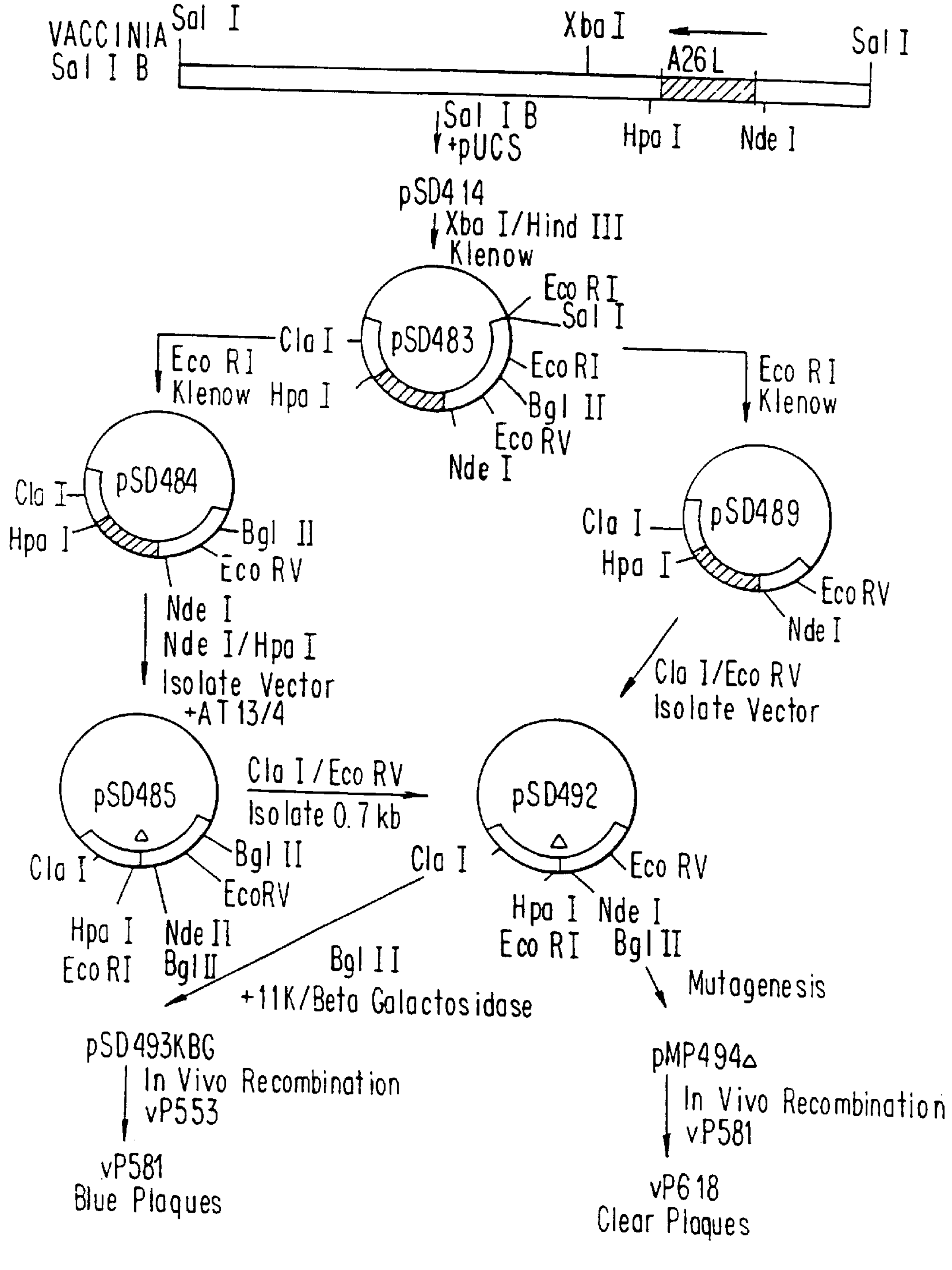
FIG. 3 schematically shows a method for the construction of plasmid pMP494Δ for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of *E. coli* polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

```
        NdeI                                                                     BglII EcoRI HpaI
ATI3  5' TATGAGTAACTTAACTCTTTTGTTAATTAAAAGTATATTCAAAAAATAAGTTATATAAATAGATCTGAATTCGTT 3'   ATI3

ATI4  3'   ACTCATTGAATTGAGAAAACAATTAATTTTCATATAAGTTTTTTATTCAATATATTTATCTAGACTTAAGCAA 5'   ATI4
```

reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of *E. coli* polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BglII cassette containing the *E. coli* Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Example 4

Construction of Plasmid pSD467 for Deletion of Hemagglutinin Gene (A56R)

Figure 4:
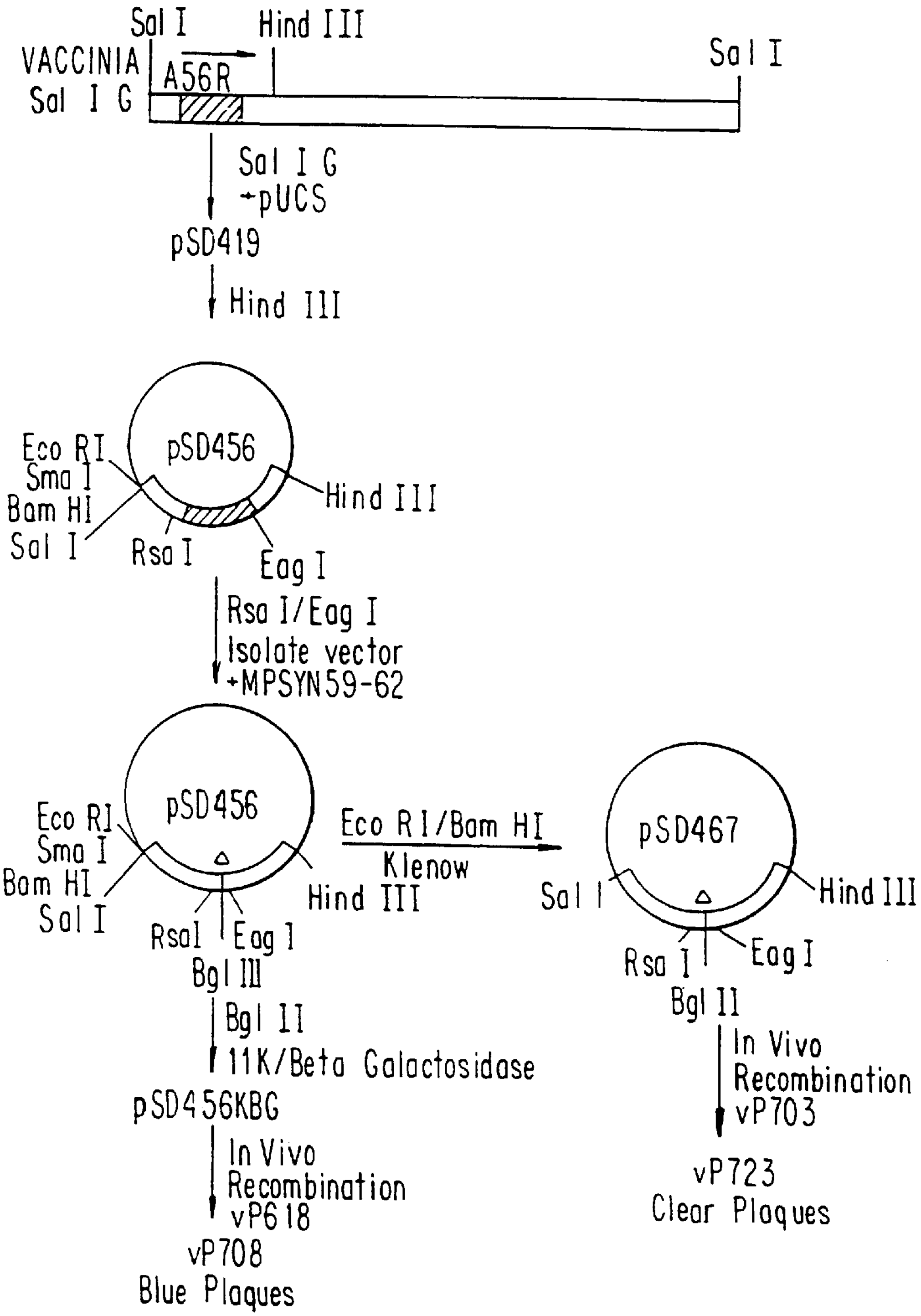
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EaqI vector fragment from pSD456 was isolated and ligated with annealed synthetic oligonucleotides MPSYN59 (SEQ ID NO:15), MPSYN62 (SEQ ID NO:16), MPSYN60 (SEQ ID NO:17), and MPSYN61 (SEQ ID NO:18)

```
                RsaI
MPSYN59   5' ACACGAATGATTTTCTAAAGTATTTGGAAAGTTTTATAGGTAGTTGATAGAACAAAATACATAATTT 3'

MPSYN62   3' TGTGCTTACTAAAAGATTTCATAAACCTTTCAAAATATCCATCAACTATCT 5'

                                                  BglII SmaI  PstI  EagI
MPSYN60   5'                TGTAAAAATAAATCACTTTTTATACTAAGATCTCCCGGGCTGCAGC     3'

MPSYN61   3' TGTTTTATGTATTAAAACATTTTTATTTAGTGAAAAATATGATTCTAGAGGGCCCGACGTCGCCGG 5'
```

reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,053]. The site of the deletion in pSD466 is indicated by a triangle in FIG. 4.

A 3.2 kb BglII/BamHI (partial) cassette containing the *E. coli* Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of *E. coli* polymerase and ligation. Recombination between vP708 and pSD467 resulted in recombinant vaccinia deletion mutant, vP723, which was isolated as a clear plaque in the presence of X-gal.

Example 5

Construction of Plasmid pMPCSK1Δ for Deletion of Open Reading Frames [C7L–K1L]

Figure 5:
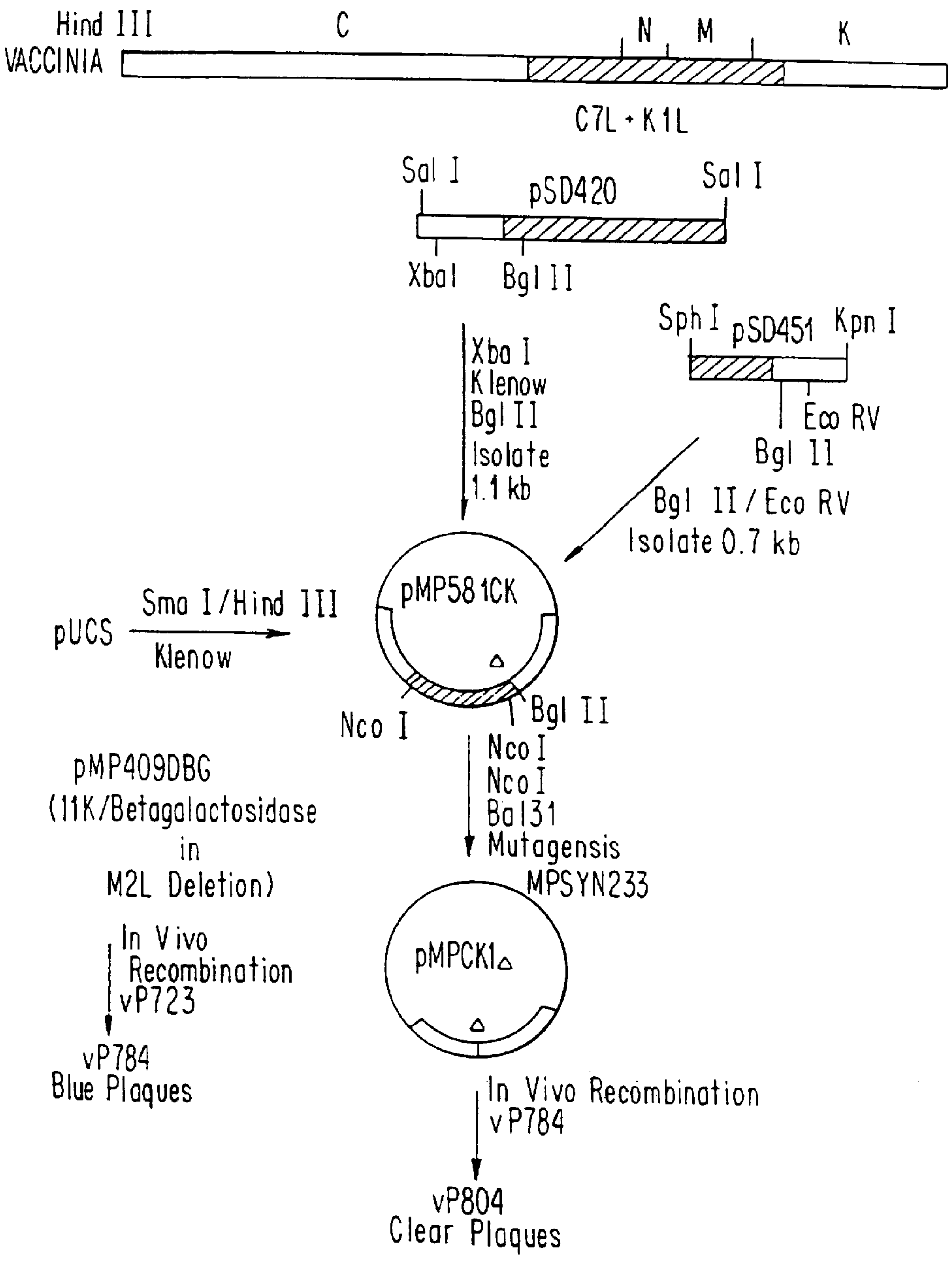
FIG. 5 schematically shows a method for the construction of plasmid pMPCK1Δ for deletion of gene cluster [C7L–K1L] and generation of recombinant vaccinia virus vP804.

Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, *E. coli* Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

```
                                                  BglII
MPSYN82 (SEQ ID NO:19) 5'  TTTCTGTATATTTGCACCAATTTAGATCTT-
                           ACTCAAAATATGTAACAATA 3'
```

The resulting plasmid, pMP409D, contains a unique BglII site inserted into the M2L deletion locus as indicated above. A 3.2 kb BamHI (partial)/BglII cassette containing the *E. coli* Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of *E. coli* polymerase. The left flanking arm consisting of vaccinia HindIII C sequences was obtained by digestion of pSD420 with XbaI (pos. 18,628) followed by blunt ending with Klenow fragment of *E. coli* polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5'-TGTCATTTAACACTATACTCATATTAATAAAAATAATATTTATT-3'. The resulting plasmid, pMPCSK1Δ, is deleted for vaccinia sequences positions 18,805–29,108, encompassing 12 vaccinia open reading frames [C7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

Example 6

Construction of Plasmid pSD548 for Deletion of Large Subunit, Ribonucleotide Reductase (I4L)

Figure 6:
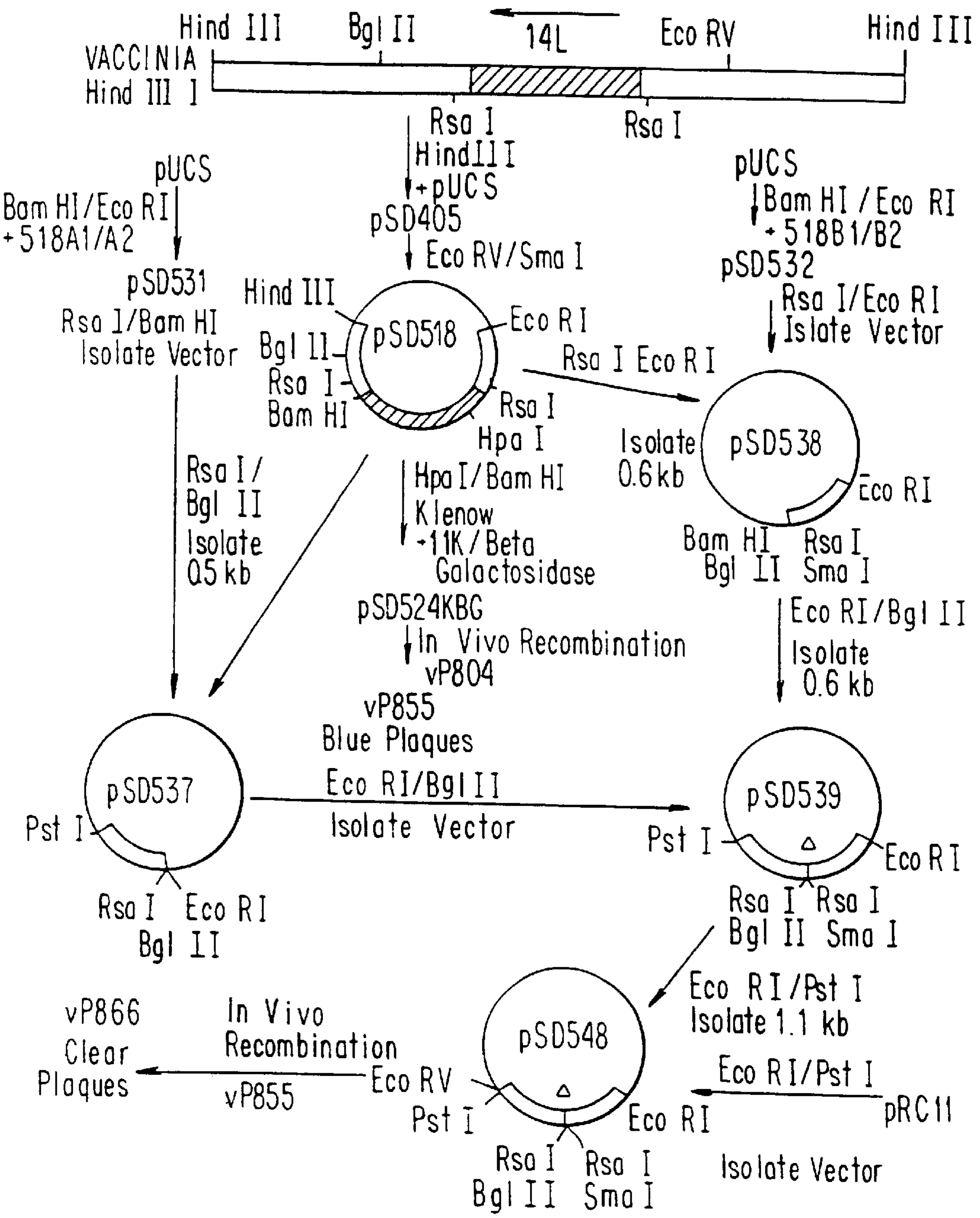
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of *E. coli* polymerase. This 4.8 kb vector fragment was ligated with a 3.2 kb SmaI cassette containing the *E. coli* Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

```
               BamHI   RsaI                                                  BglII    EcoRI
518A1       5' GATCCTGAGTACTTTGTAATATAATGATATATATTTTCACTTTATCTCATTTGAGAATAAAAAGATCTTAGG       3'     518A1

518A2       3'     GACTCATGAAACATTATATTACTATATATAAAAGTGAAATAGAGTAAACTCTTATTTTTCTAGAATCCTTAA 5'     518A2
```

forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

```
        BamHI BglII SmaI                                              RsaI   EcoRI
518B1   5' GATCCAGATCTCCCGGGAAAAAAATTATTTAACTTTTCATTAATAGGGATTTGACGTATGTAGCGTACTAGG   3,   518B1

518B2   3'    GTCTAGAGGGCCCTTTTTTTAATAAATTGAAAAGTAATTATCCCTAAACTGCATACTACGCATGATCCTTAA 5'   518B2
```

forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

Example 7

Insertion of a Rabies Glycoprotein G Gene Into NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 1) except for the presence of a polylinker region.

Figure 7:
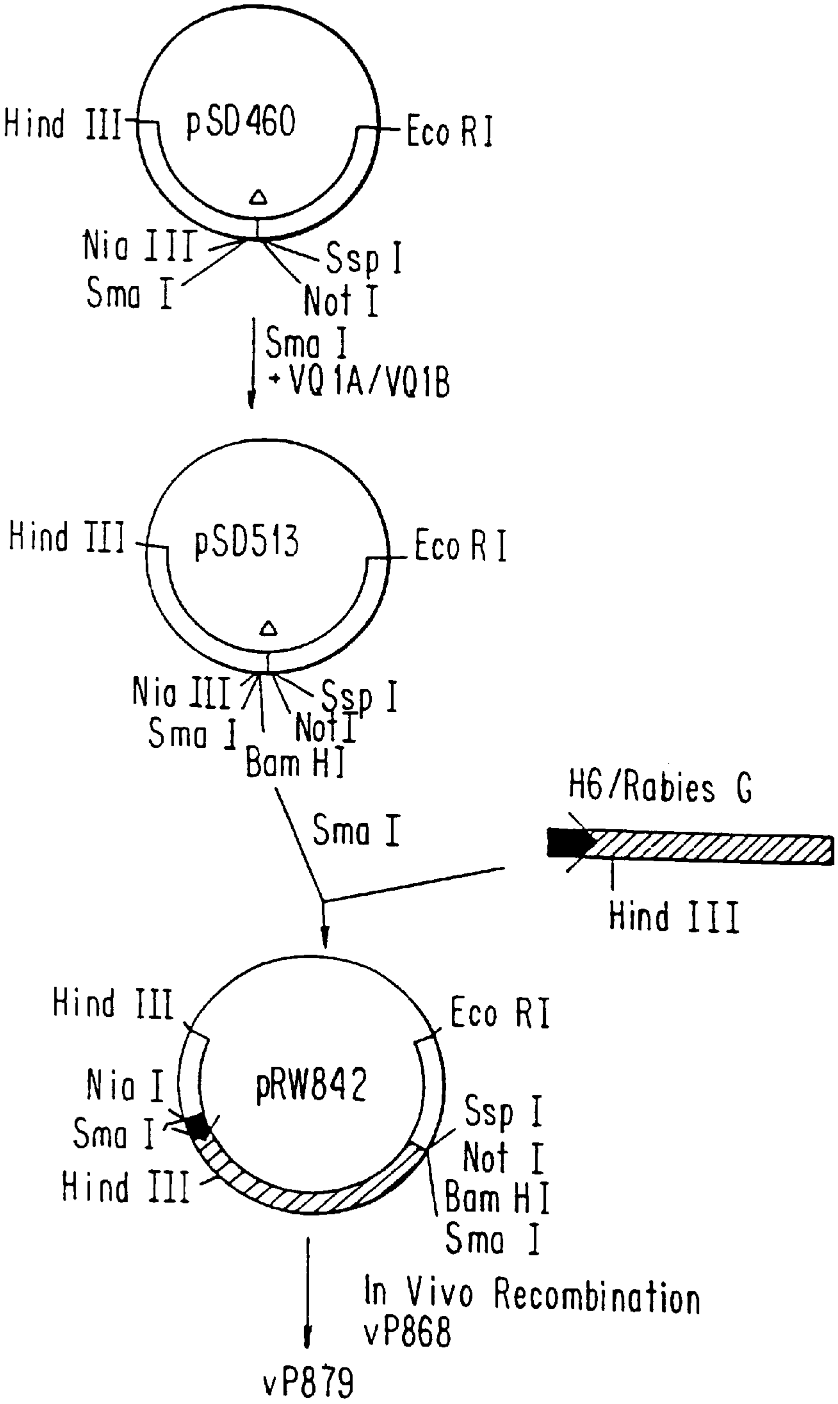
FIG. 7 schematically shows a method for the construction of plasmid pRW842 for insertion of rabies glycoprotein G gene into the TK deletion locus and generation of recombinant vaccinia virus vP879.

Referring now to FIG. 7, the polylinker region was inserted by cutting pSD460 with SmaI and ligating the plasmid vector with annealed synthetic oligonucleotides VQ1A/VQ1B (SEQ ID NO:25/SEQ ID NO:26)

```
             SmaI BglII XhoI  PstI  NarI  BamHI
VQ1A      5'  GGGAGATCTCTCGAGCTGCAGGGCGCCGGATCCTTTTTCT 3'

VQ1B      3'  CCCTCTAGAGAGCTCGACGTCCCGCGGCCTAGGAAAAAGA 5'
```

to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}P$-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

Example 8

Construction of TROVAC-NDV Expressing the Fusion and Hemagglutinin-Neuraminidase Glycoproteins of Newcastle Disease Virus This example describes the development of TROVAC, a fowlpox virus vector and, of a fowlpox Newcastle Disease Virus recombinant designated TROVAC-NDV and its safety and efficacy. A fowlpox virus (FPV) vector expressing both F and HN genes of the virulent NDV strain Texas was constructed. The recombinant produced was designated TROVAC-NDV. TROVAC-NDV expresses authentically processed NDV glycoproteins in avian cells infected with the recombinant virus and inoculation of day old chicks protects against subsequent virulent NDV challenge.

Cells and Viruses. The Texas strain of NDV is a velogenic strain. Preparation of cDNA clones of the F and HN genes has been previously described (Taylor et al., 1990; Edbauer et al., 1990). The strain of FPV designated FP-1 has been described previously (Taylor et al., 1988a). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. The stock virus used in the in vitro recombination test to produce TROVAC-NDV had been subjected to twelve passages in primary CEF cells from the plaque isolate.

Construction of a Cassette for NDV-F. A 1.8 kbp BamHI fragment containing all but 22 nucleotides from the 5' end of the F protein coding sequence was excised from pNDV81 (Taylor et al., 1990) and inserted at the BamHI site of pUC18 to form pCE13. The vaccinia virus H6 promoter previously described (Taylor et al., 1988a,b; Guo et al., 1989; Perkus et al., 1989) was inserted into pCE13 by digesting pCE13 with SalI, filling in the sticky ends with Klenow fragment of *E. coli* DNA polymerase and digesting with HindIII. A HindIII-EcoRV fragment containing the H6 promoter sequence was then inserted into pCE13 to form pCE38. A perfect 5' end was generated by digesting pCE38 with KpnI and NruI and inserting the annealed and kinased oligonucleotides CE75 (SEQ ID NO:27) and CE76 (SEQ ID NO:28) to generate pCE47.

CE75:
CGATATCCGTTAAGTTTGTATCG-
TAATGGGCTCCAGATCTTCTACCAG-
GATCCCGGTAC

CE76:
CGGGATCCTGGTAGAAGATCTGGAGC-
CCATTACGATACAAACTTAACGGATATCG.

In order to remove non-coding sequence from the 3' end of the NDV-F a SmaI to PstI fragment from pCE13 was inserted into the SmaI and PstI sites of pUC18 to form pCE23. The non-coding sequences were removed by sequential digestion of pCE23 with SacI, BamHI, Exonuclease III, SI nuclease and EcoRI. The annealed and kinased oligonucleotides CE42 (SEQ ID NO:29) and CE43 (SEQ ID NO:30) were then inserted to form pCE29.

CE42: AATTCGAGCTCCCCGGG

CE43: CCCGGGGAGCTCG

The 3' end of the NDV-F sequence was then inserted into plasmid pCE20 already containing the 5' end of NDV-F by cloning a PstI-SacI fragment from pCE29 into the PstI and SacI sites of pCE20 to form pCE32. Generation of pCE20 has previously been described in Taylor et al., 1990.

In order to align the H6 promoter and NDV-F 5' sequences contained in pCE47 with the 3' NDV-F sequences contained in pCE32, a HindIII-PstI fragment of pCE47 was inserted into the HindIII and PstI sites of pCE32 to form pCE49. The H6 promoted NDV-F sequences were then transferred to the de-ORFed F8 locus (described below) by cloning a HindIII-NruI fragment from pCE49 into the HindIII and SmaI sites of pJCA002 (described below) to form pCE54. Transcription stop signals were inserted into pCE54 by digesting pCE54 with SacI, partially digesting with BamHI and inserting the annealed and kinased oligonucleotides CE166 (SEQ ID NO:31) and CE167 (SEQ ID NO:32) to generate pCE58.

CE166: CTTTTTATAAAAAGTTAACTACGTAG

CE167: GATCCTACGTAGTTAACTTTTTATAAAAAGAGCT

A perfect 3' end for NDV-F was obtained by using the polymerase chain reaction (PCR) with pCE54 as template and oligonucleotides CE182 (SEQ ID NO:33) and CE183 (SEQ ID NO:34) as primers.

CE182: CTTAACTCAGCTGACTATCC

CE183: TACGTAGTTAACTTTTTATAAAAATCATATTTTTGTAGTGGCTC

The PCR fragment was digested with PvuII and HpaI and cloned into pCE58 that had been digested with HpaI and partially digested with PvuII. The resulting plasmid was designated pCE64. Translation stop signals were inserted by cloning a HindIII-HpaI fragment which contains the complete H6 promoter and F coding sequence from pCE64 into the HindIII and HpaI sites of pRW846 to generate pCE71, the final cassette for NDV-F. Plasmid pRW846 is essentially equivalent to plasmid pJCA002 (described below) but containing the H6 promoter and transcription and translation stop signals. Digestion of pRW846 with HindIII and HpaI eliminates the H6 promoter but leaves the stop signals intact.

Construction of Cassette for NDV-HN. Construction of plasmid pRW802 was previously described in Edbauer et al., 1990. This plasmid contains the NDV-HN sequences linked to the 3' end of the vaccinia virus H6 promoter in a pUC9 vector. A HindIII-EcoRV fragment encompassing the 5' end of the vaccinia virus H6 promoter was inserted into the HindIII and EcoRV sites of pRW802 to form pRW830. A perfect 3' end for NDV-HN was obtained by inserting the annealed and kinased oligonucleotides CE162 (SEQ ID NO:35) and CE163 (SEQ ID NO:36) into the EcoRI site of pRW830 to form pCE59, the final cassette for NDV-HN.

CE162:
AATTCAGGATCGTTCCTTTACTAGT-
TGAGATTCTCAAGGATGATGGGATT-
TAATTTTTATAAGCTTG

CE163:
AATTCAAGCTTATAAAAATTAAATC-
CCATCATCCTTGAGAATCTCAACTAG-
TAAAGGAACGATCCTG

Construction of FPV Insertion Vector. Plasmid pRW731-15 contains a 10kb PvuII-PvuII fragment cloned from genomic DNA. The nucleotide sequence was determined on both strands for a 3660 bp PvuII-EcoRV fragment and is shown in FIG. 11 (SEQ ID NO:67). The limits of an open reading frame designated here as F8 were determined. Plasmid pRW761 is a sub-clone of pRW731-15 containing a 2430 bp EcoRV-EcoRV fragment. The F8 ORF was entirely contained between an XbaI site and an SspI site in pRW761. In order to create an insertion plasmid which on recombination with TROVAC genomic DNA would eliminate the F8 ORF, the following steps were followed. Plasmid pRW761 was completely digested with XbaI and partially digested with SspI. A 3700 bp XbaI-SspI band was isolated from the gel and ligated with the annealed double-stranded oligonucleotides JCA017 (SEQ ID NO:37) and JCA018 (SEQ ID NO:38).

JCA017:5'
CTAGACACTTTATGTTTTTTAATATCCG-
GTCTTAAAAGCTTCCCGGGGATCCT-
TATACGGGGAATAAT

JCA018:5'
ATTATTCCCCGTATAAGGATCCCCCGG-
GAAGCTTTTAAGACCGGATATTAAAAAA-
CATAAAGTGT

The plasmid resulting from this ligation was designated pJCA002.

Construction of Double Insertion Vector for NDV F and HN. The H6 promoted NDV-HN sequence was inserted into the H6 promoted NDV-F cassette by cloning a HindIII fragment from pCE59 that had been filled in with Klenow fragment of *E. coli* DNA polymerase into the HpaI site of pCE71 to form pCE80. Plasmid pCE80 was completely digested with NdeI and partially digested with BglII to generate an NdeI-BglII 4760 bp fragment containing the NDV F and HN genes both driven by the H6 promoter and linked to F8 flanking arms. Plasmid pJCA021 was obtained by inserting a 4900 bp PvuII-HindII fragment from pRW731-15 into the SmaI and HindII sites of pBSSK+. Plasmid pJCA021 was then digested with NdeI and BglII and ligated to the 4760 bp NdeI-BglII fragment of pCE80 to form pJCA024. Plasmid pJCA024 therefore contains the NDV-F and HN genes inserted in opposite orientation with 3' ends adjacent between FPV flanking arms. Both genes are linked to the vaccinia virus H6 promoter. The right flanking arm adjacent to the NDV-F sequence consists of 2350 bp of FPV sequence. The left flanking arm adjacent to the NDV-HN sequence consists of 1700 bp of FPV sequence.

Development of TROVAC-NDV. Plasmid pJCA024 was transfected into TROVAC infected primary CEF cells by using the calcium phosphate precipitation method previously described (Panicali et al., 1982; Piccini et al., 1987). Positive plaques were selected on the basis of hybridization to specific NDV-F and HN radiolabelled probes and subjected to five sequential rounds of plaque purification until a pure population was achieved. One representative plaque was then amplified and the resulting TROVAC recombinant was designated TROVAC-NDV (vFP96).

Immunofluorescence. Indirect immunofluorescence was performed as described (Taylor et al., 1990) using a polyclonal anti-NDV serum and, as mono-specific reagents, sera produced in rabbits against vaccinia virus recombinants expressing NDV-F or NDV-HN.

Immunoprecipitation. Immunoprecipitation reactions were performed as described (Taylor et al., 1990) using a polyclonal anti-NDV serum obtained from SPAFAS Inc., Storrs, Conn.

The stock virus was screened by in situ plaque hybridization to confirm that the F8 ORF was deleted. The correct insertion of the NDV genes into the TROVAC genome and the deletion of the F8 ORF was also confirmed by Southern blot hybridization.

In NDV-infected cells, the F glycoprotein is anchored in the membrane via a hydrophobic transmembrane region near the carboxyl terminus and requires post-translational cleavage of a precursor, $F_0$, into two disulf ide linked polypeptides $F_1$ and $F_2$. Cleavage of $F_0$ is important in determining the pathogenicity of a given NDV strain (Homma and Ohuchi, 1973; Nagai et al., 1976; Nagai et al., 1980), and the sequence of amino acids at the cleavage site is therefore critical in determining viral virulence. It has been determined that amino acids at the cleavage site in the NDV-F sequence inserted into FPV to form recombinant vFP29 had the sequence Arg-Arg-Gln-Arg-Arg (SEQ ID NO: [39] 149) (Taylor et al., 1990) which conforms to the sequence found to be a requirement for virulent NDV strains (Chambers et al., 1986; Espion et al., 1987; Le et al., 1988; McGinnes and Morrison, 1986; Toyoda et al., 1987). The HN glycoprotein synthesized in cells infected with virulent strains of NDV is an uncleaved glycoprotein of 74 kDa. Extremely avirulent strains such as Ulster and Queensland encode an HN precursor (HNo) which requires cleavage for activation (Garten et al., 1980).

The expression of F and HN genes in TROVAC-NDV was analyzed to confirm that the gene products were authentically processed and presented. Indirect-immunofluorescence using a polyclonal anti-NDV chicken serum confirmed that immunoreactive proteins were presented on the infected cell surface. To determine that both proteins were presented on the plasma membrane, mono-specific rabbit sera were produced against vaccinia recombinants expressing either the F or HN glycoproteins. Indirect immunofluorescence using these sera confirmed the surface presentation of both proteins.

Immunoprecipitation experiments were performed by using ($^{35}S$) methionine labeled lysates of CEF cells infected with parental and recombinant viruses. The expected values of apparent molecular weights of the glycosylated forms of $F_1$ and $F_2$ are 54.7 and 10.3 kDa respectively (Chambers et al., 1986). In the immunoprecipitation experiments using a polyclonal anti-NDV serum, fusion specific products of the appropriate size were detected from the NDV-F single recombinant vFP29 (Taylor et al., 1990) and the TROVAC-NDV double recombinant vFP96. The HN glycoprotein of appropriate size was also detected from the NDV-HN single recombinant VFP-47 (Edbauer et al., 1990) and TROVAC-NDV. No NDV specific products were detected from uninfected and parental TROVAC infected CEF cells.

In CEF cells, the F and HN glycoproteins are appropriately presented on the infected cell surface where they are recognized by NDV immune serum. Immunoprecipitation analysis indicated that the $F_0$ protein is authentically cleaved to the $F_1$ and $F_2$ components required in virulent strains. Similarly, the HN glycoprotein was authentically processed in CEF cells infected with recombinant TROVAC-NDV.

Previous reports (Taylor et al., 1990; Edbauer et al., 1990; Boursnell et al., 1990a,b,c; Ogawa et al., 1990) would indicate that expression of either HN or F alone is sufficient to elicit protective immunity against NDV challenge. Work on other paramyxoviruses has indicated, however, that antibody to both proteins may be required for full protective immunity. It has been demonstrated that SV5 virus could spread in tissue culture in the presence of antibody to the HN glycoprotein but not to the F glycoprotein (Merz et al., 1980). In addition, it has been suggested that vaccine failures with killed measles virus vaccines were due to inactivation of the fusion component (Norrby et al., 1975). Since both NDV glycoproteins have been shown to be responsible for eliciting virus neutralizing antibody (Avery et al., 1979) and both glycoproteins, when expressed individually in a fowlpox vector are able to induce a protective immune response, it can be appreciated that the most efficacious NDV vaccine should express both glycoproteins.

Example 9

Construction of ALVAC Recombinants Expressing Rabies Virus Glycoprotein G

This example describes the development of ALVAC, a canarypox virus vector and, of a canarypox-rabies recombinant designated as ALVAC-RG (vCP65) and its safety and efficacy.

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence of this fragment is shown in FIG. 8 (SEQ ID NO:66) between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:39) GCTTCCCGGGAATTCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO:40)
ACTCTCAAAAGCTTCCCGGGAATTCTAGCTAGCTAGTTTTTATAAA

RW146 (SEQ ID NO:41):
GATCTTTATAAAAACTAGCTAGCTAGAATTCCCGGGAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene. Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E ((SEQ ID NO:42)–(SEQ ID NO:46)) are:

A (SEQ ID NO:42): CTGAAATTATTTCATTATCGCGATATCCGTTAAGTTTGTATCGTAATGGTTCCTCAGGCTCTCCTGTTTGT

B (SEQ ID NO:43): CATTACGATACAAACTTAACGGATATCGCGATAATGAAATAATTTCAG

C (SEQ ID NO:44): ACCCCTTCTGGTTTTTCCGTTGTGTTTTGGGAAATTCCCTATTTACACGATCCCAGACAAGCTTAGATCTCAG

D (SEQ ID NO:45): CTGAGATCTAAGCTTGTCTGGGATCGTGTAAATAGGGAATTTCCCAAAACA

E (SEQ ID NO:46): CAACGGAAAAACCAGAAGGGGTACAAACAGGAGAGCCTGAGGAAC

The diagram of annealed oligonucleotides A through E is as follows:

```
              A                      C
    --------------------------|--------------------------
    -----------------|-------------------|---------------
         B                E          D
```

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptgl55PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is (SEQ ID NO:47): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 9A and 9B). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC #CCL81) and MRC-5 cells (a fibroblast-like cell line derived from normal human fetal lung tissue ATCC #CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaqing Experiment. In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell substrates:

(1) Primary chick embryo fibroblast (CEF) cells produced from 11 day old white leghorn embryos;

(2) Vero cells—a continuous line of African Green monkey kidney cells (ATCC #CCL81); and (3) MRC-5 cells—a diploid cell line derived from human fetal lung tissue (ATCC #CCL171).

The initial inoculation was performed at an m.o.i. of 0.1 pfu per cell using three 60mm dishes of each cell substrate containing $2\times10^6$ cells per dish. One dish was inoculated in the presence of 40 $\mu$g/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 $\mu$g/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell substrate was inoculated undiluted onto three dishes of the same cell substrate (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 1 and 2.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 1 and 2 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell substrate was inoculated onto a permissive CEF monolayer and harvested at cytopathic effect (CPE) or at 7 days if no CPE was evident. The results of this experiment are shown in Table 3. Even after amplification through a permissive cell substrate, virus was only detected in MRC-5 and Vero cells for two additional passages. These results indicated that under the conditions used, there was no adaptation of either virus to growth in Vero or MRC-5 cells.

Inoculation of Macagues. Four HIV seropositive macaques were initially inoculated with ALVAC-RG as described in Table 4. After 100 days these animals were re-inoculated to determine a booster effect, and an additional seven animals were inoculated with a range of doses. Blood was drawn at appropriate intervals and sera analyzed, after heat inactivation at 560C for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with $1\times10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 $\mu$l of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats. Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 $\mu$l instilled on the surface of the right eye without scarification; (2) 100 $\mu$l as several droplets in the mouth; (3) 100 $\mu$l in each of two intradermal injection sites in the shaven skin of the external face of the right arm; and (4) 100 $\mu$l in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC #CCL81;

(b) MRC-5, human embryonic lung, ATCC #CCL 171;

(c) WISH human amnion, ATCC #CCL 25;

(d) Detroit-532, human foreskin, Downs's syndrome, ATCC #CCL 54; and (e) Primary CEF cells.

Chicken embryo fibroblast cells produced from 11 day old white leghorn embryos were included as a positive control. All inoculations were performed on preformed monolayers of $2\times10^6$ cells as discussed below.

A. Methods for DNA Analysis.

Three dishes of each cell line were inoculated at 5 pfu/cell of the virus under test, allowing one extra dish of each cell line un-inoculated. One dish was incubated in the presence of 40 μg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2\times10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 μg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of Virus Yield.

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of Expression of Rabies G Gene.

Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield. The results of titration for yield at 72 hours after inoculation at 0.1 pfu per cell are shown in Table 5. The results indicate that while a productive infection can be attained in the avian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 μg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression. To determine if any viral gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ $TCID_{50}$ per ml were serially diluted and 50 to 100 μl of dilutions inoculated into the footpad of four to six week old mice. Mice were challenged 14 days later by the intracranial route with 300 μl of the CVS strain of rabies virus containing from 15 to 43 mouse $LD_{50}$ as determined by lethality titration in a control group of mice. Potency, expressed as the $PD_{50}$ (Protective dose 50%), was calculated at 14 days post-challenge. The results of the experiment are shown in Table 6. The results indicated that ALVAC-RG was consistently able to protect mice against rabies virus challenge with a $PD_{50}$ value ranging from 3.33 to 4.56 with a mean value of 3.73 (STD 0.48). As an extension of this study, male mice were inoculated intracranially with 50 μl of virus containing 6.0 $\log_{10}$ $TCID_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ $TCID_{50}$ subcutaneously and five animals received 7.7 $\log_{10}$ $TCID_{50}$ by the same route. Animals were bled for analysis for anti-rabies antibody. Animals receiving no inoculation or 6.7 $\log_{10}$ $TCID_{50}$ of ALVAC-RG were challenged at 29 days post-vaccination with 3.7 $\log_{10}$ mouse $LD_{50}$ (dogs, in the temporal muscle) or 4.3 $\log_{10}$ mouse $LD_{50}$ (cats, in the neck) of the NYGS rabies virus challenge strain. The results of the experiment are shown in Table 7.

No adverse reactions to inoculation were seen in either cats or dogs with either dose of inoculum virus. Four of 5 dogs immunized with 6.7 $\log_{10}$ $TCID_{50}$ had antibody titers on day 14 post-vaccination and all dogs had titers at 29 days. All dogs were protected from a challenge which killed three out of four controls. In cats, three of five cats receiving 6.7 $\log_{10}$ $TCID_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ $TCID_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ $TCID_{50}$ of ALVAC-RG. Sera were analyzed for the presence of anti-rabies antibody. The results are shown in Table 8.

Four of the five monkeys naive to rabies developed a serological response by seven days post-inoculation with ALVAC-RG. All five monkeys had detectable antibody by 11 days post-inoculation. of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An anamnestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 9, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 10.

No adverse reactivity to inoculation was noted by either intramuscular or subcutaneous routes. Both chimpanzees responded to primary inoculation by 14 days and a strongly rising response was detected following re-vaccination.

TABLE 1

Sequential Passage of ALVAC in Avian and non-Avian Cells.

| | CEF | Vero | MRC-5 |
|---|---|---|---|
| Pass 1 | | | |
| Sample to[a] | 2.4 | 3.0 | 2.6 |
| t7[b] | 7.0 | 1.4 | 0.4 |
| t7A[c] | 1.2 | 1.2 | 0.4 |
| Pass 2 | | | |
| Sample to | 5.0 | 0.4 | N.D.[d] |
| t7 | 7.3 | 0.4 | N.D. |
| t7A | 3.9 | N.D. | N.D. |
| Pass 3 | | | |
| Sample to | 5.4 | 0.4 | N.D. |
| t7 | 7.4 | N.D. | N.D. |
| t7A | 3.8 | N.D. | N.D. |
| Pass 4 | | | |
| Sample to | 5.2 | N.D. | N.D. |
| t7 | 7.1 | N.D. | N.D. |
| t7A | 3.9 | N.D. | N.D. |

[a]This sample was harvested at zero time and represents the residual input virus. The titer is expressed as $\log_{10}$pfu per ml.
[b]This sample was harvested at 7 days post-infection.
[c]This sample was inoculated in the presence of 40 μg/ml of *Cytosine arabinoside* and harvested at 7 days post infection.
[d]Not detectable

TABLE 2

Sequential Passage of ALVAC-RG in Avian and non-Avian Cells

| | CEF | Vero | MRC-5 |
|---|---|---|---|
| Pass 1 | | | |
| Sample t0[a] | 3.0 | 2.9 | 2.9 |
| t7[b] | 7.1 | 1.0 | 1.4 |
| t7A[c] | 1.8 | 1.4 | 1.2 |
| Pass 2 | | | |
| Sample t0 | 5.1 | 0.4 | 0.4 |
| t7 | 7.1 | N.D.[d] | N.D. |
| t7A | 3.8 | N.D. | N.D. |
| Pass 3 | | | |
| Sample t0 | 5.1 | 0.4 | N.D. |
| t7 | 7.2 | N.D. | N.D. |
| t7A | 3.6 | N.D. | N.D. |
| Pass 4 | | | |
| Sample t0 | 5.1 | N.D. | N.D. |
| t7 | 7.0 | N.D. | N.D. |
| t7A | 4.0 | N.D. | N.D |

[a]This sample was harvested at zero time and represents the residual input virus. The titer is expressed as $log_{10}$pfu per ml.
[b]This sample was harvested at 7 days post-infection.
[c]This sample was inoculated in the presence of 40 μg/ml of *Cytosine arabinoside* and harvested at 7 days post-infection.
[d]Not detectable.

TABLE 3

Amplification of residual virus by passage in CEF cells

| | CEF | Vero | MRC-5 |
|---|---|---|---|
| a) ALVAC | | | |
| Pass 2[a] | 7.0[b] | 6.0 | 5.2 |
| 3 | 7.5 | 4.1 | 4.9 |
| 4 | 7.5 | N.D.[c] | N.D. |
| 5 | 7.1 | N.D. | N.D. |
| b) ALVAC-RG | | | |
| Pass 2[a] | 7.2 | 5.5 | 5.5 |
| 3 | 7.2 | 5.0 | 5.1 |
| 4 | 7.2 | N.D. | N.D. |
| 5 | 7.2 | N.D. | N.D. |

[a]Pass 2 represents the amplification in CEF cells of the 7 day sample from Pass 1.
[b]Titer expressed as $log_{10}$ pfu per ml
[c]Not Detectable

TABLE 4

Schedule of inoculation of rhesus macaques with ALVAC-RG (vCP65)

| Animal | | Inoculation |
|---|---|---|
| 176L | Primary: | 1 × $10^8$ pfu of vCP65 orally in TANG |
| | Secondary: | 1 × $10^7$ pfu of vCP65 plus 1 × $10^7$ pfu of vCP82[a] by SC route |
| 185 L | Primary: | 1 × $10^8$ pfu of vCP65 orally in Tang |
| | Secondary: | 1 × $10^7$ pfu of vCP65 plus 1 × $10^7$ pfu of vCP82 by SC route |
| 177 L | Primary: | 5 × $10^7$ pfu SC of vCP65 by SC route |
| | Secondary: | 1 × $10^7$ pfu of vCP65 plus 1 × $10^7$ pfu of vCP82 by SC route |

TABLE 4-continued

Schedule of inoculation of rhesus macaques with ALVAC-RG (vCP65)

| Animal | | Inoculation |
|---|---|---|
| 186L | Primary: | 5 × $10^7$ pfu of vCP65 by SC route |
| | Secondary: | 1 × $10^7$ pfu of vCP65 plus 1 × $10^7$ pfu of vCP82 by SC route |
| 178L | Primary: | 1 × $10^7$ pfu of vCP65 by SC route |
| 182L | Primary: | 1 × $10^7$ pfu of vCP65 by IM route |
| 179L | Primary: | 1 × $10^6$ pfu of vCP65 by SC route |
| 183L | Primary: | 1 × $10^6$ pfu of vCP65 by IM route |
| 180L | Primary: | 1 × $10^6$ pfu of vCP65 by SC route |
| 184L | Primary: | 1 × $10^5$ pfu of vCP65 by IM route |
| 187L | Primary | 1 × $10^7$ pfu of vCP65 orally |

[a]vCP82 is a canarypox virus recombinant expressing the measles virus fusion and hemagglutinin genes.

TABLE 5

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]Titer expressed as $log_{10}$ pfu per ml
[b]Culture incubated in the presence of 40 μg/ml of *Cytosine arabinoside*

TABLE 6

Potency of ALVAC-RG as tested in mice

| Test | Challenge Dose[a] | $PD_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse $LD_{50}$
[b]Expressed as $log_{10}$ $TCID_{50}$

TABLE 7

Efficacy of ALVAC-RG in dogs and cats

| | Dogs | | Cats | |
|---|---|---|---|---|
| Dose | Antibody[a] | Survival[b] | Antibody | Survival |
| 6.7 | 11.9 | 5/5 | 2.9 | 3/5 |
| 7.7 | 10.1 | N.T. | 8.1 | N.T. |

[a]Antibody at day 29 post inoculation expressed as the geometric mean titer in International Units.
[b]Expressed as a ratio of survivors over animals challenged

TABLE 8

Anti-rabies serological response of Squirrel monkeys inoculated with canarypox recombinants

| Monkey # | Previous Exposure | Rabies serum-neutralizing antibody[a] −196[b] | 0 | 3 | 7 | 11 | 21 | 28 |
|---|---|---|---|---|---|---|---|---|
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | |
| N.T.[g] | | | | | | | | |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $log_{10}$ $TCID_{50}$ of ALVAC
[d]Animals received 5.0 $log_{10}$ $TCID_{50}$ of vCP37
[e]Animals received 5.0 $log_{10}$ $TCID_{50}$ of ALVAC-RG
[f]Animals received 7.0 $log_{10}$ $TCID_{50}$ of ALVAC-RG
[g]Not tested.

TABLE 10-continued

Inoculation of chimpanzees with ALVAC-RG

| Weeks post-Inoculation | Animal 431 I.M. | Animal 457 S.C. |
|---|---|---|
| 12[b]/0 | 16 | 8 |
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation

Example 10

Immunization of Humans Using Canarypox Expressing Rabies Glycoprotein (ALVAC-RG; vCP65)

Figure 9A:
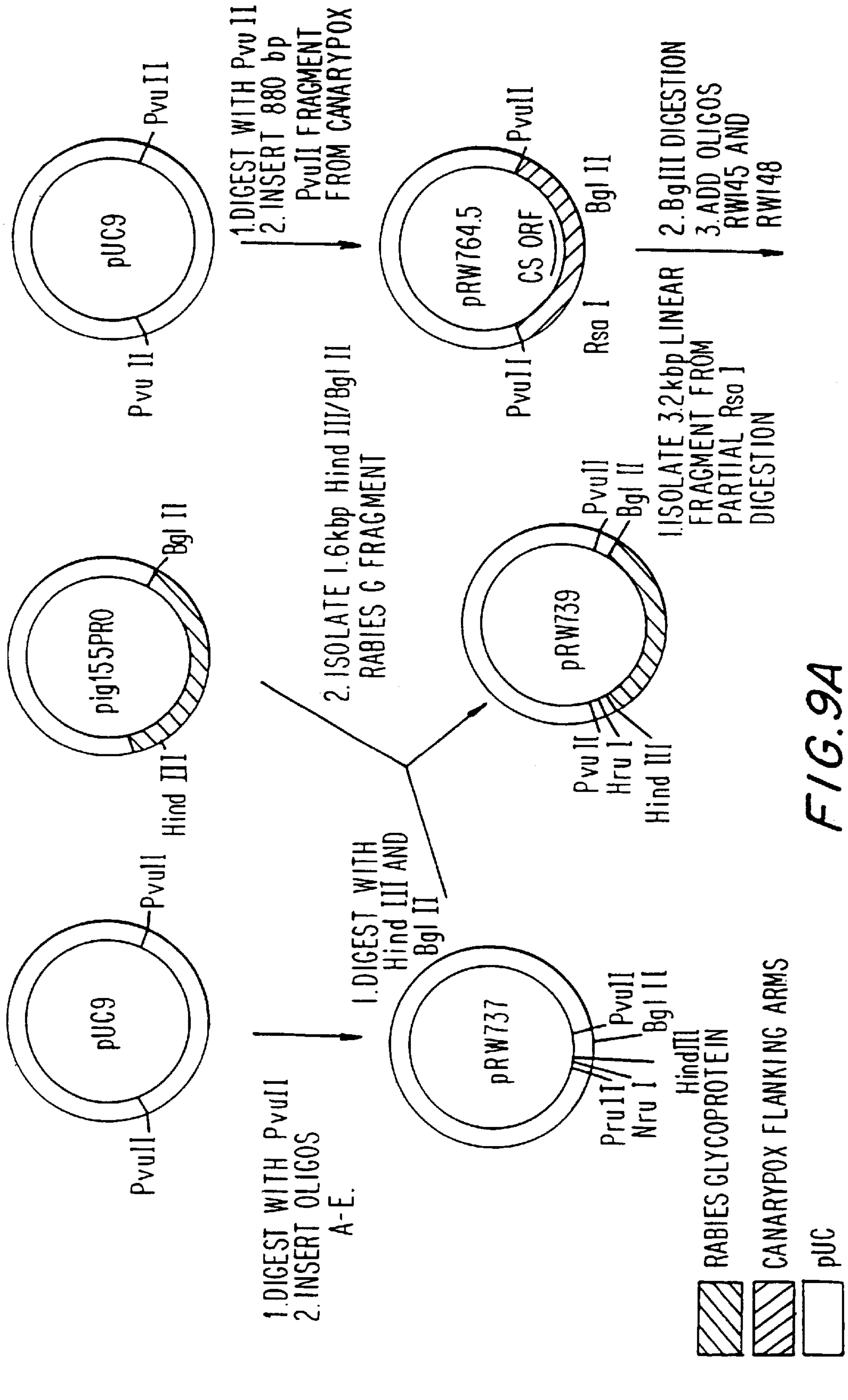
FIGS. 9A and 9B schematically show a method for the construction of recombinant canarypox virus vCP65 (ALVAC-RG)
Figure 9B:
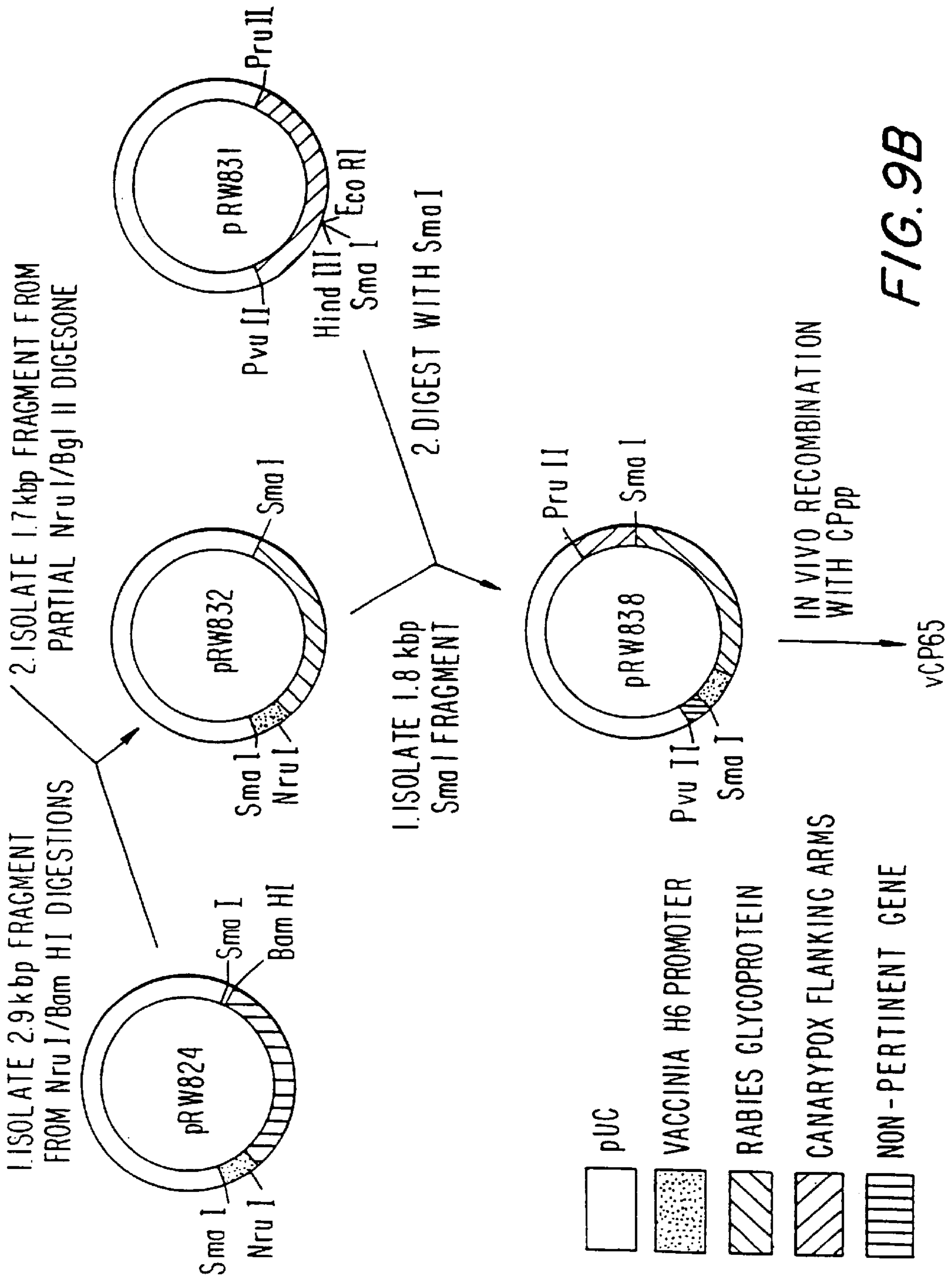

ALVAC-RG (vCP65) was generated as described in Example 9 and FIGS. 9A and 9B. For scaling-up and vaccine manufacturing ALVAC-RG (vCP65) was grown in primary CEF derived from specified pathogen free eggs. Cells were infected at a multiplicity of 0.1 and incubated at 37° C. for three days.

TABLE 9

Inoculation of rhesus macaques with ALVAC-RG[a]

| Days post-Inoculation | or/Tang 176L[b] | or/Tang 185L | SC 177L | SC 186L | SC 178L | IM 182L | SC 179L | IM 183L | SC 180L | IM 184L | OR 187L[b] |
|---|---|---|---|---|---|---|---|---|---|---|---|
| | | | Route of Primary Inoculation | | | | | | | | |
| −84 | – | – | | – | | | | | | | |
| −9 | – | – | – | – | – | | – | | | | |
| 3 | – | – | – | – | | | | | | | |
| 6 | – | – | ± | ± | | | | | | | |
| 11 | – | – | 16[d] | 128 | | | | | | | |
| 19 | – | – | 32 | 128 | – | | – | | | | |
| 35 | – | – | 32 | 512 | | | | | | | |
| 59 | – | – | 64 | 256 | | | | | | | |
| 75 | – | – | 64 | 128 | – | | – | | | | |
| 99[c] | – | – | 64 | 256 | – | | – | – | – | – | – |
| 2 | – | – | 32 | 256 | – | – | – | – | – | – | – |
| 6 | – | – | 512 | 512 | – | – | – | – | – | – | – |
| 15 | 16 | 16 | 512 | 512 | 64 | 32 | 64 | 128 | 32 | – | – |
| 29 | 16 | 32 | 256 | 256 | 64 | 64 | 32 | 128 | 32 | – | – |
| 55 | | 32 | | | | 32 | | 32 | 16 | – | |
| 57 | 16 | | 128 | 128 | 16 | | 16 | | | | – |

[a]See Table 9 for schedule of inoculations.
[b]Animals 176L and 185L received 8.0 $log_{10}$ pfu by the oral route in 5 ml Tang. Animal 187L received 7.0 $log_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an PFFI test.

TABLE 10

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and inocuity in laboratory rodents. No undesirable trait was found.

Preclinical data. Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immunoglobins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC—HDC; 2. HDC, HDC—ALVAC-RG (vCP65); 3. ALVAC-RG (vCP65), ALVAC-RG (vCP65)—HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith et al., 1973). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490 nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 11). During the primary series of immunization, fever greater than 37.7° C. was noted within 24 hours after injection in one HDC recipient (37.8° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ $TCID_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 12). Twenty eight days after the first injection all the HDC recipients had protective titers (≧0.5 IU/ml). By contrast none in groups A and B ($10^{3.5}$ and $10^{4.5}$ $TCID_{50}$) and only 2/9 in group C ($10^{5.5}$ $TCID_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 13). The pre-immune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Injection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations. FIGS. 13A–13D show graphs of rabies neutralizing antibody titers (Rapid Fluorescent Focus Inhibition Test or RFFIT, IU/ml): Booster effect of HDC and vCP65 ($10^{5.5}$ $TCID_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 13A to 13D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)—ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ $TCID_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al.; Etinger et al.).

Thus, this Example clearly demonstrates that a non-replicating poxvirus can serve as an immunizing vector in humans, with all of the advantages that replicating agents confer on the immune response, but without the safety problem created by a fully permissive virus.

TABLE 11

Reactions in the 5 days following vaccination

| vCP65 dosage (TCID50) | $10^{3.5}$ | | $10^{4.5}$ | | $10^{5.5}$ | | H D C control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 12

Rabies neutralizing antibodies (REFIT; IU/ml)
Individual titers and geometric mean titers (GMT)

| No. | TCID50/ dose | Days 0 | 7 | 28 | 35 | 56 |
|---|---|---|---|---|---|---|
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| | G.M.T. | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| | G.M.T. | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |

TABLE 12-continued

| Rabies neutralizing antibodies (REFIT; IU/ml) Individual titers and geometric mean titers (GMT) | | | | | | |
|---|---|---|---|---|---|---|
| | TCID50/ | Days | | | | |
| No. | dose | 0 | 7 | 28 | 35 | 56 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| | G.M.T. | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| | G.M.T. | <0.1 | <0.1 | 2.96 | 9.0 | 11.5* |

*p = 0.007 student t test

TABLE 13

| Canarypox antibodies: ELISA Geometric Mean Titers* | | | | | |
|---|---|---|---|---|---|
| vCP65 dosage | Days | | | | |
| TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at ½5dilution

Example 11

Comparison of the $LD_{50}$ of ALVAC and NYVAC with Various Vaccinia Virus Strains Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated for plaque forming units in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population ($LD_{50}$) was determined by the proportional method of Reed and Muench.

Comparison of the $LD_{50}$ of ALVAC and NYVAC with Various Vaccinia Virus Strains for Normal, Young Outbred Mice by the ic Route. In young, normal mice, the virulence of NYVAC and ALVAC were several orders of magnitude lower than the other vaccinia virus strains tested (Table 14). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses ($3.85\times10^8$ PFUs, ALVAC and $3\times10^8$ PFUs, NYVAC) by an undetermined mechanism by this route of inoculation.

Comparison of the $LD_{50}$ of ALVAC and NYVAC with Various Vaccinia Virus Strains for Newborn Outbred Mice by the ic Route. The relative virulence of 5 poxvirus strains for normal, newborn mice was tested by titration in an intracranial (ic) challenge model system (Table 15). With mortality as the endpoint, $LD_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, $6.3\times10^7$ PFUs, 100% mortality resulted. Mortality rates of 33.3% were observed at $6.3\times10^6$ PFUs. The cause of death, while not actually determined, was not likely of toxicological or traumatic nature since the mean survival time (MST) of mice of the highest dosage group (approximately 6.3 $LD_{50}$) was 6.7±1.5 days. When compared to WR(L) at a challenge dose of 5 $LD_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, $6\times10^8$ and $6\times10^7$ PFUs, caused 100% mortality. However, the MST of mice challenged with the highest dose, corresponding to 380 $LD_{50}$, was only 2 days (9 deaths on day 2 and 1 on day 4). In contrast, all mice challenged with the highest dose of WR-L, equivalent to 500 $LD_{50}$, survived to day 4.

TABLE 14

Calculated 50% Lethal Dose for mice by various vaccinia virus strains and for canarypox virus (ALVAC) by the ic route.

| POXVIRUS STRAIN | CALCULATED $LD_{50}$ (PFUs) |
|---|---|
| WR (L) | 2.5 |
| VC-2 | $1.26 \times 10^4$ |
| WYETH | $5.00 \times 104$ |
| NYVAC | $1.58 \times 10^8$ |
| ALVAC | $1.58 \times 10^8$ |

TABLE 15

Calculated 50% Lethal Dose for newborn mice by various vaccinia virus strains and for canarypox virus (ALVAC) by the ic route.

| POXVIRUS STRAIN | CALCULATED $LD_{50}$ (PFUs) |
|---|---|
| WR (L) | 0.4 |
| VC-2 | 0.1 |
| WYETH | 1.6 |
| NYVAC | $1.58 \times 10^6$ |
| ALVAC | $1.00 \times 10^7$ |

Example 12

Evaluation of NYVAC (vP866) and NYVAC-RG (vP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 μCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trinarchi, Griffith Laboratories, New York State Department of Health, Albany, N.Y., and a rat anti-mouse conjugate obtained from Boehringer Mannheim Corporation (Cat. #605–500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, N.J.). Three week old male Swiss Webster outbred mice, timed pregnant female Swiss Webster outbred mice, and four week old Swiss Webster nude ($nu^+nu^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$, or $10^8$ pfu of each test virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites of 0/1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 11.

Cyclophosphamide (CY) Treatment. Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per μl for untreated mice (n=4) and 4,220 cells per μl for CY-treated control mice (n=5).

Calculation of $LD_{50}$. The lethal dose required to produce 50% mortality ($LD_{50}$) was determined by the proportional method of Reed and Muench (Reed and Muench 1938).

Potency Testing of NYVAC-RG in Mice. Four to six week old mice were inoculated in the footpad with 50 to 100 μl of a range of dilutions (2.0–8.0 $log_{10}$ tissue culture infective dose 50% ($TCID_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 $LD_{50}$ of the rabies virus CVS strain (0.03 ml). On day 28, surviving mice were counted and protective does 50% ($PD_{50}$) calculated.

Figure 10:
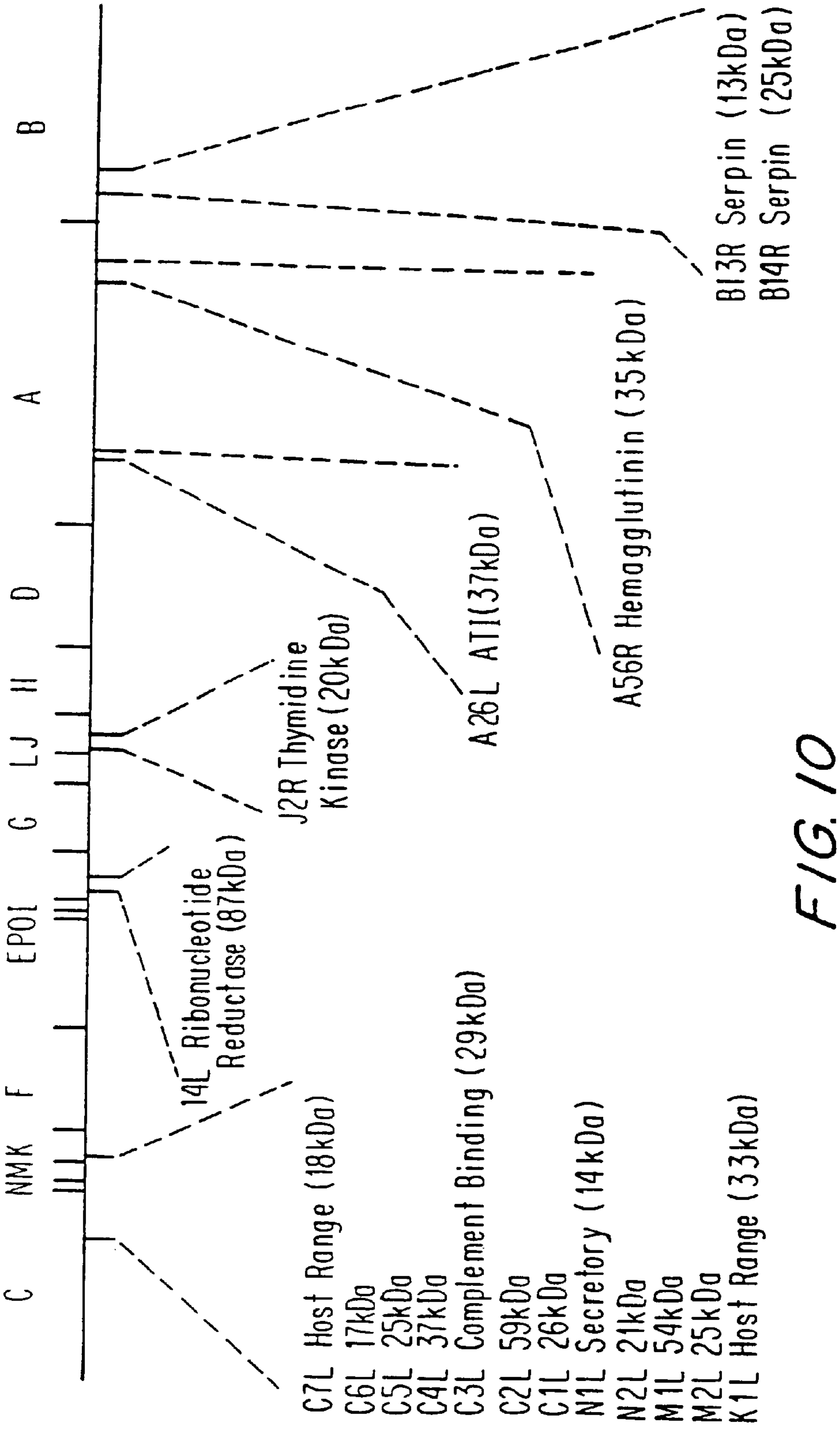
FIG. 10 shows schematically the ORFs deleted to generate NYVAC.
Figure 13A:
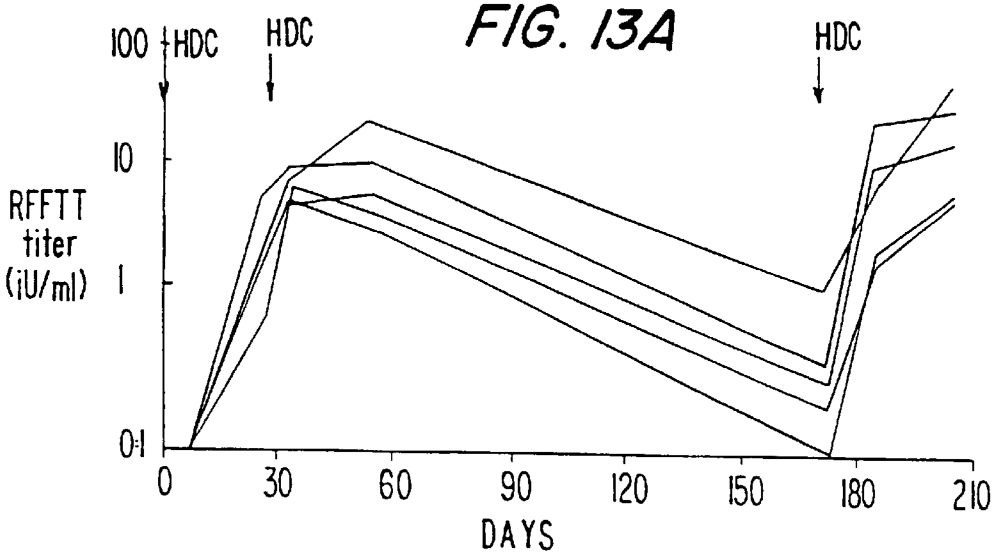
FIGS. 13A to 13D show graphs of rabies neutralizing antibody titers (RFFIT, IU/ml), booster effect of HDC and vCP65 ($10^{5.5}$ $TCID_{50}$) in volunteers previously immunized with either the same or the alternate vaccine (vaccines given at days 0, 28 and 180, antibody titers measured at days 0, 7, 28, 35, 56, 173, 187 and 208)
Figure 13C:
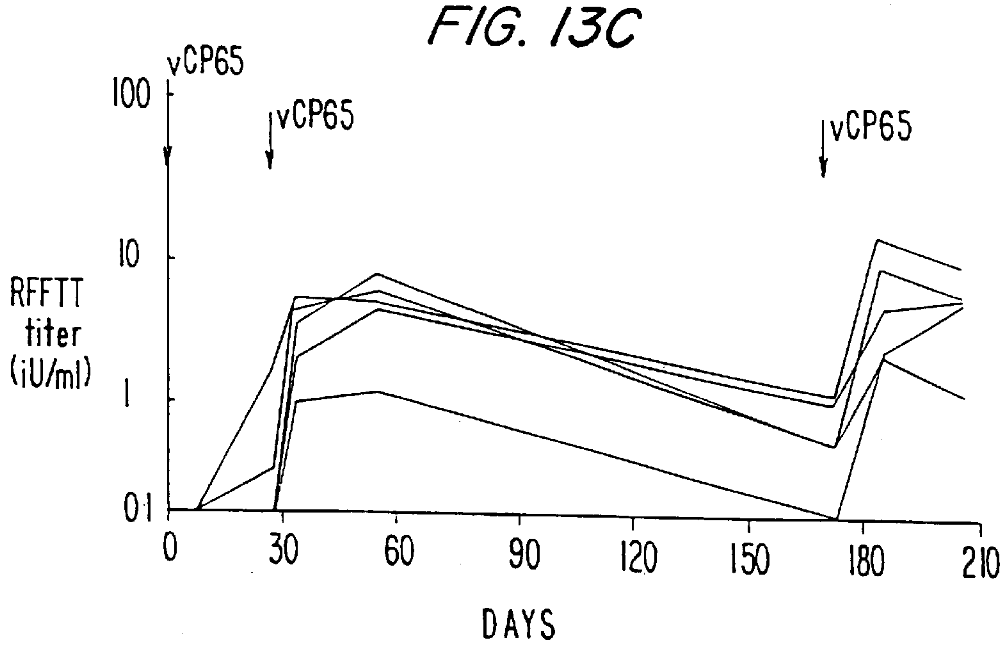
Figure 13B:
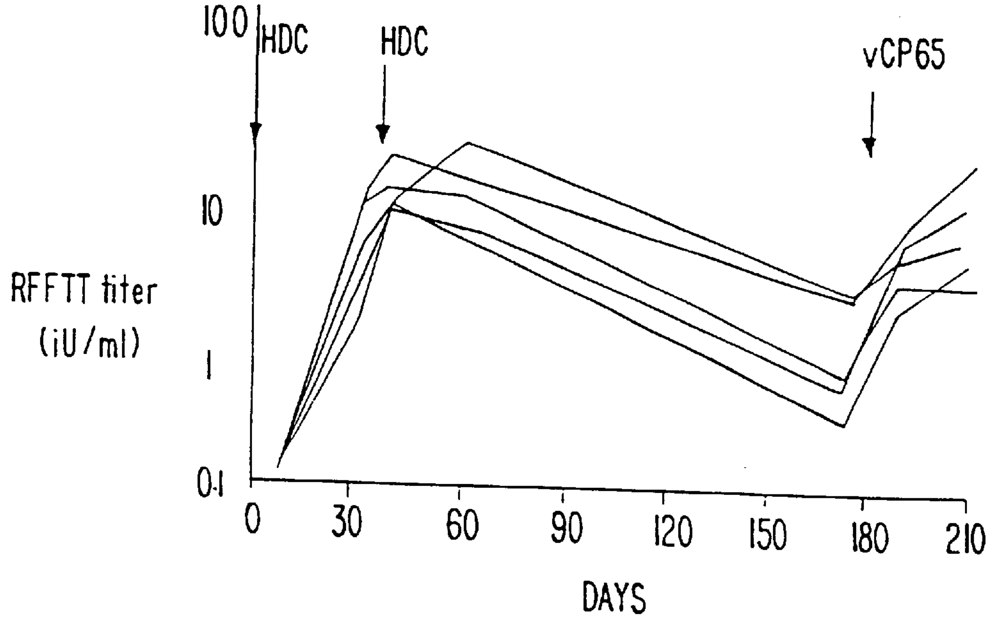
Figure 13D:
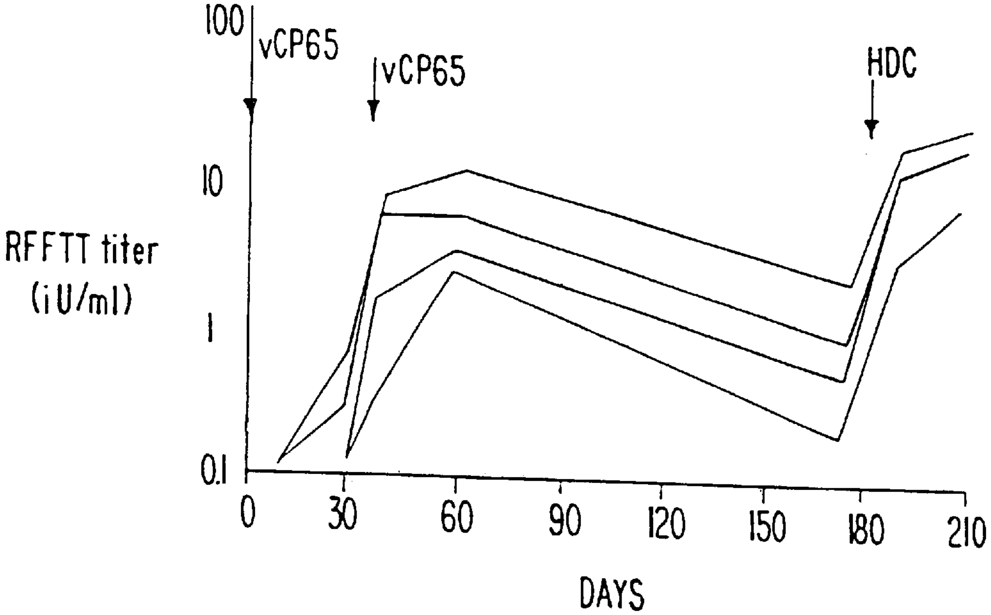

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 10 schematically depicts the ORFs deleted to generate NYVAC. At the top of FIG. 10 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 1 through 6). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 16. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contrast, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70–151) cells. Replication on these cell lines was significantly reduced when compared to virus yields obtained from NYVAC-infected CEF cells or with parental VC-2 (Table 16). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 16. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 7) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 17). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 18). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells. The results are shown in Table 18. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5\times10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5\times10^7$ or $5\times10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 19.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5\times10^7$ and $5\times10^8$ pfu) showed lesions on toes and tails, developed orchitis, and died. Mice injected with $5\times10^6$ pfu or less of WYETH showed no signs of disease or lesions.

As shown in Table 19, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5\times10^4$ to $9.5\times10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65\times10^5$ to $1.65\times10^9$) also developed pox lesions on their tails and/or their toes analogous to those of WYETH injected mice. These lesions were observed between 7–12 days post inoculation. No lesions were observed on mice injected with lower doses of WR virus, although deaths ccurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 20 demonstrates that the PDso values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 11). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 14–20). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 11, Tables 14, 15, 19). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 17 and 18). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the inocuity of NYVAC was provided by the intradermal administration on rabbit skin (Tables 17 and 18). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of specific virulence-associated genes in NYVAC prevents lesion occurrence.

Together, the results in this Example and in foregoing Examples, including Example 11, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 16) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 20). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human and veterinary applications (Tartaglia et al., 1992). Furthermore, the use of NYVAC as a general laboratory expression vector system may greatly reduce the biological hazards associated with using vaccinia virus.

By the following criteria, the results of this Example and the Examples herein, including Example 11, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 16

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |

TABLE 16-continued

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-infection expressed as a percentage of yield of VAC-2 after 72 hours on the same cell line.
[b]Titer expressed as $LOG_{50}$ pfu per ml.
[c]Sample was incubated in the presence of 40 μg/ml of *cytosine arabinoside*.
[d]Not determined.
*ATCC #CCL25 Human amnionic cells.

TABLE 17

Induration and ulceration at the site of intradermal inoculation of the rabbit skin

| VIRUS STRAIN | DOSE[a] | INDURATION Size[b] | INDURATION Days[c] | ULCERATION Size | ULCERATION Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a]pfu of indicated vaccinia virus in 0.1 ml PBS inoculated intradermally into one site.
[b]mean maximum size of lesions ($mm^2$)
[c]mean time after inoculation for complete healing of lesion.
[d]no lesions discernable.

TABLE 18

Persistence of poxviruses at the site of intradermal inoculation

| Virus | Inoculum Dose | Total Virus Recovered |
|---|---|---|
| WR | 8.0a | 6.14 |
| | 7.0 | 6.26 |
| | 6.0 | 6.21 |
| WYETH | 8.0 | 3.66 |
| | 7.0 | 4.10 |
| | 6.0 | 3.59 |

TABLE 18-continued

| Persistence of poxviruses at the site of intradermal inoculation | | |
|---|---|---|
| Virus | Inoculum Dose | Total Virus Recovered |
| VC-2 | 8.0 | 4.47 |
| | 7.0 | 4.74 |
| | 6.0 | 3.97 |
| NYVAC | 8.0 | 0 |
| | 7.0 | 0 |
| | 6.0 | 0 |

[a]expressed as $log_{10}$ pfu.

TABLE 19

| Virulence studies in immunocompromised mice | | |
|---|---|---|
| | $LD_{50}$[a] | |
| Poxvirus Strain | Nude mice | Cyclophosphamide treated mice |
| WR | 422 | 42 |
| VC-2 | $>10^9$ | $<1.65 \times 10^5$ |
| WYETH | $1.58 \times 10^7$ | $1.83 \times 10^6$ |
| NYVAC | $>5.50 \times 10^8$ | $7.23 \times 10^8$ |
| ALVAC | $>10^9$ | $>5.00 \times 10^{8b}$ |

[a]Calculated 50% lethal dose (pfu) for nude or cyclophosphamide treated mice by the indicated vaccinia viruses and for ALVAC by intraperitoneal route.
[b]5 out of 10 mice died at the highest dose of $5 \times 10^8$ pfu.

TABLE 20

| Comparative efficacy of NYVAC-RG and ALVAC-RG in mice | |
|---|---|
| Recombinant | $PD_{50}$[a] |
| VV-RG | 3.74 |
| ALVAC-RG | 3.86 |
| NYVAC-RG | 3.70 |

[a]Four to six week old mice were inoculated in the footpad with 50–100 μl of a range of dilutions (2.0–8.0 $log_{10}$ tissue culture infection dose 50% ($TCID_{50}$) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus corresponding to 15 lethal dose 50% ($LD_{50}$) per mouse. At day 28, surviving mice were counted and a protective dose 50% ($PD_{50}$) was calculated.

Example 13

Construction of Trovac Recombinants Expressing the Hemagglutinin Glycoproteins of Avian Influenza Viruses This Example describes the development of fowlpox virus recombinants expressing the hemagglutinin genes of three serotypes of avian influenza virus.

Cells and Viruses. Plasmids containing cDNA clones of the H4, H5 and H7 hemagglutinin genes were obtained from Dr. Robert Webster, St. Jude Children's Research Hospital, Memphis, Tenn. The strain of FPV designated FP-1 has been described previously (Taylor et al., 1988a, b). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIH5 (vFP89) and TROVAC-AIH4 (vFP92) had been further amplified though 8 passages in primary CEF cells. The stock virus used to produce TROVAC-AIH7 (vFP100) had been further amplified through 12 passages in primary CEF cells.

Construction of Fowlpox Insertion Plasmid at F8 Locus. Plasmid pRW731.15 contains a 10 kbp PvuII-PvuII fragment cloned from TROVAC genomic DNA. The nucleotide sequence was determined on both strands for a 3659 bp PvuII-EcoRV fragment. This sequence is shown in FIG. 11 (SEQ ID NO:67). The limits of an open reading frame designated in this laboratory as F8 were determined within this sequence. The open reading frame is initiated at position 495 and terminates at position 1887. A deletion was made from position 779 to position 1926, as described below.

Plasmid pRW761 is a sub-clone of pRW731.15 containing a 2430 bp EcoRV-EcORV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:37) and JCA018 (SEQ ID NO:38).

JCA017 (SEQ ID NO:37) 5' CTAGACACTTTATGTTTTTTAATATCCGGTCTTAAAAGCTTCCCGGGGATCCTTATACGGGGAATAAT 3'

JCA018 (SEQ ID NO:38) 5' ATTATTCCCCGTATAAGGATCCCCCGGGAAGCTTTTAAGACCGGATATTAAAAAACATAAAGTGT 3'

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al. 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO:48) and RW179 (SEQ ID NO:49) were cut with EcoRV and BamHI and inserted between the EcoRV and BamHI sites of JCA004 to form pRW846.

```
RW178             5' TCATTATCGCGATATCCGTGTTAACTAGCTA
(SEQ ID NO:48):   GCTAATTTTTATTCCCGGGATCCTTATCA 3'

RW179             5' GTATAAGGATCCCGGGAATAAAAATTAGCT
(SEQ ID NO:49):   AGCTAGTTAACACGGATATCGCGATAATGA 3'
```

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Fowlpox Insertion Plasmid at F7 Locus. The original F7 non-de-ORFed insertion plasmid, pRW731.13, contained a 5.5 kb FP genomic PvuII fragment in the PvuII site of pUC9. The insertion site was a unique HincII site within these sequences. The nucleotide sequence shown in FIG. 12 (SEQ ID NO:68) was determined for a 2356 bp region ncompassing the unique HincII site. Analysis of this sequence revealed that the unique HincII site (FIG. 12, underlined) was situated within an ORF encoding a polypeptide of 90 amino acids. The ORF begins with an ATG at position 1531 and terminates at position 898 (positions marked by arrows in FIG. 12).

The arms for the de-ORFed insertion plasmid were derived by PCR using pRW731.13 as template. A 596 bp arm (designated as HB) corresponding to the region upstream from the ORF was amplified with oligonucleotides F73PH2 (SEQ ID NO:50) (5'-GACAATCTAAGTCCTATATTAGAC-3') and F73PB (SEQ ID NO:51) (5'-GGATTTTTAGGTAGACAC-3'). A 270 bp arm (designated as EH) corresponding to the region downstream from the ORF was amplified using oligonucleotides F75PE (SEQ ID NO:52) (5'-TCATCGTCTTCATCATCG-3') and F73PH1 (SEQ ID NO:53) (5'-GTCTTAAACTTATTGTAAGGGTATACCTG-3').

Fragment EH was digested with EcoRV to generate a 126 bp fragment. The EcoRV site is at the 3'-end and the 5'-end was formed, by PCR, to contain the 3' end of a HincII site. This fragment was inserted into pBS-SK (Stratagene, La Jolla, Calif.) digested with HincII to form plasmid pF7D1. The sequence was confirmed by dideoxynucleotide sequence analysis. The plasmid pF7D1 was linearized with ApaI, blunt-ended using T4 DNA polymerase, and ligated to the 596 bp HB fragment. The resultant plasmid was designated as pF7D2. The entire sequence and orientation were confirmed by nucleotide sequence analysis.

The plasmid pF7D2 was digested with EcoRV and BglII to generate a 600 bp fragment. This fragment was inserted into pBS-SK that was digested with ApaI, blunt-ended with T4 DNA polymerase, and subsequently digested with BamHI. The resultant plasmid was designated as pF7D3. This plasmid contains an HB arm of 404 bp and a EH arm of 126 bp.

The plasmid pF7D3 was linearized with XhoI and blunt-ended with the Klenow fragment of the *E. coli* DNA polymerase in the presence of 2 mM dNTPs. This linearized plasmid was ligated with annealed oligonucleotides F7MCSB (SEQ ID NO:54) (5'-AACGATTAGTTAGTTACTAAAAGCT-TGCTGCAGCCCGGGTTTTTTATTAGTTTAGTTAGTC-3') and F7MCSA (SEQ ID NO:55) (5'-GACTAACTAACTAATAAAAAACCCGGGCTGCAGC AAGCTTTTTGTAACTAACTAATCGTT-3'). This was performed to insert a multiple cloning region containing the restriction sites for HindIII, PstI and SmaI between the EH and HB arms. The resultant plasmid was designated as pF7DO.

Construction of Insertion Plasmid for the H4 Hemagglutinin at the F8 Locus. A cDNA copy encoding the avian influenza H4 derived from A/Ty/Min/833/80 was obtained from Dr. R. Webster in plasmid pTM4H833. The plasmid was digested with HindIII and NruI and blunt-ended using the Klenow fragment of DNA polymerase in the presence of dNTPs. The blunt-ended 2.5 kbp HindIII-NruI fragment containing the H4 coding region was inserted into the HincII site of pIBI25 (International Biotechnologies, Inc., New Haven, Conn.). The resulting plasmid pRW828 was partially cut with BanII, the linear product isolated and recut with HindIII. Plasmid pRW828 now with a 100 bp HindIII-BanII deletion was used as a vector for the synthetic oligonucleotides RW152 (SEQ ID NO:56) and RW153 (SEQ ID NO:57). These oligonucleotides represent the 3' portion of the H6 promoter from the EcoRV site and align the ATG of the promoter with the ATG of the H4 cDNA.

```
RW152      5' GCACGGAACAAAGCTTATCGCGATATCCGTTA
(SEQ ID    AGTTTGTATCGTAATGCTATCAATCACGATTCTGTTC
NO:56):    CTGCTCATAGCAGAGGGCTCATCTCAGAAT 3'

RW153      5' ATTCTGAGATGAGCCCTCTGCTATGAGCAGGA
(SEQ ID    ACAGAATCGTGATTGATAGCATTACGATACAAACTTA
NO:57):    ACGGATATCGCGATAAGCTTTGTTCCGTGC 3'
```

The oligonucleotides were annealed, cut with BanII and HindIII and inserted into the HindIII-BanII deleted pRW828 vector described above. The resulting plasmid pRW844 was cut with EcoRV and DraI and the 1.7 kbp fragment containing the 3' H6 promoted H4 coding sequence was inserted between the EcoRV and HincII sites of pRW846 (described previously) forming plasmid RW848. Plasmid pRW848 therefore contains the H4 coding equence linked to the vaccinia virus H6 promoter in the de-RFed F8 locus of fowlpox virus.

Construction of Insertion Plasmid for H5 Hemagglutinin at the F8 Locus. A cDNA clone of avian influenza H5 derived from A/Turkey/Ireland/1378/83 was received in plasmid pTH29 from Dr. R. Webster. Synthetic oligonucleotides RW10 (SEQ ID NO:58) through RW13 (SEQ ID NO:61) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

```
RW10       5' GAAAAATTTAAAGTCGACCTGTTTTGTTGAGT
(SEQ ID    TGTTTGCGTGGTAACCAATGCAAATCTGGTC
NO:58):    ACT 3'

RW11       5' TCTAGCAAGACTGACTATTGCAAAAAGAAGCA
(SEQ ID    CTATTTCCTCCATTACGATACAAACTTAACG
NO:59):    GAT 3'

RW12       5' ATCCGTTAAGTTTGTATCGTAATGGAGGAAA
(SEQ ID    TAGTGCTTCTTTTTGCAATAGTCAGTCTTGCTAGAAG
NO:60):    TGACCAGATTTGCATTGGT 3'

RW13       5' TACCACGCAAACAACTCAACAAAACAGGTCG
(SEQ ID    ACTTTAAATTTTTCTGCA 3'
NO:61):
```

The oligonucleotides were annealed at 95° C. for three minutes followed by slow cooling at room temperature. This results in the following double strand structure with the indicated ends.

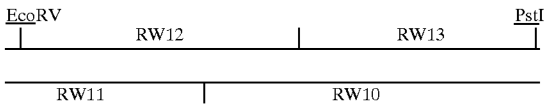

Cloning of oligonucleotides between the EcoRV and PstI sites of pRW742B resulted in pRW744. Plasmid pRW742B contains the vaccinia virus H6 promoter linked to a non-pertinent gene inserted at the HincII site of pRW731.15 described previously. Digestion with PstI and EcoRV eliminates the non-pertinent gene and the 3'-end of the H6 promoter. Plasmid pRW744 now contains the 3' portion of the H6 promoter overlapping the ATG of avian influenza H5. The plasmid also contains the H5 sequence through the 5' SalI site and the 3' sequence from the H5 stop codon (containing a DraI site). Use of the DraI site removes the H5 3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recut with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp PRW759 EcoRV-DraI fragment containing the 3' H6 promoter and the H5 gene was inserted between the EcoRV and HincII sites of pRW846 (previously described). The resulting plasmid pRW849 contains the H6 promoted avian influenza virus H5 gene in the de-ORFed F8 locus.

Construction of Insertion Vector for H7 Hemagglutinin at the F7 Locus. Plasmid pCVH71 containing the H7 hemagglutinin from A/CK/VIC/1/85 was received from Dr. R. Webster. An EcoRI-BamHI fragment containing the H7 gene was blunt-ended with the Klenow fragment of DNA polymerase and inserted into the HincII site of pIBI25 as PRW827. Synthetic oligonucleotides RW165 (SEQ ID NO:62) and RW166 (SEQ ID NO:63) were annealed, cut with HincII and StyI and inserted between the EcoRV and StyI sites of pRW827 to generate pRW845.

| | |
|---|---|
| RW165 (SEQ ID NO:62): | 5' GTACAGGTCGACAAGCTTCCCGGGTATCGCG ATATCCGTTAAGTTTGTATCGTAATGAATACTCAAAT TCTAATACTCACTCTTGTGGCAGCCATTCACACAAAT GCAGACAAAATCTGCCTTGGACATCAT 3' |
| RW166 (SEQ ID NO:63): | 5' ATGATGTCCAAGGCAGATTTTGTCTGCATTTG TGTGAATGGCTGCCACAAGAGTGAGTATTAGAATTTG AGTATTCATTACGATACAAACTTAACGGATATCGCGA TACCCGGGAAGCTTGTCGACCTGTAC 3' |

Oligonucleotides RW165 (SEQ ID NO:62) and RW166 (SEQ ID NO:63) link the 3' portion of the H6 promoter to the H7 gene. The 3' non-coding end of the H7 gene was removed by isolating the linear product of an ApaLI digestion of pRW845, recutting it with EcoRI, isolating the largest fragment and annealing with synthetic oligonucleotides RW227 (SEQ ID NO:64) and RW228 (SEQ ID NO:65). The resulting plasmid was pRW854.

| | |
|---|---|
| RW227 (SEQ ID NO:64): | 5' ATAACATGCGGTGCACCATTTGTATAT AAGTTAACGAATTCCAAGTCAAGC 3' |
| RW228 (SEQ ID NO:65): | 5' GCTTGACTTGGAATTCGTTAACTTATA TACAAATGGTGCACCGCATGTTAT 3' |

The stop codon of H7 in PRW854 is followed by an HpaI site. The intermediate H6 promoted H7 construct in the de-ORFed F7 locus (described below) was generated by moving the pRW854 EcoRV-HpaI fragment into pRW858 which had been cut with EcoRV and blunt-ended at its PstI site. Plasmid pRW858 (described below) contains the H6 promoter in an F7 de-ORFed insertion plasmid.

The plasmid pRW858 was constructed by insertion of an 850 bp SmaI/HPaI fragment, containing the H6 promoter linked to a non-pertinent gene, into the SmaI site of pF7DO described previously. The non-pertinent sequences were excised by digestion of pRW858 with EcoRV (site 24 bp upstream of the 3'-end of the H6 promoter) and PstI. The 3.5 kb resultant fragment was isolated and blunt-ended using the Klenow fragment of the *E. coli* DNA polymerase in the presence of 2 mM dNTPs. This blunt-ended fragment was ligated to a 1700 bp EcoRV/HpaI fragment derived from pRW854 (described previously). This EcoRV/HpaI fragment contains the entire AIV HA (H7) gene juxtaposed 3' to the 3'-most 24 bp of the VV H6 promoter. The resultant plasmid was designated pRW861.

The 126 bp EH arm (defined previously) was lengthened in pRW861 to increase the recombination frequency with genomic TROVAC DNA. To accomplish this, a 575 bp AccI/SnaBI fragment was derived from pRW 731.13 (defined previously). The fragment was isolated and inserted between the AccI and NaeI sites of pRW861. The resultant plasmid, containing an EH arm of 725 bp and a HB arm of 404 bp flanking the AIV H7 gene, was designated as pRW869. Plasmid pRW869 therefore consists of the H7 coding sequence linked at its 5' end to the vaccinia virus H6 promoter. The left flanking arm consists of 404 bp of TROVAC sequence and the right flanking arm of 725 bp of TROVAC sequence which directs insertion to the de-ORFed F7 locus.

Development of TROVAC-Avian Influenza Virus Recombinants. Insertion plasmids containing the avian influenza virus HA coding sequences were individually transfected into TROVAC infected primary CEF cells by using the calcium phosphate precipitation method previously described (Panicali et al., 1982; Piccini et al., 1987). Positive plaques were selected on the basis of hybridization to HA specific radiolabelled probes and subjected to sequential rounds of plaque purification until a pure population was achieved. One representative plaque was then amplified to produce a stock virus. Plasmid pRW849 was used in an in vitro recombination test to produce recombinant TROVAC-AIH5 (vFP89) expressing the H5 hemagglutinin. Plasmid pRW848 was used to produce recombinant TROVAC-AIH4 (vFP92) expressing the H4 hemagglutinin. Plasmid pRW869 was used to produce recombinant TROVAC-AIH7 (vFP100) expressing the H7 hemagglutinin.

Immunofluorescence. In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked $HA_1$ and $HA_2$ subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIH5, H4 hemagglutinin in TROVAC-AIH4 and H7 hemagglutinin in TROVAC-AIH7 was confirmed by indirect immunofluorescence. Expression of the H5 hemagglutinin was detected using a pool of monoclonal antibodies specific for the H5HA. Expression of the H4HA was analyzed using a goat monospecific anti-H4 serum. Expression of the H7HA was analyzed using a H7 specific monoclonal antibody preparation.

Immunoprecipitation. It has been determined that the sequence at and around the cleavage site of the hemagglutinin molecule plays an important role in determining viral virulence since cleavage of the hemagglutinin polypeptide is necessary for virus particles to be infectious. The hemagglutinin proteins of the virulent H5 and H7 viruses possess more than one basic amino acid at the carboxy terminus of HA1. It is thought that this allows cellular proteases which recognize a series of basic amino acids to cleave the hemagglutinin and allow the infectious virus to spread both in vitro and in vivo. The hemagglutinin molecules of H4 avirulent strains are not cleaved in tissue culture unless exogenous trypsin is added.

In order to determine that the hemagglutinin molecules expressed by the TROVAC recombinants were authentically processed, immunoprecipitation experiments were performed as described (Taylor et al., 1990) using the specific reagents described above.

Immunoprecipitation analysis of the H5 hemagglutinin expressed by TROVAC-AIH5 (vFP89) showed that the glycoprotein is evident as the two cleavage products $HA_1$ and $HA_2$ with approximate molecular weights of 44 and 23 kDa, respectively. No such proteins were precipitated from uninfected cells or cells infected with parental TROVAC. Similarly immunoprecipitation analysis of the hemagglutinin expressed by TROVAC-AIH7 (vFP100) showed specific precipitation of the $HA_2$ cleavage product. The $HA_1$ cleavage product was not recognized. No proteins were specifically precipitated from uninfected CEF cells or TROVAC infected CEF cells. In contrast, immunoprecipitation analysis of the expression product of TROVAC-AIH4 (vFP92) showed expression of only the precursor protein $HA_0$. This is in agreement with the lack of cleavage of the hemagglutinins of avirulent subtypes in tissue culture. No H4 specific proteins were detected in uninfected CEF cells or cells infected with TROVAC. Generation of recombinant virus by recombination, in situ hybridization of nitrocellulose filters and screening for B-galactosidase activity are as previously described (Panicali et al., 1982; Perkus et al., 1989).

Example 14

Generation of an ALVAC Recombinant Expressing HIV1 gag (+pro) (IIIB), gp120(MN) (+ transmembrane) Epitopes A plasmid, pHXB2D, containing HIV1 (IIIB) cDNA sequence (Ratner et al, 1985), was obtained from Robert Gallo (NCI, NIH). The sequence encoding the 5'-end of the gag gene was cloned between vaccinia virus tk flanking arms. This was accomplished by cloning the 1,625 bp BglII fragment of pHXB2D, containing the 5'-end of the gag gene, into the 4,075 bp BglII fragment of pSD542VCVQ. The plasmid generated by this manipulation is called pHIVG2.

The 3'-end of the gag gene was then cloned into pHIVG2. This was accomplished by cloning a 280 bp ApaI-BamHI PCR fragment, containing the 3'-end of the gag gene, into the 5,620 bp ApaI-BamHI fragment of pHIVG2. (This PCR fragment was generated from the plasmid, pHXB2D, with the oligonucleotide primers, HIVP5 (SEQ ID NO:69; 5'-TGTGGCAAAGAAGGGC-3') and HIVP6 (SEQ ID NO:70; 5'-TTGGATCCTTATTGTGACGAGGGGTC-3').) The plasmid generated by this manipulation is called pHIVG3.

The I3L promoter was then cloned upstream of the gag gene. This was accomplished by cloning the oligonucleotides, HIVL17 (SEQ ID NO:71;

5'-GATCTTGAGATAAAGTGAAAATATATATCATTATATTACAAAGTACAATTATTTAGTTTAATCATGGGTGCGAGAGCGTCAGTATTAAGCGGGGGAGAATTAGAT-3') and HIVL18 (SEQ ID NO:72; 5'-CGATCTAATTCTCCCCCGCTTAATACTGACGCTCTCGCACCCATGATTAAACCTAAATAATTGTACTTTGTAATATAATGATATATATTTTCACTTTATCTCAA-3'), encoding the vaccinia virus I3L promoter and the 58-end of the gag gene, into the 5,540 bp partial BglII-ClaI fragment of pHIVG3. The plasmid generated by this manipulation is called pHIVG4.

The portion of the gag gene encoding p24, p2, p7 and p6 was then eliminated. This was accomplished by cloning the oligonucleotides, HIVL19 (SEQ ID NO:73; 5'-CTGACACAGGACACAGCAATCAGGTCAGCCAAAATTACTAATTTTTATCTCGAGGTCGACAGGACCCG-3') and HIVL20 (SEQ ID NO:74; 5'-GATCCGGGTCCTGTCGACCTCGAGATAAAAATTAGTAATTTTGGCTGACCTGATTGCTGTGTCCTGTGTCAG-3'), into the 4,450 bp partial PvuII-BamHI fragment of pHIVG4. The plasmid generated by this manipulation is called pHIVG5.

The remainder of the gag gene, as well as the pol gene, was then cloned downstream of the p17 "gene". This was accomplished by cloning the 4,955 bp ClaI-SalI fragment of pHXB2D, containing most of the gag gene and all of the pol gene, into the 4,150 bp ClaI-SalI fragment of pHIVG5. The plasmid generated by this manipulation is called pHIVG6.

Extraneous 3'-noncoding sequence was then eliminated.

This was accomplished by cloning a 360 bp AflII-BamHI PCR fragment, containing the 3'-end of the pol gene, into the 8,030 bp AflII-BamHI fragment of pHIVG6. (This PCR fragment as generated from the plasmid, pHXB2D, with the oligonucleotide primers, HIVP7 (SEQ ID NO:75; 5'-AAGAAAATTATAGGAC-3') and HIVP8 (SEQ ID NO:76; 5'-TTGGATCCCTAATCCTCATCCTGT-3').) The plasmid generated by this manipulation is called pHIVG7.

The I3L-promoted gag and pol genes were then cloned between canary pox C3 flanking arms. This was accomplished by cloning the 4,360 bp partial BglII-BamHI fragment of pHIVG7, containing the I3L-promoted gag and pol genes, into the BamHI site of pVQH6CP3L. The plasmid generated by this manipulation is called pHIVGE14.

The H6-promoted HIVlgp120(MN)(+transmembrane) "gene" (Gurgo et al, 1988) was then cloned into pHIVGE14. This was accomplished by cloning the 1,700 bp NruI-SmaI fragment of pC5HIVMN120T, containing the gp120(+ transmembrane) "gene", into the 11,400 bp NruI-SmaI fragment of pHIVGE14. The plasmid generated by this manipulation is called pHIVGE14T.

Most of the pol gene was then removed. This was accomplished by cloning a 540 bp ApaI-BamHI PCR fragment, containing the 3'-end of the HIV1 protease "gene", into the 10,000 bp ApaI-BamHI fragment of pHIVGE14T. (This PCR fragment was generated from the plasmid, pHIVG7, with the oligonucleotide primers, HIVP5 and HIVP37 (SEQ ID NO:77; 5'-AAAGGATCCCCCGGGTTAAAAATTTAAAGTGCAACC-3').) This manipulation removes most of the pol gene, but leaves the protease "gene" intact. The plasmid generated by this manipulation is called pHIV32. The DNA sequence of pHIV32 (SEQ ID NOS: 78 and 79) is shown in FIGS. 14A–14C which shows the nucleotide sequence of the H6-promoted HIV1 gp120(+transmembrane) gene and the I3L-promoted HIV1 gag(+pro) gene contained in pHIV32: gag (+pro) and gp120 (+transmembrane)

| FEATURES | From | To/ Span | | Description |
|---|---|---|---|---|
| frag | 1 | 56 | | C3 flanking arm |
| frag | 162 | 76 | (C) | HIV1 (IIIB) env transmembrane region |
| frag | 1728 | 163 | (C) | HIV1 (MN) gp120 gene |
| frag | 1853 | 1729 | (C) | vaccinia H6 promoter |
| frag | 1925 | 1983 | | vaccinia I3L promoter |
| frag | 1984 | 3746 | | HIV1 (IIB) gag/pro gene |
| frag | 3753 | 3808 | | C3 flanking arm |

The DNA sequence of the ALVAC C3 flanking arm (SEQ ID NOS: 80 and 81) is shown in FIGS. 15A–F. FIGS. 15A to 15F show the nucleotide sequence of the C3 locus in pVQH6CP3L:

C3 LOCUS pVQH6CP3L

| FEATURES | From | To/Span | Description |
|---|---|---|---|
| frag | 1 | 1460 | C3 flanking arm |
| frag | 1461 | 1501 | Cloning sites |
| frag | 1630 | 1502 | H6 promoter |
| frag | 1717 | 4291 | C3 flanking arm |

pHIV32 was used in vitro recombination with ALVAC as the rescuing virus to yield vCP205.

Example 15

Generation of an ALVAC Recombinant Expressing HIV1 gag (+pro) (IIIB), gp120 (MN) (+ transmembrane) and 2 nef(BRU) Epitopes Expression cassettes encoding two nef CTL epitopes, CTL1 (amino acids 66–147) and CTL2 (amino acids 182–206) (Wain-Hobson et al, 1985; Nixon and McMichael, 1991), were then inserted into vCP205. The insertion plasmid, p2–60-HIV.3, containing the nef CTL epitopes, was generated by the following procedure. The I3L-promoted CTL2 epitope was cloned into pBSH6. This was accomplished by cloning a 255 bp PCR HindIII-XhoI fragment, containing the I3L-promoted CTL2 epitope, into the 3,100 bp HindIII-XhoI fragment of pBSH6. (The 255 bp PCR fragment was generated by the following procedure. A 216 bp PCR fragment, containing the I3L-promoter and the 5'-end of the CTL2 epitope, was generated from the plasmid, pMPI3H, with the oligonucleotide primers, VQPCRI3 (SEQ ID NO: 82;

5'-ATCATCAAGCTTAATTAATTAGTTATTAGACAAGGTGAAAACGAAACTATTTGTAGCTTAATTATTAGACATCATGCAGTGGTTAAAC-3') and I3PCRCTL (SEQ ID NO: 83;

5'-CTAGCTACGTGATGAAATGCTAATCTAGAATCAAATCTCCACTCCATGATTAAACCTAAATAATTGTAC-3'). This 216 bp PCR fragment was then used as a template in a second PCR reaction with the oligonucleotide primers, VQPCRI3 and CTLPCR (SEQ ID NO: 84;

5'-GAATTCCTCGAGGATCCTCTAGATTAACAATTTTTAAAATATTCAGGATGTAATTCTCTAGCTACGTGATGAAATGC-3'), to generate the PCR fragment, containing the I3L-promoted CTL2 epitope, that was digested with HindIII and XhoI and cloned into pBSH6). The plasmid generated by this manipulation is called p2–60-HIV.1.

The H6-promoted CTL1 epitope was then cloned into p2–60-HIV.1. This was accomplished by cloning a 290 bp NruI-EcoRI fragment, containing the H6-promoted CTL1 epitope, into the 3,300 bp NruI-EcoRI fragment of p2–60-HIV.1. (The 290 bp NruI-EcoRI fragment was generated by the following procedure. A 195 bp PCR fragment, containing the H6-promoter and the 5'-end of the CTL1 epitope, was generated from the plasmid, pH6T2, with the oligonucleotide primers, H6PCR1 (SEQ ID NO: 85; 5'-ACTACTAAGCTTCTTTATTCTATACTTAAAAAGTG-3') and NCCPCR1 (SEQ ID NO: 86;

5'-CAGCTGCTTTGTAAGTCATTGGTCTTAAAGGTACTTGAGGTGTTACTGGAAAACCTACCATTACGATACAAACTTAACGGATATCGCG-3'). This 195 bp PCR fragment and the oligonucleotides, NCC174A (SEQ ID NO: 87;

5'-ACTTACAAAGCAGCTGTAGATCTTTCTCACTTTTTAAAAGAAAAAGGAGGTTTAGAAGGGCTAATTCATTCTCAACGAAGACAAGATATTCTTGATTTGTGG-3') and NCC174B (SEQ ID NO: 88;

5'-CCACAAATCAAGAATATCTTGTCTTCGTTGAGAATGAATTAGCCCTTCTAAACCTCCTTTTTCTTTTAAAAAGTGAGAAAGATCTACAGCTGCTTTGTAAGT-3'), were then used as templates in a second PCR reaction with the oligonucleotide primers, H6PCR1 and NCCPCR2 (SEQ ID NO: 89;

5'-CTGCCAATCAGGAAAATATCCTTGTGTATGATAAATCCACAAATCAAGAATATC-3'). The resulting 317 bp PCR fragment, containing the H6-promoter and most of the CTL1 epitope, and the oligonucleotides, NCC291A (SEQ ID NO: 90;

5'-GGATATTTTCCTGATTGGCAGAATTACACACCAGGACCAGGAGTCAGATACCCATTAACCTTTGGTTGGTGCTACAAGC-3') and NCC291B (SEQ ID NO: 91;

5'-GCTTGTAGCACCAACCAAAGGTTAATGGGTATCTGACTCCTGGTCCTGGTGTGTAATTCTGCCAATCAGGAAAATATCC-3'), were then used as templates in a third PCR reaction with the oligonucleotide primers, H6PCR1 and NCCPCR3 (SEQ ID NO: 92;

5'-ACTACTGAATTCTCGAGAAAAATTATGGTACTAGCTTGTAGCACCAACC-3'), to generate the PCR fragment, containing the H6-promoted CTL1 epitope, that was digested with NruI and EcoRI and cloned into p2–60-HIV.1) The plasmid generated by this manipulation is called p2–60-HIV.2.

The I3L-promoted CTL2 and H6-promoted CTL1 epitopes were then cloned between canarypox C6 flanking arms. This was accomplished by cloning the 640 bp XhoI fragment of p2–60-HIV.2, containing the two (2) nef CTL epitopes, into the XhoI site of pC6L. The plasmid generated by this manipulation is called p2–60-HIV.3. The DNA sequence of p2–60-HIV.3 (SEQ ID NOS: 93–96) is shown in FIG. 16. FIG. 16 shows the nucleotide sequence of the I3L-promoted nef CTL2 epitope and H6-promoted nef CTL1 epitope contained in p2–60-HIV.3:

NEF CTL epitopes

| FEATURES | From | To/Span | | Description |
|---|---|---|---|---|
| frag | 1 | 51 | | C6 Left Arm |
| pept | 175 | 98 | (C) | nef CTL2 |
| frag | 275 | 176 | (C) | I3L promoter |
| frag | 337 | 460 | | H6 promoter |
| pept | 461 | 709 | 1 | nef CTL1 |
| frag | 751 | 801 | | C6 Right Arm |

The DNA sequence of the ALVAC C6 flanking arm (SEQ ID NOS: 97 and 98) is shown in FIGS. 17A–C. FIGS. 17A to 17C show the nucleotide sequence of the C6 locus in pC6L:

C6 LOCUS pC6L

| FEATURES | From | To/Span | Description |
|---|---|---|---|
| frag | 1 | 381 | C6 flanking arm |
| frag | 382 | 447 | Cloning sites |
| frag | 448 | 1615 | C6 flanking arm |

p2–60HIV.3 was used in in vitro recombination experiments with vCP205 as the rescuing virus to yield vCP264.

Example 16

Generation of an ALVAC Recombinant Expressing HIV1 gag (+pro) (IIIB), gp120 (MN) (+ transmembrane) and 2 nef (BRU) and 3 pol (IIIB) CTL Epitope Containing Regions Expression cassettes encoding three (3) pol CTL epitopes, pol1 (amino acids 172–219), pol2 (amino acids 325–383) and pol3 (amino acids 461–519) (Ratner et al, 1985; Nixon and McMichael, 1991), were then inserted into vCP264. The insertion plasmid, pC5POLT5A, containing the three (3) pol CTL epitopes, was generated by cloning a 948 bp XhoI-BamHI fragment, containing the H6-promoted pol1 epitope, the I3L-promoted pol2 epitope and the 42K-promoted pol3 epitope, into the 2,940 bp XhoI-BamHI fragment of pBSK$^+$. (The 948 bp XhoI-BamHI fragment was generated by the following procedure. A 183 bp PCR fragment, containing the pol1 epitope, was generated from the plasmid, pHXB2D, with the oligonucleotide primers, P1A (SEQ ID NO: 99;

5'-TTTGTATCGTAATGATTGAGACTGTACCAGTAAAATTAAAGCC-3') and P1B (SEQ ID NO: 100;

5'-GGGCTGCAGGAATTCTAATCAATTAAGGCCCAATTTTTGAAATTTTCCCTTCCTTTTCCATCTCTG-3'). A 224 bp PCR fragment, containing the pol2 epitope, was generated from the plasmid, pHXB2D, with the oligonucleotide primers, P2A (SEQ ID NO: 101;

5'-ACAAAGTACAATTATTTAGGTTTAATCATGGCAATATTCCAAAGTAGCATGAC-3') and P2B (SEQ ID NO: 102;

5'-ATCATCCTCGAGAAAAATTAGGTAAGTCCCCCCTCAACAGATG-3'). A 236 bp PCR fragment, containing the pol3 epitope, was generated from the plasmid, pHXB2D, with the oligonucleotide primers, P3A (SEQ ID NO: 103;

5'-AAAATATATAATTACAATATAAAATGCCACTAACAGAAGAAGCAGAGCTAGAACTGGC-3') and P3B (SEQ ID NO: 104;

5'-ATCATCTCTAGACTCGAGGATCCATAAAAATTATCCTGTTTTCAGATTTTTAAATGGCTC-3'). A 340 bp PCR fragment, containing the I3L and H6 promoters (in a head-to-head configuration) was generated from the plasmid, p2–60-HIV.2, with the oligonucleotide primers, P2IVH (SEQ ID NO: 105;

5'-GTCATGCTACTTTTGAATATTGCCATGATTAAACCTAAATAATTGTACTTTG-3')

and IVHP1 (SEQ ID NO: 106;

5'-TTTAATTTTACTGGTACAGTCTCAATCATTACGATACAAACTTAACGGATATCGCG-3'). A 168 bp PCR fragment, containing the 42K promoter, was generated from the plasmid, pVQ42KTh4.1, with the oligonucleotide primers, EPS42K (SEQ ID NO: 107;

5'-AATTGATTAGAATTCCTGCAGCCCGGGTCAAAAAAATATAAATG-3') and 42KP3B (SEQ ID NO: 108;

5'-CCAGTTCTAGCTCTGCTTCTTCTGTTAGTGGCATTTTATATTGTAATTATATATTTTC-3'). A 511 bp PCR fragment, containing the H6 promoter and I3L-promoted pol2 epitope, was generated by using the 224 bp PCR fragment, containing the pol2 epitope, and the 340 bp PCR fragment, containing the I3L and H6 promoters, as templates in a PCR reaction with the oligonucleotide primers, P2B and IVHP1. A 347 bp PCR fragment, containing the 42K-promoted pol3 epitope, was generated by using the 168 bp PCR fragment, containing the 42K promoter, and the 236 bp PCR fragment, containing the pol3 epitope, as templates in a PCR reaction with the oligonucleotide primers, IPS42K and P3B. A 506 bp PCR fragment, containing the pol1 epitope and the 42K-promoted pol3 epitope, was generated by using the 183 bp PCR fragment, containing the pol1 epitope, and the 347 bp PCR fragment, containing the 42K-promoted pol3 epitope, as templates in a PCR reaction with the oligonucleotide primers, P1A and P3B. A 977 bp PCR fragment, containing the H6-promoted pol1 epitope, the I3L-promoted pol2 epitope and the 42K-promoted pol3 epitope, was generated by using the 511 bp PCR fragment, containing the H6 promoter and I3L-promoted pol2 epitope, and the 506 bp PCR fragment, containing the pol1 epitope and 42K-promoted pol3 epitope, as templates in a PCR reaction with the oligonucleotide primers, P2B and P3B. The 977 bp PCR fragment was then digested with XhoI and BamHI and cloned into the 2,940 bp XhoI-BamHI fragment of pBSK+.) The plasmid generated by this manipulation is called pBSPOLT5.

Nucleotide sequence analysis of pBSPOLT5 indicated that there was an error in the pol2 epitope. In order to correct this mistake, the 948 bp XhoI-BamHI fragment, containing the H6-promoted pol1 epitope, the I3L-promoted pol2 epitope and the 42K-promoted pol3 epitope, was used as a template in a PCR reaction with the oligonucleotide primers, I3PCR1 (SEQ ID NO: 109; 5'-ATCATCGGATCCAAGCTTACATCATGCAGTGG-3') and FIXPOL2 (SEQ ID NO: 110;

5'-ATCATCCTCGAGCTATTCAATTAGGTTGTAAGTCCCCACCTCAAC-3'). The resulting PCR fragment, containing the corrected I3L-promoted pol2 epitope, was digested with HindIII and XhoI and cloned into the 3,650 bp HindIII-XhoI fragment of pBSPOLT5. The plasmid generated by this manipulation is called pBSPOLT5A.

The H6-promoted pol1 epitope, I3L-promoted pol2 epitope and 42K-promoted pol3 epitope was then cloned between canary pox C5 flanking arms. This was accomplished by cloning the 897 bp BamHI-XhoI fragment of pBSPOLT5A, containing the H6-promoted pol1 epitope, the I3L-promoted pol2 epitope and the 42K-promoted pol3 epitope, into the 4,675 bp BamHI-XhoI fragment of pNC5L-SP5. The plasmid generated by this manipulation is called pC5POLT5A. The DNA sequence of pC5POLT5A (SEQ ID NOS: 111–115) is shown in FIGS. 18A–B. FIGS. 18A to 18B shows the nucleotide sequence of the 13L-promoted pol2 epitope, H6-promoted pol1 epitode and 42K-promoted pol3 epitope contained in pC5POLT5a:

POL CTL epitopes

| FEATURES | From | To/Span | | Description |
|---|---|---|---|---|
| frag | 1 | 50 | | C5 Left Arm |
| pept | 272 | 92 | (C) | POL 2 |
| frag | 372 | 273 | (C) | I3L promoter |
| frag | 377 | 500 | | H6 promoter |
| pept | 501 | 647 | 1 | POL1 |
| frag | 676 | 782 | | _42K promoter |
| pept | 783 | 962 | 1 | POL 3 |
| frag | 986 | 1035 | | C5 Right Arm |

The DNA sequence of the ALVAC C5 flanking arm (SEQ ID NOS: 116 and 117) is shown in FIGS. 19A–C. FIGS. 19A to 19C show the nucleotide sequence of the C5 locus in pNC5L-SP5:

C5 LOCUS
pNC5L-SP5

| FEATURES | From | To/Span | Description |
|---|---|---|---|
| frag | 1 | 1549 | C5 flanking arm |
| frag | 1550 | 1637 | Cloning sites |
| frag | 1638 | 2049 | C5 flanking arm |

pC5POLT5A was used in in vitro recombination experiments with vCP264 as the rescuing virus to yield vCP300.

Example 17

Restriction and Immunoprecipitation Analyses

Restriction enzyme analysis was performed to confirm that the HIV1 sequences in vCP300 are in the proper loci. ALVAC, vCP205, vCP264 and vCP300 DNA were digested with HindIII, PstI or XhoI and the resultant fragments fractionated on an agarose gel. When the sizes of the resulting fragments were compared, it was determined that, as expected, the gag(+pro) and gp120(+transmembrane) genes were inserted into the C3 locus, the nef epitopes were inserted into the C6 locus and the pol epitopes were inserted into the C5 locus.

Immunoprecipitation analysis was performed to determine whether vCP300 expresses authentic HIV1 gag and gp120(+transmembrane) gene products. HeLa cell monolayers were either mock infected or infected at an m.o.i. of 10 pfu/cell with ALVAC or vCP300. Following an hour adsorption period, the inoculum was aspirated and the cells were overlayed with 2 mls of modified Eagle's medium (minus methionine) containing 2% fetal bovine serum and [$35_S$]-methionine (20 μCi/ml). Cells were harvested at 18 hrs post-infection by the addition of 1 ml 3×buffer A (3% NP-40, 30 mM Tris (pH7.4), 3 mM EDTA, 0.03% Na Azide and 0.6 mg/ml PMSF) and 50 ul aprotinin, with subsequent scraping of the cell monolayers. Lysates from the infected cells were analyzed for HIV1 gag and gp120(+transmembrane) gene expression using serum from HIV1-seropositive individuals (obtained from New York State Department of Health). The sera was bound to Protein A-sepharose in an overnight incubation at 4° C. Following this incubation period, the material was washed 4× with 1×buffer A. Lysates, precleared with normal human sera and protein A-sepharose, were then incubated overnight at 4° C. with the HIV1-seropositive human sera bound to protein A-sepharose. After the overnight incubation period, the samples were washed 4× with 1×buffer A and 2× with a $LiCl_2$/urea buffer. Precipitated proteins were dissociated from the immune complexes by the addition of 2×Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography. This analysis indicated that HIV1 gag and gp120(+transmembrane) gene products were precipitated from vCP300-infected cells, but were not precipitated from mock infected or ALVAC-infected cells.

Expression of the nef and pol epitopes in vCP300-infected cells has not been confirmed because no epitope specific serological reagents are yet available. Nucleotide sequence analysis, however, has confirmed that the nef and pol sequences cloned into vCP300 are correct. PCR fragments, containing the nef and pol expression cassettes, were generated from vCP300 DNA. Nucleotide sequence analysis of these fragments indicated that the nef and pol sequences are correct.

vCP205 expresses the same cell surface-associated form of HIV1 gp120 as expressed by vCP300. The immunogenicity of this gene product, as expressed by vCP205, has been assayed in small laboratory animals.

Example 18

Immunogenicity Studies

Groups of two rabbits or guinea pigs were inoculated intramuscularly (im) with $10^8$ pfu of ALVAC, vCP205, or with 0.1 mg of peptide CLTB-36 (GPKEPFRDYVDRFYKNKRKRIHIGPGRAFYTTKN) (SEQ ID NOS: 118) adjuvanted with 0.05 mg of QS-21 according to the schedule below (Table 21).

Table 21. Immunization schedule for rabbits and guinea pigs inoculated with ALVAC, vCP205, or with peptide CLTB-36 in QS-21.

INOCULATION

| GROUP | WEEK 0 | WEEK 4 | WEEK 8 |
|---|---|---|---|
| 1 | ALVAC | ALVAC | CLTB-36/QS-21 |
| 2 | vCP205 | vCP205 | vCP205 |
| 3 | vCP205 | vCP205 | CLTB-36/QS-21 |
| 4 | CLTB-36/QS-21 | CLTB-36/QS-21 | CLTB-36/QS-21 |

Each rabbit and guinea pig was bled prior to the first inoculation and at 2-week intervals following the first inoculation through week 14. Serum was prepared from each blood sample and stored at −70° C. until use. Each serum was tested for antibody responses to recombinant HIV MN/BRU hybrid gp160 or to 25-mer synthetic HIV MN gp120 V3 loop (American Bio-Technologies, Inc. Cambridge, Mass., product #686010) by kinetics enzyme-linked immunosorbant assay (KELISA).

Figure 20:
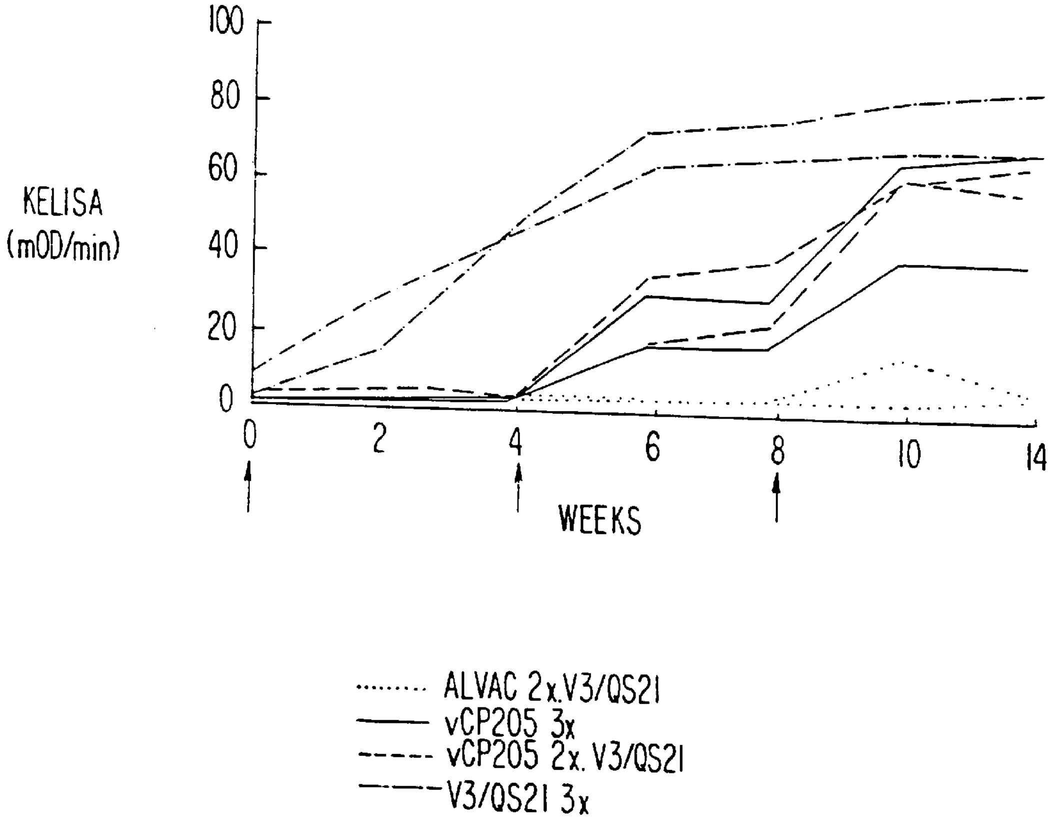
FIG. 20 shows the rabbit antibody responses to the HIV envelope glycoprotein following immunization with ALVAC, vCP205, or with peptide CLTB-36.

Rabbits immunized with vCP205 (Group 2) produced the highest levels of anti-gp160 antibodies (FIG. 20). Rabbits were immunized according to the schedule in Table 21 (arrows in FIG. 20) and bled at 2 week intervals. Each serum was diluted 1:100 in dilution buffer and tested for reactivity with purified recombinant HIV MN/BRU gp160 using a kinetics ELISA. Both rabbits in this group began producing gp160 reactive antibodies after a single inoculation. Boosting with subsequent inoculations produced only minor increases in antibody levels. Rabbits inoculated twice with vCP205 and boosted with peptide CLTB-36 in QS-21 adjuvant (Group 3) apparently failed to make anti-gp160 antibodies when compared to control rabbits (Group 1). Of the rabbits immunized three times with peptide CLTB-36 in QS-21, only one responded by generating gp160-specific antibodies. The one responsive rabbit (A353) began producing gp160 antibodies only after the third immunization.

Figure 21:
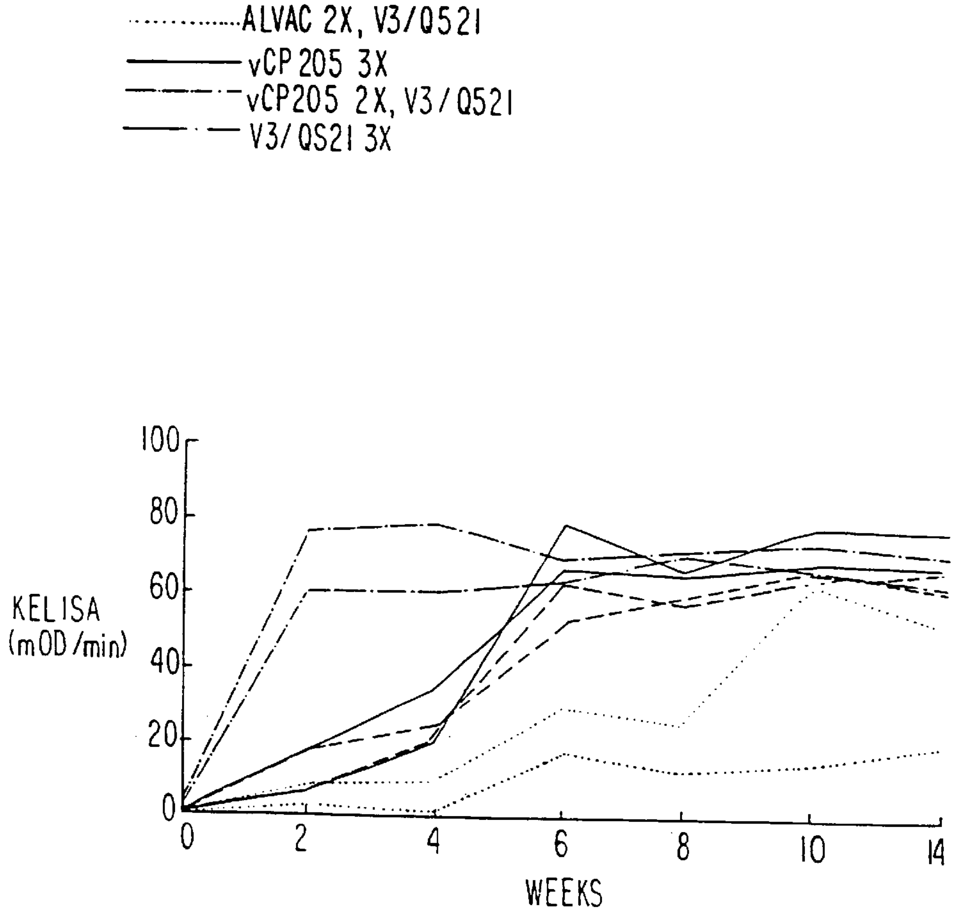
FIG. 21 shows the rabbit antibody responses to the HIV MN V3 loop following immunization with ALVAC, vCP205, or with peptide CLTB-36.

Rabbits immunized only with peptide CLTB-36 would not be expected to generate broadly reactive gp160 -specific antibodies since the peptide contains only a small portion of the envelope glycoprotein, the V3 loop. Thus, sera were tested for reactivity to a peptide containing 25 amino acids of the HIV MN V3 loop (FIG. 21). Rabbits were immunized according to the schedule in Table 21 (arrows in FIG. 22)

and bled at 2 week intervals. Each serum was diluted 1:100 in dilution buffer and tested for reactivity with a 25-mer synthetic peptide representing the HIV MN gp120 V3 loop (CNKRKRIHIGPGRAFYTTKNIIGTIC; (SEQ ID NO: 119) American Bio-Technologies, Inc. Cambridge, Mass., product #686010) using a kinetics ELISA. As before, the highest V3 antibody responses were found in the sera of rabbits inoculated three times with vCP205. Two inoculations with vCP205 followed by peptide CLTB-36 in QS-21 produced anti-V3 antibody responses, but not as high as Group 2 rabbits. Also, as before, only one rabbit responded to three inoculations with peptide CLTB-36 in QS-21.

Figure 22:
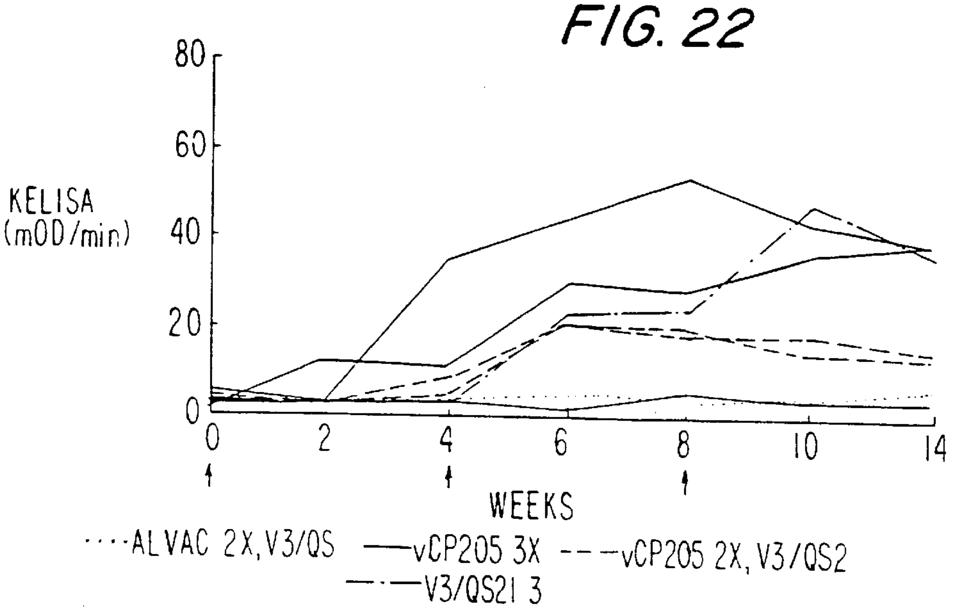
FIG. 22 shows the guinea pig antibody responses to the HIV envelope glycoprotein following immunization with ALVAC, vCP205, or with peptide CLTB-36.

Guinea pigs in all groups, including one animal in Group 1, produced antibodies that reacted with HIV gp160 (FIG. 22). Guinea pigs were immunized according to the schedule in Table 21 (arrows in FIG. 22) and bled at 2 week intervals. Each serum was diluted 1:100 in dilution buffer and tested for reactivity with purified recombinant HIV MN/BRU gp160 using a kinetics ELISA. The single animal in Group 1 that responded did so only after inoculation with peptide CLTB-36 in QS-21 adjuvant. Antibody levels in the sera of all guinea pigs in Groups 2, 3, and 4 were similar. Most of the guinea pigs responded to a single inoculation by producing gp16o antibodies.

Figure 23:
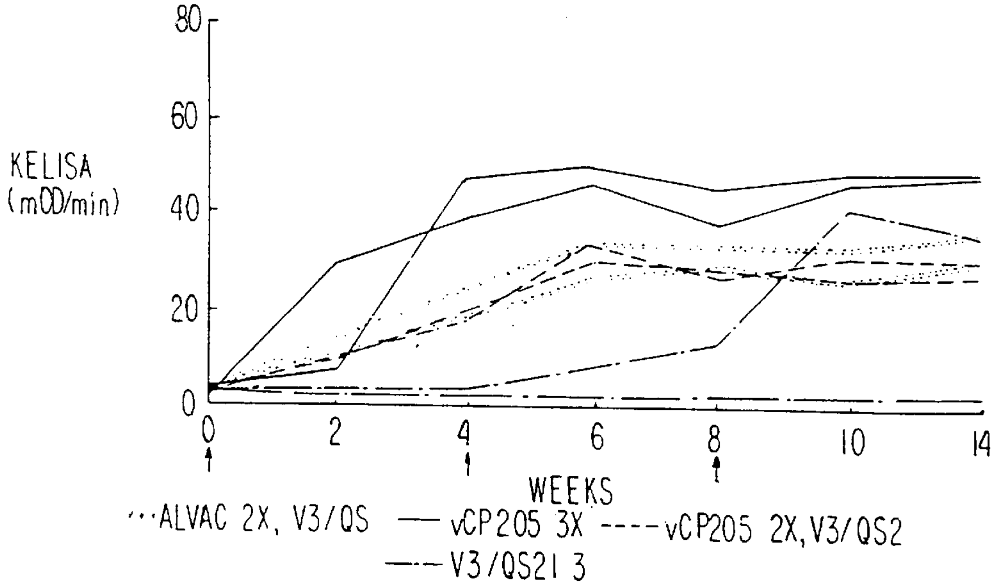
FIG. 23 shows the guinea pig antibody responses to the HIV MN V3 loop following immunization with ALVAC, vCP205, or with peptide CLTB-36.

Similar results were seen using a HIV MN V3 25-mer peptide as the KELISA antigen (FIG. 23). Guinea pigs were immunized according to the schedule in Table 21 (arrows in FIG. 23) and bled at 2 week intervals. Each serum was diluted 1:100 in dilution buffer and tested for reactivity with a 25-mer synthetic peptide representing the HIV MN gp120 V3 loop (CNKRKRIHIGPGRAFYTTKNIIGTIC (SEQ ID NO: 120) American Bio-Technologies, Inc. Cambridge, Mass., product #686010) using a kinetics ELISA. A single inoculation of peptide CLTB-36 in QS-21 elicited V3 antibody responses which were boosted by second and third inoculations. Two inoculations with vCP205 were necessary to induce V3 antibody responses which was boosted to higher levels by the third inoculation of vCP205 or CLTB-36 in QS-21.

Figure 24:
FIG. 24 shows in vitro stimulation of HIV-1-specific CTLs from PBMCs of an HIV-seropositive individual—Patient 1.
Figure 25:
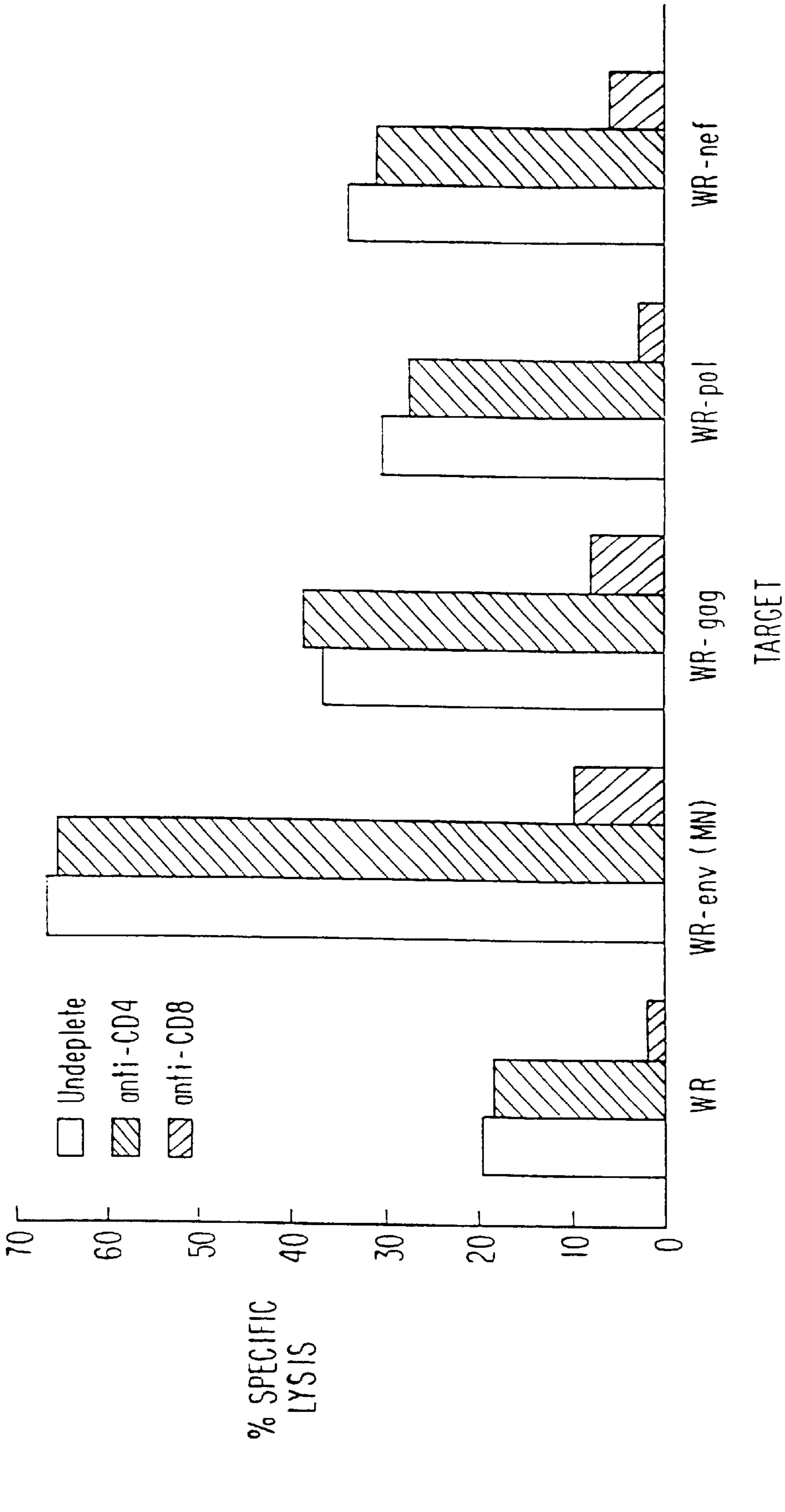
FIG. 25 is as in FIG. 24 but with Patient 2.

Expression and immunogenicity of the Nef and Pol CTL epitopes expressed by vCP300 is demonstrated by the following in vitro assays. Fresh PBMC samples were derived from HIV-seropositive individuals. Twenty-percent of these cells were inoculated with vCP300 at an m.o.i. of 10. Two hours post-infection the cells were washed and mixed with autologous, uninoculated PBMCs at a ratio of uninoculated/inoculated of 10:1. (Seeding density equaled $1.5\times10^6$ cells/ml). On day 0, exogenous IL-7 was added at a final concentration of 1000 U/ml. On day three, the addition of an exogenous source of IL-7 and IL-2 was added at a final concentration of 1000U/ml and 220 U/ml, respectively. After 12 days in culture, the in vitro stimulated cell population was used in a standard $^{51}$Cr-release assay using autologous Epstein-Barr virus-transformed B cells infected with vaccinia virus (WR) recombinants expressing HIV-1 proteins as targets. The results from assays obtained using an Effector/Target (E/T) cell ratio of 20:1 are shown in FIGS. 24 and 25 and expressed as percent specific lysis. The combined results demonstrate the ability of vCP300-infected PBMCs to stimulate HIV-1, Env-, Gag-, Pol-, and Nef-specific cytolytic activity. Further, abrogation of the cytolytic activities by anti-CD8 monoclonal antibodies demonstrates that the nature of the cell mediating the cytolytic activities are classical $CD8^+$ CTLs.

In summary, the inoculation of rabbits and guinea pigs with the HIV ALVAC recombinant canarypox virus, vCP205, elicited antibodies to the HIV envelope glycoprotein and a region of the HIV envelope glycoprotein associated with neutralization of HIV, the gp120 V3 loop region. The expression and immunogenicity of the vCP300 expressed Env, Gag, Pol and Nef encoded products is demonstrated by the in vitro stimulation of $CD8^+$ CTLs from seropositive individuals. Thus, vCP205 and vCP300 and precursors to these recombinants and expression products and DNA from these recombinants are useful, as described above.

Example 19

Generation OF vCP1307; an ALVAC Recombinant Expressing a from of HIV1 gp120+TM with 2 ELDKWA Epitopes Inserted into the gp120 V3 Loop vCP1307, an ALVAC recombinant expressing HIV1 gp120+TM with 2 ELDKWA epitopes from HIV1 gp41 inserted into the gp120 V3 loop region, was generated by the following procedure. The sequence encoding part of the ELDKWA elements and V3 loop was cloned into pBSK+ (Stratagene, LaJolla, Calif.). This was accomplished by cloning a 225 bp EcoRI-SacI-digested PCR fragment, containing part of the ELDKWA-V3 loop sequence, into the 2,900 bp EcoRI-SacI fragment of pBSK+. (This PCR fragment was generated from the plasmid, pBSHIVMN120T, with the primers, HIVP72 (SEQ ID NO: 121; 5'-TTATTACCATTCCAAGTACTATT-3') and HIVP74 (SEQ ID NO: 122) 5'-TCTGTACA AATTAATTGTACAAGACCCAACTACGAGCTCGACAAATGGGCCCATATAGGACCAGGGAGAGAATTGGATAAGTGGGCGAATATAATAGGAACTATAAGAC-3').) The plasmid generated by this manipulation is called pHIV55.

[pBSHIVMN120T, a plasmid containing the H6-promoted HIV1 gp120+TM gene, was generated by the following procedure. A plasmid, pMN1.8-9, containing a cDNA copy of the HIV1 (MN) env gene, was obtained from Marvin Reitz (NCI, NIH). An early transcription termination signal sequence, $T_5NT$, in the env gene was modified. This was accomplished by cloning a 1,100 bp KpI-EcoRI-digested PCR fragment, containing the T5NT-modified 5'-end of the env gene, into the 2,900 bp KpnI-EcoRI fragment of pBSK+. (This PCR fragment was generated from the plasmid, pMN1.8-9, with the oligonucleotides, HIVMN6 (SEQ ID NO: 123; 5'-GGGTTATTAATGATCTGTAG-3') and HIV3B2 (SEQ ID NO: 124; 5'-GAATTACAGTAGAAGAATTCCCCTCCACAATTAAAAC-3').) The plasmid generated by this manipulation is called pBSMIDMN.

The $T_5NT$-modified 5'-end of the env gene was then cloned upstream to the rest of the env gene. This was accomplished by cloning the 1,025 bp KpnI-EcoRI fragment of pBSMIDMN, containing the $T_5NT$-modified 5'-end of the env gene, into the 4,300 bp KpnI-EcoRI fragment of pBS3MN. (pBS3MN was generated by cloning a 430 bp EcoRI-SacI-digested PCR fragment, containing a central portion of the env gene, and a 1,050 bp SacI-XbaI-digested PCR fragment, containing the 3'-end of the env gene, into the 2,900 bp EcoRI-XbaI fragment of pBSK+. The 430 bp PCR fragment was generated from the plasmid, pMN1.8-9, with the oligonucleotides, HIV3B1 (SEQ ID NO: 125; 5'-GTTTTAATTGTGGAGGGGAATTCTTCTACTGTAATTC-3') and HIVMN4 (SEQ ID NO: 126; 5'-ATCATCGAGCTCCTATCGCTGCTC-3'). The 1,050 bp PCR fragment was generated from the plasmid, pMN1.8-9, with the oligonucleotides, HIVMN5 (SEQ ID NO: 127;

5'-ATCATCGAGCTCTGTTCCTTGGGTTCTTAG-3') and HIVMN3P (SEQ ID NO: 128; 5'-ATCATCTCTAGAATAAAAATTATAGCAAAGCCCTTTCCAAGCC-3').) The plasmid generated by this manipulation is called pBSMID3MN.

The H6 promoter (Perkus et al., 1989) was then cloned upstream to the env gene. This was accomplished by cloning the 320 bp KpnI fragment of pH6IIIBE, containing the H6 promoter linked to the 5'-end of the HIV1 (IIIB) env gene, and the 2,450 bp KpnI-XbaI fragment of pBSMID3MN, containing the bulk of the HIV1 (MN) env gene, into the 2,900 bp KpnI-XbaI fragment of pBSK+. The plasmid generated by this manipulation is called pH6HMNE.

The sequence encoding gp41 was then replaced with the sequence encoding the HIV1 env transmembrane (TM) region. This was accomplished by cloning a 480 bp EcoRI-XbaI-digested PCR fragment, containing the 3'-end of the gp120 gene and the HIV1 env transmembrane region, into the 4,200 bp EcoRI-XbaI fragment of pH6HMNE. (This PCR fragment was generated from the PCR fragment, PCR-MN11, and oligonucleotides, HIVTM1 (SEQ ID NO: 129; 5'-TTATTCATAATGATAGTAGGAGGCTTGGTAGGTTAAGAATAGTTTTTGCTGTACTCTCTGTAGTGAATAGAGTTAGGCAGGGATAA-3') and HIVTM2 (SEQ ID NO: 130; 5'-TTATCCCTGCCTAACTCTATTCACTACAGAGAGTACAGCAAAAACTATTCTTAAACCTACCAAGCCTCCTACTATCATTATGAATAA-3'), with the oligonucleotides, HIV3B1 (SEQ ID NO: 125) and HIVTM3 (SEQ ID NO: 131; 5'-ATCATCTCTAGAATAAAAATTATCCCTGCCTAACTCTATTCAC-3'). PCR-MN11 was generated from the plasmid, pH6HMNE, with the oligonucleotides, HIV3B1 (SEQ ID NO: 125) and HIVMN18 (SEQ ID NO: 132; 5'-GCCTCCTACTATCATTATGAATAATCTTTTTTCTCTCTG-3').) The plasmid generated by this manipulation is called pBSHIVMN120T.]

Another part of the sequence encoding the ELDKWA epitopes and V3 loop was then cloned into pBSK+. This was accomplished by cloning a 300 bp HindIII-SacI-digested PCR fragment, containing part of the ELDKWA-V3 loop sequence, into the 2,900 bp HindIII-SacI fragment of pBSK+. (This PCR fragment was generated from the plasmid, pBSHIVMN120T, with the primers, HIVP69 (SEQ ID NO: 133; 5'-TGATAGTACCAGCTATAGGTTGAT-3') and HIVP75 (SEQ ID NO: 134; 5'-TTTGTCGAGCTCGTAGTTGGGTCTTGTACAATT-3').) The plasmid generated by this manipulation is called pHIV56.

The ELDKWA-V3 loop sequences from pHIV55 and pHIV56 were then cloned into the H6-promoted gp120+TM gene. This was accomplished by cloning the 225 bp EcoRI-SacI fragment of pHIV55 and the 300 bp HindIII-SacI fragment of pHIV56, containing the ELDKWA-V3 loop sequences, into the 4,300 bp EcoRI-HindIII fragment of pBSHIVMN120T. The plasmid generated by this manipulation is called pHIV57.

The H6-promoted gp120+TM construct containing the ELDKWA epitopes was then cloned between C5 flanking arms. This was accomplished by cloning the 1,700 bp NruI-XbaI fragment of pHIV57, containing the H6-promoted gp120+TM (with ELDKWA epitopes) gene, into the 4,700 bp NruI-XbaI fragment of pSIVGC15. (pSIVGCl5 contains the H6-promoted SIV env gene cloned between C5 flanking arms.) The plasmid generated by this manipulation is called pHIV59. The DNA sequence of the H6-promoted gp120+TM (with ELDKWA epitopes) gene in pHIV59 is shown in FIG. 26.

pHIV59 was used in in vitro recombination experiments with ALVAC as the rescuing virus to yield vCP1307.

FACS analysis was performed to determine whether HIV1 gp120+TM (with ELDKWA epitopes) was expressed on the surface of vCP1307-infected cells. $5\times10^6$ HeLa-S3 cells in S-MEM (Sigma M-8028 Joklik suspension media) were infected at an m.o.i. of 5 pfu/cell with ALVAC, vP1286 (a WR recombiant expressing HIV1 gp120+TM) or vCP1307. Following a 60 minute adsorption period at 37° C., the cells were washed with 10 mls of S-MEM and centrifuged at 1,000 RPM for 5 minutes. The samples were then resuspended in 1 ml of S-MEM, transferred to 5 ml Sarstadt tubes and placed on a rotator at 37° C. After 18 hours, 200 ul aliquots ($1\times10^6$ cells) were placed in polypropylene tubes and washed with 3 mls of PBS-CMF (with 0.2% $NaN_3$+0.2% BSA). The supernatant was then decanted and the pellet was resuspended in 100 ul of a 1:100 dilution of sera from HIV1-seropositive humans (obtained from the New York State Dept. of Health) or a 1:100 dilution of a human monoclonal antibody specific for the ELDKWA epitope, IAM41–2F5 (obtained from Viral Testing Systems Corp., Houston, Tex.). The samples were incubated at 4° C. for 60 minutes, washed two times with PBS-CMF (with 0.2% $NaN_3$+0.2% BSA) and centrifuged at 1,000 RPM for 5 minutes. The supernatant was decanted and the pellet was resuspended in a 1:100 dilution of goat anti-human FITC (obtained from Boehringer Mannheim). The samples were incubated at 4° C. for 30 minutes, washed twice with PBS-CMF (with 0.2% $NaN_3$+0.2% BSA) and analyzed on a Facscan flow cytometer. A gene product containing the ELDKWA epitope was expressed at low levels on the surface of vCP1307-infected cells, but was not expressed on the surface of ALVAC-infected or vP1286-infected cells (FIG. 27, lower panel). A gene product reactive with the HIV1-seropositive sera was expressed on the surface of vP1286-infected cells and vCP1307-infected cells, but was not expressed on the surface of ALVAC-infected cells (FIG. 27, upper panel). These results indicate that the ELDKWA epitope of the HIV1 gp120+TM (with ELDKWA epitopes) gene product is expressed on the surface of vCP1307-infected cells, consistent with the fact that a portion of the V3 loop of this gene product has been replaced with ELDKWA epitopes.

Immunoprecipitation analysis was performed to determine whether vCP1307 expresses a form of gp120+TM which contains an immunogenic ELDKWA epitope. HeLa cell monolayers were infected at an m.o.i. of 10 pfu/cell with ALVAC (the parental virus), vP1286 (a WR recombinant expressing HIV1 gp120+TM) or vCP1307. Following an hour adsorption period, the inoculum was removed and the cells were overlayed with 2 mls of modified Eagle's medium (minus cysteine and methionine) containing 2% dialyzed fetal bovine serum and [$^{35}$S]-TRANS label (30 $\mu$Ci/ml). The lysates were harvested at 18 hrs post-infection by addition of 1 ml 3×buffer A (450 mM NaCl, 3% NP-40, 30 mM Tris (pH=7.4), 3 mM EDTA, 0.03% Na-Azide and 0.6 mg/ml PMSF) and analyzed for expression of 1) the ELDKWA epitope, using a 1:100 dilution of a human monoclonal antibody specific for the ELDKWA epitope, IAM41-2F5 (obtained from Viral Testing Systems Corp., Houston, Tex.) and 2) HIV1 gene products, using a 1:100 dilution of sera from HIV1-seropositive humans (obtained from the New York State Dept. of Health). Lysates, precleared with normal human sera and a protein A-sepharose complex, were incubated overnight at 4° C. with an IAM41-2F5-protein A-sepharose complex or an HIV1-seropositive sera-protein A-sepharose complex. The samples were washed 4× with 1×buffer A and 2× with a $LiCl_2$/urea buffer. Precipitated proteins were dissociated from the immune complexes by the addition of 2×Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1 M Na-salicylate for fluorography. Proteins of the appropriate size were precipitated with the monoclonal antibody to the ELDKWA epitope from vCP1307-infected cells, but were not precipitated from ALVAC-infected cells or vP1286-infected cells. Furthermore, proteins of the appropriate size were precipitated with the human HIV1-seropositive sera from vP1286-infected cells and vCP1307-infected cells, but were not precipitated from ALVAC-infected cells. These results indicate that vCP1307 expresses a form of gp120+TM which contains an antigenic ELDKWA epitope.

Example 20

Generation of vP1313; a NYVAC Recombinant Expressing a form of HIV1 gp120+TM with 2 ELDKWA Epitopes Inserted Into the gp120 V3 Loop vP1313, a NYVAC recombinant expressing HIV1 gp120+TM with 2 ELDKWA epitopes from HIV1 gp41 inserted into the gp120 V3 loop, was generated by the following procedure. The sequence encoding part of the ELDKWA epitopes and V3 loop was cloned into pBSK+. This was accomplished by cloning a 225 bp EcoRI-SacI-digested PCR fragment, containing part of the ELDKWA-V3 loop sequence, into the 2,900 bp EcoRI-SacI fragment of pBSK+. (This PCR fragment was generated from the plasmid, pBSHIVMN120T, with the primers, HIVP72 (SEQ ID NO: 144; 5'-TTATTACCATTCCAAGTACTATT-3') and HIVP74 (SEQ ID NO: 145; 5'-TCTGTACAAATTA ATTGTACAAGACCCAACTACGAGCTCGACAAATG GGCCCATATAGGACCAGGGAGAGAATTGGATAA GTGGGCGAATATAATAGGAACTATAAGAC-3').) The plasmid generated by this manipulation is called pHIV55.

[pBSHIVMN120T, a plasmid containing the H6-promoted HIV1 gp120+TM gene, was generated by the following procedure. A plasmid, pMN1.8-9, containing a cDNA copy of the HIV1 (MN) env gene, was obtained from Marvin Reitz (NCI, NIH). An early transcription termination signal sequence, $T_5NT$, in the env gene was modified. This was accomplished by cloning a 1,100 bp KpnI-EcoRI-digested PCR fragment, containing the $T_5NT$-modified 5'-end of the env gene, into the 2,900 bp KpnI-EcoRI fragment of pBSK+. (This PCR fragment was generated from the plasmid, pMN1.8-9, with the oligonucleotides, HIVMN6 (SEQ ID NO: 146; 5'-GGGTTATTAATGAT CTGTAG-3') and HIV3B2 (SEQ ID NO: 124; 5'-GAATTACAGTAGAAGAATTCCCCT CCACAATTAAAAC-3').) The plasmid generated by this manipulation is called pBSMIDMN.

The $T_5NT$-modified 5'-end of the env gene was then cloned upstream to the rest of the env gene. This was accomplished by cloning the 1,025 bp KpnI-EcoRI fragment of pBSMIDMN, containing the $T_5NT$-modified 5'-end of the env gene, into the 4,300 bp KpnI-EcoRI fragmnent of pBS3MN. (pBS3MN was generated by cloning a 430 bp EcoRI-SacI-digested PCR fragment, containing a central portion of the env gene, and a 1,050 bp SacI-XbaI-digested PCR fragment, containing the 3'-end of the env gene, into the 2,900 bp EcoRI-XbaI fragment of pBSK+. The 430 bp PCR fragment was generated from the plasmid, pMN1.8-9, with the oligonucleotides, HIV3B1 (SEQ ID NO: 125; 5'-GTTTTAATTGTGGAGGGGAATTCTTCTAC TGTAATTC-3') and HIVMN4 (SEQ ID NO: 126; 5'-ATCATCGAGCTCCTATCGCTGCTC-3'). The 1,050 bp PCR fragment was generated from the plasmid, pMN1.8-9, with the oligonucleotides, HIVMN5 (SEQ ID NO: 127; 5'-ATCATCGAGCTCTGTTCCTTGGGTTCTTAG-3') and HIVMN3P (SEQ ID NO: 128; 5'-ATCATCTCTAGAATAAAAATTATAGCAAAGCCC TTTCCAAGCC-3').) The plasmid generated by this manipulation is called pBSMID3MN.

The H6 promoter was then cloned upstream to the env gene. This was accomplished by cloning the 320 bp KpnI fragment of pH6IIIBE, containing the H6 promoter linked to the 5'-end of the HIV1 (IIIB) env gene, and the 2,450 bp KpnI-XbaI fragment of pBSMID3MN, containing the bulk of the HIV1 (MN) env gene, into the 2,900 bp KpnI-XbaI fragment of pBSK+. The plasmid generated by this manipulation is called pH6HMNE.

The sequence encoding gp41 was then replaced with the sequence encoding the HIV1 env transmembrane (TM) region. This was accomplished by cloning a 480 bp EcoRI-XbaI-digested PCR fragment, containing the 3'-end of the gp120 gene and the HIV1 env transmembrane region, into the 4,200 bp EcoRI-XbaI fragment of pH6HMNE. (This PCR fragment was generated from the PCR fragment, PCR-MN11, and oligonucleotides, HIVTM1 (SEQ ID NO: 129; 5'-TTATTCATAATGATAGTAGGAGGCTTGGTAGGT TTAAGAATAGTTTTTGCTGTACTCTCTGTAGTG AATAGAGTTAGGCAGGGATAA-3') and HIVTM2 (SEQ ID NO: [125] 130; 5'-TTATCCCTGC CTAACTCTATTCACTACAGAGAGTACAGCAAAA ACTATTCTTAAACCTACCAAGCCTCCTACTATCA TTATGAATAA-3'), with the oligonucleotides, HIV3B1 (SEQ ID NO: [131] 125) and HIVTM3 (SEQ ID NO: [125] 131; 5'-ATCATCTCTAGAATAAAAATTATCCCTGCCTAACT CTATTCAC-3'). PCR-MN11 was generated from the plasmid, pH6HMNE, with the oligonucleotides, HIV3B1 (SEQ ID NO: 125) and HIVMN18 (SEQ ID NO: 132; 5'-GCCTCCTACTATCATTATGAATAATCTTTTTTCTC TCTG-3').) The plasmid generated by this manipulation is called pBSHIVMN120T.]

Another part of the sequence encoding the ELDKWA epitopes and V3 loop was then cloned into pBSK+. This was accomplished by cloning a 300 bp HindIII-SacI-digested PCR fragment, containing part of the ELDKWA-V3 loop sequence, into the 2,900 bp HindIII-SacI fragment of pBSK+. (This PCR fragment was generated from the plasmid, pBSHIVMN120T, with the primers, HIVP69 (SEQ ID NO: 133; 5'-TGATAGTACCAGCTATAGGTTGAT-3') and HIVP75 (SEQ ID NO: 134; 5'-TTTGTCGAGCTCGTAGTTGGGTCTTGTACAATT-3') .) The plasmid generated by this manipulation is called pHIV56.

The ELDKWA-V3 loop sequences from pHIV55 and pHIV56 were then cloned into the H6-promoted gp120+TM gene. This was accomplished by cloning the 225 bp EcoRI-SacI fragment of pHIV55 and the 300 bp HindIII-SacI fragment of pHIV56, containing the ELDKWA-V3 loop sequences, into the 4,300 bp EcoRI-HindIII fragment of pBSHIVMN120T. The plasmid generated by this manipulation is called pHIV57.

The H6-promoted gp120+TM construct containing the ELDKWA epitopes was then cloned between C5 flanking arms. This was accomplished by cloning the 1,700 bp NruI-XbaI fragment of pHIV57, containing the H6-promoted gp120+TM (with ELDKWA epitopes) gene, into the 4,700 bp NruI-XbaI fragment of pSIVGC15. (pSIVGC15 contains the H6-promoted SIV env gene cloned between C5 flanking arms) The plasmid generated by this manipulation is called pHIV59.

The H6-promoted gp120+TM (with ELDKWA epitopes) gene was then cloned between I4L flanking arms. This was accomplished by cloning the 1,850 bp BamHI-SmaI fragment of pHIV59, containing the H6-promoted gp120+TM (with ELDKWA epitopes) gene, into the 3,600 bp BamHI-SmaI fragment of pSD550VC. The plasmid generated by this manipulation is called pHIV60. The DNA sequence of the H6-promoted gp120+TM (with ELDKWA epitopes) gene in pHIV60 is shown in FIG. 28.

pHIV60 was used in in vitro recombination experiments with NYVAC as the rescuing virus to yield vP1313.

FACS analysis was performed to determine whether HIV1 gp120+TM (with ELDKWA epitopes) was expressed on the surface of vP1313-infected cells. $5\times10^6$ HeLa-S3 cells in S-MEM (Sigma M-8028 Joklik suspension media) were infected at an m.o.i. of 5 pfu/cell with NYVAC, vP1286 (a WR recombinant expressing HIV1 gp120+TM) or vP1313. Following a 60 minute adsorption period at 37° C., the cells were washed with 10 mls of S-MEM and centrifuged at 1,000 RPM for 5 minutes. The samples were then resuspended in 1 ml of S-MEM, transferred to 5 ml Sarstadt tubes and placed on a rotator at 37° C. After 18 hours, 200 ul aliquots ($1\times10^6$ cells) were placed in polypropylene tubes and washed with 3 mls of PBS-CMF (with 0.2% $NaN_3$+ 0.2% BSA). The supernatant was then decanted and the pellet was resuspended in 100 ul of a 1:100 dilution of sera from HIV1-seropositive humans (obtained from the New York State Dept. of Health), or a 1:100 dilution of a human monoclonal antibody specific for the ELDKWA epitope, IAM41-2F5 (obtained from Viral Testing Systems Corp. Houston, Tex.). The samples were incubated at 4° C. for 60 minutes, washed two times with PBS-CMF (with 0.2% $NaN_3$+0.2% BSA) and centrifuged at 1,000 RPM for 5 minutes. The supernatant was decanted and the pellet was resuspended in a 1:100 dilution of goat anti-human FITC (obtained from Boehringer Mannheim). The samples were incubated at 4° C. for 30 minutes, washed twice with PBS-CMF (with 0.2% $NaN_3$+0.2% BSA) and analyzed on a Facscan flow cytometer. A gene product containing the ELDKWA epitope was expressed on the surface of vP1313-infected cells, but was not expressed on the surface of NYVAC-infected or vP1286-infected cells (FIG. 29, lower panel). A gene product reactive with the HIV1-seropositive sera was expressed on the surface of vP1286-infected cells and vP1313-infected cells, but was not expressed on the surface of NYVAC-infected cells (FIG. 29, upper panel). These results indicate that the ELDKWA epitope of the HIV1 gp120+TM (with ELDKWA epitopes) gene product is expressed on the surface of vP1313-infected cells, consistent with the fact that a portion of the V3 loop of this gene product has been replaced with ELDKWA epitopes.

Immunoprecipitation analysis was performed to determine whether vP1313 expresses a form of gp120+TM which contains an immunogenic ELDKWA epitope. HeLa cell monolayers were infected at an m.o.i. of 10 pfu/cell with NYVAC (the parental virus), vP1286 (a WR recombinant expressing HIV1 gp120+TM) or vP1313. Following an hour adsorption period, the inoculum was removed and the cells were overlayed with 2 mls of modified Eagle's medium (minus cysteine and methionine) containing 2% dialyzed fetal bovine serum and [$^{35}$S]-TRANS label (30 $\mu$Ci/ml). The lysates were harvested at 18 hrs post-infection by addition of 1 ml 3×buffer A (450 mM NaCl, 3% NP-40, 30 mM Tris (pH=7.4), 3 mM EDTA, 0.03% Na-Azide and 0.6 mg/ml PMSF) and analyzed for expression of 1) the ELDKWA epitope, using a 1:100 dilution of a human monoclonal antibody specific for the ELDKWA epitope, IAM41-2F5 (obtained from Viral Testing Systems Corp., Houston, Tex.) and 2) HIV1 gene products, using a 1:100 dilution of sera from HIV1-seropositive humans (obtained from the New York State Dept. of Health). Lysates, precleared with normal human sera and a protein A-sepharose complex, were incubated overnight at 4° C. with an IAM41-2F5-protein A-sepharose complex or an HIV1-seropositive sera-protein A-sepharose complex. The samples were washed 4× with 1×buffer A and 2× with a $LiCl_2$/urea buffer. Precipitated proteins were dissociated from the immune complexes by the addition of 2×Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1 M Na-salicylate for fluorography. Proteins of the appropriate size were precipitated with the monoclonal antibody to the ELDKWA epitope from vP1313-infected cells, but were not precipitated from NYVAC-infected cells or vP1286-infected cells. Furthermore, proteins of the appropriate size were precipitated with the human HIV1-seropositive sera from vP1286-infected cells and vP1313-infected cells, but were not precipitated from NYVAC-infected cells. These results indicate that vP1313 expresses a form of gp120+TM which contains an immunogenic ELDKWA epitope.

Example 21

Generation of vP1319; a COPAK Recombinant Expressing a form of HIV1 gp120+TM with 2 ELDKWA Epitopes Inserted Into the gp120 V3 Loop vP1319, a COPAK recombinant expressing HIV1 gp120+TM with 2 ELDKWA epitopes from HIV1 gp41 inserted into the gp120 V3 loop, was generated by the following procedure. The sequence encoding part of the ELDKWA epitopes and V3 loop was cloned into pBSK+. This was accomplished by cloning a 225 bp EcoRI-SacI-digested PCR fragment, containing part of the ELDKWA-V3 loop sequence, into the 2,900 bp EcoRI-SacI fragment of pBSK+. (This PCR fragment was generated from the plasmid, pBSHIVMN120T, with the primers, HIVP72 (SEQ ID NO: 121; 5'-TTATTACCATTCCAAGTACTATT-3') and HIVP74 (SEQ ID NO: 122; 5'-TCTGTACAAATTAATT GTACAAGACCCAACTACGAGCTCGACAAATGGG CCCATATAGGACCAGGGAGAGAATTGGATAAGTGG GCGAATATAATAGGAACTATAAGAC-3').) The plasmid generated by this manipulation is called pHIV55.

[pBSHIVMN120T, a plasmid containing the H6-promoted HIV1 gp120+TM gene, was generated by the following procedure. A plasmid, pMN1.8-9, containing a cDNA copy of the HIV1 (MN) env gene, was obtained from Marvin Reitz (NCI, NIH). An early transcription termination signal sequence, $T_5NT$, in the env gene was modified. This was accomplished by cloning a 1,100 bp KpnI-EcoRI-digested PCR fragment, containing the $T_5NT$-modified 5'-end of the env gene, into the 2,900 bp KpnI-EcoRI fragment of pBSK+. (This PCR fragment was generated from the plasmid, pMN1.8-9, with the oligonucleotides, HIVMN6 (SEQ ID NO: 123; 5'-GGGTTATTAATGATCTGTAG-3') and HIV3B2 (SEQ ID NO: 124; 5'-GAATTACAGTAGAAGAATTCCCCTCC ACAATTAAAAC-3').) The plasmid generated by this manipulation is called PBSMIDMN.

The $T_5NT$-modified 5'-end of the env gene was then cloned upstream to the rest of the env gene. This was accomplished by cloning the 1,025 bp KpnI-EcoRI fragment of pBSMIDMN, containing the $T_5NT$-modified 5'-end of the env gene, into the 4,300 bp KpnI-EcoRI fragmnent of pBS3MN. (pBS3MN was generated by cloning a 430 bp EcoRI-SacI-digested PCR fragment, containing a central portion of the env gene, and a 1,050 bp SacI-XbaI-digested PCR fragment, containing the 3'-end of the env gene, into the 2,900 bp EcoRI-XbaI fragment of pBSK+. The 430 bp PCR fragment was generated from the plasmid, pMN1.8-9, with the oligonucleotides, HIV3B1 (SEQ ID NO: 125; 5'-GTTTTAATTGTGGAGGGGAATTCTTCTACTGTA ATTC-3') and HIVMN4 (SEQ ID NO: 126; 5'-ATCATCGAGCTCCTATCGCTGCTC-3'). The 1,050 bp PCR fragment was generated from the plasmid, pMN1.8-9, with the oligonucleotides, HIVMNS (SEQ ID NO: 127; 5'-ATCATCGAGCTCTGTTCCTTGGGTTCTTAG-3') and HIVMN3P (SEQ ID NO: 128; 5'-ATCATCTCTAGAATAAAAATTATAGCAAAGCCCT TTCCAAGCC-3').) The plasmid generated by this manipulation is called pBSMID3MN.

The H6 promoter was then cloned upstream to the env gene. This was accomplished by cloning the 320 bp KpnI fragment of pH6IIIBE, containing the H6 promoter linked to the 5'-end of the HIV1 (IIIB) env gene, and the 2,450 bp KpnI-XbaI fragment of pBSMID3MN, containing the bulk of the HIV1 (MN) env gene, into the 2,900 bp KpnI-XbaI fragment of pBSK+. The plasmid generated by this manipulation is called pH6HMNE.

The sequence encoding gp41 was then replaced with the sequence encoding the HIV1 env transmembrane (TM) region. This was accomplished by cloning a 480 bp EcoRI-XbaI-digested PCR fragment, containing the 3'-end of the gp120 gene and the HIV1 env transmembrane region, into the 4,200 bp EcoRI-XbaI fragment of pH6HMNE. (This PCR fragment was generated from the PCR fragment, PCR-MN11, and oligonucleotides, HIVTM1 (SEQ ID NO: 129; 5'-TTATTCATAATGATAGTAGGAGGCTTGGTAGGT TTAAGAATAGTTTTTGCTGTACTCTCTGTAGTGAAT AGAGTTAGGCAGGGATAA-3') and HIVTM2 (SEQ ID NO: 130; 5'-TTATCCCTGCCTAACTCTATTCACTAC AGAGAGTACAGCAAAAACTATTCTTAAACCTAC- CAAGCCTCCTACTATCATTATGAATAA-3'), with the oligonucleotides, HIV3B1 (SEQ ID NO: 125) and HIVTM3 (SEQ ID NO: 131; 5'-TCATCTCTAGAATAAAAATTAT CCCTGCCTAACTCTATTCAC-3'). PCR-MN11 was enerated from the plasmid, pH6HMNE, with the oligonucleotides, HIV3B1 (SEQ ID NO: 125) and HIVMN18 (SEQ ID NO: 132; 5'-GCCT CCTACTATCATTATGAATAATCTTTTTTCTCTCTG-3').) The plasmid generated by this manipulation is called pBSHIVMN120T.]

Another part of the sequence encoding the ELDKWA epitopes and V3 loop was then cloned into pBSK+. This was accomplished by cloning a 300 bp HindIII-SacI-digested PCR fragment, containing part of the ELDKWA-V3 loop sequence, into the 2,900 bp HindIII-SacI fragment of pBSK+. (This PCR fragment was generated from the plasmid, pBSHIVMN120T, with the primers, HIVP69 (SEQ ID NO: 133; 5'-TGATAGTACCAGCTATAGGTTGAT-3') and HIVP75 (SEQ ID NO: 134; 5'-TTTGTCGAGCTCGTAGTTGGGTCTTGTACAA TT-3').) The plasmid generated by this manipulation is called pHIV56.

The ELDKWA-V3 loop sequences from pHIV55 and pHIV56 were then cloned into the H6-promoted gp120+TM gene. This was accomplished by cloning the 225 bp EcoRI-SacI fragment of pHIV55 and the 300 bp HindIII-SacI fragment of pHIV56, containing the ELDKWA-V3 loop sequences, into the 4,300 bp EcoRI-HindIII fragment of pBSHIVMN120T. The plasmid generated by this manipulation is called pHIV57.

The H6-promoted gp120+TM construct containing the ELDKWA epitopes was then cloned between C5 flanking arms. This was accomplished by cloning the 1,700 bp NruI-XbaI fragment of pHIV57, containing the H6-promoted gp120+TM (with ELDKWA epitopes) gene, into the 4,700 bp NruI-XbaI fragment of pSIVGC15. (pSIVGC15 contains the H6-promoted SIV env gene cloned between C5 flanking arms.) The plasmid generated by this manipulation is called pHIV59.

The H6-promoted gp120+TM (with ELDKWA epitopes) gene was then cloned between COPAK flanking arms. This was accomplished by cloning the 1,850 bp BamHI-SmaI fragment of pHIV59, containing the H6-promoted gp120+TM (with ELDKWA epitopes) gene, into the 4,600 bp BamHI-SmaI fragment of pSD553VC. The plasmid generated by this manipulation is called pHIV61. The DNA sequence of the H6-promoted gp120+TM (with ELDKWA epitopes) gene in pHIV61 is shown in FIG. 30.

pHIV61 was used in in vitro recombination experiments with COPAK as the rescuing virus to yield vP1319.

Figure 31A:
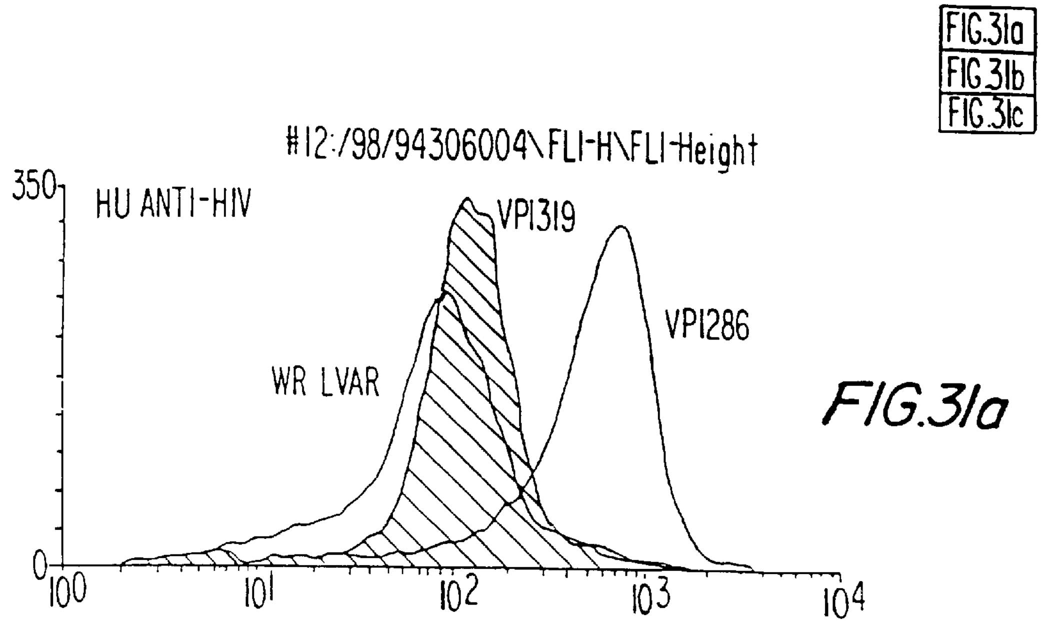
FIG. 31 shows the FACS analysis of vP1319-infected cells (FACS analysis was performed on HeLa cells infected with WR, vP1286 or vP1319 with sera from HIV1-seropositve humans (upper panel), a human monoclonal antibody specific for the ELDKWA epitope, IAM41-2F5 (middle panel) or a mouse monoclonal antibody specific for the V3 loop, 50.1 (lower panel))
Figure 31B:
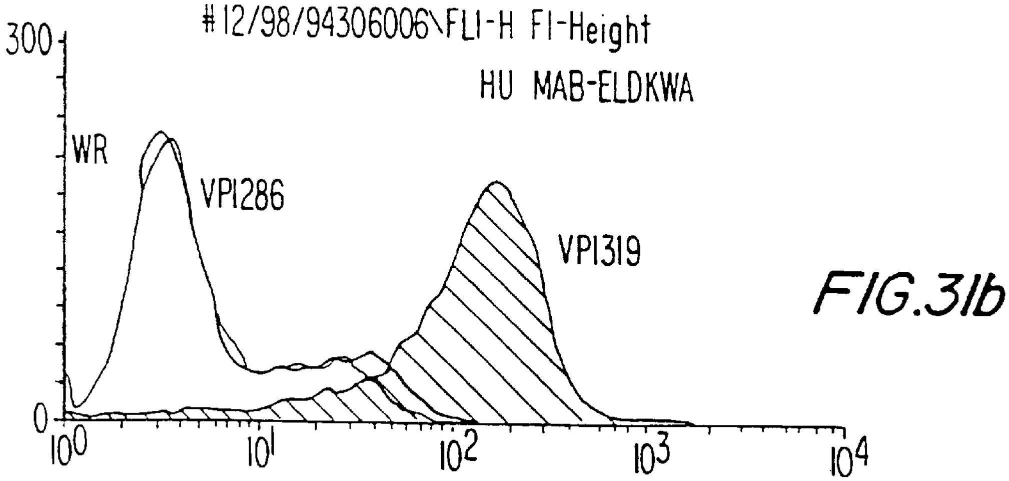
Figure 31C:
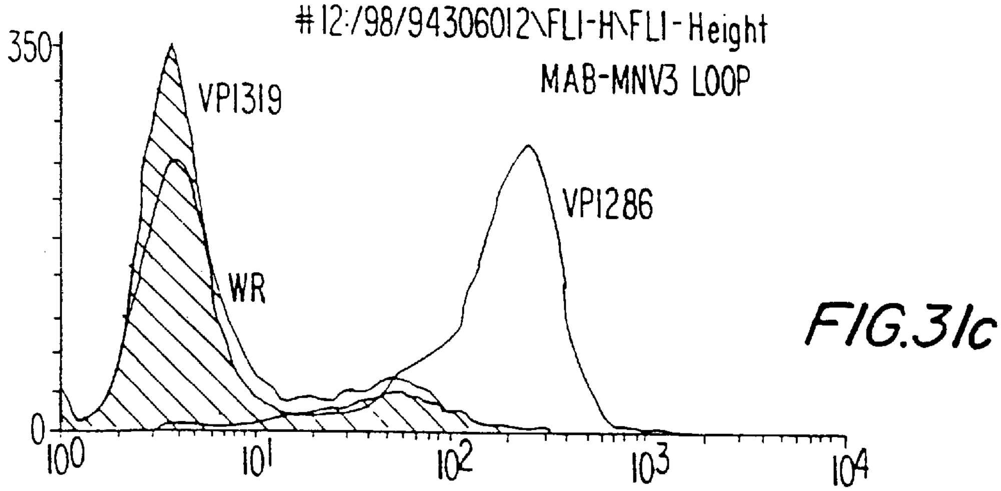

FACS analysis was performed to determine whether HIV1 gp120+TM (with ELDKWA epitopes) was expressed on the surface of vP1319-infected cells. $5\times10^6$ HeLa-S3 cells in S-MEM (Sigma M-8028 Joklik suspension media) were infected at an m.o.i. of 5 pfu/cell with WR, vP1286 (a WR recombiant expressing HIV1 gp120+TM) or vP1319. Following a 60 minute adsorption period at 37° C., the cells were washed with 10 mls of S-MEM and centrifuged at 1,000 RPM for 5 minutes. The samples were then resuspended in 1 ml of S-MEM, transferred to 5 ml Sarstadt tubes and placed on a rotator at 37° C. After 18 hours, 200 ul aliquots ($1\times10^6$ cells) were placed in polypropylene tubes and washed with 3 mls of PBS-CMF (with 0.2% $NaN_3$+ 0.2% BSA). The supernatant was then decanted and the pellet was resuspended in 100 ul of a 1:100 dilution of sera from HIV1-seropositive humans (obtained from the New York State Dept. of Health), a 1:500 dilution of a mouse monoclonal antibody specific for the HIV1 (MN) V3 loop, 50.1 (obtained from M. Robert-Guroff, NCI, NIH.) or a 1:100 dilution of a human monoclonal antibody specific for the ELDKWA epitope, IAM41–2F5 (obtained from Viral Testing Systems Corp., Houston, Tex.). The samples were incubated at 4° C. for 60 minutes, washed two times with PBS-CMF (with 0.2% $NaN_3$+0.2% BSA) and centrifuged at 1,000 RPM for 5 minutes. The supernatant was decanted and the pellet was resuspended in a 1:100 dilution of goat anti-human FITC or goat anti-mouse FITC (obtained from Boehringer Mannheim). The samples were incubated at 4° C. for 30 minutes, washed twice with PBS-CMF (with 0.2% $NaN_3$+0.2% BSA) and analyzed on a Facscan flow cytometer. A gene product containing the ELDKWA epitope was expressed on the surface of vP1319-infected cells, but was not expressed on the surface of WR-infected cells or vP1286-infected cells (FIG. 31, middle panel). A gene product containing the V3 loop was expressed on the surface of vP1286-infected cells, but was not expressed on the surface of WR-infected cells or vP13l9-infected cells (FIG. 31, lower panel). A gene product reactive with the HIV1-seropositive sera was expressed on the surface of vP1286-infected cells and vP1319-infected cells, but was not expressed on the surface of WR-infected cells (FIG. 31, upper panel). This analysis indicated that 1) the ELDKWA epitope of the HIV1 gp120+TM (with ELDKWA epitopes) gene product is expressed on the surface of vP1319-infected cells and 2) the gene product expressed on the surface of vP1319-infected cells does not contain a wild-type V3 loop, consistent with the fact that the V3 loop of this gene product has been replaced with ELDKWA epitopes.

Immunoprecipitation analysis was performed to determine whether vP1319 expresses a form of gp120+TM which contains an immunogenic ELDKWA epitope. HeLa cell monolayers were infected at an m.o.i. of 10 pfu/cell with NYVAC (the parental virus), vP1286 (a WR recombinant expressing HIV1 gp120+TM) or vP1319. Following an hour adsorption period, the inoculum was removed and the cells were overlayed with 2 mls of modified Eagle's medium (minus cysteine and methionine) containing 2% dialyzed fetal bovine serum and [$^{35}$S]-TRANS label (30 $\mu$Ci/ml). The lysates were harvested at 18 hrs post-infection by addition of 1 ml 3×buffer A (450 mM NaCl, 3% NP-40, 30 mM Tris (pH=7.4), 3 mM EDTA, 0.03% Na-Azide and 0.6 mg/ml PMSF) and analyzed for expression of 1) the ELDKWA epitope, using a 1:100 dilution of a human monoclonal antibody specific for the ELDKWA epitope, IAM41-2F5 (obtained from Viral Testing Systems Corp., Houston, Tex.) and 2) HIV1 gene products, using a 1:100 dilution of sera from HIV1-seropositive humans (obtained from the New York State Dept. of Health). Lysates, precleared with normal human sera and a protein A-sepharose complex, were incubated overnight at 4° C. with an IAM41-2F5-protein A-sepharose complex or an HIV1-seropositive sera-protein A-sepharose complex. The samples were washed 4× with 1×buffer A and 2× with a $LiCl_2$/urea buffer. Precipitated proteins were dissociated from the immune complexes by the addition of 2×Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1 M Na-salicylate for fluorography. Proteins of the appropriate size were precipitated with the monoclonal antibody to the ELDKWA epitope from vP1319-infected cells, but were not precipitated from NYVAC-infected cells or vP1286-infected cells. Furthermore, proteins of the appropriate size were precipitated with the human HIV1-seropositive sera from vP1286-infected cells and vP1319-infected cells, but were not precipitated from NYVAC-infected cells. These results indicate that vP1319 expresses a form of gp120+TM which contains an immunogenic ELDKWA epitope.

Since vCP1307, vP1313 and vP1319 each express the ELDKWA epitope in an immunogenic configuration, these recombinants have numerous utilities, as do the expression products, antibodies elicited thereby, and DNA from these recombinants, as discussed above.

Example 22

Inocuity and the Immunogenicity of vCP205 in Mcacques Inoculated by Intramuscular Route Experimental Animals:

Species: *Macaca fascicularis* (adult, wild caught)

Number: 8

Sex: Males

Origin: Mauritius Island considered free of Herpes B, Filovirus and Tuberculosis. Previous history: polio experiments.

Diet and drinking water: Commercial diet and fruits; tap water ad libitum.

Four male Cynomolgus macaques were inoculated five times, at one month intervals, with one dose of ALVAC-HIV (vCP205) (containing $10^{5.8}$ $TCID_{50}$/dose) by intramuscular route. The injections caused neither symptoms nor lesions. Body weight of monkeys was not altered by the injections. Four control animals were injected with placebo. (Mixture of DMEM-F12 medium (25%), Lactoglutamate (25%) and freeze-drying substrate (50%)). General condition was monitored daily and injection sites were observed on days 1, 2, 3, 4 and 7 after each inoculation. Body weights were recorded once a week.

Blood samples were collected in EDTA blood collection Vacutainer® tubes (Becton-Dickinson, Meyland, France) for hematological analyses, in lithium-heparin microvette CB 100 tubes (Sarstedt, Nümbrecht, Germany) for biochemical analysis and in tubes with serum separator SST Vacutainer® tubes (Becton-Dickinson, Meylan, France) for serological analyses (MON:TSA.034.00). Samplings were done on days 0, 3, 7, 14, 28, 31, 35, 42, 56, 59, 63, 70, 84, 87, 91, 98, 112, 115, 119, 126 and 140. Anesthesia (Ketamine, 20 mg/kg, intramuscular) was used for clinical examinations and blood sampling.

Hematological and biochemical analysis were carried out with the VET TEST 8008 Apparatus. Anti-HIV gp160, p24 proteins and V3 peptide antibodies were titered according to an ELISA technique. Maxisorp F96 NUNC plates wells were coated for 1 hour at 37° C., with one of the following antigens diluted in 0.1 M carbonate buffer, pH 9.6:

130 ng per well of purified gp160 MN/BRU (from recombinant vaccinia containing 30% of cleaved gp160 and no $alpha_2$ macroglobulin), 200 ng of V3MN peptide, 130 ng of purified "p24" HIV (*E. coli*, P25 LAI isolate, batch 672Cl, Transgene).

All incubations were carried out in a final volume of 100 $\mu$l , followed by 3 washings performed with phosphate buffered saline, pH 7.1–0.1% Tween 20. Plates were blocked for 1 hour at 37° C. with 150 $\mu$l of phosphate buffered saline pH 7.1–0.05% Tween 20–5% (W/V) powdered skim milk (Gloria).

Serial threefold dilutions of the sera, ranging from 1/50 to 1/12150, in phosphate buffered saline—0.05% Tween 20–5% (W/V) powdered skim milk, were added to the wells and incubated for 90 min at 37° C.

After washing, anti-monkey IgG peroxidase conjugate (Cappel, goat IgG fraction), diluted 1/3000 in phosphate buffered saline—0.5% Tween 20–5% powdered skim milk, was added and the plates incubated for another 90 min at 37° C. The plates, washed four times, were incubated in the dark for 30 min at room temperature with the substrate O-phenylenediamine dihydrochloride (Sigma tablets). The substrate was used at the concentration of 1.5 mg/ml in 0.05 M phosphate citrate buffer, pH 5.0 containing 0.03 containing 0.03% sodium perborate (Sigma capsules).

The reactions were stopped with 50 $\mu$l of 4N $H_2SO_4$. The optical density was measured at 490–650 nm with an automatic plate reader (Vmax, Molecular Devices). The antibody titers were calculated according to the formula:

$$\text{Titer} = \log\frac{OD_{490\text{-}650} \times 10}{\text{l/dilution}} \left(\text{OD value range: 0.2 to 1}\right)$$

Neutralizing antibody assay determines the dilution of serum that prevents the development of syncytia in 50% of microwells infected with 10 $TCID_{50}$ of HIV MN. The MN strain was obtained from F. Barre-Sinoussi and propagated in CEM clone 166 cells.

Sera were decomplemented and twofold serial dilutions in RPMI beginning 1/10 were prepared. Equal volumes of serum dilution and HIV suspension (500 $\mu$l each) were mixed and incubated for 2 h at 37° C. The HIV suspension had been adjusted to contain $10^2$ to $10^{2.5}$ $TCID_{50}$ per ml.

Prior to use, indicator CEMss cells were plated in microwells coated with poly-L-lysine, and incubated for 1 h at 37° C. Culture medium was removed and replaced with the virus/serum mixtures (100 μl/well, 6 wells per dilution). After 1 h incubation at 37° C. culture medium was added to each well and the plates were incubated at 37° C. All incubations were in a $CO_2$ 5% incubator.

Seven and 14 days later, the cultures were examined under the microscope and wells showing syncytia were recorded. Neutralizing 50% titer was computed according to SPEARMAN and KÄRBER and expressed as the $\log_{10}$ of the end-point. As a confirmation, supernatants of the cultures were collected on day seven, pooled for each dilution and assayed for RT activity. Each assay includes an infectivity titration of the virus suspension, titration of antibody in a reference serum and a set of uninfected microwells as negative controls.

Results:

A majority of the parameters selected to monitor hematological and biochemical status varied within normal limits, including: erythrocyte number, mean corpuscle volume, hematocrite, creatinin and alanine aminotransferase.

Some variations were seen, which cannot be attributed to the repeated immunizations with ALVAC-HIV (vCP205): i) unexplained lymphocytosis on weeks 8 and 9 in both the test and the control groups; ii) a decreased level of hemoglobin in both groups on weeks 17 and 20 and in control groups; ii) a decreased level of hemoglobin in both groups on weeks 17 and 20 and in controls on week 9; iii) erratic high values of the aspartate aminotransferase in two control monkeys and last; iv) irregular trombocytes counts caused by microcoagulation of some specimens.

The anti-HIV immune response induced by vCP205 was assessed by ELISA tests using purified gp160 MN/BRU (from recombinant vaccinia), V3MN synthetic peptide and p24 (from *E. coli*, LAI isolate). All the animals developed antibodies against gp160 and V3, and 2/4 against p24. The positive anti-HIV immune response usually appeared after 2, or maximum, 3 injections. Subsequent vCP205 inoculations mainly maintained (sometimes slightly increased) the antibody levels and improved homogeneity of the response between macaques. Highest antibody titers were usually observed two weeks after each inoculation, followed by a decrease until the next booster. Neutralizing antibodies against HIV/MN were detectable in all immunized monkeys.

Figure 32A:
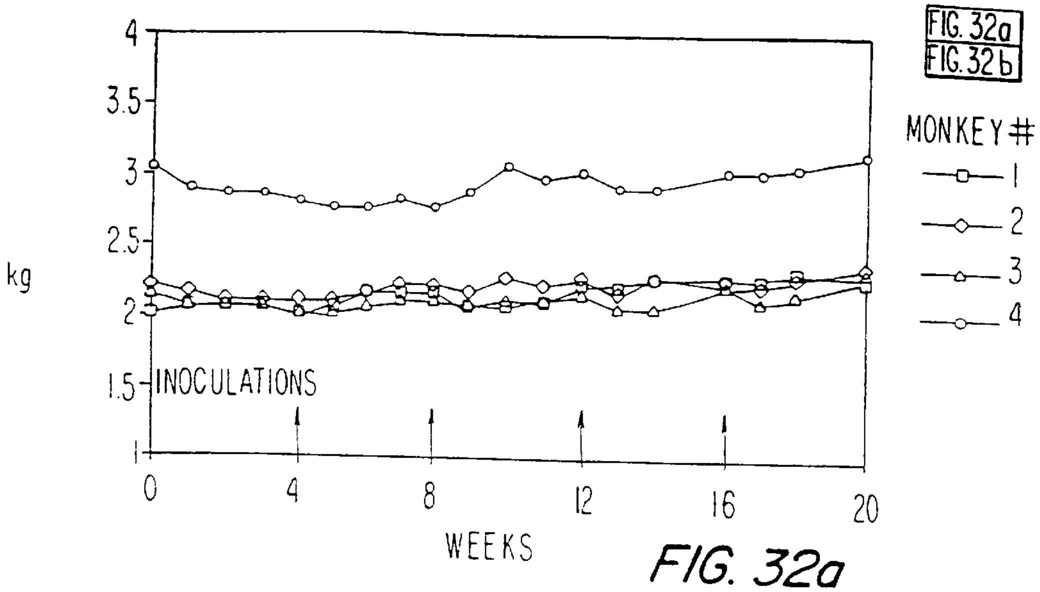
Figure 32B:
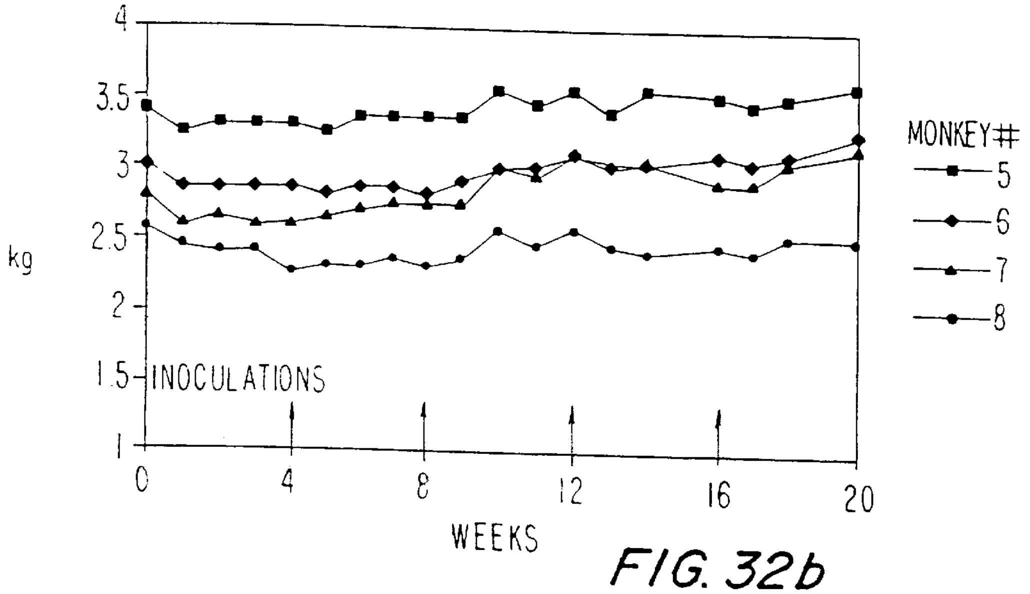

Clinical observation: neither erythema nor edema were reported at the site of inoculation. Body weights were stable in control monkeys and in ALVAC-HIV (vCP205) recipients (FIG. 32).

Figures 1, 2, 3, 4, 33A:
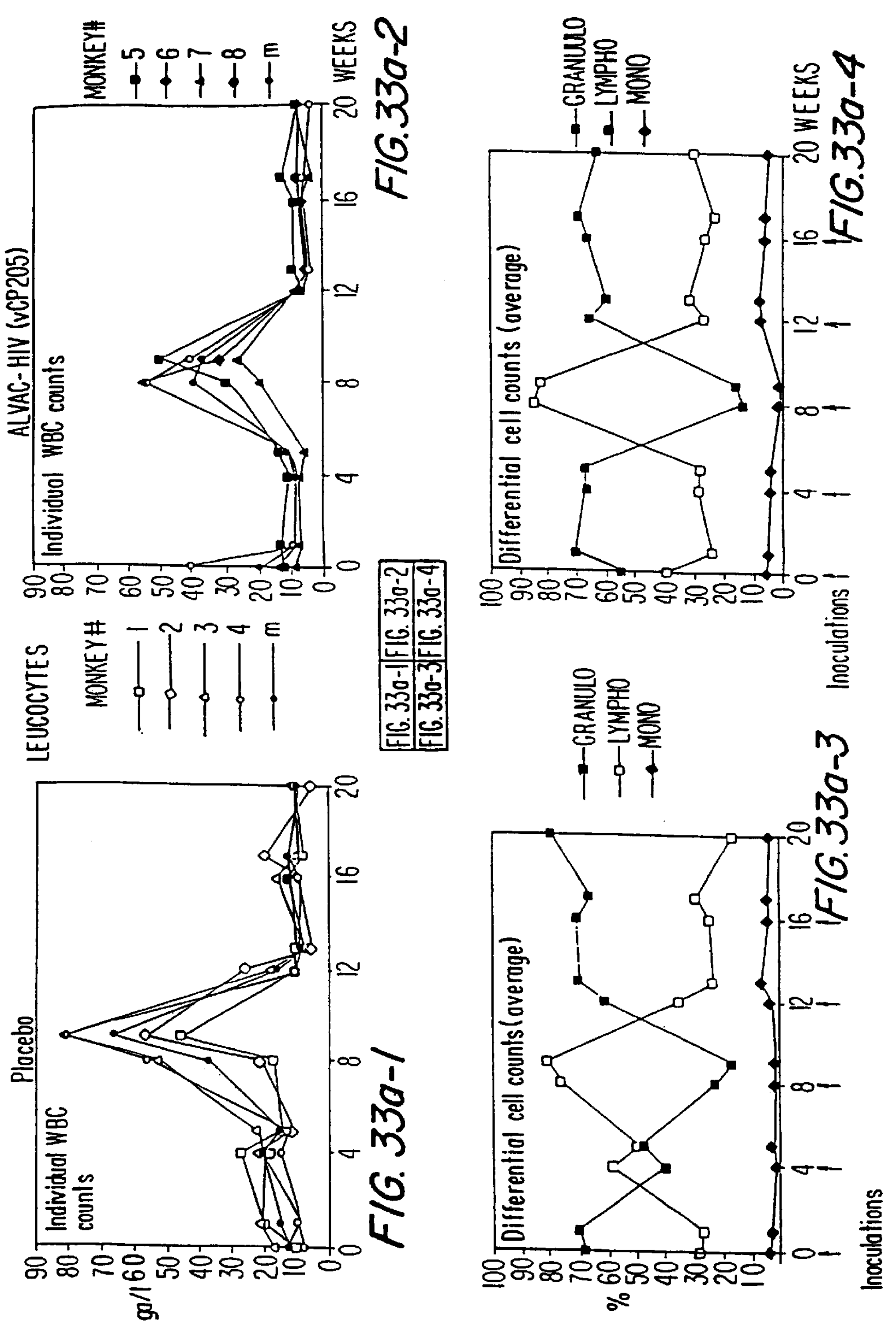

Hematological analyses: Leucocyte counts were greatly modified in both control and tested animals on weeks 8 and 9 with formula inversion (FIG. 33*a*). This fact, noted in both groups, is without correlation with the viral injections.

Figures 1, 2, 3, 4, 33B:
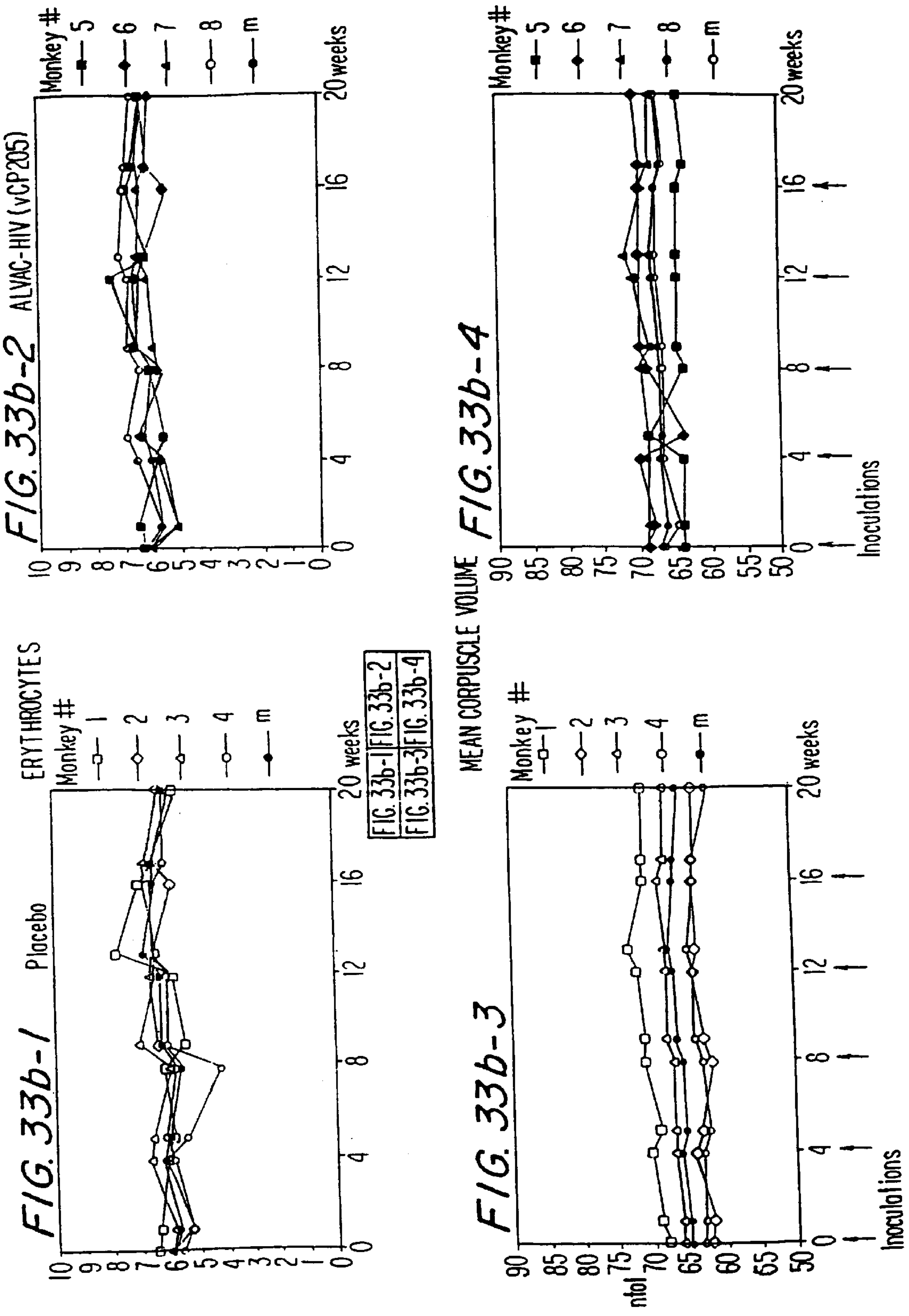
Figures 1, 2, 3, 4, 33C:
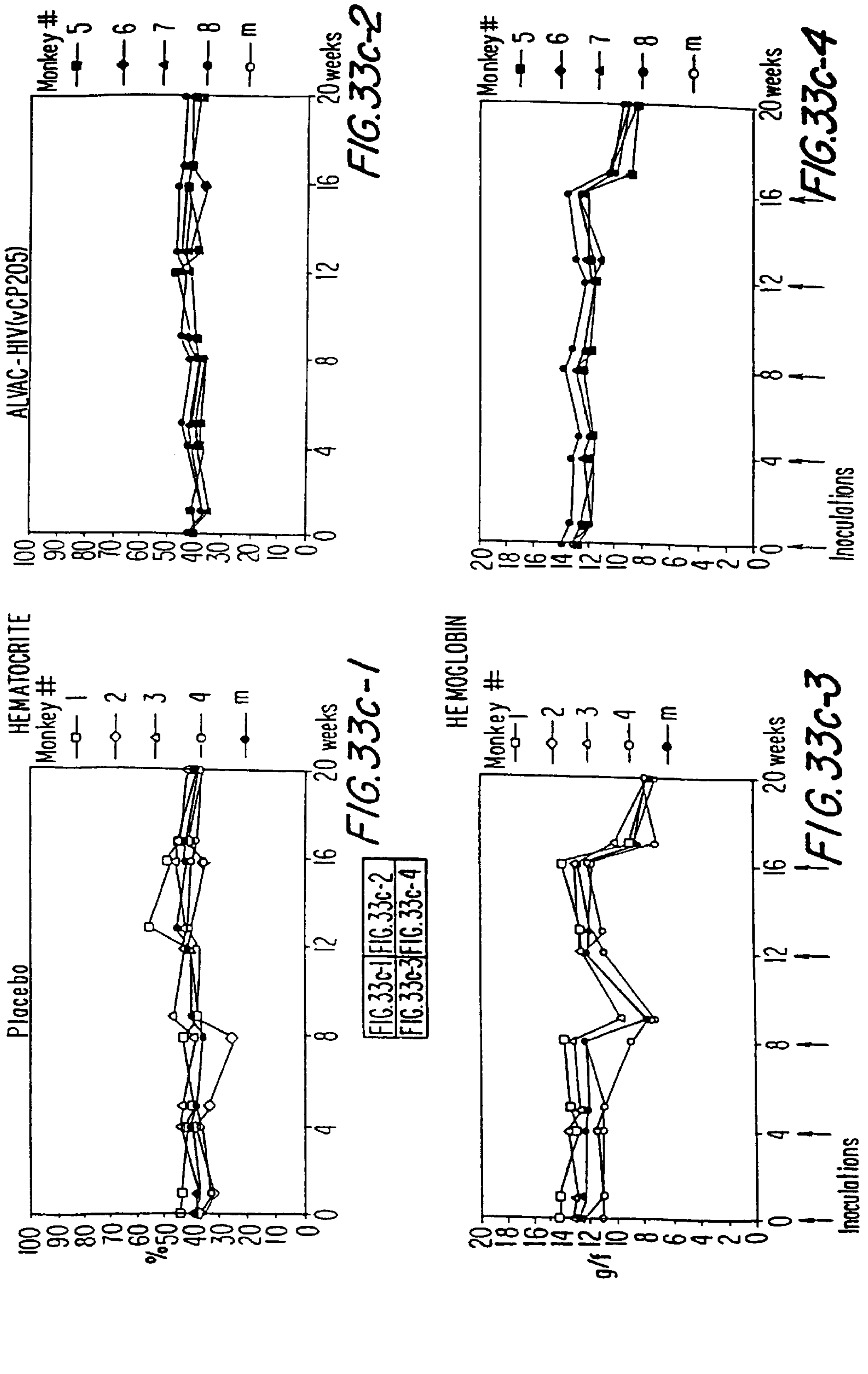

Erythrocyte number, corpuscle mean volume and hematocrite varied within normal limits but hemoglobin showed some discrepancy on weeks 9, 17 and 20 in controls and on weeks 17 and 20 in animals inoculated with ALVAC-HIV (vCP205) (FIGS. 33*b* and *c*). Thrombocytes values varied depending on the sampling quality (microcoagulation) (FIG. 33*c*).

Figure 34A:
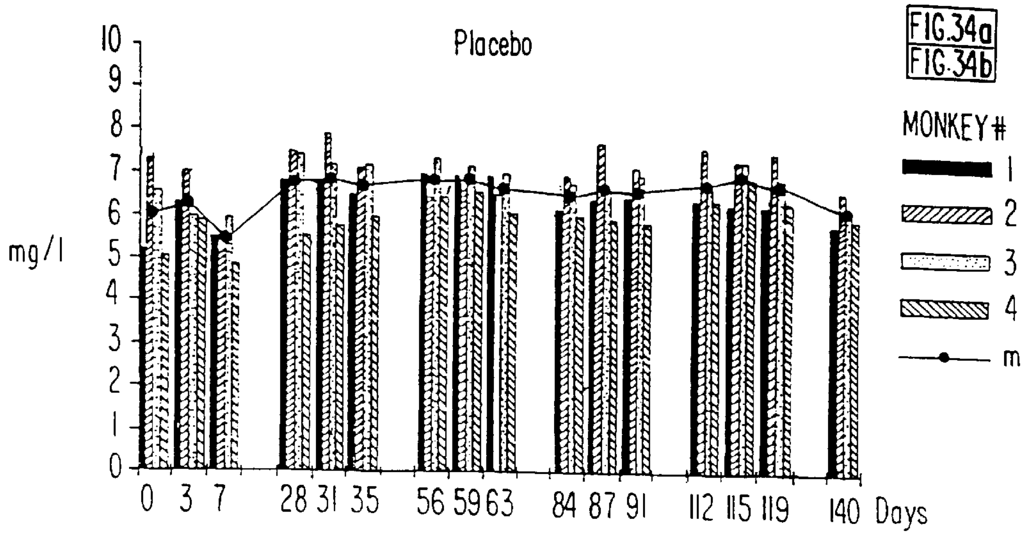
Figure 34B:
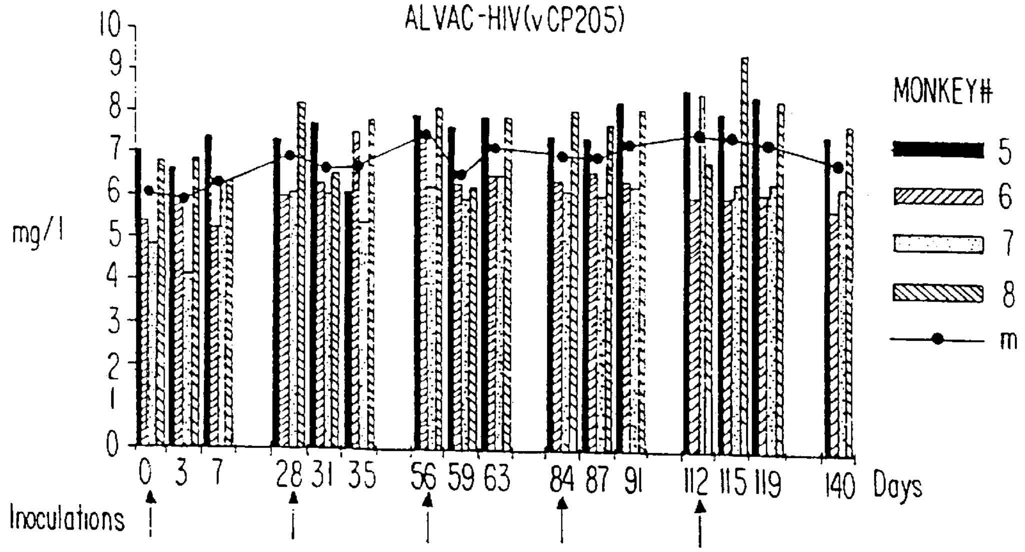
FIG. 34*b*: top=sodium, lower=potassium; keying same as FIG. 43*a*.

Biochemical analyses: Creatinin and ALAT (SGPTransaminase) did not vary significantly after the reiterated inoculations FIGS. 34 and 36). The AST (SGOTransaminase) values presented variations particularly important in control monkeys #3 and 2 respectively on week 5 and 8–9 (FIG. 35).

Serological analyses (considering the ELISA titers of the negative control group of macaques sera, the negative detection threshold of the serological response was considered to be, in log10: 1.56±0.24, 1.92±0.12 and 2.18±0.34, for gp160, V3 and p24 respectively): gp160 and V3 specific response (FIGS. 37*a*–37*b*, 38*a*–38*b*): the kinetics of antibody of gp160 was similar to that to V3. The magnitude of the latter was slightly weaker (mean titer at week 20 of 4.37 versus 8.84).

Figure 37A:
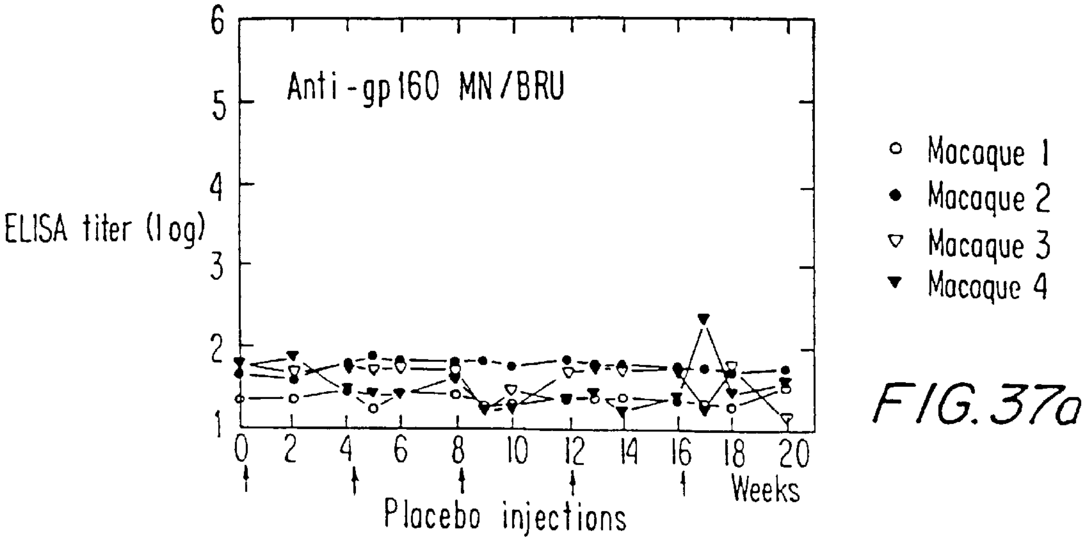
Figure 37B:
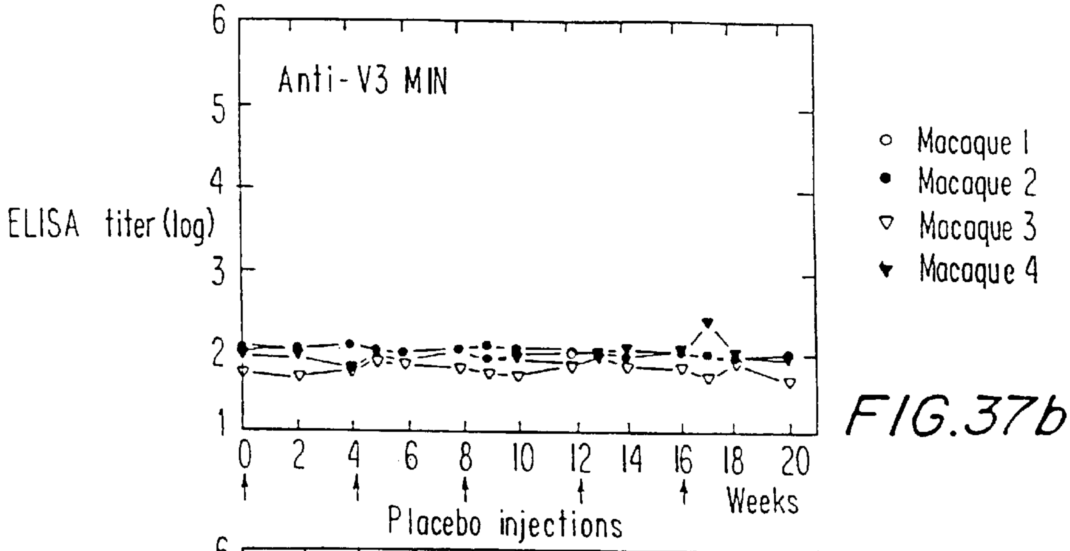
Figure 37C:
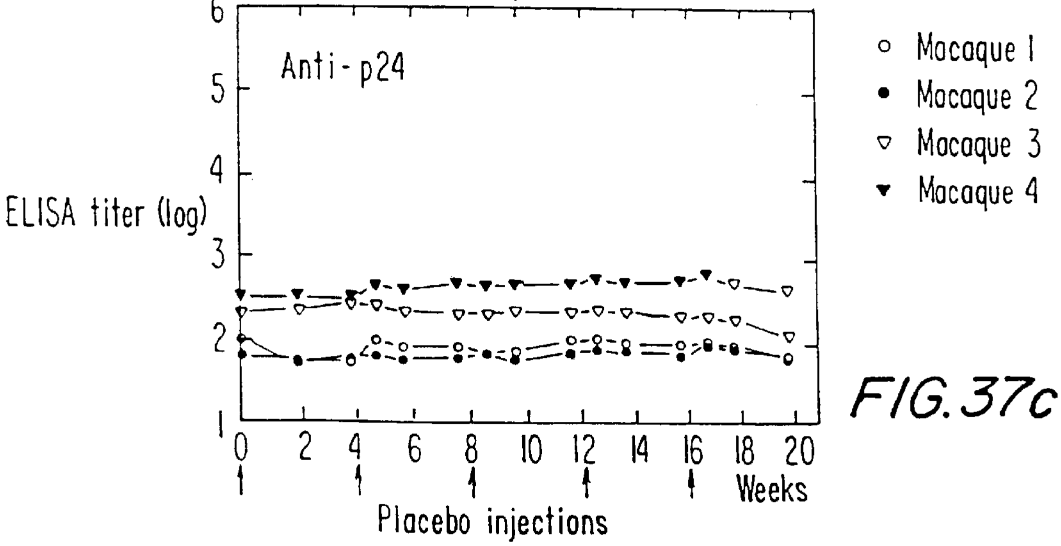
Figure 38A:
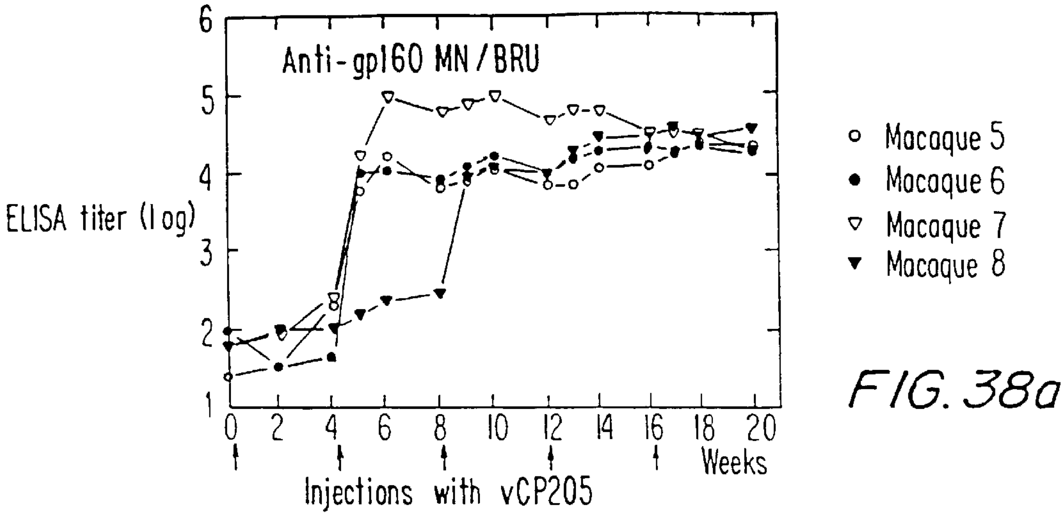
Figure 38B:
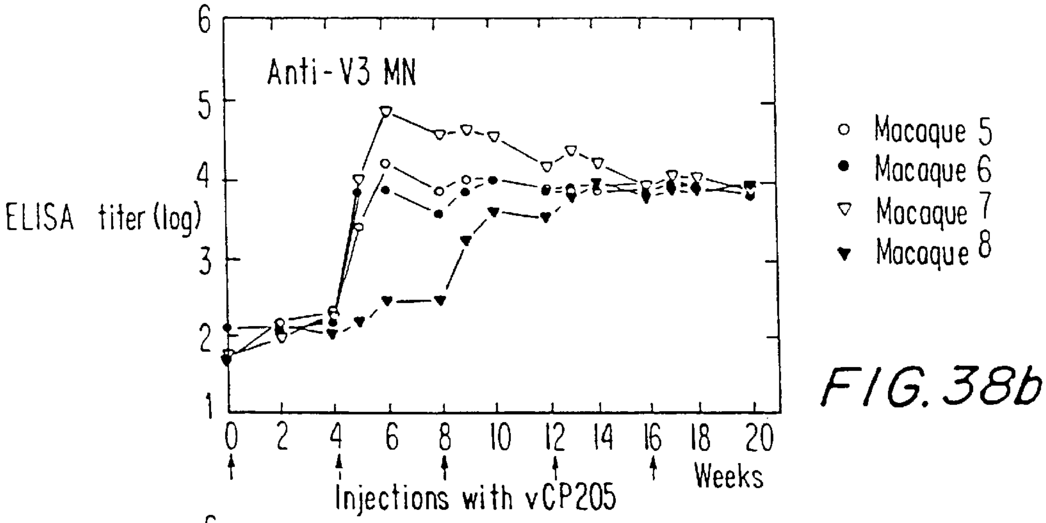
Figure 38C:
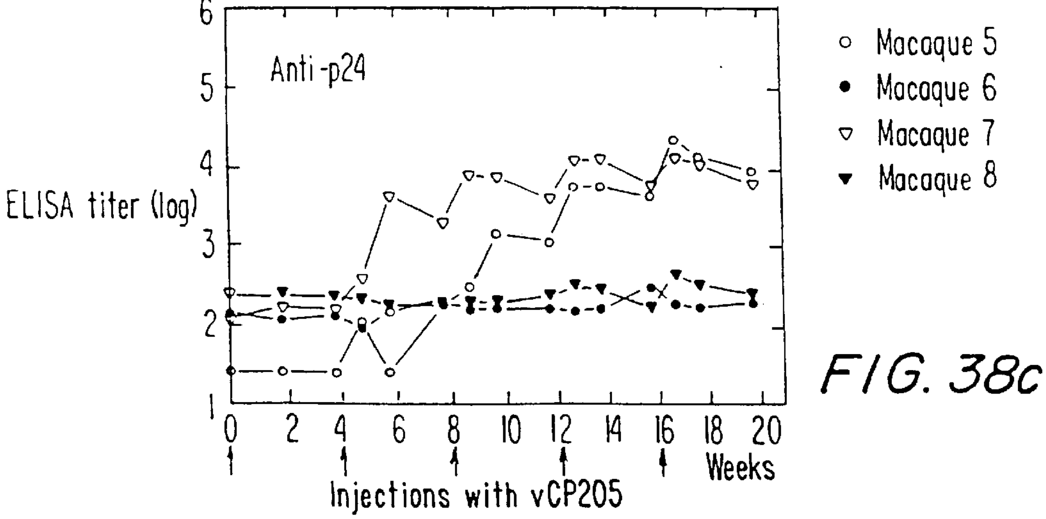

Two injections were necessary to induce a detectable immune response. Three monkeys showed a maximum response after the second injection; the fourth one required three (gp160) or four (V3) injections to do so. During the four week interval between injections, antibody titers consistently increased then faded, to be boosted by the next inoculation. While there were significant individual differences in the responses to the initial injections, the responses leveled out as the experiment progressed.

p24 a specific response (FIGS. 37*c*, 38*c*): a response was observed for 2 macaques (macaques 5 and 7) out of 4 after respectively 2 and 3 injections of vCP205. This is in contrast with a guinea-pig test in which no anti-p24 antibodies were detected in any inoculated animal groups. As with anti-gp160 and anti-V3 antibodies, titers fluctuated up and down between injections and individual differences progressively disappeared. Unlike that of gp160 and V3, the anti-p24 antibody profile did not reach a plateau.

Figure 39:
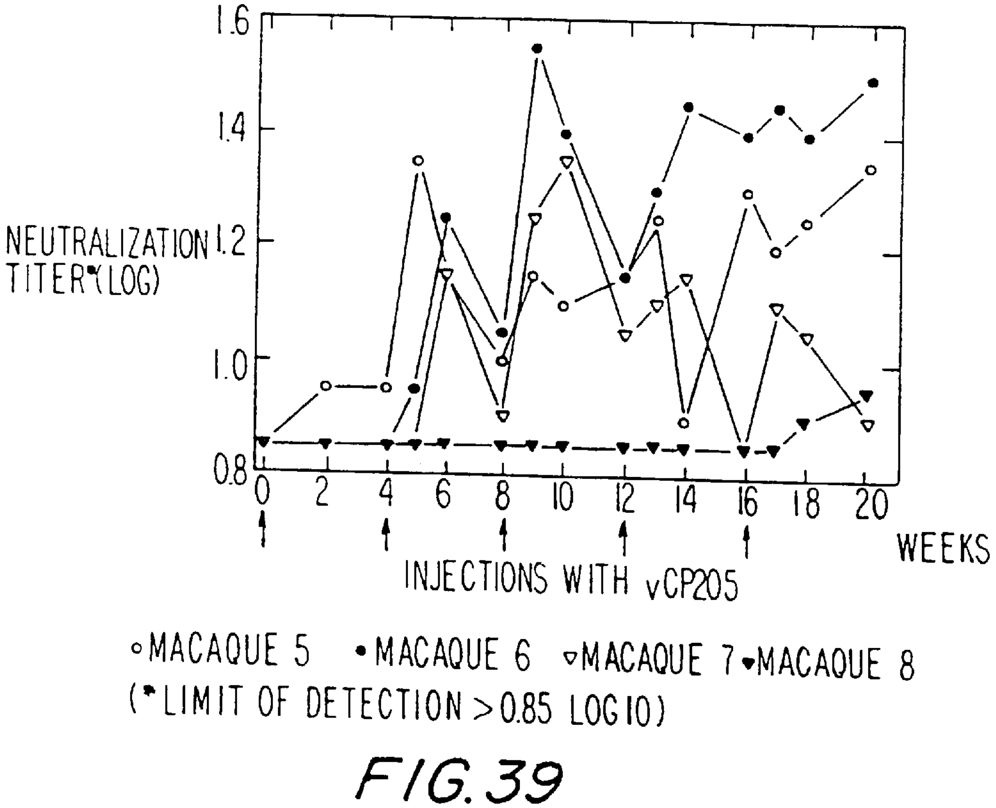
FIG. 39 shows anti-HIV1 (MN) neutralizing antibodies in monkeys inoculated with vCP205 (keying same as FIG. 38*a–c*); and, FIGS. 40, 41*a*, 41*b*, 41*c*, 42, 43*a*, 43*b*, 43*c*, 43*d*, 44*a*, 44*b*, 45*a*, 45*b*, 46*a*, 46*b*, 47*a*, and 47*b* show leucocyte counts (FIG. 40), blood counts (erythrocytes FIG. 41*a*, hematocrite FIG. 41*b*, reticulocytes FIG. 41*c*), prothrombin (FIG. 42), biochemical results (total cholesterol, total proteins, glucose FIG. 43*a*; sodium, potassium FIG. 43*b*; creatinine, bilirubin FIG. 43*c*; SGOTransaminase, SGPTransaminase, alkaline phosphatase FIG. 43*d*), gp160 MN/BRU ELISA (control FIG. 44*a*, test animals FIG. 44*b*), V3 MN ELISA (control FIG. 46*a*, test animals FIG. 46*b*), and nef ELISA (control FIG. 47*a*, test animals FIG. 47*b*) in monkeys inoculated with vCP300 and a placebo (FIG. 40: layout same as FIG. 33*a*; keying same as FIG. 33*a*, except in upper panels, mean is dotted circle (left) and open circle (right) and in lower panels decimal instead of percentage and darkened square=neutro, open diamond=eosino, and darkened triangle=baso.

Neutralizing antibody: as shown in FIG. 39, all four monkeys with vCP205 developed detectable levels of neutralizing antibody against HIV (MN). One of them tested positive after one injection, two after the second injection and the last one required five administrations. It is noteworthy that the latter animal also showed the slowest kinetics of ELISA antibody. The levels of neutralizing activity are relatively modest (1/10 to 1/30 in arithmetical expression) and, likewise ELISA measurements, went up and down in the intervals between injections.

Effect of a late boost with the proteins gp160 and p24: The four monkeys were boosted 7 weeks post the last injection of vCP205 with 200 μg of gp160 and 200 μg of p24 proteins in incomplete Freund's adjuvant (Montanide ISA51) to raise hyperimmune reference sera; this caused a pronounced increase (at least 10-fold) in antibody titers, suggesting that the plateau seen in the ELISA analysis were not the limit of response.

The immunization regimen induced high levels of binding antibody to gp160 MN/BRU and V3 MN peptide, and low but definite neutralizing antibody. Serological results showed higher antibody levels than those observed in macaques inoculated with ALVAC-HIV (vCP125) and one booster (instead of two) was sufficient to obtain a good anamnestic type response. This Example shows that vCP205 and expression products thereof, antibodies therefrom, and DNA from vCP205, can be used as described above.

Example 23

Inocuity and Immunogenicity of vCP300 in Macaques

Experimental Animals:

Species: *Macaca fascicularis*

Number: 8

Sex: Males

Origin: Mauritius Island considered without Herpes B, Filovirus and tuberculosis.

Four male Cynomolgus macaques were immunized five times, at one month intervals, with one dose of ALVAC-HIV (vCP300) (containing $10^{6.16}$ $TCID_{50}$/dose) by intramuscular route. Four control animals were injected with placebo. As a sixth injection, all the animals received ALVAC-HIV (vCP300) by intravenous route. The regimen was as follows:

Group #1

Product: Placebo

Route: Intramuscular alternately in the left or right deltoid muscle

Volume: 1 ml

Number of injections: 5 (on weeks 0, 4, 8, 12 and 16).

Group #2

Product: ALVAC-HIV

Route: Intramuscular alternately in the left or right deltoid muscle.

Volume: 1 ml.

Dose: $10^{6.16}$ $TCID_{50}$.

Number of injections: 5 (on weeks 0, 4, 8, 12 and 16).

Groups #1 and #2

On week 20

Product: ALVAC-HIV (vCP300)

Route: Intravenous

Volume: 1 ml

Dose: $10^{6.16}$ $TCID_{50}$.

Number of injections: 1.

Clinical observations: Injection site was observed on days 1, 2, 3, 4 and 7 following each inoculation. Animals were weighed once a week. Samplings: Blood samples were taken under ketamin anesthesia from the femoral vein. Blood was collected in the following order in Vacutainer tubes (Becton Dickinson, Meylan, France):

1) 1.8 ml in 0.129M buffered sodium citrated tube (prothrombine).
2) 1 ml in 5 mg sodium fluoride and 4 mg potassium oxalate tube (glucose).
3) 2 ml in 0.17M EDTA $K_3$ tube (hematological analyses).
4) 2 to 3 ml in tubes for serum separation with inert barrier material and clot activator (biochemical and serological analyses).

Samplings were done on days 0, 3, 7, 14, 28, 31, 35, 42, 56, 59, 63, 70, 84, 87, 91, 98, 112, 119, 126, 140 and 143.

Dosages:

Hematological analyses included: blood counts and differential leucocyte counts, hemoglobin, thrombocytes, prothrombin, reticulocytes and sedimentation rate.

Biochemical analyses included: sodium, potassium, glucose, alkalin phosphatases, cholesterol, total proteins and electrophoresis, transaminases SGOT and SGPT.

Serological analyses: Anti-HIV gp160 glycoprotein, p24 protein, V3 peptide and nef protein antibodies were titrated according to a modification of the ELISA technique:

Maxisorp F96 NUNC plates wells were coated for 1 hour at 37° C., then overnight at 4° C., with one of the following antigens diluted in 0.1 M carbonate buffer, pH 9.6:

130 ng per well of purified gp160 MN/BRU (from recombinant vaccinia VVTG 5156), 200 ng of V3MN peptide, 130 ng of purified p24 HIV (*E. coli*, p25 LAI isolate, batch 672Cl, Transgene).

All incubations were carried out in a final volume of 100 $\mu$l, followed by 3 washings performed with phosphate buffered saline, pH 7.1–0.1% Tween 20. Plates were blocked for 1 hour at 37° C. with 150 $\mu$l of phosphate buffered saline pH 7.1–0.05% Tween 20–5% (W/V) powdered skim milk (Gloria). Serial threefold dilutions of the sera, ranging from 1/50 to 1/12150 or 1/500 to 1/121500, in phosphate buffered saline—0.05% Tween 20–5% (W/V) powdered skim milk, were added to the wells and incubated for 90 min. at 37° C.

After washing, anti-monkey IgG peroxidase conjugate (Cappel, goat IgG fraction), diluted 1/3000 in phosphate buffered saline—0.05% Tween 20–5% powdered skim milk, was added and the plates incubated for another 90 min. at 37° C. The plates, washed four times, were incubated in the dark for 30 min. at room temperature with the substrate O-phenylenediamine dihydrochloride (Sigma tablets), the substrate was used at the concentration of 1.5 mg/ml in 0.05 M phosphate citrate buffer, pH 5.0 containing 0.03% sodium perborate (Sigma capsules). The reactions were stopped with 50 $\mu$l of 4N $H_2SO_4$.

The optical density was measured at 490–650 nm with an automatic plate reader (Vmax, Molecular Devices). The blanks were substracted and the values of the duplicates averaged. The antibody titers were calculated for the OD value range of 0.2 to 1.2, from the regression curve of a standard anti-gp160 and anti-p24 hyperimmune serum of guinea-pig which was present on each ELISA plate. The titer of the standard serum had been previously determined according to the formula:

$$\text{Titer} = \log\frac{OD_{490\text{–}650} \times 10}{\text{l/dilution}}\left(\text{OD value range: 0.2 to 1.2}\right)$$

Since no standard monkey anti-nef serum was available, the determination of anti-nef antibodies was performed by including in the test a reference monoclonal mouse antibody (anti-nef HIV1 ALI, MATG0020, Transgene) as an internal positive control. Anti-mouse IgG peroxidase conjugate (Amersham) diluted 1/5000, was then used and sera titers were calculated using the formula mentioned above.

Results:

The injections caused neither symptoms nor lesions. Body weight of monkeys was not altered by the injections. Hematological parameters did not vary significantly and biochemical analyses showed no alteration of kidneys and liver functions.

Hematological results: Variations, when present, were similar in pattern and in range in the placebo and in the vaccinee groups.

Figures 40A, 40B, 40C, 40D:
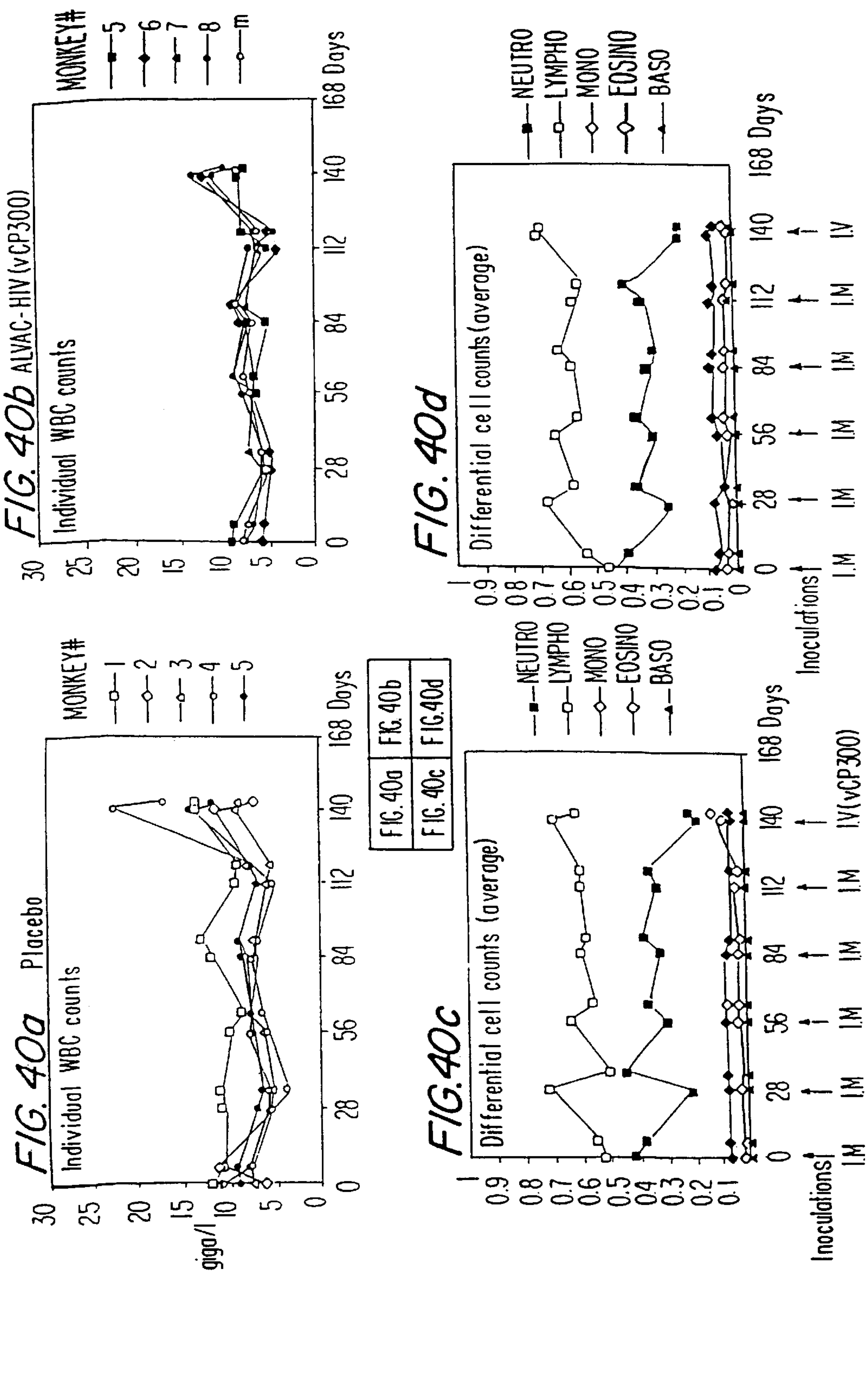
Figures 1, 3, 4, 41A:
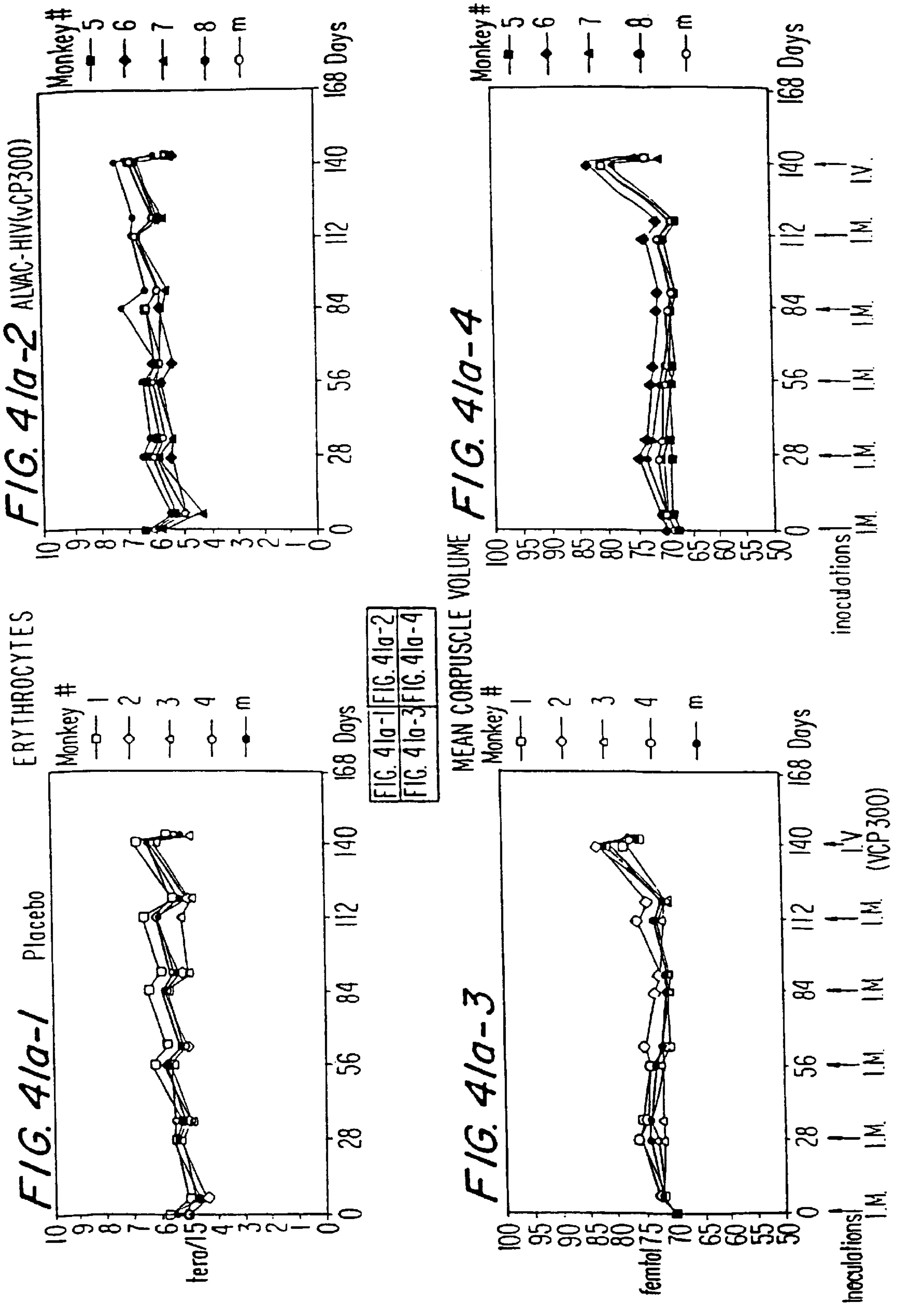
FIG. 41*a*: layout same as FIG. 33*b*, keying same as FIG. 33*a*, except mean is dotted circle (left) and open circle (right).
Figures 3, 4, 41B:
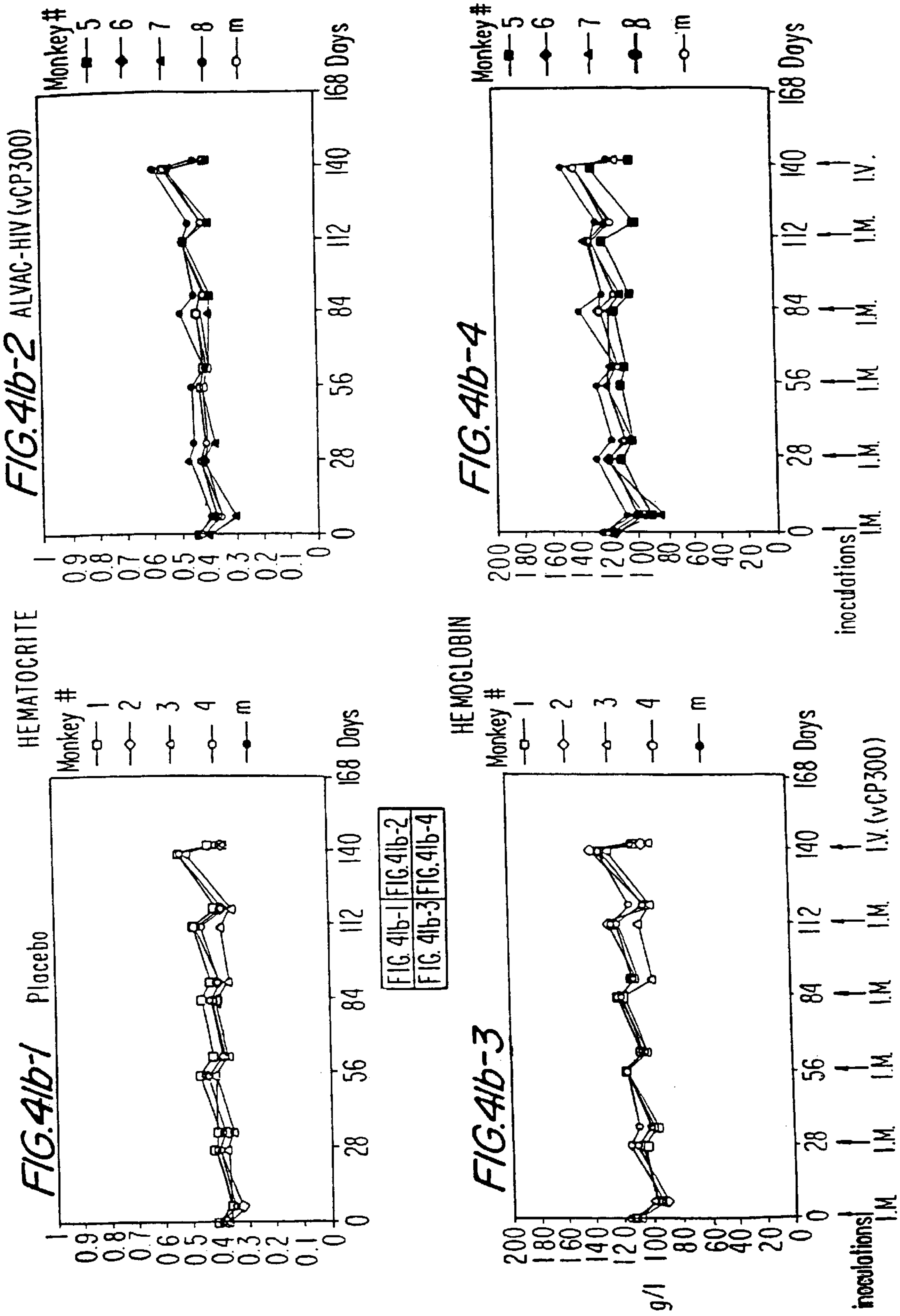
FIG. 41*b*: layout same as FIG. 33*c*, keying same as FIG. 41*a*.
Figure 4I:
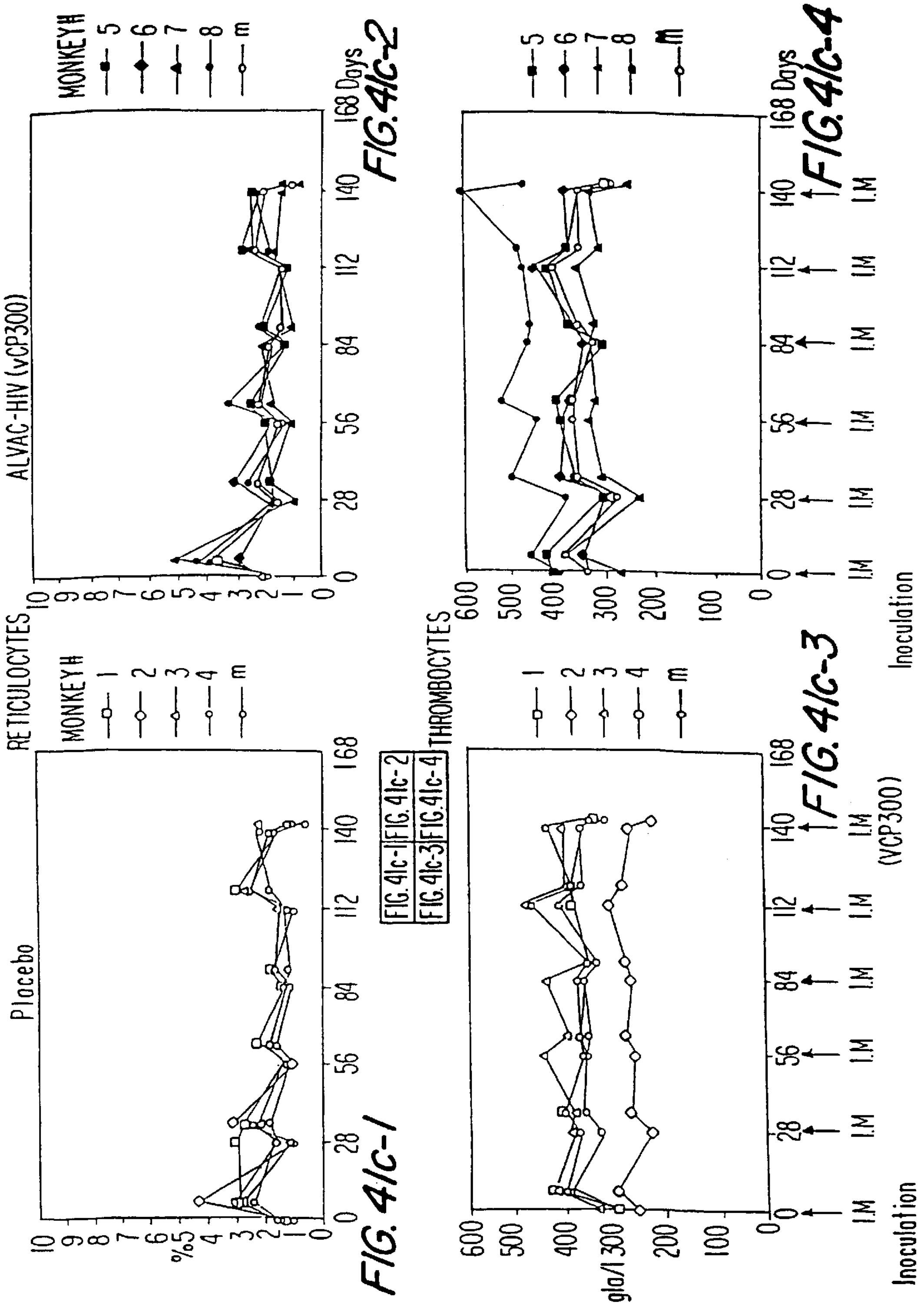
Figure 42A:
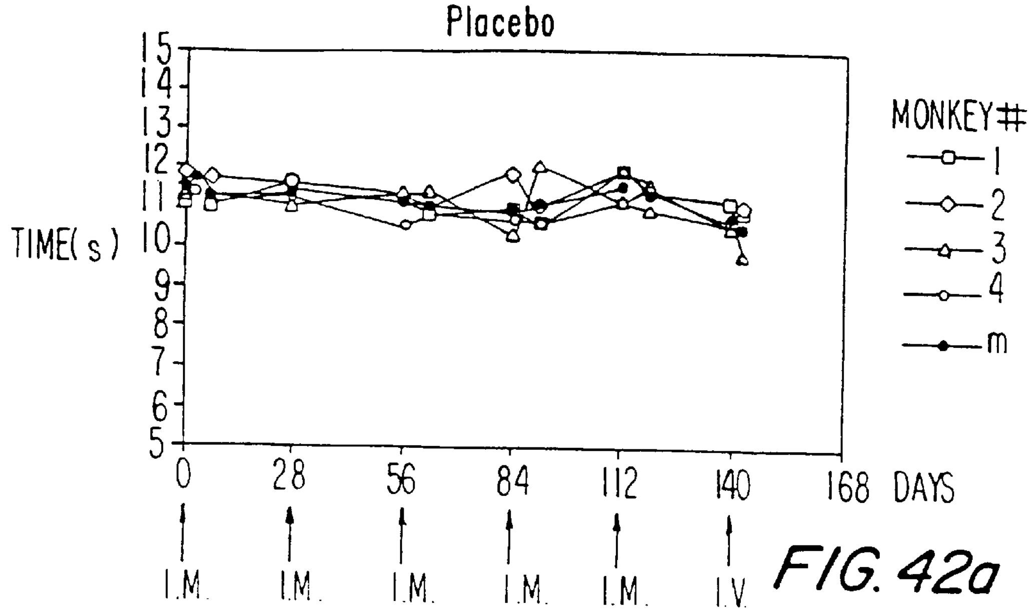
FIG. 42: upper panel=placebo, lower panel=vCP300, keying same as FIG. 41*c*.
Figure 42B:
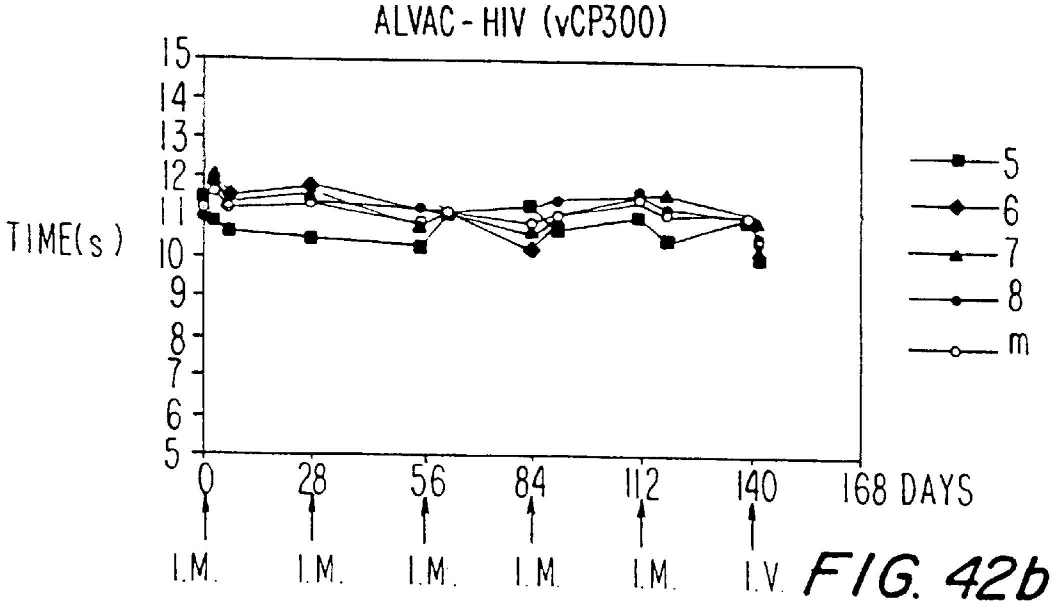

Individual WBC counts varied within normal limits. Differential WBC counts often showed a diminution of lyphocytes 3 days after the blood samplings (FIG. 40). Erythrocyte counts, hematocrite and hemoglobin transiently descreased after each blood sampling contrary to reticulocyte counts which increased regularly after the puncture (FIGS. 41*a*, 41*b*, 41*c*). Mean corpuscle volume was stable in all the animals except an increase on day 140. Thrombocyte counts showed some variations (FIG. 41) but prothrombin level was stable (FIG. 42). There was no sign of anemia in either group. Sedimentation rate was 1 mm after one hour in all the samples.

Biochemical results: For a better interpretation of the variations observed, a standard serum (pool of 18 macaque sera) was analyzed at the beginning (Std a) and at the end (Std p) of each series of samples to be tested.

Figures 1, 43B:
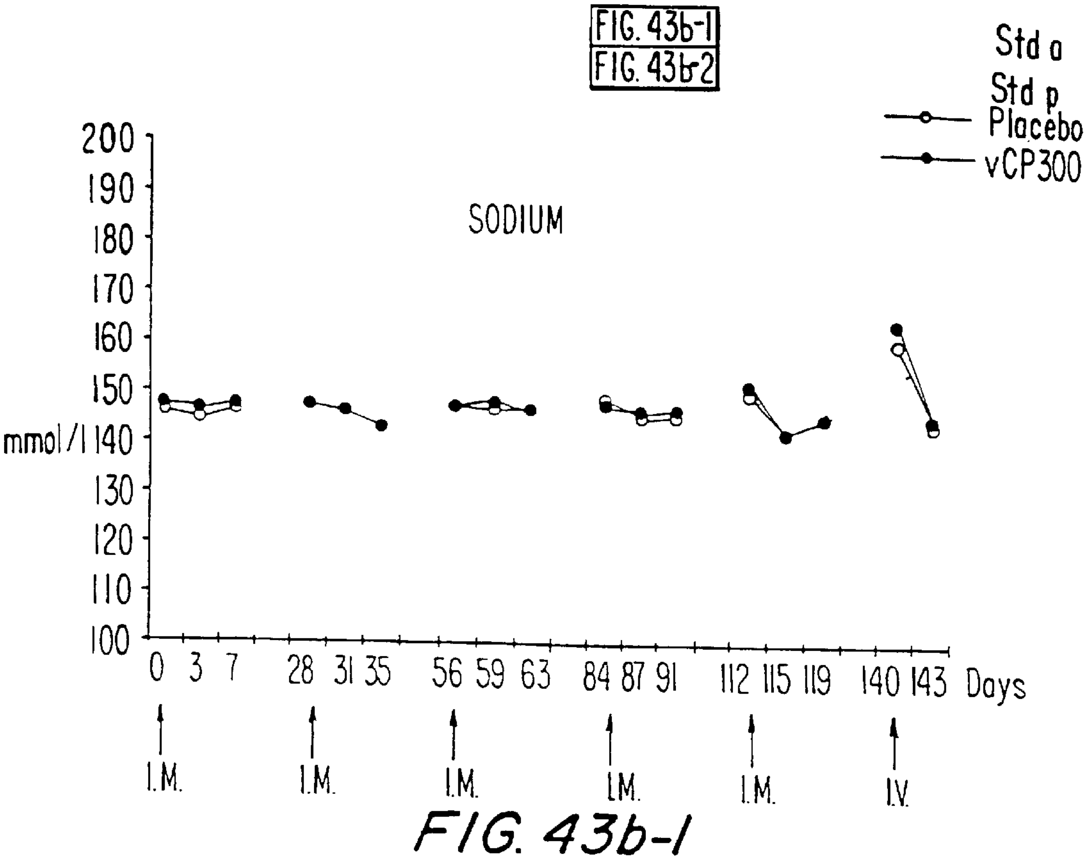
Figures 2, 43B:
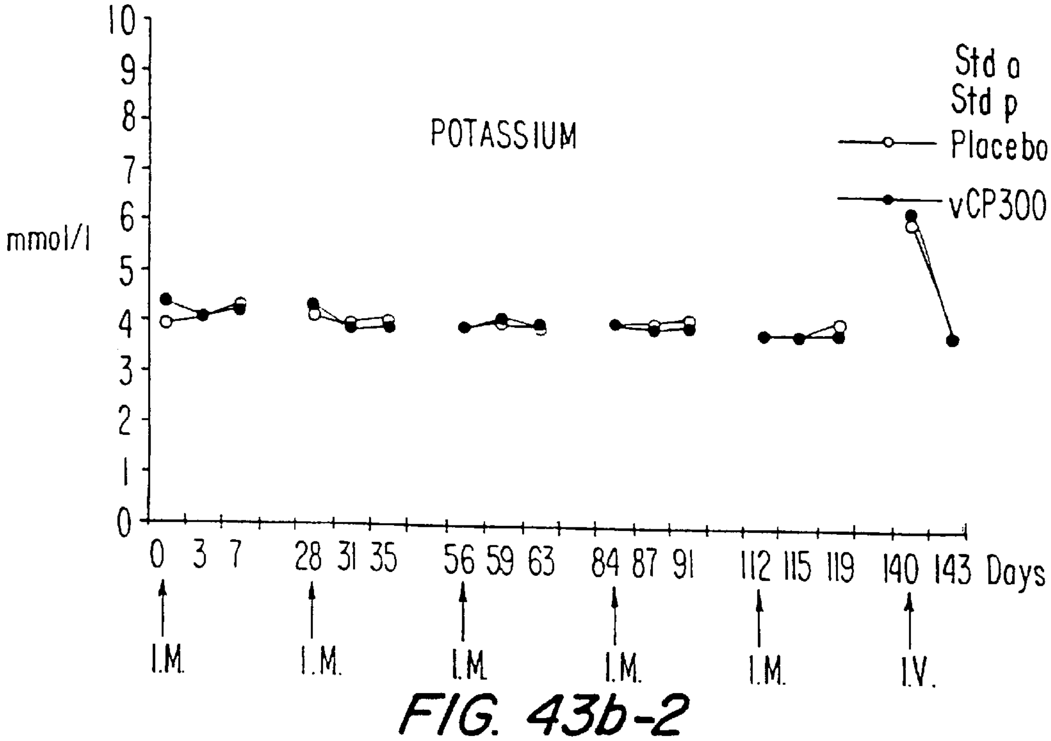
Figure 44A:
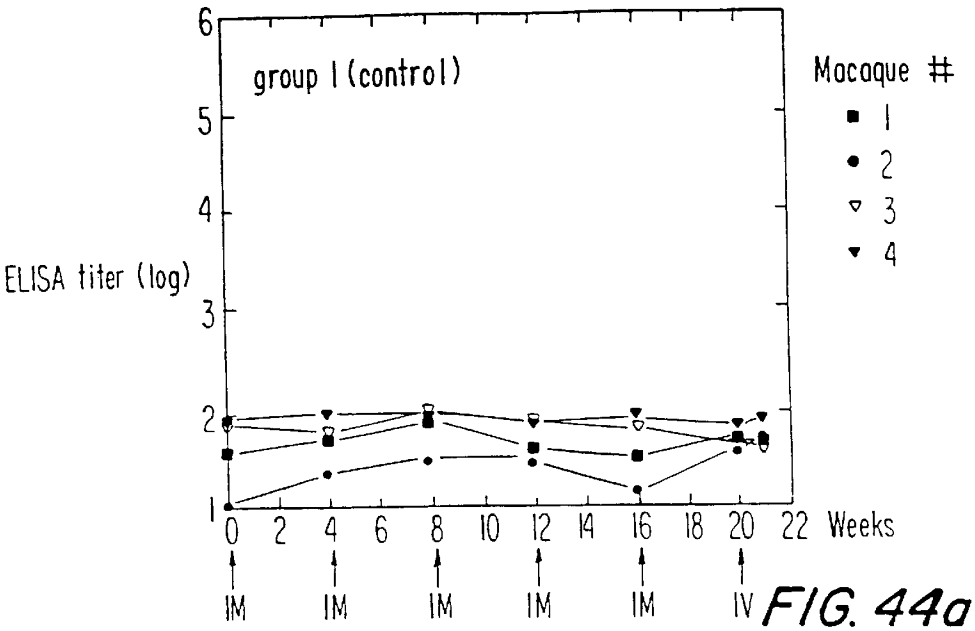
FIGS. 44*a*, 44*b*: gp160 MN/BRU ELISA, control and vCP300, respectively; keying same as FIGS. 37*a* and 38*a*, respectively.
Figure 44B:
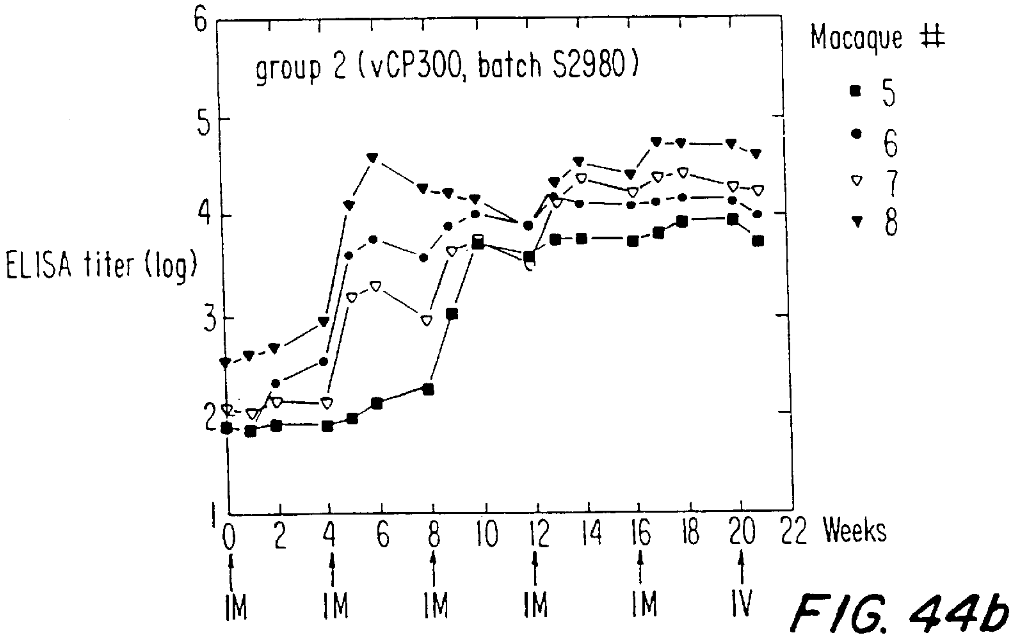
Figure 45A:
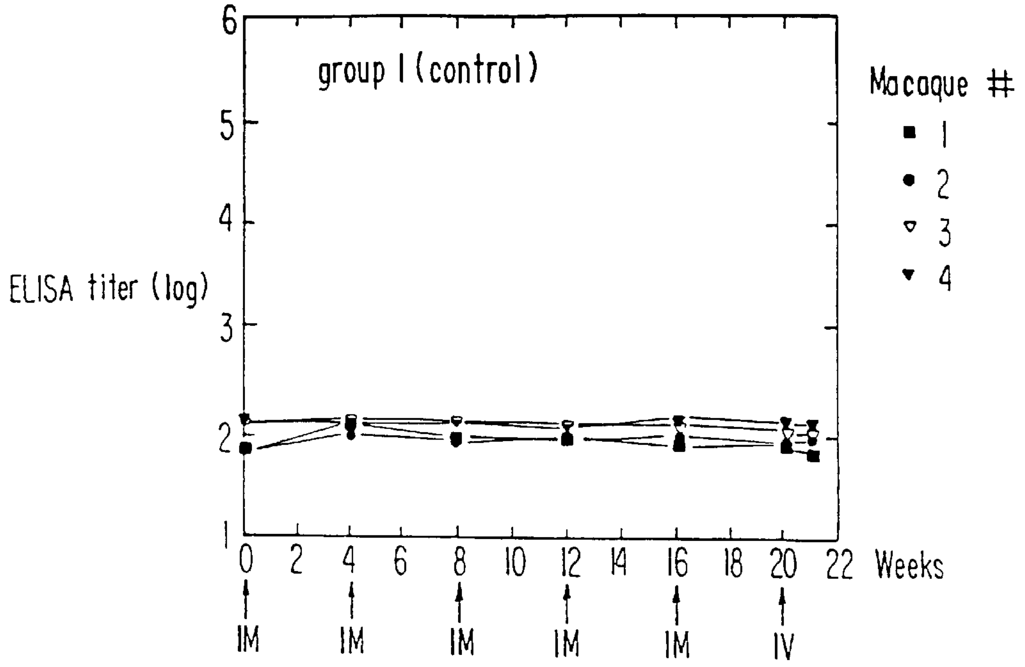
FIGS. 45*a*, 45*b*: V3 MN ELISA, control and vCP300, respectively; keying same as FIGS. 37*b* and 38*b*, respectively.
Figure 45B:
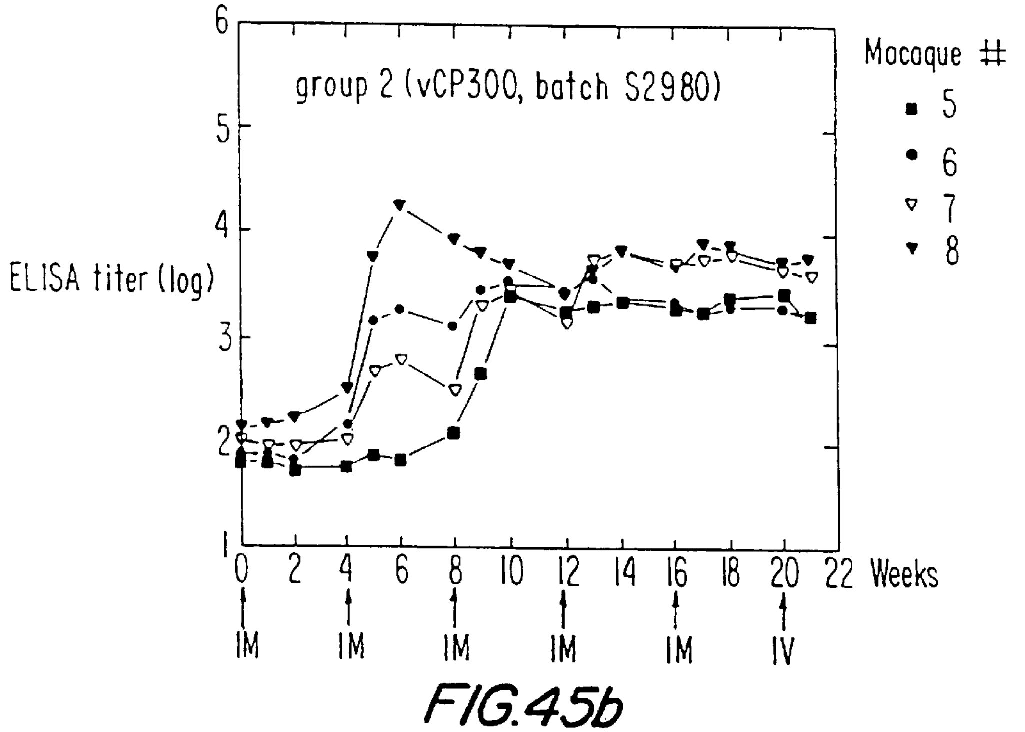

Cholesterol values varied in the same way in controls and in test group (FIGS. 43*a* and 43*b*).

Sodium and potassium were stable after all the injections but, as for total proteins and glucose, there was a great rising on day 140. On that day, blood specimens were drawn prior to the intravenous injection without anesthesia (so that clinical reactions could be monitored without interference); the change observed in several biological parameters was likely due to the stress associated with handling and sampling in the absence of anesthesia (FIGS. 43*a* and 43*b*). Electrophoresis profiles (data not shown) were very similar in all the samples. Creatinine, bilirubin, glutamic oxaloacetic and glutamic pyruvic transaminases and alkalin phosphatases varied within normal limits and always in the same direction in both control and test groups (FIGS. 43*c* and 43*d*). Kidneys and liver functions were therefore not affected by the inoculations of ALVAV-HIV (vCP300).

Figure 46A:
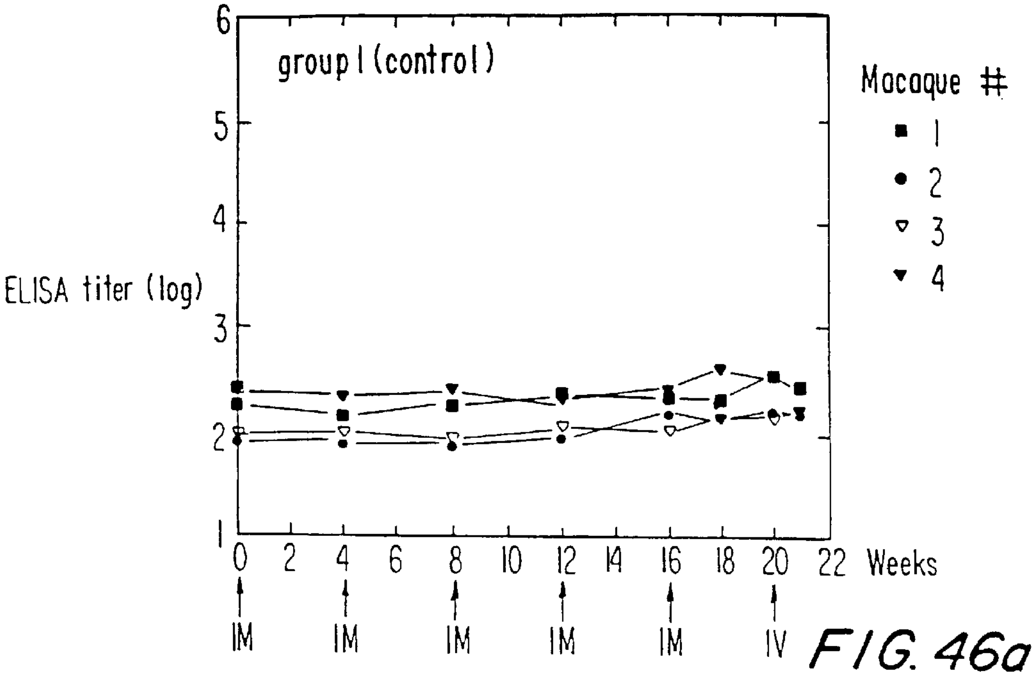
FIGS. 46*a*, 46*b*: p34 ELISA, control and vCP300, respectively; keying same as FIGS. 37*c* and 38*c*, respectively.
Figure 46B:
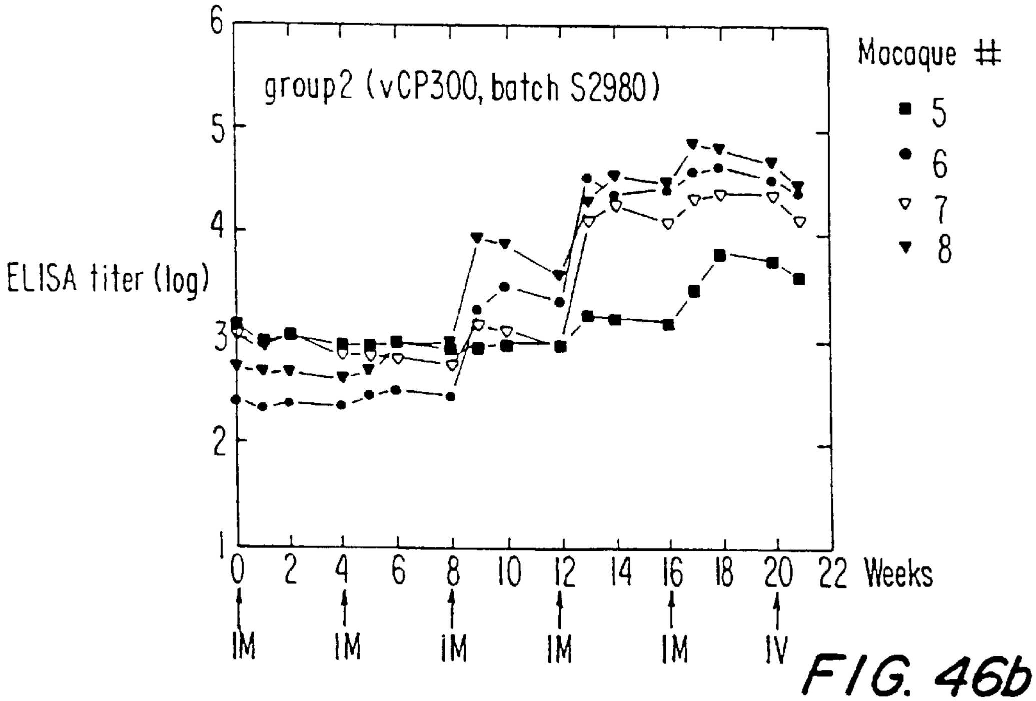
Figure 47A:
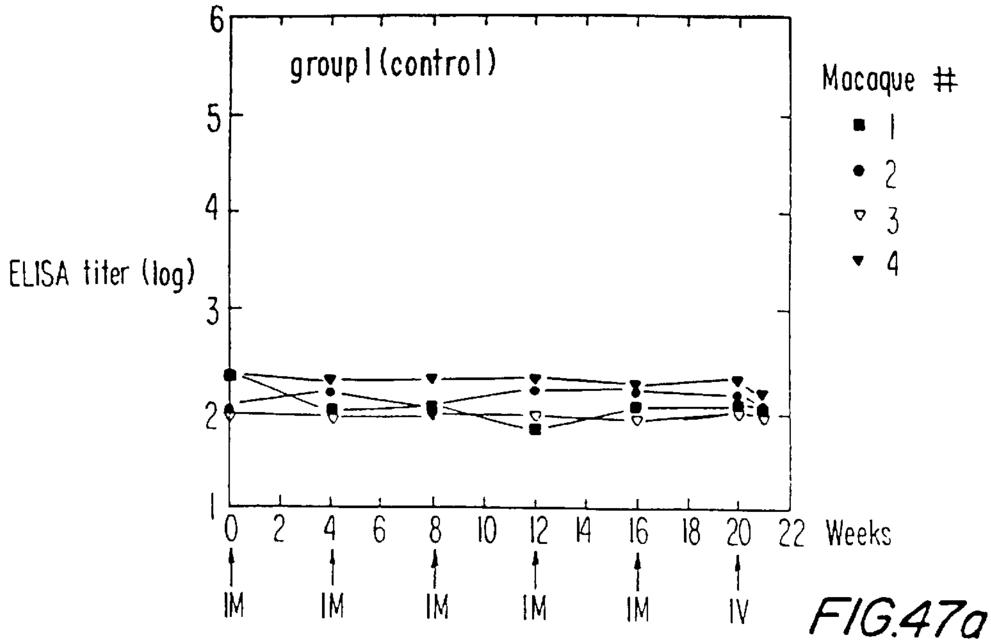
FIGS. 47*a*, 47*b*, nef ELISA, control and vCP300, respectively; keying as in FIGS. 44*a*–46*b*).
Figure 47B:
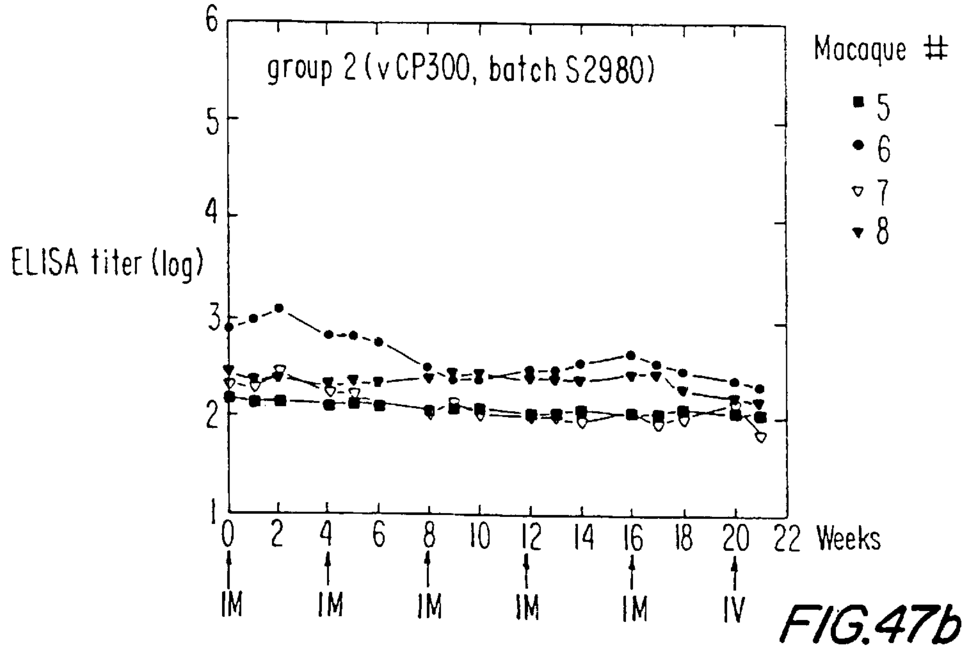

Serological results: Two (macaques #6, 7, 8) or three (macaque #5) injections were necessary to induce detectable anti-gp160 and anti-V3 responses (FIGS. 44*a*, 44*b*, 45*a*, 45*b*). Two weeks after the second injection, these responses were variable between animals (anti-gp160 titers fluctuating between 2 to 4.6 logs). This response heterogeneity was smoothed out by the third injection. The subsequent intramuscular injections mainly maintained or increased the titers which reached around 4.3 and 3.6 for respectively anti-gp160 and anti-V3 antibodies after the fourth to fifth injection. Detectable anti-p24 antibodies (FIGS. 46*a*, 46*b*) were observed after three (macaques #6, 8) to four (macaque #7) or five (macaque 5) vCP300 intramuscular injections. The animals with the highest anti-gp160 /V3 titers exhibited the highest anti-p24 (≈4.3 on week 18 post-primoimmunization). None of the animals raised anti-nef antibodies (FIGS. 47*a*, 47*b*).

The immune response induced by vCP300 was assessed by analyzing in ELISA the anti-HIV-1 gp160, V3, p24 and nef sera antibodies.

All the animals developed antibodies against gp160, V3 and p24: significant anti-gp160 or V3 responses were obtained after 2 or at most 3 intramuscular injections. Subsequent inoculations maintained or increased the antibody levels. Anti-p24 responses were detected after 3 to 5 injections and each inoculation of vCP300 increased the levels. No anti-nef antibodies could be detected in any of the animals.

The highest antibody titers were usually observed two weeks after each intramuscular injection, followed by a decrease until the next boost.

These serological results are very close to those obtained with ALVAC-HIV (vCP205) which expressed the same proteins but no CTL epitopes. Two minor differences can be pointed out in this exmaple with vCP300: slightly lower anti-gp160 /V3 antibody titers (≈0.2 to 0.5 log), and higher anti-p24 responses (all macaques positive, higher sera titers). Because of the individual variations between animals, these differences were not deemend significant. No indication of hypersensitivity was seen following intravenous inoculation. No side effects were recorded. This regimen induced high levels of binding antibodies to gp160 (though lower than with vCP205), V3 and p24 antigens. This Example shows that vCP300 and expression products thereof, antibodies therefrom, and DNA from vCP300 can be used as described above.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Altenburger, W., C-P. Suter and J. Altenburger, Archives Virol. 105, 15–27 (1989).
2. Avery, R. J., and J. Niven., Infect. and Immun. 26, 795–801 (1979).
3. Bachacher, A., Predl, R., Strutzenberger, K., Steinfellner, W., Trkola, A., Purtscher, M., Gruber, G., Tauer, C., Steindl, F., Jungbauer, A. and Katinger, H. AIDS Research and Human Retroviruses 10, 359–369 (1994).
4. Behbehani, A. M., Microbiological Reviews 47, 455–509 (1983).
5. Bergoin, M., and Dales, S., In Comparative Virology, eds. K. Maramorosch and E. Kurstak, (Academic Press, N.Y.) pp. 169–205 (1971).
6. Berman, P., Eastman, D., Wilkes, D., Nakamura, G., Gregory, T., Schwartz, D., Gorse, G., Belshe, R., Clements, M. and Byrn, R., AIDS 8, 591–601 (1994).
7. Berman, P., Gregory, T., Riddle, L., Nakamura, G., Champe, M., Porter, J., Wurm, F., Hershberg, R., Cobb, E. and Eichberg, J., Nature 345, 622–625 (1990).
8. Bertholet, C., Drillien, R., and Wittek, R., Proc. Natl. Acad. Sci. USA 82, 2096–2100 (1985).
9. Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300. (1990c).
10. Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23, 305–316 (1990b).
11. Boursnell, M. E. G., P. F. Green, J. I. A. Campbell, A. Deuter, R. W. Peters., F. M. Tomley, A. C. R. Samson, P. Chambers, P. T. Emmerson, and M. M. Binns, J. Gen. Virol. 71, 621–628 (1990a).
12. Broliden, P.-A., von Gegerfelt, A., Clapham, P., Rosen, J., Fenyo, E-M., Wahren, B. and Broliden, K., Proc. Natl. Acad. Sci. USA 89, 461–465 (1992).
13. Buller, R. M. L., Chakrabarti, S., Cooper, J. A., Twardzik, D. R., and Moss, B., J.Virol. 62, 866–874 (1988).
14. Buller, R. M. L., G. L. Smith, Cremer, K., Notkins, A. L., and Moss, B., Nature 317, 813–815 (1985).
15. Cadoz, M., A. Strady, B. Meignier, J. Taylor, J. Tartaglia, E. Paoletti and S. Plotkin, The Lancet, 339, 1429 (1992).
16. Chambers, P., N. S. Millar, and P. T. Emmerson, J. Gen. Virol. 67, 2685–2694 (1986).
17. Child, S. J., Palumbo, G. J., Buller, R. M. L., and Hruby, D. E. Virology 174, 625–629 (1990).
18. Clewell, D. B. and D. R. Helinski, Proc. Natl. Acad. Sci. USA 62, 1159–1166 (1969).
19. Clewell, D. B., J. Bacteriol 110, 667–676 (1972).
20. Colinas, R. J., R. C. Condit and E. Paoletti, Virus Research 18, 49–70 (1990).
21. Conley, A., Kessler, J., Boots, L., Tung, J.-S., Arnold, B., Keller, P., Shaw, A. and Emini, E., Proc. Natl. Acad. Sci. USA 91, 3348–3352 (1994).
22. Cooney E. L., Corrier A. C., Greenberg P. D., et al., Lancet 337, 567–572 (1991).
23. Cox, W. I., Tartaglia, J., and E. Paoletti. Virology 195, 845–850 (1993).
24. Dreyfuss, G., Adam, S. A., and Choi, Y. D., Mol. Cell. Biol. 4, 415–423 (1984).
25. Edbauer, C., R. Weinberg, J. Taylor, A. Rey-Senelonge, J. F. Bouquet, P. Desmettre, and E. Paoletti, Virology 179, 901–904 (1990).
26. Emini, E., Schleif, W., Nunberg, J., Conley, A., Eda, Y., Tokiyoshi, S., Putney, S., Matsushita, S., Cobb, K., Jett, C., Eichberg, J., and K. Murthy, Nature 355, 728–730 (1992).
27. Engelke, D. R., Hoener, P. A., and Collins, F. S., Proc. Natl. Acad. Sci. USA 85, 544–548 (1988).
28. Espion, D., S. de Henau, C. Letellier, C.-D. Wemers, R. Brasseur, J. F. Young, M. Gross, M. Rosenberg, G. Meulemans and A. Burny, Arch. Virol. 95, 79–95 (1987).
29. Fenner, F., Virology 5, 502–529 (1958).
30. Flexner, C., Hugen, A., and Moss, B., Nature 330, 259–262 (1987).

31. Fries et al., 32nd Interscience Conference on Antimicrobial Agents and Chemotherapy, Anaheim, Calif. (October 1992).
32. Fultz, P., Nara, P., Barre-Sinoussi, F., Chaput, A., Greenberg, M., Muchmore, E., Kieny, M.-P. and Girard, M. Science 256, 1687–1689 (1992).
33. Funahashi, S., T. Sato and H. Shida, J. Gen. Virol. 69, 35–47 (1988).
34. Garten, W., Kohama, T., and H-D. Klenk. J. Gen. Virol. 51, 207–211 (1980).
35. Ghendon, Y. Z., and Chernos, V. I., Acta Virol. 8, 359–368 (1964).
36. Gillard, S., Spehner, D., Drillien, R., and Kirn, A., Proc. Natl. Acad. Sci. USA 83, 5573–5577 (1986).
37. Girard, M., Kieny, M.-P., Pinter, A., Barre-Sinoussi, F., Nara, P., Kolbe, H., Kusui, K., Chaput, A., Reinhart, T., Muchmore, E., Ronco, J., Kaczorek, M., Gomard, E., Gluckman, J.-C. and Fultz, P., Proc. Natl. Acad. Sci. USA 88, 542–546 (1991).
38. Goebel, S. J., Johnson, G. P., Perkus, M. E., Davis, S. W., Winslow, J. P., Paoletti, E., Virology 179, 247–266 (1990a).
39. Goebel, S. J., G. P. Johnson, M. E. Perkus, S. W. Davis, J. P. Winslow and E. Paoletti, Virology 179, 517–563 (1990b).
40. Golding, H., Robey, F., Gates, F., Linder, W., Beining, P., Hoffman, T. and Golding, B., J. Exp, Med. 167, 914–923 (1988).
41. Golding, H., Shearer, G., Hillman, K., Lucas, P., Manischewitz, J., Zajac, R., Clerici, M., Gress, R., Boswell, R. and Golding, B., J. Clin. Invest. 83, 1430–1435 (1989).
42. Goldstein, D. J. and S. K. Weller, Virology 166, 41–51 (1988).
43. Guo, P., Goebel, S., Davis, S., Perkus, M. E., Languet, B., Desmettre, P., Allen, G., and Paoletti, E., J. Virol. 63, 4189–4198 (1989).
44. Guo et al., J. Virol. 64, 2399–2406 (1990).
45. Hammond, S., Bollinger, R., Stanhope, P., Quinn, T., Schwartz, D., Clements, M. and Siliciano, R., J. Exp. Med. 176, 1531–1542 (1992).
46. Hanson, C., AIDS Research and Human Retroviruses 10, 645–648 (1994).
47. Homma, M., and M. Ohuchi, J. Virol. 12, 1457–1465 (1973).
48. Hruby, D. E. and L. A. Ball, J. Virol. 43, 403–409 (1982).
49. Hruby, D. E., R. A. Maki, D. B. Miller and L. A. Ball, Proc. Natl. Acad. Sci. USA 80, 3411–3415 (1983).
50. Hu, S.-L., Abrams, K., Barber, G., Morn, P., Zarling, J., Langlois, A., Kuller, L., Morton, W. and Benveniste, R., Science 255, 456–459 (1992).
51. Ichihashi, Y. and Dales, S., Virology 46, 533–543 (1971).
52. Itamura, S., H. Iinuma, H. Shida, Y. Morikawa, K. Nerome and A. Oya, J. Gen. Virol. 71, 2859–2865 (1990).
53. Jacobson, J. G., D. A. Leib, D. J. Goldstein, C. L. Bogard, P. A. Schaffer, S. K. Weller and D. M. Coen, Virology 173, 276–283 (1989).
54. Jamieson, A. T., G. A. Gentry and J. H. Subak-Sharpe, J. Gen. Virol. 24, 465–480 (1974).
55. Katinger, H., Muster, T., Buchacher, A., Trkola, A., Purtscher, M., Gruber, G., Steindl, F., Himmler, G., Jungbauer, A. and Ruker, F., Septieme Colloque Des Cent Gardes—1992, 299–303 (1992).
56. Kato, S., M. Takahashi, S. Kameyama and J. Kamahora, Biken's 2, 353–363 (1959).
57. Kieny, M. P., Lathe, R., Drillien, R., Spehner, D., Skory, S., Schmitt, D., Wiktor, T., Koprowski, H., and Lecocq, J. P., Nature (London) 312, 163–166 (1984).
58. Klasse, P., Pipkorn, R. and Blomberg, J., Proc. Natl. Acad. Sci. USA 85, 5225–5229 (1988).
59. Konishi et al., Virology 190, 454–458 (1992).
60. Kotwal, G. J., S. N. Isaacs, R. McKenzie, M. M. Frank and B. Moss, Science 250, 827–830 (1990).
61. Kotwal, G. J., A. W. Hugin and B. Moss, Virology 171, 579–587 (1989a).
62. Kotwal, G. J. and Moss, B., Nature (Lond.) 335, 176–178 (1988).
63. Kotwal, G. J. and B. Moss, J. Virol. 63, 600–606 (1989b).
64. Le, L., R. Brasseur, C. Wemers, G. Meulemans, and A. Burny, Virus Genes 1, 333–350 (1988).
65. Mandecki, W., Proc. Natl. Acad. Sci. USA 83, 7177–7182 (1986).
66. Maniatis, T., Fritsch, E. F., and Sambrook, J. In Molecular cloning: a laboratory manual, (Cold Spring Harbor Laboratory, Cold Spring Harbor, N.Y.) (1982).
67. Matthews, R. E. F., Intervirology 17, 42–44 (1982).
68. McGinnes, L. W., and T. G. Morrison, Virus Research 5, 343–356 (1986).
69. Merz, D. C., A. Scheid, and P. Choppin, J. Exper. Med. 151, 275–288 (1980).
70. Miller, M., Warmerdam, M., Gaston, I., Greene, W. and Feinberg, M., J. Exp. Med. 179, 101–113 (1994).
71. Morgan, A. J., M. Mackett, S. Finerty, J. R. Arrand, F. T. Scullion and M. A. Epstein, J. Med. Virol. 25, 189–195 (1988).
72. Moss, B., E. Winters and J. A. Cooper, J. Virol. 40, 387–395 (1981).
73. Nagai, Y., T. Yoshida, M. Hamaguchi, H. Naruse, M. Iinuma, K. Maeno, and T. Matsumoto, Microbiol. Immunol. 24, 173–177 (1980).
74. Nabel et al., Tibtech, May 1993, 11:211–215.
75. Nagai, Y., H. D. Klenk, and R. Rott, Virology 72, 494–508 (1976).
76. Norrby, E., and Y. Gollmar, Infect. and Immun. 11, 231–239 (1975).
77. Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).
78. Palumbo, G. J., Pickup, D. J., Fredrickson, T. N., Mcintyre, L. J., and Buller, R. M. L., Virology 172, 262–273 (1989).
79. Panicali, D. and E. Paoletti, Proc. Natl. Acad. Sci. USA 79, 4927–4931 (1982).
80. Panicali, D., Davis, S. W., Mercer, S. R., and Paoletti, E., J. Virol. 37, 1000–1010 (1981).
81. Patel, D. D. and Pickup, D. J., EMBO 6, 3787–3794 (1987).
82. Patel, D. D., Ray, C. A., Drucker, R. P., and Pickup, D. J., Proc. Natl. Acad. Sci. USA 85, 9431–9435 (1988).
83. Perkus, M. E., D. Panicali, S. Mercer and E. Paoletti, Virology 152, 285–297 (1986).
84. Perkus, M., Limbach, K. and Paoletti, E., Journal of Virology 63, 3829–3836 (1989).
85. Perkus, M. E., A. Piccini, B. R. Lipinskas and E. Paoletti, Science 229, 981–984 (1985).
86. Perkus, M. E., Limbach, K., and Paoletti, E., J. Virol. 63, 3829–3836 (1989).
87. Perkus, M. E., Goebel, S. J., Davis, S. W., Johnson, G. P., Limbach, K., Norton, E. K., and Paoletti, E., Virology 179, 276–286 (1990).
88. Perkus, M. E., S. J. Goebel, S. W. Davis, G. P. Johnson, E. K. Norton and E. Paoletti, Virology 180, 406–410 (1991).
89. Pialoux et al., Aids Research and Human Retroviruses, 11(3):373–81 (1995).

90. Piccini, A., M. E. Perkus, and E. Paoletti, Methods in Enzymology 153, 545–563 (1987).
91. Pickup, D. J., B. S. Ink, B. L. Parsons, W. Hu and W. K. Joklik, Proc. Natl. Acad. Sci. USA 81, 6817–6821 (1984).
92. Pickup, D. J., B. S. Ink, W. Hu, C. A. Ray and W. K. Joklik, Proc. Natl. Acad. Sci. USA 83, 7698–7702 (1986).
93. Robinson, W., Kawamura, T., Gorny, M., Lake, D., Xu, J.-Y., Matsumoto, Y., Sugano, T., Masuho, Y., Mitchell, W., Hersh, E. and Zolla-Pazner, S., Proc. Natl. Acad. Sci. USA 87, 3185–3189 (1990).
94. Sanger, F., Nickel, S. Coulson, A. R., Proc. Natl. Acad. Sci. 74, 5463–5467 (1977).
95. Schmidtt, J. F. C. and H. G. Stunnenberg, J. Virol. 62, 1889–1897 (1988).
96. Seligmann, E. B., In Laboratory Techniques in Rabies, eds. M. M. Kaplan and H. Koprowski, (World Health Organization, Geneva) pp. 279–285 (1973).
97. Shafferman, A., Lennox, J., Grosfeld, H., Sadoff, J., Redfield, R. and Burke, D., AIDS Res. Hum. Retroviruses 5, 33–39 (1989).
98. Shapira, S. K., Chou, J., Richaud, F. V. and Casadaban, M. J., Gene 25, 71–82 (1983).
99. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
100. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
101. Shida, H., Virology 150, 451–462 (1986).
102. Slabaugh, M., N. Roseman, R. Davis and C. Mathews, J. Virol. 62, 519–527 (1988).
103. Smith, J. S., P. A. Yager and G. M. Baer, In Laboratory Techniques in Rabies, eds. M. M. Kaplan and H. Koprowski (WHO Geneva) pp. 354–357 (1973).
104. Spear, G., Takefman, D., Sharpe, S., Ghassemi, M. and Zolla-Pazner, S., Virology 204, 609–615 (1994).
105. Spina, C., Kwoh, T., Chowers, M., Guatelli, J. and Richman, D., J. Exp. Med. 179, 115–123 (1994).
106. Stanberry, L. R., S. Kit and M. G. Myers, J. Virol. 55, 322–328 (1985).
107. Tabor, S. and C. C. Richardson, Proc. Natl. Acad. Sci. USA 84, 4767–4771 (1987).
108. Tartaglia, J., Perkus, M. E., Taylor, J., Norton, E. K., Audonnet, J.-C., Cox, W. I., Davis, S. W., Van Der Hoeven, J., Meignier, B., Riviere, M., Languet, B., Paoletti, E., Virology 188, 217–232 (1992).
109. Tartaglia, J., R. Gettig & E. Paoletti, Virology (In press).
110. Tartaglia, J., J. Taylor, W. I. Cox, J.-C. Audonnet, M. E. Perkus, A. Radaelli, C. de Giuli Morghen, B. Meignier, M. Riviere, K. Weinhold & E. Paoletti, In AIDS Research Reviews, W. Koff, F. Wong-Staal & R. C. Kenedy, Eds., Vol. 3, Marcel Dekker, NY, pp. 361–378 (1993a).
111. Tartaglia, J. & E. Paoletti, In Immunochemistry of Viruses, II. The Basis for Serodiagnosis and Vaccines. M. H. V. van Regenmortel & A. R. Neurath, Eds. 125–151. Elsevier Science Publishers, Amsterdam (1990b).
112. Tartaglia, J., Jarrett, O., Desmettre, P., Paoletti, E. (1993b) J. Virol. 67, 2370–2375 (1993).
113. Tartaglia, J., Pincus, S., Paoletti, E., Critical Reviews in Immunology 10, 13–30 (1990a).
114. Taylor, J., Weinberg, R., Kawaoka, Y., Webster, R. G., and Paoletti, E., Vaccine 6, 504–508 (1988a).
115. Taylor, J., C. Trimarchi, R. Weinberg, B. Languet, F. Guillemin, P. Desmettre and E. Paoletti, Vaccine 9, 190–193 (1991b).
116. Taylor, G., E. J. Stott, G. Wertz and A. Ball, J. Gen. Virol. 72, 125–130 (1991a).
117. Taylor, J., R. Weinberg, B. Lanquet, P. Desmettre, and E. Paoletti, Vaccine 6, 497–503 (1988b).
118. Taylor, J., R. Weinberg, J. Tartaglia, C. Richardson, G. Alkhatib, D. Briedis, M. Appel, E. Norton & E. Paoletti, Virology 187, 321–328 (1992).
119. Taylor, J., Edbauer, C., Rey-Senelonge, A., Bouquet, J.-F., Norton, E., Goebel, S., Desmettre, P., Paoletti, E., J. Virol. 64, 1441–1450 (1990).
120. Toyoda, T., T. Sakaguchi, K. Imai, N. M. Inocencio, B. Gotoh, M. Hamaguchi, and Y. Nagai, Virology 158, 242–247 (1987).
121. Webster et al., Vaccine, 1994, 12(16): 1495–1498.
122. Weir, J. P. and B. Moss, J. Virol. 46, 530–537 (1983).
123. Yuen, L., and Moss, B., Proc. Natl. Acad. Sci. USA 84, 6417–6421 (1987).
124. Zhou, J., L. Crawford, L. McLean, X. Sun, M. Stanley, N. Almond and G. L. Smith, J. Gen. Virol. 71, 2185–2190 (1990).

---

What is claimed is:

1. A recombinant poxvirus comprising exogenous DNA encoding at least one Lentivirus epitope, wherein the poxvirus is a vaccinia virus having J2R, B13R+B14R, A26L, A56R, C7L–K1L and I4L are deleted from the virus; or a thymidine kinase gene, a hemorrhagic region, an A type inclusion body region, a hemagglutinin gene, a host range region, and a large subunit, ribonucleotide reductase are deleted from the virus;

or the poxvirus is a NYVAC recombinant virus;

and wherein the exogenous DNA encodes:

HIV1 gag(+pro)(IIIB), gp120(MN)(+transmembrane) and two nef(BRU)CTL epitopes; or gp120(MN)(+transmembrane) and two ELDKWA (SEQ ID NO: 147) epitopes in the gp120 V3 loop region; or HIV1 gag(+pro)(IIIB) and gp120(MN)(+ transmembrane); or HIV1 gag(+pro)(IIIB), gp120(MN)(+transmembrane) and two nef(BRU) and three pol(IIIB) CTL epitope containing regions; or at least one of: HIV1 gag(+pro)(IIIB), gp120(MN)(+ transmembrane), nef(BRU)CTL, pol(IIIB)CTL, and ELDKWA (SEQ ID NO: 147) or LDKW (SEQ ID NO: 148) epitopes.

2. The recombinant poxvirus of claim 1 wherein wherein the exogenous DNA encodes HIV1 gag(+pro)(IIIB), gp120 (MN)(+transmembrane) and two nef(BRU)CTL epitopes.

3. The recombinant poxvirus of claim 2 wherein the two nef(BRU)CTL epitopes are CTL1 and CTL2.

4. The recombinant poxvirus of claim 1 wherein the exogenous DNA encodes gp120(MN)(+transmembrane) and two ELDKWA (SEO ID NO: 147) epitopes in the gp120 V3 loop region.

5. The recombinant poxvirus of claim 1 wherein the exogenous DNA encodes HIV1 gag(+pro)(IIIB) and gp120 (MN)(+transmembrane).

6. The recombinant poxvirus of claim 1 wherein the exogenous DNA encodes HIV1 gag(+pro)(IIIB), gp120 (MN)(+transmembrane) and two nef(BRU) and three pol (IIIB) CTL epitope containing regions.

7. The recombinant poxvirus of claim 6 wherein the two nef(BRU)CTL and three pol(IIIB)CTL epitopes are: CTL1, CTL2, pol1, pol2 and pol3.

8. The recombinant poxvirus of claim 1 which is a NYVAC recombinant virus.

9. The recombinant poxvirus of claim 1 wherein the exogenous DNA codes for at least one of: HIV1 gag(+pro) (IIIB), gp120(MN)(+transmembrane), nef(BRU)CTL, pol (IIIB)CTL, and ELDKWA (SEQ ID NO: 147) or LDKW (SEQ ID NO: 148) epitopes.

10. The recombinant poxvirus of claim 9 wherein the exogenous DNA codes for HIV1 gag(+pro)(IIIB), gp120 (MN)(+transmembrane), two nef(BRU)CTL and three pol (IIIB)CTL epitopes; or, two ELDKWA (SEO ID NO: 147) epitopes.

11. The recombinant poxvirus of claim 10 wherein the two nef(BRU)CTL and three pol(IIIB)CTL epitopes are: CTL1, CTL2, pol1, pol2 and pol3.

12. The recombinant poxvirus of claim 9 wherein the ELDKWA (SEQ ID NO: 147) or LDKW (SEQ ID NO: 148) epitopes are expressed as part of a region of gp120 or a region of gp160.

13. The virus of claim 12 wherein the ELDKWA (SEQ ID NO: 147) or LDKW (SEQ ID NO: 148) epitopes are expressed as part of gp120 V3.

14. A recombinant poxvirus which is vP1313.

15. A immunogenic composition comprising a recombinant poxvirus as claimed in claim 1 and a carrier.

16. A method for expressing a Lentivirus gene product comprising infecting a suitable host cell with a recombinant poxvirus as claimed in claim 1.

17. A method for inducing an immunogical response to a Lentivirus gene product comprising administering a recombinant poxvirus as claimed in claim 1.

18. A method for inducing an immunogical response to a Lentivirus gene product comprising administering a composition as claimed in claim 15.

19. A method for inducing an immunogical response to a Lentivirus gene product comprising administering a recombinant poxvirus comprising exogenous DNA encoding at least one Lentivirus epitope, wherein the poxvirus is a vaccinia virus having J2R, B13R+B14R, A26L, A56R, C7L–K1L and I4L are deleted from the virus; or a thymidine kinase gene, a hemorrhagic region, an A type inclusion body region, a hemagglutinin gene, a host range region, and a large subunit, ribonucleotide reductase are deleted from the virus;

or the poxvirus is a NYVAC recombinant virus; and said method further comprising subsequently administering an antigen derived from a Lentivirus, whereby the administation of the recombinant poxvirus is a priming administration and the administration of the antigen derived from the Lentivirus is a booster administration.

20. The method of claim 18 further comprising subsequently administering an antigen derived from Lentivirus, whereby the administation of the composition is a priming administration and the administration of the antigen derived from Lentivirus is a booster administration.

21. The method of claim 19 wherein the Lentivirus is human immunodeficiency virus.

22. A recombinant poxvirus which is vP1319.

23. The method of claim 17 further comprising subsequently administering an antigen derived from Lentivirus, whereby the administation of the composition is a priming administration and the administration of the antigen derived from Lentivirus is a booster administration.

* * * * *